(12) United States Patent
Burton et al.

(10) Patent No.: US 7,774,052 B2
(45) Date of Patent: Aug. 10, 2010

(54) METHODS AND APPARATUS FOR MONITORING CONSCIOUSNESS

(75) Inventors: David Burton, Victoria (AU); Eugene Zilberg, Victoria (AU)

(73) Assignee: Compumedics Limited, Abbotsford (AU)

( * ) Notice: Subject to any disclaimer, the term of this patent is extended or adjusted under 35 U.S.C. 154(b) by 1085 days.

(21) Appl. No.: 10/731,816

(22) Filed: Dec. 9, 2003

(65) Prior Publication Data

US 2004/0193068 A1   Sep. 30, 2004
US 2010/0076333 A9   Mar. 25, 2010

Related U.S. Application Data

(63) Continuation of application No. PCT/AU2002/000776, filed on Jun. 13, 2002.

(51) Int. Cl.
*A61B 5/04* (2006.01)

(52) U.S. Cl. ........................ 600/544; 600/545
(58) Field of Classification Search .......... 600/544–546
See application file for complete search history.

(56) References Cited

U.S. PATENT DOCUMENTS

| | | | | |
|---|---|---|---|---|
| 4,201,224 A | * | 5/1980 | John | 600/544 |
| 4,869,264 A | * | 9/1989 | Silberstein | 600/544 |
| 5,069,221 A | | 12/1991 | Smith et al. | |
| 5,263,489 A | * | 11/1993 | Johnson et al. | 600/546 |
| 5,307,818 A | * | 5/1994 | Segalowitz | 600/509 |
| 5,320,109 A | * | 6/1994 | Chamoun et al. | 600/544 |
| 5,566,067 A | | 10/1996 | Hobson et al. | |
| 5,730,146 A | * | 3/1998 | Itil et al. | 600/545 |
| 5,782,874 A | * | 7/1998 | Loos | 607/2 |
| 5,813,993 A | | 9/1998 | Kaplan et al. | |
| 6,032,064 A | | 2/2000 | Devlin et al. | |
| 6,052,619 A | * | 4/2000 | John | 600/544 |

(Continued)

FOREIGN PATENT DOCUMENTS

WO   9810701 A1   3/1998

(Continued)

OTHER PUBLICATIONS

International Search Report, International Application No. PCT/AU02/00776 (Jun. 13, 2002), WO 02/100267 (Dec. 19, 2002).

*Primary Examiner*—Patricia C Mallari
*Assistant Examiner*—Karen E Toth
(74) *Attorney, Agent, or Firm*—Sughrue Mion, PLLC

(57) ABSTRACT

The systems of the present invention provide improved accuracy in monitoring, analysing, detecting, predicting and/or providing alerts and alarms associated with depth of anaesthesia, depth of consciousness, hypnotic state, sedation depth, fatigue or vigilance of a subject, with as few as 3 surface electrodes. The systems incorporate real-time phase, amplitude and frequency analysis of a subject's electro-encephalogram. The systems weight outputs of various types of analyses to produce an integrated analysis or display for precise indication or alert to users of the systems including anaesthetists, nurses and other medical personnel, transport drivers and machine workers. The systems weight the outputs of one or more analysis algorithms including combinations of simultaneous, real-time R&K analysis, AEP spectral analysis-SEF-MF, Bi-coherence analysis, initial wave analysis, auditory response, arousal analysis, body movement analysis, 95% spectral edge analysis and anaesthetic phase and spectral energy variance measurement in association with a subject's state of consciousness.

15 Claims, 54 Drawing Sheets

U.S. PATENT DOCUMENTS

| | | | |
|---|---|---|---|
| 6,117,075 A * | 9/2000 | Barnea | 600/300 |
| 6,217,627 B1 * | 4/2001 | Vyskocil et al. | 55/492 |
| 6,385,486 B1 * | 5/2002 | John et al. | 600/544 |
| 6,493,576 B1 * | 12/2002 | Dankwart-Eder | 600/544 |
| 6,556,861 B1 * | 4/2003 | Prichep | 600/544 |
| 6,560,479 B2 * | 5/2003 | van Drongelen | 600/544 |
| 6,728,564 B2 * | 4/2004 | Lahteenmaki | 600/383 |
| 6,966,650 B2 * | 11/2005 | Hu et al. | 351/205 |
| 2002/0173729 A1 * | 11/2002 | Viertio-Oja et al. | 600/544 |
| 2003/0069510 A1 * | 4/2003 | Semler | 600/509 |
| 2003/0181821 A1 * | 9/2003 | Greenwald et al. | 600/544 |
| 2004/0243017 A1 * | 12/2004 | Causevic | 600/544 |
| 2005/0065427 A1 * | 3/2005 | Magill et al. | 600/407 |

FOREIGN PATENT DOCUMENTS

| | | |
|---|---|---|
| WO | WO 98/43536 | 10/1998 |

* cited by examiner

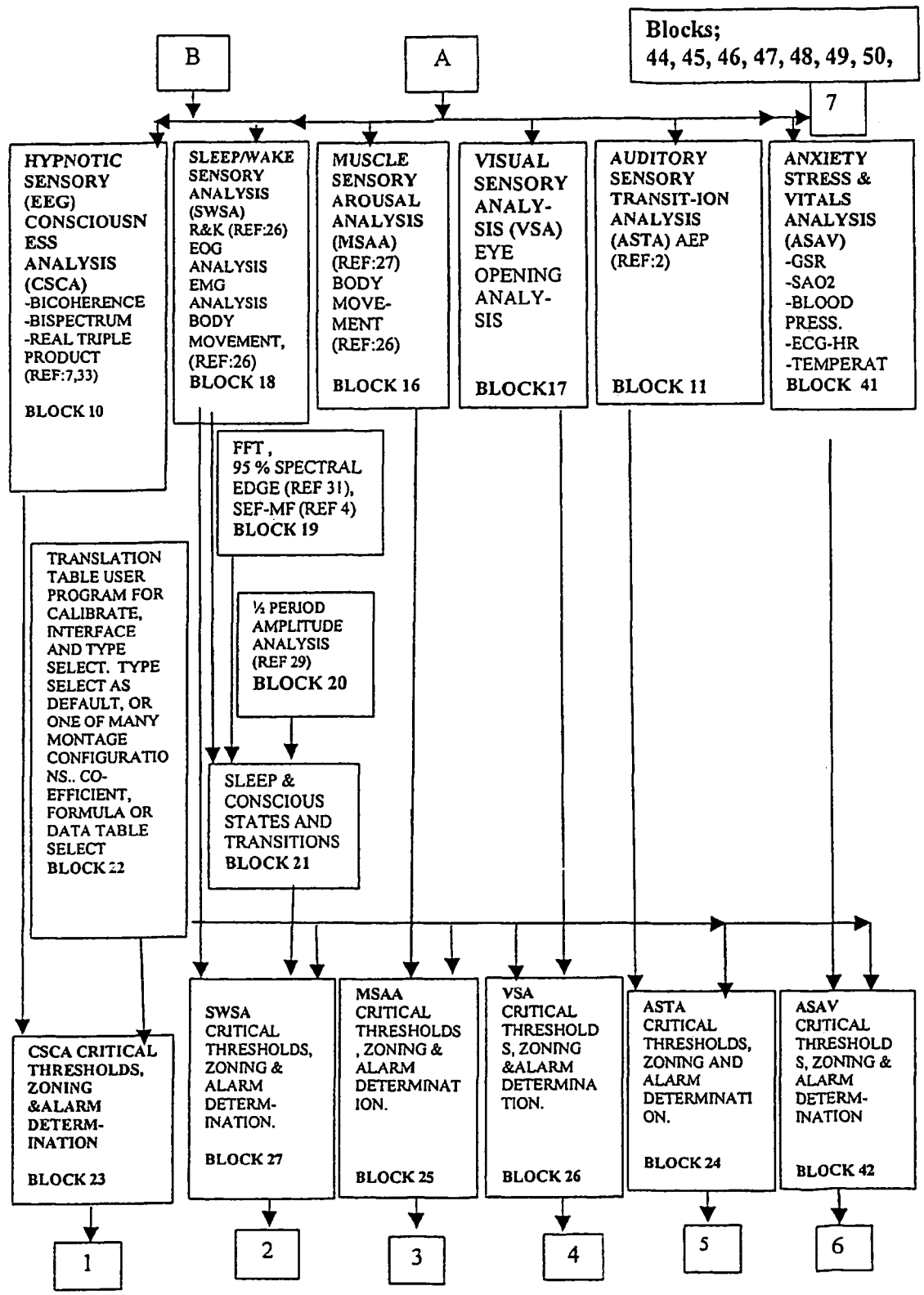
FIG 18 (cont)(i)

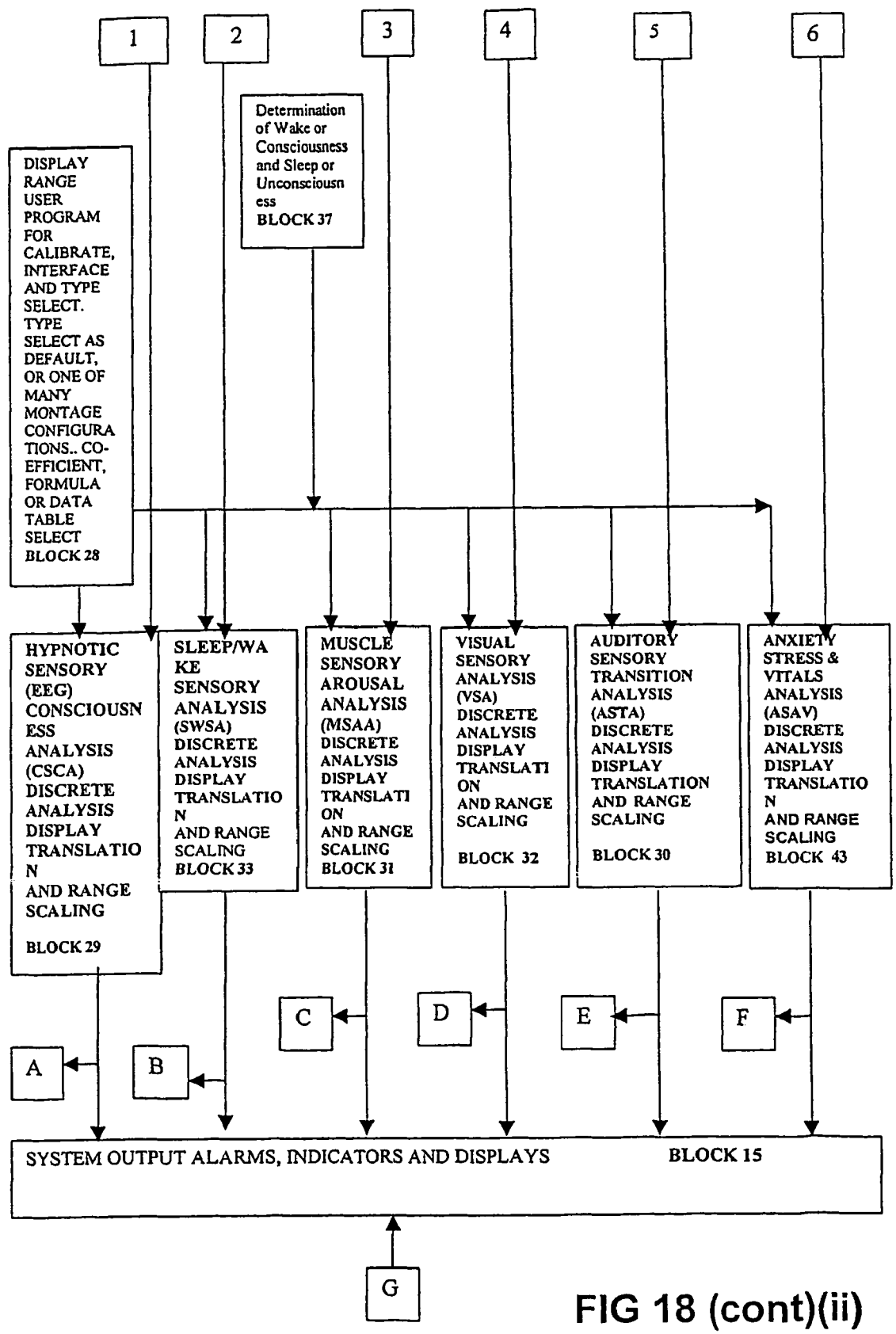
FIG 18 (cont)(ii)

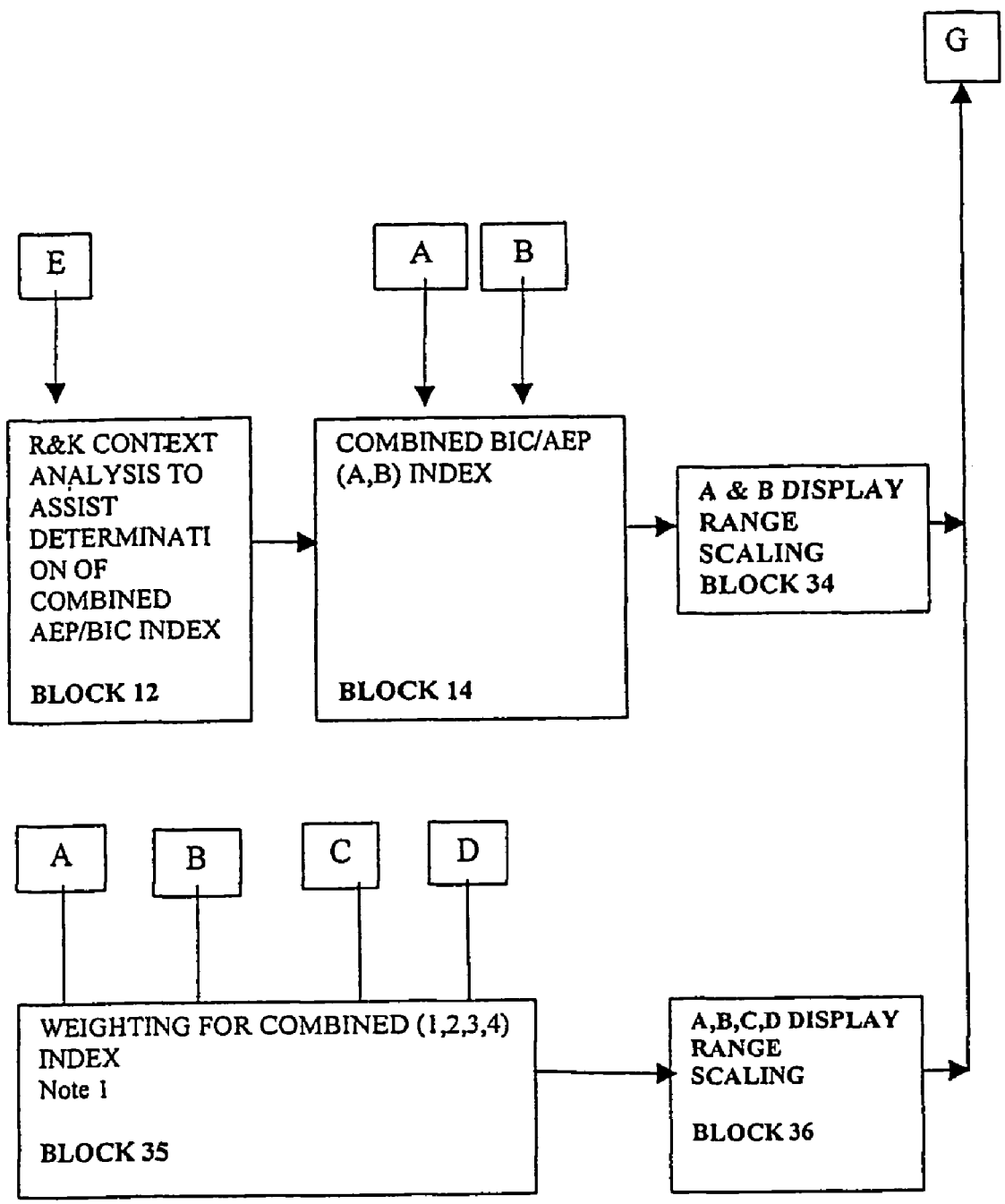
FIG 18 (cont)(iii)

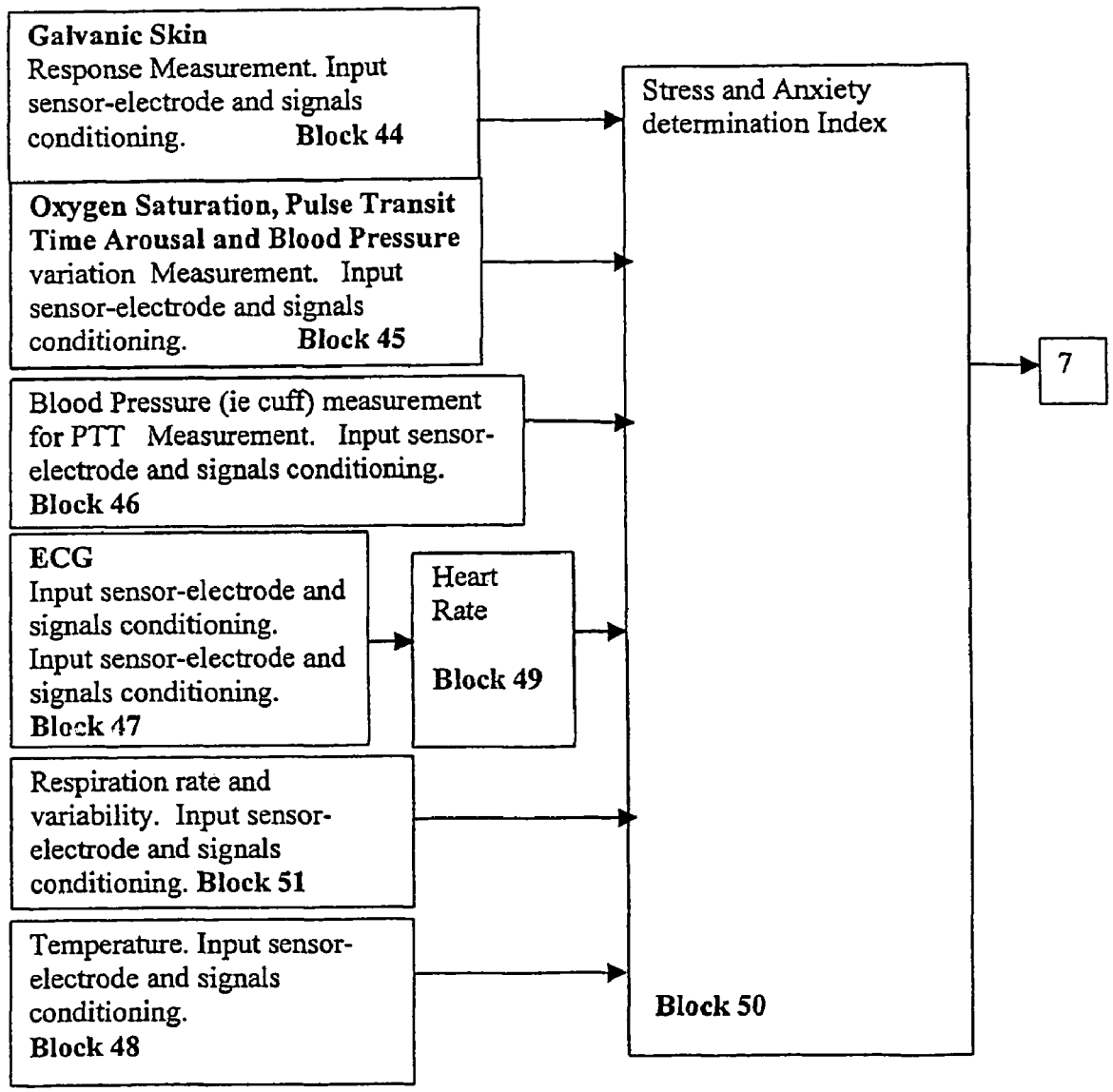
FIG 18 (cont)(iv)

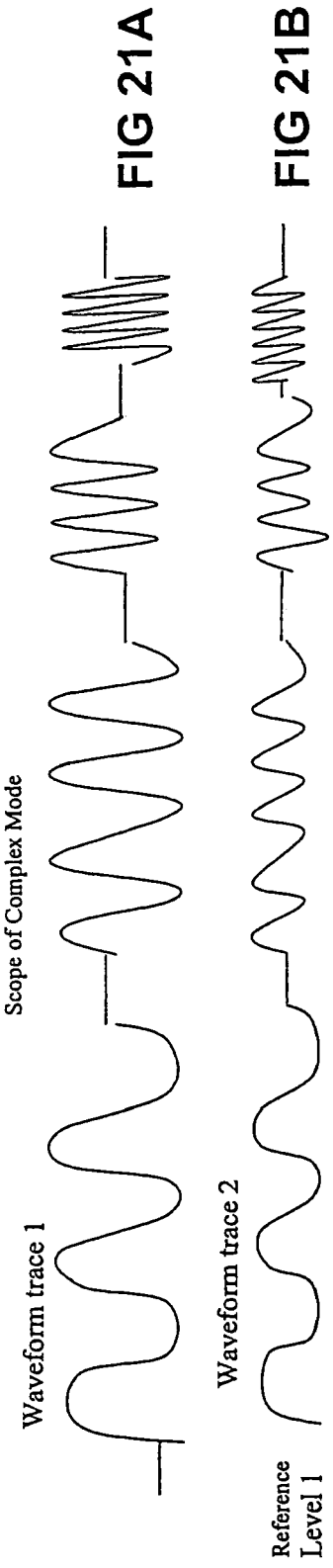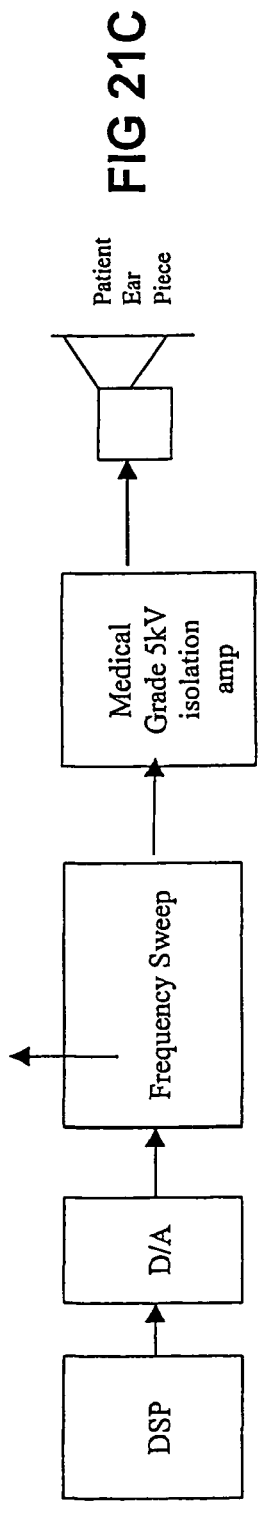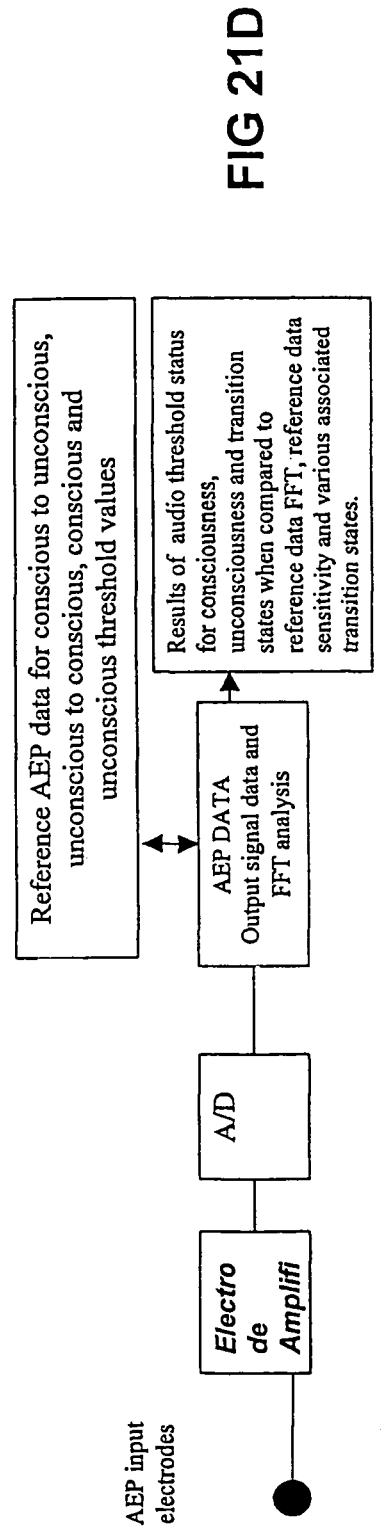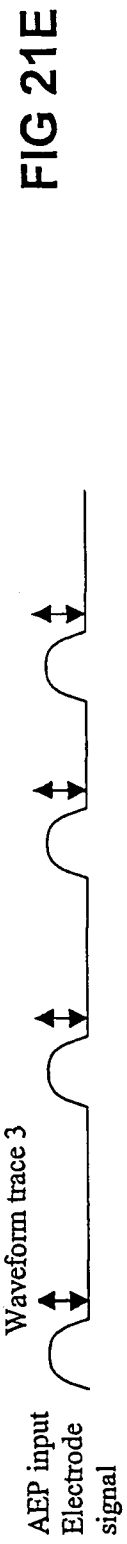
FIG 21A
FIG 21B
FIG 21C
FIG 21D
FIG 21E

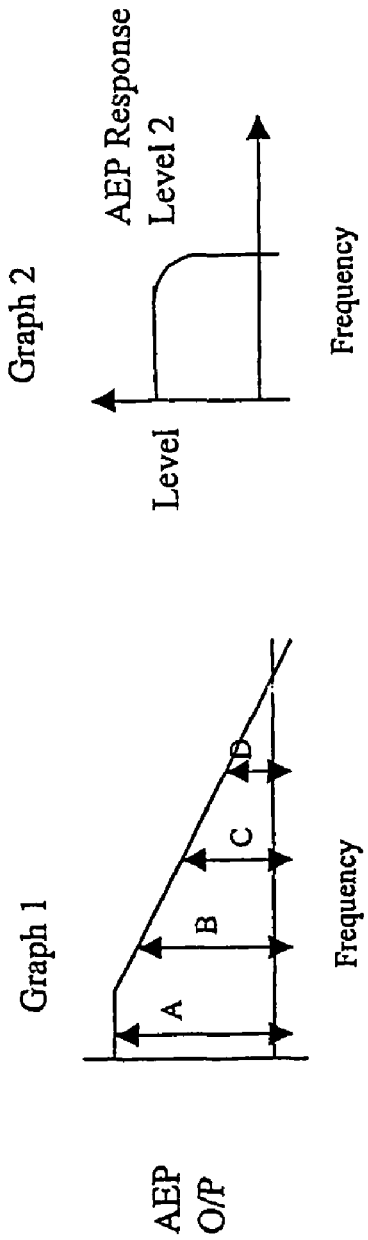
FIG 21F
FIG 21G
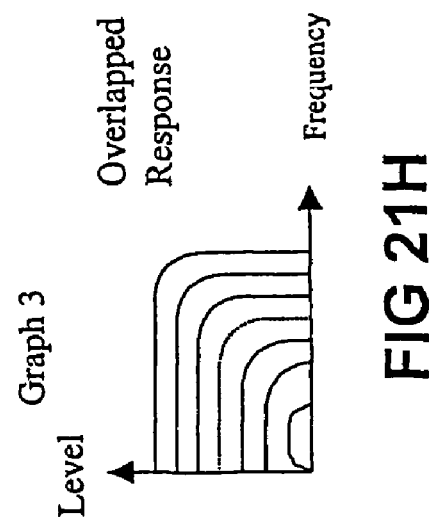
FIG 21H

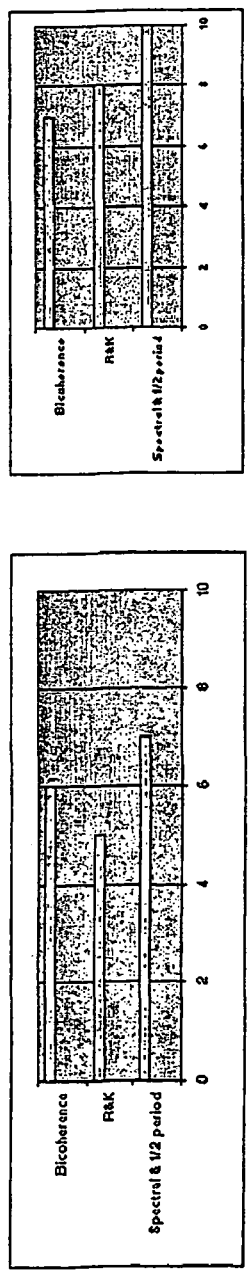
FIG 22A — Context Analysis Method
FIG 22B — Context Analysis Probability
FIG 22a / FIG 22b — Validate
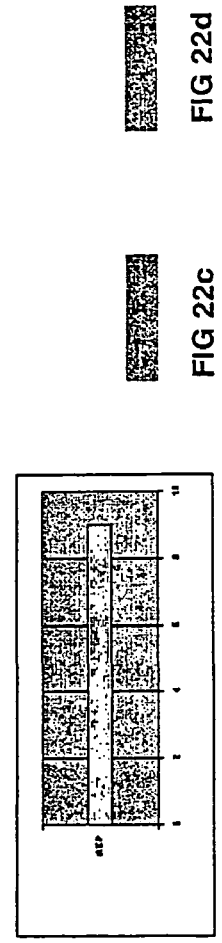
FIG 22C — Transition Analysis Method
FIG 22D — Transition Analysis Probability
FIG 22c / FIG 22d — Validate
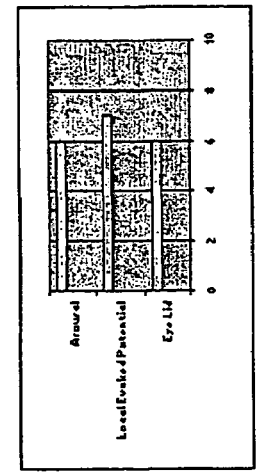
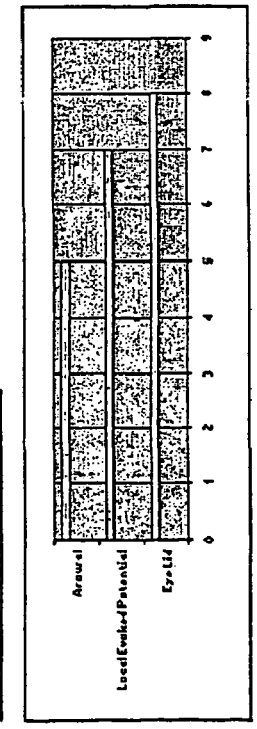
FIG 22E — Movement Analysis Method
FIG 22F — Movement Analysis Probability
FIG 22e / FIG 22f — Validate

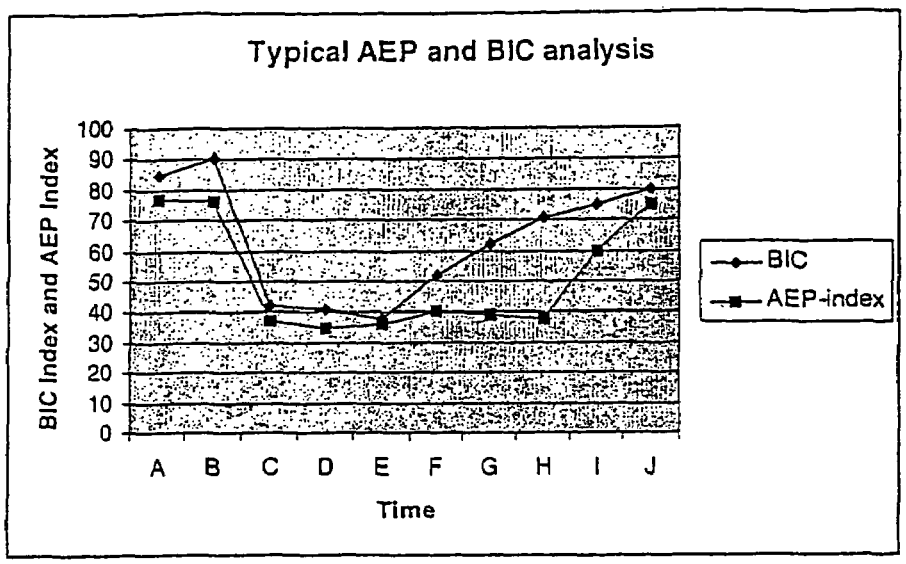
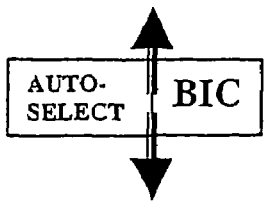
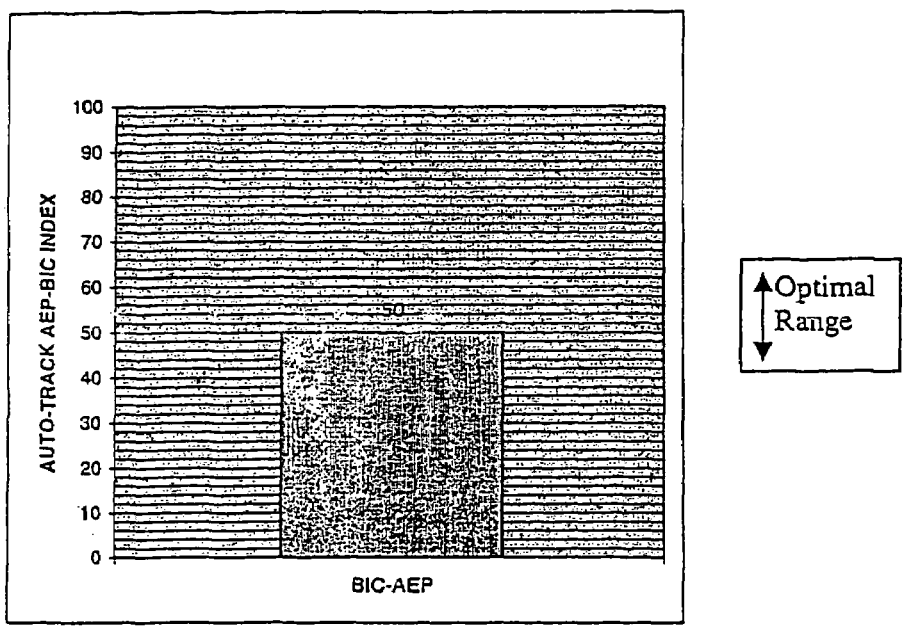
FIG 23A

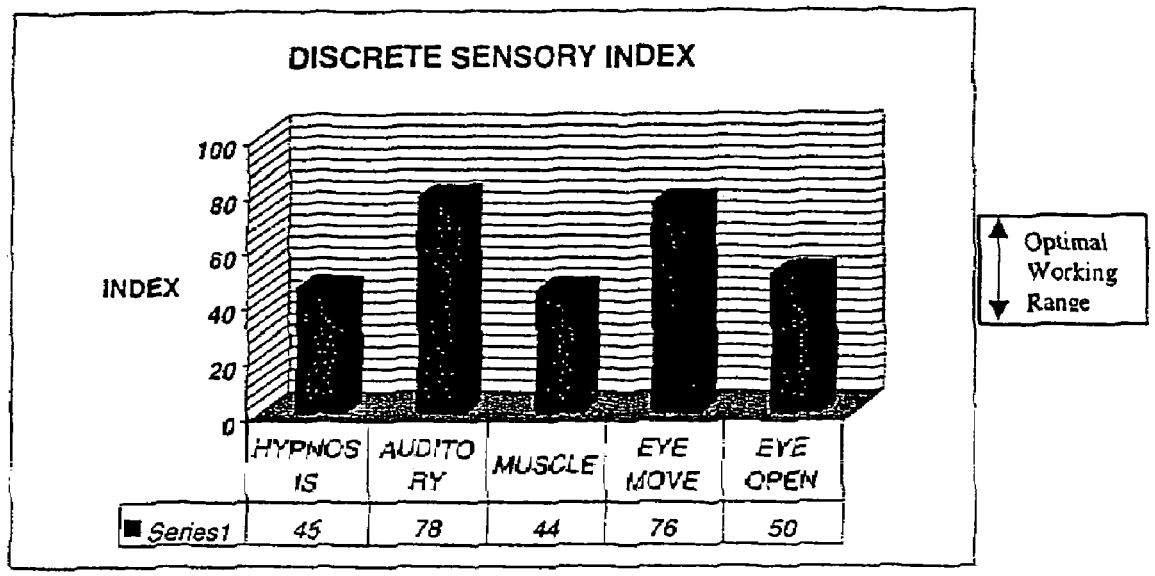
VERY POOR-RED
OPTIMAL-GREEN
POOR-ORANGE
CURRENT CONSCIOUS STATE- CONSCIOUS
TRANSITION STATUS-    CONSCIOUS TO UNCONSCIOUS
SIGNAL VALIDATION HINT    : CHECK BIC + ELECTRODE
ANALYSIS VALIDATION HINT : BIC ANALYSIS LOW QUALITY
FIG 23B

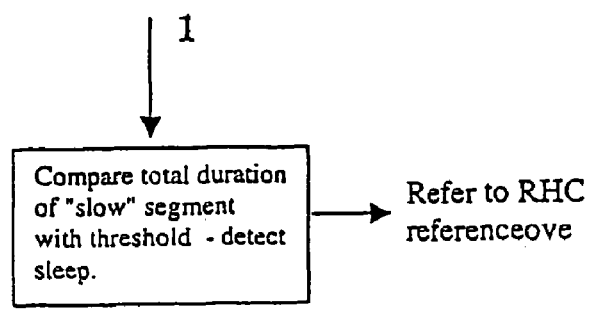

↓ 1

Compare total duration of "slow" segment with threshold - detect sleep. → Refer to RHC referenceove

 Note 1. we do not apply glitch element sleep analysis is corrupted due to excessive fast frequency noise or artefact signal corruption (this fast frequency artefact can be created by generation of muscle movement)

Note 2.

IE. Instead of this example being interpreted as alpha it may ( due to glitch) be interpreted as beta and generate errors in sleep state assessment.

FIG 27 (cont)

Input data for S=1, S=2, S=3 .......S=n-1, S=n

| Input Analysis Type | S=1 input data |
|---|---|
| 1 | 26 |
| 2 | 79 |
| 3 | 89 |
| 4 | 56 |
| 5 | 33 |

Output Data

| Input Analysis Type | S=1 input data |
|---|---|
| 1 | 26 |
| 2 | 33 |
| 3 | 78 |
| 4 | 57 |
| 5 | 30 |

→ 78

Where S = data sample
S1 = data sample 1
Where n = total number of data samples

FIG 30B

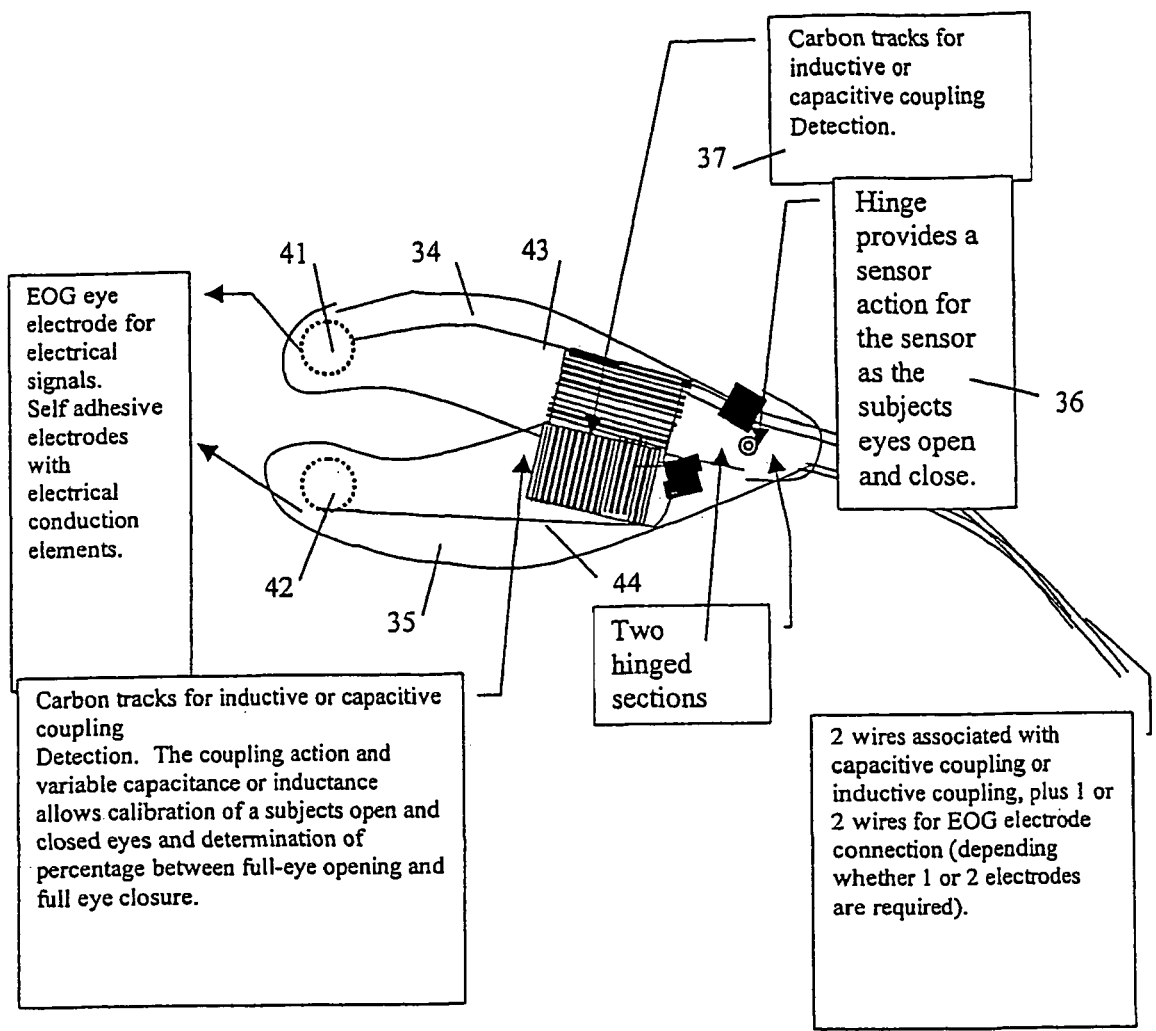
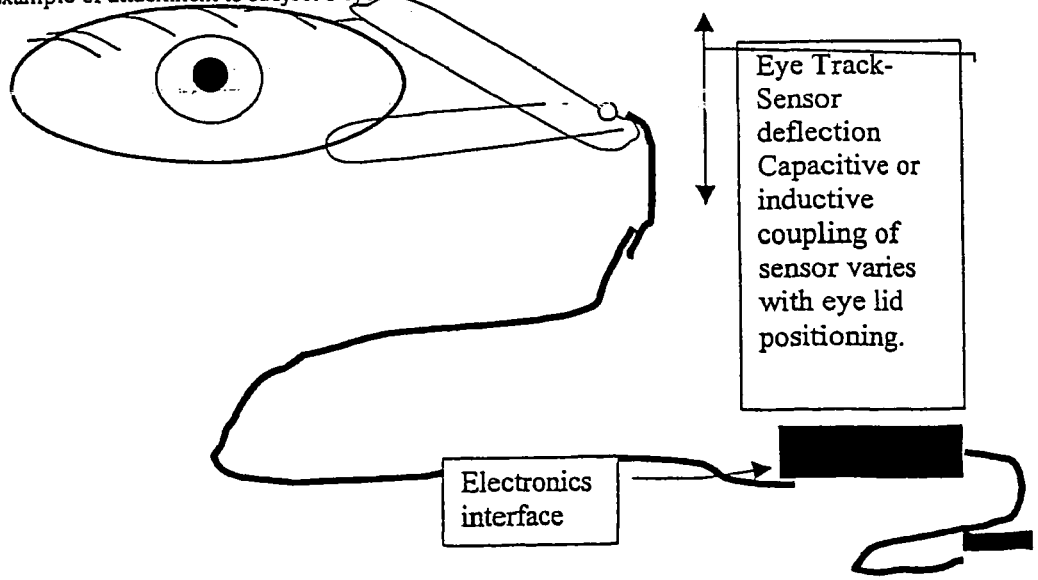
FIG 34A

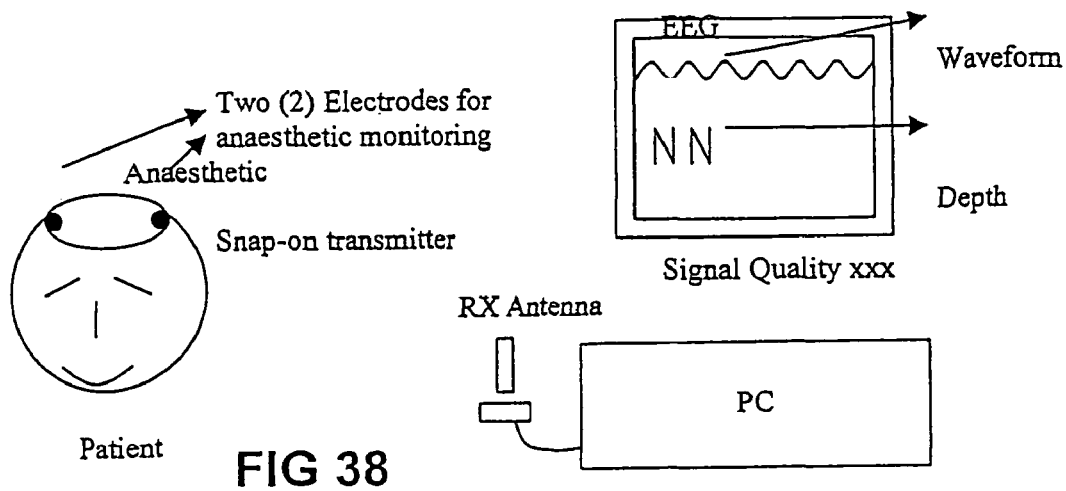

FIG 38

Version where active electrode is positioned via very short wires to a convenient location point such as under a head cap or other.

Wireless module with in-direct attach format where wireless module attaches via small wires and press-stud, clip or slide in type connection formats direct to or electrode substrate or electrodes, which are in attached to patient. In this format the in-direct attachment provides increased interference dure to longer interconnecting wire distances.

FIG 46

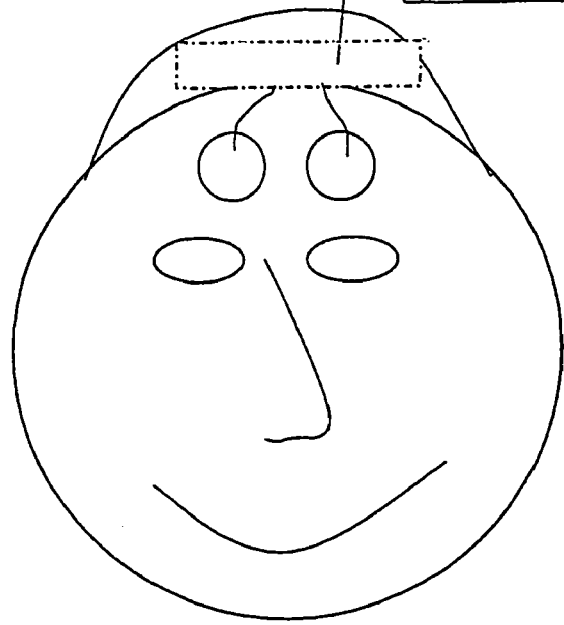

US 7,774,052 B2

METHODS AND APPARATUS FOR MONITORING CONSCIOUSNESS

This is a continuation of International Application No. PCT/AU2002/000776, filed Jun. 13, 2002.

FIELD OF THE INVENTION

The present invention relates to diverse methods and apparatus including systems incorporating same, for selectively monitoring the state of mind, or state of consciousness of human and other sentient subjects. More particularly the present invention relates to novel sensors and suites of sensors for accurately monitoring, sensing, tracking, analysing, storing, logging and/or displaying data related to combinations of physiological senses of a sentient subject. The physiological senses may include mind state and arousal of the subject including frequency, phase, amplitude and/or activity of one or more electro-encephalogram (EEG) signals.

The apparatus may be used in various configurations for applications including, inter alia, depth of consciousness, depth of unconsciousness, depth of anaesthesia, state of a subject's alertness, depth of sedation, hypnotic state, state of concentration, state of vigilance and state of attention. In a particular application, the system of the present invention may be adapted to monitor a subject for depth of anaesthesia and/or present state of consciousness during anaesthesia administration so that e.g. the subject may be properly sedated during a medical procedure. In addition, various data collecting and processing techniques are described pursuant to the systems of the present invention, as well as dynamic, re-configurable and adaptable display configurations for such data. An operator may reference such data as most optimally relates to the application (or applications) set forth herein in readily understandable format including suitable alarm signalling, threshold monitoring and the like.

The systems may utilize sleep analysis, EEG bispectral analysis (incorporating bi-coherence) and audio evoked potential (AEP) analysis in an integrated fashion for improved monitoring of, inter alia, a subject's consciousness, audio sensory systems, movement, arousal, muscle activity, eye movement, eye opening, stress and anxiety levels, vital sign parameters, and/or audio-visual recall. The monitoring systems preferably are arranged such that associated physiological electrode attachments are minimized.

The present invention is related to systems disclosed in PCT application AU99/01166 filed on 24 Dec. 1999 entitled "Vigilance Monitoring System", the disclosure of which is incorporated herein by cross reference.

BACKGROUND OF THE INVENTION

William Thomas Gordon Morton first demonstrated what is today referred to as surgical anaesthesia. However, a comprehensive or detailed understanding of how anaesthesia works is still unknown today. It is known that anaesthesia acts upon the central nervous system by reacting with membranes of nerve cells in the brain in order to shut down responses such as sight, touch and awareness, but the precise mechanisms and affects of this sensory process are still a subject of research.

In Australia about 1 million people a year undergo general anaesthesia. Of these 1 million people about 5 people die each year, as a direct result of the anaesthesia, while about 3000 more will be inadequately anaesthetised. These inadequately anaesthetised people will experience a range of symptoms from hearing recall while undergoing a medical procedure, sight recall from premature recovery and the early opening of eyes, stress and anxiety from experiencing paralysis. Some degree of mental awareness to the medical procedure being instigated, memory recall from having some degree of consciousness, and operation mishaps can occur in cases where the subject's state of paralysis is not adequate leading to movement of the subject's body during incision, for example.

A typical general anaesthetic procedure may involve a pre-medication or sedative, after which the patient is wheeled into the operating theatre where the anaesthetist applies a blood-pressure measurement cuff to the patient's arm, an oximeter probe to the patient's finger for the measurement of oxygen saturation, and ECG or electrocardiogram leads to a patient's chest for monitoring of heart-rate.

An intravenous cannula is then inserted into the patient's arm, and a mixture of drugs are infused into the blood-stream in order to put the patient to sleep, control pain and relax muscles. Within about 30 seconds the patient will typically transition from a state of consciousness to unconsciousness. Once the patient is unconscious, the anaesthetist typically reverts the patient to a gas delivery mask, which contains an "inhalation" anaesthetic that is breathed, by the patient through the mask. The patient may also be attached to a ventilator that will assist or support the patient's ventilation during the operation. The surgeon's intent is to commence the medical operation procedure when the patient is unconsciousness and can feel no pain.

The current state of the art provides an array of systems to monitor a patient whilst undergoing anaesthetic drug delivery, but none of these accommodate monitoring and validation of the range of sensory parameters satisfactory to monitor for "shut-down" or unconscious state of neural recall (including state of hypnosis, unconsciousness and sleep), auditory recall state (including Audio Evoked Potential and complex frequency and sensitivity state), muscle paralysis, movement and arousal state (including arousal and body movement analysis), visual recall state, (including eye opening and eye movement analysis state), anxiety and stress state (including temperature, blood-pressure, oxygen saturation-SA02, heart-rate variability, skin galvanometry resistance analysis).

Some prior art systems provide analysis of unconsciousness state (Aspect Monitoring) and other systems analyse electro-encephalograph signal activity (Physiometrix). Moreover experiments have been conducted and apparatus devised to monitor audio response (Audio Evoked Potential) together with a range of neurological analysis. However, the working of the brain's responses to anaesthetics and subsequent "shut-down" of the body's sensory systems still remains a mystery.

The system of the present invention may measure not only the state of consciousness of the sentient subject but also various states of sensory systems. In particular emphasis may be applied to measurement and monitoring of the sensory systems that are potentially most vulnerable to incidence of recall during an anaesthetic procedure. The HCM system of the present invention may provide a primary measure or guide to a clinician for optimal anaesthetic drug dosage by monitoring consciousness (such as associated with EEG and BSAEP parameter measurement), while also providing a "last line of defence" by monitoring the subject's sensory systems including sight, hearing, movement, taste and sound, for minimizing risk of recall associated with an anaesthetic/medical procedure.

Allan Rechtschaffen and Anthony Kales, describe in "A Manual of Standardized Terminology, Techniques and Scoring System for Sleep Stages of Human Subjects", Brain Information Service/Brain Research Institute, University of California Los Angeles, Calif. 90027, (R&K) (34) a method of scoring human sleep physiology. Further descriptions of the behaviour of the brain's electrical energy in terms of half-period amplitude analysis are disclosed by Burton and Johns in AU Patent 632932, the disclosure of which is incorporated herein by cross reference (45).

These earlier techniques were utilised for defining stages of a human's sleep and were predominantly applied to a subject in sleep, as recognised by conventional stages of sleep including stage 1, stage 2, stage 3, stage 4 and REM sleep (as distinct from hypnotic or in-depth of anaesthesia states). In particular the first stage of sleep detection with R&K standardised sleep staging techniques relies upon specific physiological sequences of events, such as the subject's rolling of the eyes or slow moving electro occulogram and changes in the electro-encephalogram frequency spectrum. It is apparent that significant changes in human physiology leading to the subject entering stage one of sleep represent a dramatic change in a subject's state of consciousness. This dramatic state of consciousness may be too late in detection where the aim is, for example, to determine onset of a lack of vigilance for a pilot of an aircraft or other critical job function. In other circumstances a subject could enter a hypnotic state where the driver of a car, for example, lapses into a type of "trance" and the state of vigilance and the subject's environment could become critical and highly dangerous. The phases of human physiology periods (leading up to stage 1) of non-sleep are not specifically described in R&K teachings.

Even hospitals such as Melbourne's Alfred Hospital, which demonstrated one of the world's lowest reported incidences of consciousness under general anaesthesia, still have an incidence rate of 1 in 1000 patients (91). The chances of being aware and experiencing pain are even lower but the consequences can be devastating. Side effects of consciousness while under anaesthesia can range from nightmares to recall of pain, stress, visual and audio recall during a medical procedure.

The HCM system of the present invention may address these limitations by providing specialised R&K and bicoherence monitoring during application of general anaesthesia. The HCM system may also provide methods of artefact rejection to allow more precise monitoring and analysis of neurological and other bicoherence and sleep variables from the subject.

Until now there has been no way to determine whether a patient is asleep during a medical procedure, according to University of Sydney-Australia's Web site, introductory paper on anaesthesia (92).

In 1942 Canadian anaesthetists discovered that neuromuscular blocking drugs could be developed. Sir Walter Raleigh had known in 1596 that the indigenous people of Bolivia had been using an American plant derivative called curare to cause paralysis. Since 1942 these drugs have revolutionised surgery, particularly abdominal and chest operations where muscle contraction had made cutting and stitching almost impossible.

By deactivating the muscles, anaesthetists can make lighter and safer anaesthetic drugs whilst still keeping the patient unconscious. These muscle blocking drugs are now used in up to half of all operations. However, the downside of the application of these muscle drugs is that a patient is paralysed so that conscious or unconscious movement is impossible. In circumstances where a patient is awakening or is in a state of consciousness during a medical procedure, the patient is unable to move and defend him/herself or alert anyone of a potentially horrific experience that the patient may be encountering.

Anaesthetists tend to overestimate the amount of anaesthetic drug usage by up to 30%. This overestimation has consequences in relation to a patient's health, recovery time and financial costs to health services (94).

The HCM system of the present invention may address the limitations of the prior art by providing an apparatus and method for monitoring and analysing arousal and body movement of a patient throughout anaesthesia. Furthermore the HCM system may provide means to position electrodes and sensors for monitoring arousal and body movements from any location on the patient's body. If, for example, a chest operation requires extreme absence from movement due to a critical incision procedure, electrodes or sensors may be placed around sensitive chest muscles non-invasively or via inter-operative methods.

The challenge to monitor for appropriate or optimum anaesthesia is demonstrated with classic experiments such as that of psychiatrist Bernard Levin in 1965, when 10 patients who were read statements during anaesthesia, later had no recall of the statements when questioned after surgery. However, of the same patients under hypnosis four could quote the words verbatim and another four could remember segments, but became agitated and upset during questioning (95). An adequately anaesthetised patient should not "feel", "smell", "see" or "taste" anything until they regain consciousness (96).

In 1998 Dr David Adams of New York's Mount Sinai Medical Centre replayed audio tapes of paired words (boy/girl, bitter/sweet, ocean/water . . . ) to 25 unconscious heart surgery patients. Approximately four days after the operation, the patients listened to a list of single words. Some of these words had been played while they were unconscious during their former operation. The patients were asked to respond to each word with the first word that came into their minds. The patients were found to be significantly better at free-associating the word pairs they had already encountered than those they had not. It was apparent that the patients had heard the information and remembered it (97).

It appears that while a smaller number of patient's have conscious memories of their experiences on the operating table, a larger number have unconscious recollections. While positive messages during surgery may have desired consequences others can have undesirable results (98).

The HCM system of the present invention addresses the limitations of the prior art by providing in one form an apparatus and method for monitoring auditory sensory system while the patient is undergoing anaesthesia. Furthermore the HCM system may provide a comprehensive means of analysing both frequency response and sensitivity response of one or both auditory sensory systems of the patient during anaesthesia. This may provide monitoring and a means of replay as evidence of the state of the subjects auditory system throughout anaesthesia to reduce the risk of auditory recall.

The HCM system of the present invention may provide a method and apparatus for monitoring and/or analysing a patient's eye movement and eye opening to minimise or eliminate the risk of visual recall after anaesthesia.

The HCM system may provide a method and apparatus for monitoring a patient's stress and anxiety levels together with a range of vital parameters to minimize the risk that the patient is undergoing undue stress, anxiety and health conditions during anaesthesia, and subsequently reducing or eliminating the incidence of these states.

Previous studies present a relationship between human treatment and changes in physiological states, as associated with anxiety or stress. In particular such studies link respiration rate, skin resistance and finger pulse volume to anxiety (53). Other studies present relationships between salivary cortisol levels and activities accompanying increased cardiovascular activity (54).

Studies also present relationships between heart rate variability (HRV), and people reporting anxiety and perceived stress and between a subject's blood pressure and heart rate, and activities associated with increased stress (55, 56, 57). Vagal modulation of heart-rate period was found to be sensitive to a person's emotional stress. Other studies present relationships between a subject's blood pressure and heart rate, and activities associated with increased stress (58).

The HCM system of the present invention may measure, analyse and display in near real-time graphical or numerical representation of skin resistance, oxygen saturation, pulse-transit-time arousal, blood pressure, heart rate, heart rate variability and temperature. Furthermore, the HCM system may measure, monitor and analyse these variables and present an index and/or other graphical and tabular display means, to assist an anaesthetist or other medical personnel in the assessment of a subject's depth of anaesthesia.

The HCM system of the present invention may record, monitor and analyse in near real-time effects of cortisol salivary content and changes thereof as an indicator of stress or anxiety, as may be associated with increased heart rate as may occur with premature awaking during anaesthesia.

The HCM system of the present invention may also measure, analyse and display in near real-time graphical or numerical representation of vagal modulation of heart-rate period. Furthermore, the HCM system may measure, monitor and analyse this variable which may be represented in terms of HRV frequency de-composed into various frequency components; i.e. LF-0.05-0.15 Hz, HF-0.15-0.5 Hz, using spectral analysis; and may present an index and/or other graphical and tabular display means, to assist an anaesthetist or other medical personnel in assessing a subject's depth of anaesthesia.

The HCM system of the present invention may record, monitor and analyse in near real-time effects of blood pressure and heart rate, and changes thereof as an indicator of stress or anxiety as may be associated with changes in blood pressure and heart rate, as may occur with premature awaking during anaesthesia.

The current field of sleep medicine is not precise in scoring or quantifying human sleep physiology. The degree of "inter-scorer" agreement in determining sleep classification of human physiology is of the order of 80 to 90%. Monitoring and analysing the state of a patient during anaesthesia treatment, and subsequent accurate determination of the patient's state depth of anaesthesia at any point in time is important to ensure efficacy of the patient's anaesthetic treatment. To this end, accurately defining the mechanisms, sequence or sensitivity of the sentient mind "shutting down" or re-awakening as associated with vigilance or response to administration of anaesthetics including the mind's recall of such events is important for ensuring optimal administration of anaesthetic agents. The science and knowledge associated with sleep staging or scoring of human sleep is still relatively primitive in terms of understanding the mechanisms of sleep and consciousness. In particular it appears that the science and knowledge associated with details and the sequence of "shutting down" of consciousness and human sensory systems including sight, hearing, smell, consciousness and muscle activity or arousal necessary to avoid potential recall of a patient's experiences associated with anaesthesia, is still relatively young and inexperienced.

The HCM system of the present invention recognizes the prior art limitations, and addresses them by providing a system which may be configured to monitor and analyse combinations of a subject's sensory systems during, inter alia, an anaesthesia procedure.

The HCM system may improve the probability of determining a subject's consciousness by applying two or more independent methods of analysis including bi-coherence based analysis and Brain Stem Audio Evoked Potential or Steady State Evoked Potential based analysis, and arbitrating, cross-checking and integrating results of the two or more methods of analysis using a further independent method of EEG analysis such as spectral based EEG analysis, including optimised bi-spectral analysis and optimised R&K sleep-wake analysis, to improve accuracy in determining the consciousness status of the subject. In conjunction with determining the consciousness status of the subject, the system may analyse consciousness/hypnosis/vigilance with the aid monitoring and analysis of brain waves together with various combinations of sensory monitoring and analysis including auditory, muscle movement and/or arousal including micro-arousal, eye opening & eye movement.

Other parameters, which may optionally be included in depth-of-anaesthesia monitoring and analysis determination, include anxiety & stress levels, heart rate variability, galvanomic skin resistance, temperature, respiration rate variability and blood pressure and/or oxygen saturation.

The HCM system of the present invention may include an apparatus for monitoring, analysing, recording and replaying a subject's consciousness state in conjunction with critical physiological sensory status of the subject. In this context critical refers to sensory systems that are critical for minimising the risk of recalling the experience or senses, associated with a medical procedure while under anaesthesia.

The combinations of multiple sensory monitoring and analysis may include a provision for a user to configure, select or operate the system with one or more channels of input data from a subject together with a range of system set-ups or montages, consistent with the complexity of signal attachment to the subject, the critical nature of the monitoring including the duration of an operation and risk associated with administration of anaesthesia or muscle paralysis medication to the subject, the skill and training or experience of the user, the sensitivity of the subject to anaesthetic or muscle paralysis medication, and variability of different subjects in relation to susceptibility to premature awakening or consciousness including recall of auditory or visual stimuli, anxiety or arousal.

The HCM system of the present invention may provide unique wireless connected electrode systems to reduce conventional wiring and risk of entanglement In some instances patient or subject specific data may substantially affect monitoring or analysis methods associated with the monitoring system. To the applicants knowledge, no one has linked critical parameters such as weight, age and sex of a patient to sensitivity and weighting of depth of anaesthesia monitoring. The HCM system of present invention may include a capability to adapt weighting or sensitivity of the analysis to the physiological parameters being monitored. An example of this may include the manner in which the weight or sex of a subject affects the optimal band of concentration of an anaesthetic agent.

The HCM system of the present invention may utilise data associated with the subject, such that its sensitivity or important thresholds may be adjusted from one subject to the next. In this context "utilisation" of data refers to compensation of critical display threshold levels and sensitivity of various user displays. In other-words the user displayed thresholds and associated variations in sensitivity may be changed in accordance with critical (for example, in depth of anaesthesia monitoring) sensitivity to certain anaesthetic agents.

Surface electrode connections have been applied in the past to monitoring applications associated with various physiological parameters. However one problem with surface electrode connections is that the quality of the connection to the subject can deteriorate due to a number of conditions including patient sweat, movement or drying out of the connecting electrolyte solution between electrode and subject. The problem of electrode quality may be more critical in applications such as those associated with intensive care and operating theatre environments, than is the case with depth of anaesthesia monitoring systems. To date, no one has used connection of redundant electrodes, automatic validation of electrode connection quality and validation by way of routine impedance measurements and other signal validation techniques (refer FIG. 18—MFD Block 7) including automatic substitution of poor electrode connections with redundant or spare electrode connections (refer FIG. 35—IAMES or FIG. 37—ISES). The system of the present invention may include redundant electrodes together with integrated electrode-sensors and wireless/rechargeable electrode-sensors to minimize the number of electrodes and sensors (as few as 3 sensor-electrodes in some embodiments) for depth of anaesthesia monitoring and analysis (where the quantity, reliability and simplicity of electrode-sensor attachments may be highly critical) including monitoring and analysis of physiological states such as mind-state, auditory sensory, visual sensory, arousal sensory, anxiety sensory and vital states.

Eye movement sensors (such as piezo or PVD movement sensors) and electrodes (such as EOG) have been used in the past for detecting eye movement or eye-lid movement respectively. However one problem associated with depth of anaesthesia monitoring is that some patients awaken prematurely during a medical procedure and opening of the eyes can lead to distressing views and subsequent recall or nightmare occurrences. A further problem exists where the patient may litigate in such instances, in which case an objective and accurate recording of the patient's state and amount of eye opening may be important. A system that allows the user to calibrate such an eye-opening sensor would also be of value. The HCM system of the present invention may provide such a sensor (refer FIG. 34—EOS) for detecting in a calibrated manner a degree of eye opening of a subject.

In accordance with general literature a predominant prior art method for detecting anaesthesia is bi-coherence analysis of EEG waveforms. Aspect Monitoring, which is a main supplier of in-depth anaesthesia monitoring systems deploys this technique. Aspect Monitoring has trademark applications for BIS and Bi-spectral Index. Bi-spectral Index is based on the technique of bi-coherence analysis.

Functioning of the brain in the transition of states from consciousness to subconsciousness and from unconsciousness to consciousness is recognised as a non-linear transition in relation to the generation of electrical brain activity. Accordingly, the bi-coherence method of monitoring EEG has been shown to be an affective method for predicting the state of consciousness and the subsequent state of depth of anaesthesia.

However, even with improved analysis of EEG data as described above, another prior art limitation exists. This limitation is related to the fact that while the combined frequency and phase analysis of EEG data may provide an improved method for monitoring a patient's state of consciousness, it has been found (4) that Audio Evoked Potential (AEP) provides a more informative measure of a subject's transition from unconsciousness to consciousness, while EEG based bi-spectrum analysis provides a more informative measure from consciousness to unconsciousness. Accordingly, the HCM system of the present invention may automatically detect whether the patient is transitioning from consciousness to unconsciousness or visa versa and may apply or weight bispectrum analysis (bicoherence/bispectrum/triple product) or AEP analysis (such as Brain Stem Auditory Evoked Potential-BAEP) respectively.

The HCM System addresses the limitations of the prior art by applying R&K analysis as a type of "independent arbitration" agent for determining which analysis type is optimal, based on the context and sequence of analysis change or transitions. For example, R&K detection of wake state, suggests a probable transition from consciousness to unconsciousness, which in turn suggests that the optimal or higher weighting of consciousness state determination should be derived from BIC (bi-spectral analysis incorporating bi-coherence) analysis. In contrast, R&K detection of a sleep state (stage 1, 2, 3, 4, REM, for example) suggests a probable transition from unconsciousness to consciousness, which in turn suggests that optimal or higher weighting of consciousness state determination should be derived from AEP analysis.

Barr and colleagues describe in British Journal of Anaesthesia June 2000 (1), a Coherence index (CHI) used to assess depth of anaesthesia during fentanyl and midazolam anaesthesia for coronary bypass surgery in which BIP decreased during anaesthesia, but varied considerably during surgery. Schraag and colleagues describe in Anesth Analg April 2000 (2), "that both BIP and AEPi are reliable means for monitoring the level of unconsciousness during propofol infusion. However, AEPi proved to offer more discriminatory power in the individual patient. The implication is that both the coherence index of the electroencephalogram and the auditory evoked potentials index are good predictors of the level of sedation and unconsciousness during propofol infusion. However, the auditory evoked potentials index offers better discriminatory power in describing the transition from the conscious to the unconscious state in the individual patient."

Gajraj R J describes in British Journal of Anaesthesia May 1999 (3), "Comparison of bi-spectral EEG analysis and auditory evoked potentials for monitoring depth of anaesthesia during propofol anaesthesia." In this study, Gajraj & colleagues compared the auditory evoked potential index (AEPindex) and bi-spectral index (BIS) for monitoring depth of anaesthesia in spontaneously breathing surgical patients." "The average awake values of AEP-Index were significantly higher than all average values during unconsciousness but this was not the case for BIS. BIS increased gradually during emergence from anaesthesia and may therefore be able to predict recovery of consciousness at the end of anaesthesia. AEP-Index was more able to detect the transition from unconsciousness to consciousness."

Gajraj R J, describes in Br J Anaesth January 1998 (30), "Analysis of the EEG bispectrum, auditory evoked potentials and the EEG power spectrum during repeated transitions from consciousness to unconsciousness." In this study, Gajraj & colleagues describe: "We have compared the auditory evoked potential (AEP) index (a numerical index derived from the AEP), 95% spectral edge frequency (SEF), median frequency (MF) and the bi-spectral index (BIS) during alternating periods of consciousness and unconsciousness produced by target-controlled infusions of propofol." "Our findings suggest that of the four electrophysiological variables, AEP index was best at distinguishing the transition from unconsciousness to consciousness and therefore may be able to predict the transition unconsciousness to consciousness."

The HCM system of the present invention may address the limitation of prior art methods of EEG sleep analysis, by applying multiple independent methods of analysis and processing including methods based on auditory evoked potential (AEP) index (a numerical index derived from the AEP), 95% spectral edge frequency (SEF), median frequency (MF) and coherence index (CHI) and R&K sleep staging, together with a unique method of context analysis to provide improved decision making with respect to which of the multiple analysis processes are most suitable for optimal tracking of each phase of the monitored stages of consciousness.

Witte H, describes in: Neurosci Lett November 1997 (5), "Analysis of the interrelations between a low-frequency and a high-frequency signal component in human neonatal EEG during quiet sleep." In this study, Witte and colleagues describe: "It can be shown that dominant rhythmic signal components of neonatal EEG burst patterns (discontinuous EEG in quiet sleep) are characterised by a quadratic phase coupling (coherence analysis). A so-called 'initial wave' (narrow band rhythm within a frequency range of 3-12 Hz) can be demonstrated within the first part of the burst pattern. The detection of this signal component and of the phase coupling is more successful in the frontal region. By means of amplitude demodulation of the 'initial wave' and a subsequent coherence analysis the phase coupling can be attributed to an amplitude modulation, i.e. the envelope curve of the 'initial wave' shows for a distinct period of time the same qualitative course as the signal trace of a 'lower' frequency component (0.75-3 Hz)."

The HCM system of the present invention may address the limitation of categorisation of neonatal neurological patterns by including within the decisions of sleep-wake categorisation information such as the age of a subject. In turn this information may be used to weight analysis processes within the neurological data. In the above case the age of the subject may prompt the analysis processes to recognise unique markers such as 'initial wave' and to use recognition of these unique markers to provide improved accuracy for categorising and detecting EEG patterns and associated sleep staging of neonatal human subjects.

It is apparent that no one singular method for determining a subject's state of vigilance is appropriate. R&K standardised criteria for sleep staging can be important in recognizing a subject's sleep state, coherence analysis can accurately describe a patient's transition from wake to sleep, auditory response can describe a subject's transition from sleep to wake, "initial wave" can assist in detecting a subject's transition into hypnotic state, and movement detection can describe a subjects state of rest or relaxation. Furthermore, accuracy in detecting and tracking a subject's vigilance state can be improved by recognizing a subject's age and in appropriate cases utilizing a subject's personalised calibration and learning functions. While conventional methods of vigilance analysis as described above, each have specific benefits associated with various forms of sleep state, hypnotic or vigilant state, the HCM system of the present invention is designed to incorporate concurrent or selective combinations of analysis in accordance with the users specific requirements.

The HCM system of the present invention recognises that the linear amplitude and spectral analysis methods utilised by R&K for sleep state analysis of a subject are indifferent to the non-linear coherence analysis method more suited for entry and exit from sleep or hypnotic states of the subject.

The HCM system of the present invention may utilise any combination of spectral edge frequency analysis, Coherence analysis, R&K standardised sleep staging criteria, auditory response monitoring, initial wave monitoring, arousal analysis and specialised input parameters derived from the calibration or specific subject configuration and system configurations such as the subject's sex and age data. A learning function and application of neural networks may provide a means for the system to weight the vigilance analysis format in a manner which is most appropriate for a specific subjects vigilant state such as wake, sleep, and transition from wake to sleep or sleep to wake.

The HCM system of the present invention may analyse a subject's neurological data for purpose of coherence analysis and R&K spectral analysis that may also include electro-occulogram and electro-myogram physiological data. In particular the HCM system may process transition stages of the subject's vigilance to determine the most appropriate method of analysis and display of the subject's hypnotic, sleep or vigilance state.

For example, the subject may be detected as being in wake state by means of R&K analysis (preferred method for sleep/wake detection), followed by on-set of hypnotic state (preferred method of monitoring and analysing exit of hypnotic/sleep state) as detected by the coherence index, enter sleep state by means of R&K analysis stage 1 detection (preferred method for sleep/wake detection), exit sleep state by means of firstly R&K wake state detection, and then tracking depth of hypnotic state by means of AEP index and auditory response (preferred method of monitoring and analysing exit of hypnotic/sleep state).

The HCM system of the present invention may automatically allocate an optimal processing means for determining a subjects transition of consciousness state or sleep state by applying simultaneously one or more processing techniques for determining the most appropriate measure of the subjects state in accordance with the transition of the subjects consciousness.

Furthermore the HCM system may include frequency analysis (R&K analysis) (34) spectral analysis-SEF-MF, ½ period analysis (46), (FFT) as a means to determine the transition and the current state of a subject in order to determine which method of consciousness analysis (BIP, AEP for example) is the most accurate and subsequent indicator for identifying and tracking the subject's vigilant state.

An ideal embodiment of the present invention may provide an independent measure of both sleep state and brain activity in both wake and sleep states. Furthermore the ideal embodiment may detect when a non-valid sleep state was recognised (per International standard R&K) so that brain activity or consciousness measures should be utilised (BIP and AEP index). Furthermore the ideal embodiment may include a simple non-ambiguous readout for users of the system.

The HCM system of the present invention includes improved analysis of depth of anaesthesia/consciousness/patient state with optimised sleep-wake R&K analysis, optimised bi-spectral analysis and optimised AEP analysis. Phase based analysis may be combined with frequency band-amplitude analysis (spectral analysis) to provide an improvement on phase only or frequency based analysis (refer FIGS. 16, 17, 18, 34, 35, 37, 41, 42, 45).

To the applicants knowledge no one has used combinations of Sleep-wake ½ period analysis or other forms of R&K or modified R&K analysis, unique artefact processing (refer FIG. 18—MFD block 21) combined with specially weighted (in accordance with empirical clinical data) and optimised bi-coherence, triple product and bi-spectral index (refer FIG. 18—MFD Block 10), and AEP analysis to improve the accuracy in determining the state of a subject's consciousness.

The HCM system may, within a single monitoring device and single electrode device, simultaneously provide a combination of analysis types (and displays thereof including BIS analysis, AEP index analysis, estimated R&K analysis, arousal analysis, eye movement analysis and eye opening analysis.

A common problem with frequency-based analysis methods (be it sleep-wake or bicoherence/bispectrum/triple product) in analysing neurological data, is that the results of the aforementioned types of analyses can change significantly with seemingly stable physiological conditions. For example, substantial increases in EEG activity in the 12 to 18 Hz (theta) frequency band may be observed with administration of anaesthetic agents in the low to medium concentrations, but high doses of the same agents may lead to sudden reduced activity in the 12-18 Hz frequency band and increased activity in the 0.5-3.5 Hz band, followed by burst suppression at extremely high concentrations. Similarly, bicoherence/bispectrum/triple product analysis relies upon "relatively new principles" for determining the subject's state of consciousness. In contrast, a well documented and validated method for sleep staging such as presented by R&K, utilises analysis techniques which, although being highly validated, are subject to misleading frequency effects, as described above. Apparatus based on the R&K method combines real-time optimised (34, 45) R&K analysis with optimised bi-spectral analysis to increase accuracy beyond conventional Bi-spectral Index™ (52). Application of optimised spectral analysis may provide a meaningful basis for determining consciousness state, where R&K analysis has been formulated to provide sleep stage (or depth of sleep) or wake state (referred to herein as sleep-wake analysis) as opposed to varying degrees of subconsciousness, as a subject approaches sleep or an unconscious state. R&K analysis on the other hand may provide a well validated method for determining a subject's depth of sleep. Furthermore modified R&K analysis (refer FIG. 18—MFD Block 10) may improve artefact rejection, making determination of the patient state more reliable or less dependent on artefacts or noise, often evident during monitoring of a patient. The artefacts may include sweat artefact, amplifier blocking artefact, and mains noise signal intrusion, for example. The HCM system of the present invention may weight optimised R&K and optimised bi-spectral analysis in accordance with the strengths and weaknesses of each of these processes to provide overall improved accuracy and probability of determining the subject's depth or state of anaesthesia.

The HCM system of the present invention may reduce the effects of over reliance on frequency based changes of neurological data from a patient, by utilising both frequency based EEG (sleep-wake analysis) and phase based EEG analysis (bicoherence/bispectrum/triple product).

The HCM system may provide automatic selection or weighting of BIC and AEP analysis by means of R&K or similar frequency based analysis as an arbitration agent in the decision path for weighting analysis types.

The HCM System may be adapted to automatically detect whether the patient is transitioning from consciousness to unconsciousness or visa versa and to apply or weight bi-spectrum analysis (bi-coherence/bi-spectrum/triple) or audio evoked potential analysis (such as Brain Stem Auditory Evoked Potential-BAEP) respectively.

The system of the present invention may monitor and detect the state of the subjects consciousness. In particular real-time and concurrent processes ideally suited to both non-linear and linear analysis techniques may be applied. The system may include bi-coherence (non-linear) analysis for depth of consciousness monitoring in conjunction with Audio Evoked Potential (more linear based) analysis for monitoring transition of a subject between conscious and unconscious states. The system may provide improved monitoring and analysis for application in detection, system alerts and alarms associated with depth of anaesthesia, hypnotic state, sedation depth, fatigue or vigilance of a subject, with as few as 3 surface electrodes. Combined or separate indexes or display methods may provide accurate tracking of the subject's state of consciousness and transition of conscious state. The system of the present invention may assign patient states of sleep, wake, depth of consciousness, depth of anaesthesia and vigilance in accordance with analysis states derived from a combination of analysis types, including in particular BIC and AEP based analysis. Prior art systems (such as Aspect Monitoring) are limited as they are not as precise or responsive as an AEP, arousal or EEG activity based system for detecting transition and AEP responsiveness to transition but not as gradual a measure (as BIC) for predicting consciousness state.

However a limitation of this prior art method is that the gradual change of the bicoherence measure may, by nature of the type of the non-linear analysis prevent a clear or significant emphasis of the subject's transition state. The transition state is when the subject changes from consciousness to unconsciousness or visa versa. This is a critical state when monitoring a subjects depth of anaesthesia as a subject who is on the verge of waking up may need urgent administration of anaesthesia in order to avoid a serious incident such as the subject awakening during a surgical operation.

For example, a time based curve or graph of the bi-coherence processed signal can produce a relatively gradual and consistent change when compared to other validated methods of consciousness monitoring, such as Audio Evoked Potential (AEP) monitoring techniques.

In the case of AEP monitoring, a subject wears a headphone attachment and is presented with audio stimulus clicks, while at the same time the auditory nerve is monitored. By monitoring the amplitude of the response of the monitored (via non-invasive surface electrodes attached to a subject's near ear) auditory nerve signal and averaging this signal by summing a sequence of overlaid traces of this auditory signal, it is possible to measure a degree of the subject's consciousness. In this particular example consciousness may be determined by a measure of the subjects hearing responses. One advantage of this method is that it is recognised to provide superior transition state information, where the transition state is the actual determinant of whether the subject is in a state of consciousness or unconsciousness. A disadvantage of this method is that the state of transition based on AEP analysis is relatively sudden due to the sudden response of the auditory nerve during the transition of a subject's state from unconsciousness to consciousness (30). However, an advantage is the explicit or obvious nature of the data curve transition between the two states.

Therefore the recognised methods of tracking consciousness and unconsciousness of a subject each have different advantages and disadvantages (33).

However the applicant is not aware of any prior art system or method that is able to provide an ideal solution. Such solution would need to have non-linear gradual measurement and prediction abilities associated with bi-coherence analysis, together with immediate indication associated with the transition state as depicted by AEP analysis.

The HCM system of the present invention may automatically detect whether the patient is transitioning from consciousness to unconsciousness or visa versa and apply or weight bi-spectrum analysis (bi-coherence/bi-spectrum/triple product) or audio evoked potential analysis (such as Brain Stem Auditory Evoked Potential-BSAEP) respectively. The HCM system may address prior art imitations by applying R&K analysis as a type of "independent arbitration" agent for determining which analysis type is optimal, based on the context and sequence of analysis change or transitions. For example, R&K detection of wake state, suggests a probable transition from consciousness to unconsciousness, which in turn suggests that optimal or higher weighting of consciousness state determination should be derived from the BIC (bi-spectral analysis incorporating bi-coherence) analysis. In contrast, R&K detection of a sleep state (stage 1, 2, 3, 4, REM, for example) suggests a probable transition from unconsciousness to consciousness, which in turn suggests that optimal or higher weighting of consciousness state determination should be derived from AEP analysis.

An ideal system for monitoring depth of anaesthesia or vigilance or depth of sedation or hypnotic state should be able to present a single or simple index, display reference or monitoring technique which clearly depicts both a prediction of depth of anaesthesia and a current state and transition of states of a subject. In particular the ideal system should be able to utilise a method of combining AEP and bi-coherence analysis techniques into a single monitoring measure. The HCM system of the present invention may achieve this scenario by weighting the AEP transition state and the bi-coherence analysis value so that a single combined reference is obtained.

The HCM system may weight the transition state heavily when a subject transitions his/her mind-state from unconsciousness to consciousness (AEP, arousal and eye opening wake analysis is heavily weighed) so that an anaesthetist can have a guide in predicting the depth of anaesthesia utilising the bi-coherence factor, but if the subject changes or approaches a change in state as indicated via AEP analysis, the anaesthetist may be given immediate and obvious display indication and can avert a potentially serious incident such as the subject awakening during a surgical operation.

The HCM system of the present invention may assign patient states of sleep, wake, depth of consciousness, depth of anaesthesia and vigilance in accordance with analysis states derived from a combination of analysis types including R&K analysis (34), AEP (30), spectral analysis-SEF-MF (4), Bi-coherence (BIC) analysis (33), initial wave analysis (5), auditory response (4,30), arousal analysis (35) and body movement analysis (34,26), 95% spectral edge analysis (36) and anaesthetic phase and spectral energy variance measurement in association with a subject's state of consciousness (30), Pulse Transient Time (PTT) based arousal detection (31), PTT measure and PTT based blood-pressure reference measure, PTT based heart rate and blood pressure with simple non-invasive oximeter (31, 32), PAT analysis for sympathetic arousal detection (104-108), EEG spike-Kcomplex-wave-activity-event categorisation (47) and bio-blanket-heart-temperature-PTT blood-pressure-respiration-breathing sound (49).

The HCM system of the present invention may include automatic consciousness state context determination (refer FIGS. 16, 17, 18, 34, 35, 37, 41, 42, 45). The HCM system may provide trend or sequence analysis with improved qualification of a subject's depth or level of various mind states by incorporating preliminary analysis or preview analysis context determination. In particular the HCM system may apply concurrently and in real-time EEG frequency (26,30,36,47), EEG phase (33) and EEG amplitude analysis (30).

For the purpose of "context" determination, the HCM system may apply concurrently and in real-time a combination of methods of analysis including R&K analysis (34, 45,46), AEP (30), spectral analysis-SEF-MF (4,30), Bi-coherence (BIC) analysis (33), initial wave analysis (5), Auditory Evoked Response (30), arousal analysis (35) and body movement analysis (34), 95% spectral edge analysis (36) and anaesthetic phase and spectral energy variance measurement in association with a subject's state of consciousness. (36), Pulse Transient Time (PTT) based arousal detection (31, 32), PTT measure and PTT based blood-pressure reference measure, PTT based heart rate and blood pressure with simple non-invasive oximeter, PAT analysis for sympathetic arousal detection (104-108), EEG spike-K-complex-wave-activity-event categorisation (47) and bio-blanket-heart-temperature-PTT blood-pressure-respiration-breathing sound (49), to determine the context of a subject's state of mind. In particular the "context" may include that a subject is in a state of wake or consciousness and whether or not the subject is entering or approaching a state of unconsciousness or sleep, for example. Where a subject is in a state of unconsciousness or sleep, an ideal depth and state of consciousness monitoring system may emphasise or highly weight a change of state where (for example), this change of state could represent a subject awakening during an operation procedure, for example.

There are a number of limitations associated with current standards for staging human sleep (R&K standardised sleep criteria) (34). Some of these limitations arise, for example, from the fact that it has been found that infants exhibit higher amplitude of EEG frequency bands such as deltawave than do more elderly patients. It has also been found that in infants conventional methods of scoring sleep are not an accurate indication of the child's sleep physiology.

The HCM system of the present invention may address the limitation of prior art methods of EEG sleep analysis with an ability to concurrently analyze and process a selection of, or combination of methods of sleep/hypnosis/arousal/vital signs monitoring including:

R&K analysis (34),
EEG pattern recognition
AEP (30),
spectral analysis-SEF-MF (4),
Bi-coherence (BIC) analysis (33),
initial wave analysis (5),
auditory response (30),
arousal analysis (35),
body movement analysis (34),
95% spectral edge analysis (36),
anaesthetic phase and spectral energy variance measurement in association with a subject's state of consciousness. (30),
Pulse Transient Time (PTT) based arousal detection (31),
PTT measure and PTT based blood-pressure reference measure (31,32),
PTT based heart rate and blood pressure with simple non-invasive oximeter (31,32)
PAT analysis for sympathetic arousal detection (104-108),
EEG spike-K-complex-wave-activity-event categorization (47),
bio-blanket-heart-temperature-PTT blood-pressure-respiration-breathing sound (49).

In addition to the above analysis techniques the HCM system of the present invention may access any combination of one or more of the above analysis techniques concurrently and determine the:
context,
physiological vigilance or sleep or wake or consciousness transition; and
predict "probability of transition" of a subject's vigilance state.

The "context and predictive" analysis includes providing a validation of the subject's sleep or hypnotic state by referencing a combination of the above analysis techniques in terms of the current vigilance phase and a trend or sequence vigilance phase. If, for example the HCM system determines that the subjects current vigilance state does not qualify for classification under conventional rules as depicted by R&K analysis (34), but was detected by way of BIC coherence analysis (33) as progressing to a deeper stage of hypnotic state or a deeper state of unconsciousness (as with deeper state of in-depth anaesthesia state), then the HCM system may make a more accurate decision based on predictions from the context of the R&K and BIC analysis past and current trend data. In this particular case the prediction may be that the subject is entering a phase of deeper unconsciousness or hypnotic state (by way of no R&K state and BIC analysis), and accordingly has a higher probability of predicting that the subject is more likely to be approaching a transition of unconsciousness to consciousness. This aforementioned prediction may alert the HCM system that the most accurate method of analysis in the phase from unconsciousness to consciousness is likely to be Auditory Evoked Potential response. The HCM system present may "self-adapt" the analysis method in accordance to the sequence of the subject's vigilance state transitions in order to provide improved accuracy for monitoring a subjects vigilance or to more appropriately classify same into a sleep, hypnotic or consciousness state of the subject being monitored. "Self adaptation" in this context refers to the capability of the HCM system to initially weight vigilance analysis towards BIC as the preferred method for analysing a subject's transition from wake to unconsciousness, and then subsequently weight Audio Evoked Potential response as the preferred method of analysing a patient's transition from unconsciousness to consciousness.

The HCM system of the present invention may determine the most probable transition states by evaluating the trend or sequence of data output from more than one analysis type. Example of vigilance transition states include:
consciousness to unconsciousness
unconsciousness to consciousness
sleep to wake
wake to sleep
deepening of unconsciousness (or hypnotic) state
exiting of unconsciousness (or hypnotic) state
Examples of analysis types that may be automatically allocated based on a subject's current vigilance transition state and current state include:

| TRANSITION STATES | AUTOMATIC PREFERRED ANALYSIS TYPE |
|---|---|
| Consciousness to unconsciousness | BIP |
| Unconsciousness to consciousness | AEP |
| Sleep to wake | 1)R&K, 2)BIC |
| Wake to sleep | 1)R&K, 2)BIC |
| Deepening of unconsciousness (or hypnotic) state | BIC |
| Exiting of unconsciousness (or hypnotic) state | AEP |

| CURRENT STATE | AUTOMATIC PREFERRED ANALYSIS TYPE FOR STATE CLARIFICATION |
|---|---|
| Consciousness or wake | 1)BIC, 2)R&K |
| Unconsciousness | AEP |
| Sleep state | R&K |
| Wake state or consciousness | 1)BIC, 2)R&K |

The HCM system of the present invention may take into account the instantaneous and trend analysis outputs from one or more analysis type to determine a subjects most probable transition state and may then select the most qualified or accurate analysis type as the primary decision weighting of a subject's state of consciousness (hypnotic state), wake, sleep or vigilance.

The HCM system of the present invention may include a learning capability and pattern recognition to enable different combinations of analysis type and different combinations of trends of analysis, to determine the most appropriate analysis type for determining the patient's vigilance.

Furthermore the HCM system of the present invention may recognise combinations of analysis output to improve accuracy of detecting a subject's vigilant state or transition of the subject's vigilant state.

The HCM system of the present invention may apply both FFT and ½ period amplitude analysis in consecutive 1 second intervals (can be set to greater values, particularly where lower frequency response characteristics are being utilized). The FFT analysis (i.e. 95% spectral edge (36)) has an advantage of providing power distribution of the EEG signal frequencies but the disadvantage of not presenting mixed frequency EEG signals for assessment under scoring criteria such as per R&K analysis EEG (34,45,46). An example of where ½ period amplitude analysis may provide an advantage over frequency analysis is where a 30 second epoch contains a high amplitude Delta wave and the Delta wave does not constitute greater than 50% of the 30 second epoch, but due to excessively high amplitude of the Delta wave, would appear to dominate the 30 second epoch. In this case use of FFT would suggest that this epoch is, say stage 4 (greater than 50% of the epoch time with high amplitude Delta wave in accordance with R&K analysis (34,45,46). However if for example, the epoch consisted of greater than 50% of the epoch in Alpha EEG waves as would be more evident (than FFT analysis) with ½ period amplitude analysis then this epoch should in accordance with R&K human sleep scoring criteria, not be scored as stage 4 of sleep. In other words the ½ period amplitude analysis more correctly represents the method of scoring sleep in accordance with R&K than FFT in such instances and utilization of FFT and ½ period analysis (45) may provide improved accuracy for determining a subject's consciousness state (33) and sleep state (34) in the HCM system.

The HCM system of the present invention may include automatic Input Signal Validation, Optimisation & Compensation (ASVC) including automatic substitution of poor quality electrode connections (refer FIGS. 17, 18,34,35,37,41,42, 45). This function may enable the system to automatically validate input signals (physiological variables in the present application but applicable to other industries involving monitoring or analysis of signals in general) of a subject's monitored variables. Validation may be by way of automatic impedance measurement, frequency response, mains interference, signal to noise and signal distortion and other measured signal characteristics as part of the analysis algorithm for monitoring, detecting or predicting a subject's state of consciousness, sedation or vigilance.

Furthermore the HCM system of the present invention may automatically determine signal conditions during operation of the system, and invoke subsequent signal processing to compensate or reduce artefacts caused by unwanted signal distortion or interference such as noise. Furthermore, in order to allow the system to display to the user on-going signal validation and signal quality issues, signal status and subsequent compensation (or signal correction), signal trends or progressive deterioration of signal quality and existing signal quality issues, both current and trend signal status may be displayed in real-time and stored, with both modified and compensated signal data.

The HCM system of the present invention may provide trace ability (or an audit trail) of all signal modifications so that the system user can validate any automatic signal compensation decisions both in real-time and in later study review. A further feature of the HCM system is a capability to provide the user qualification, at all times, relating to detected signal deterioration and subsequent signal compensation. A further capability may allow the user of the HCM system to automatically or manually (upon the user's discretion or agreement with qualification of signal deterioration and proposed compensation) invoke signal compensation for optimising or improving signal quality. Due to time synchronised (with recorded signals) trace ability (audit trail) of signal validation and subsequent signal compensation, modified signals may be revoked (unmodified) to original signal format where required.

Furthermore, signal validation may provide a means to allow the system to optimise signal quality for improved application of various signal-processing algorithms.

The system of the present invention may adapt or re-assign redundant or spare electrode channels in substitution of identified poor quality signal channels. In particular the system may automatically alert a user of the quality of all attached electrodes and sensors. Where any poor signal quality is detected the system may advise the user of recommendations or hints to quickly identify and resolve signal quality problems.

Surface electrode connections have been applied in the past for various physiological parameters and monitoring applications. However one problem associated with surface electrode connections is that the quality of the connection to the patient can deteriorate as a result of a number of conditions including patient sweat, movement, or the drying out of the connecting electrolyte solution between electrode and patient. In particular the problems of electrode quality may be particularly critical in applications such as those associated with intensive care and operating theatre environments, as is the case with depth of anaesthesia monitoring systems.

To the applicant's knowledge, no one has used connection of redundant electrodes, automatic electrode connection quality and validation by way of routine impedance measurements and other signal validation techniques (refer FIG. 18—MFD Block 7) and automatic substitution of poor electrode connections with the redundant (spare) electrode connections (refer FIG. 35 (IAMES) or 37 ISES)). The system of the present invention may utilise redundant electrode systems together with integrated electrode-sensors and wireless/rechargeable electrode-sensors to minimize the quantity of electrodes and sensors (as few as 3 sensor-electrodes) for depth of anaesthesia monitoring (where the quantity, reliability and simplicity of electrode-sensor attachments is very critical) and analysis including mind-state, auditory sensory, visual sensory, arousal sensory, anxiety sensory and vital signs physiological states.

The system of the present invention may include automatic Analysis Validation, Compensation, Optimisation, Adaptation of Format and Analysis and Probability Assignment (AAVCOAFA)(refer FIGS. 16, 17,18,34,35,37,41,42,45). The system may adapt algorithms for determining the subject's state of consciousness (and vulnerability to anaesthesia procedure recall) while simultaneously in substantively real-time allowing the system to determine and display to the user the signal analysis methods being deployed (such as R&K derived from optimised BIC—outer malar bone surface electrodes—as opposed to C3 EEG signal) signals status, trends or progressive deterioration of signals (such as detailed in (AVCOADSP), or analysis quality caused by, for example, input signal connection deterioration, or connection of improved signal inputs. In other words the system may determine the most appropriate (accurate and reliable) analysis method (algorithm type) by way of validating input signal quality and automatically or manually activate a changed analysis method or format that is the most suitable for the validated signal channels. The analysis methods may be determined according to presence, status and quality of the patient signals being monitored.

A further capability of automatic analysis validation is that the system may adapt or re-assign variants or substitute analysis formats where the existing analysis format requires change, such as when an input channel connection(s) deteriorate.

The system may automatically alert the user of the quality and probability of the applied analysis processes. The system may also advise the user of recommendations or hints to quickly identify and resolve analysis validation deterioration or issues.

The HCM system of the present invention may display to the user on-going analysis validation status, progressive deterioration of analysis quality and subsequent analysis variation or analysis compensation due to signal deterioration, for example.

Furthermore once analysis types have been activated, weighting techniques may be applied in order to determine the probability associated with different analysis methods. For example, BIC (outer malbar bone, surface electrode placement) derived R&K EEG analysis does not produce as high a probability as C3 (surface electrode) derived R&K EEG analysis.

The HCM system of the present invention may provide an automatic analysis format linked to signal validation, such as in the case of sleep and wake analysis where the analysis parameters applied may depend on the validated signals. If, for example, only EEG outer malbar electrodes are validated, then frequency optimised EEG outer malbar signals may be utilized for analysis, as opposed to more complex analysis signal combinations including EMG and EOG signals.

The system of the present invention may include Patient Data-Linked Analysis (PDA)(refer FIGS. 16, 17, 18,34,35, 37,41,42,45). The system may adapt the analysis algorithms used for determining a subject's state of consciousness (and vulnerability to anaesthesia procedure recall) in accordance with critical data such as the subject's body mass index (weight, height), sex and age. Such Patient Data-Linked (PDA) analysis may enable patient specific data such as the subject's body mass index, age, sex, medical history and other relevant information to be utilised in analysis algorithms for monitoring, detecting or predicting the state of consciousness, sedation or vigilance of the subject.

Patient specific data is entered in prior art patient monitoring systems. However in some instances patient specific data can substantially affect monitoring or analysis methods associated with the monitoring system. To the applicants knowledge, no one has linked critical parameters such as weight, age and sex of a patient to the sensitivity and weighting of depth of anaesthesia monitoring. The HCM system of the present invention may change the weighting or sensitivity of analysis of the physiological parameters being monitored. An example of this is where the weight or sex of a subject affects (in accordance with empirical clinical data), the optimal band of operation of a given concentration of an anaesthetic agent, due to the effects that sex and weight have on these parameters.

The HCM system of the present invention may utilise certain patient data, which may vary the sensitivity or important thresholds associated with variations between one patient and the next. The "utilisation" of this data refers to compensation, for example, of critical display threshold levels and sensitivity of various user displays. These user display thresholds and associated sensitivity variations may change in accordance with critical applications, for example when using the system to monitor sensitivity of depth of anaesthesia to certain anaesthetic agents.

Table A below shows one example of Patient Specific Data Entry Parameters:

TABLE A

PATIENT SPECIFIC INPUT DATA

Age:
Weight:
Height:
SEX:
BMI:
History file:
Calibration file:
Calibration-file anesthetic type:

The system of the present invention may include Calibration-Linked Analysis (refer FIGS. 16, 17,18,34,35,37,41,42, 45). The system may adapt the analysis algorithms used for determining a subject's state of consciousness (and vulnerability to anaesthesia procedure recall) in accordance with the subject's critical calibration data, such as how the subject responds to various preliminary or pre-test studies. This "calibration data" may include thresholds and parameters derived from a specific patient's preliminary study, in order to determine the characteristics of the subject's physiological parameters for more accurate consideration of variations between different subjects.

This capability may be important where, for example, a subject undergoes a critical operation. To minimise the risk associated with anaesthesia administration, a preliminary calibration study can be conduced. This study may include a capability to store tables of values or specific drug administration versus analysis state (BIC/AEP/R&K/95% spectral edge or other) coefficients or specific analysis values associated with varying degrees of drug administration. The system of the present invention may include localized or general motor and sensory nerve and muscle response and arousal analysis (refer FIGS. 16, 17, 18,34,35,37,41-45). The system may adapt algorithms used for determining a subject's state of consciousness (and vulnerability to anaesthesia procedure recall) in accordance with monitoring and detection of the subject's arousals (typically detected from shifts in frequency and amplitude in monitored signals) or muscle responses (for example during an operation or medical procedure). The system may apply this data as an alert or detection means for the subject's transition state or physiological and mind-state response to a medical procedure and a means of consciousness state detection. In other words the muscle changes or arousal events may be indicative of muscle responses of the subject, which in turn may indicate the subjects localised anaesthesia effectiveness or the subject's state of consciousness and local muscle response.

In particular localised monitoring and detection of muscle movement or activity may provide a means to localise the arousal and muscle monitoring, relative to the responsive or sensitive areas associated with a medical procedure, and consequently may provide immediate feedback where an anaesthetised area of a subject indicates muscle or nerve responses consistent with inadequate anaesthetic drug administration. The system may include accurate monitoring and recording of the effect of local anaesthetic by detecting the subject's motor and sensory responses in conjunction or time-linked with an incision or other medical procedure. The latter feature may provide a means of monitoring and analysing both the state of a subject's mind and the response from selected ear related (cochlear) procedures where a subject's state of anaesthesia and performance or response of the auditory system can be monitored and analysed throughout an operation procedure. Industry standard techniques (for example, Canadian Task Force)(35) for detecting arousals may be utilized in the system of the present invention.

The HCM system of the present invention may include an electrical stimulus pulse (evoked potential) and test of the nerve or muscle response of a subject while undergoing an operation or medical procedure. The electrical stimulus pulse may be applied at a selected excitation location on the subject's body, and the response (nerve or muscle) can function in a dual-monitoring mode whereby determining the subjects state of consciousness or vigilance (as in depth of anaesthesia monitoring) and determining the response and performance of selected muscles or nerves of the subject may be performed simultaneously. This "dual-monitoring" function may be particularly useful when a subject is undergoing a delicate and precise medical operation or procedure.

The system of the present invention may include an Integrated Anaesthesia Monitoring Electrode System (IAMES) (refer FIGS. 16, 17,18,34,35,37,38,41-45). IAMES may be wired or wireless. IAMES may include a simple, low cost and minimally intrusive electrode system, which may be disposable or reusable with a connector interface to a replaceable EAS. Alternatively EAS may be integrated with a Wireless Electronic Module (WEM). A version which is completely disposable would typically be lower in cost and may not in some lower cost options, include a wireless interface. The lower cost completely disposable versions may include a low cost data logging system with low cost display means. Low cost display means for completely disposable versions, may include once of display output for index measure, for example, or digital interface or data card for information retrieval.

The IAMES system may be divided into two components including an electrode attachment system (EAS) and the WEM section. Completely disposable systems may include integrated WEM and EAS sections for further cost reduction.

The EAS system is a remote patient attached electrode transceiver monitoring station, which contains a means of inputting patient data to the WEM module (refer below). EAS includes a code identification system allowing system configuration to be set up in accordance with the specific electrode type (i.e. EEG, EOG, EMG, EEG or other).

EAS includes conductive surfaces which may be easily attached to a patient's skin surface for electrical pick-up of physiological variables associated with a subject including a combination of left and right, outer malbar placed electrodes for detecting typical bicoherence EEG variables, left and right outer carantheous eye electrodes for detecting EOG electrical signal associated with eye movements, chin submental EMG electrodes for detecting the subject's chin muscle activity and state of restfulness, A1 or A2 electrodes (dependent on the format of the electrode system) for providing an electro-physiological reference signal and eye lid position sensors for detecting eye opening activity and percentage of eye opening.

A combination (hybrid) system may provide R&K and/or bicoherence signal attachment in one wireless hybrid device, thus opening up avenues for large scale home monitoring of sleep disorders, more critical applications such as medical procedures and operations or vigilance monitoring of workers or air/land/sea transport personnel. Options may include sub-mental EMG and/or auditory sound output devices (earpiece, headphones or speaker) and/or auditory signal pick-up devices (surface electro-physiological electrode).

A Wireless Electronic Module (WEM) system may include a small, low power and lightweight module designed to snap connect to an EAS module. The WEM module may provide the following functions:

- interface for one or more channels of patient data emanating from the EAS module;
- electrode and sensor amplification (DSP and/or analogue methods);
- filtering (DSP and/or analogue methods);
- calibration testing including generation of one or more (different wave-shapes, frequency and amplitude) local test waveforms;
- impedance measurement;
- signal quality measurement;
- input DC offset measurement;
- wireless data transceiving and DSP or micro-controller data processing capabilities; and
- reference code identification detailing electrode type (e.g. EEG, EOG, EMG, EEG or other).

The WEM transceiver module may transmit physiological signals and various test data such as the impedance value across the electrode signals, quality measure of signal or data such as a reference code detailing electrode type (i.e. EEG, EOG, EMG, EEG or other). The EAS transceiver module may also receive various control and test commands such as requests to measure impedance, generation of test or calibration waveforms, a measure of signal quality and other data.

The WEM system may be powered via any combination of rechargeable or single use batteries, self powered electrodes with a capability of charging via RF or EMF induction during use or as a charging procedure.

A WEM module may be directly attached to an EAS module, or it may be attached to an EAS module via an intermediate wireless link or wired attachment. Alternatively, patient worn or patient attached device(s) such as headband, headcap or hat, wrist-worn or other devices may incorporate an EAS and/or WEM module.

The WEM module may be self powered with Radio Frequency or Electromagnetic frequency providing a power supplement. The latter system may utilise radio or electromagnetic signals as a means for recharging the power source in the WEM module.

The IMES device may be wirelessly linked to close proximity or distant monitoring systems equipped with a wireless data interface capability to IMES. Close proximity monitoring devices may include the headrest of a car seat where a self-powered IMES system (typically EMF power recharge system) may be wirelessly linked to a transceiver device contained within the driver's seat headrest or other convenient or appropriate location(s). The WEM may be wirelessly linked to remote computer devices wherein WEM data may be stored, displayed and/or analysed. The remote WEM device may also provide a controlled interface to the WEM module for calibration and impedance testing. WEM may also be wirelessly linked to mobile phones or wireless modems or a network interface including an Internet connection.

The IMES device, when incorporated with local (incorporated in WEM module) or remote (wireless or wire-linked) BIC analysis may provide analysis for detecting vehicle or machine operator vigilance with a wireless electrode option.

The system of the present invention may include an Eye Opening Sensor (EOS)(refer FIGS. 34, 35,37,42). The EOS system may provide an improved device for sensing and measuring Eye Opening. Eye movement sensors (such as piezo or PVD movement sensors) and electrodes (such as EOG) have been used in the past for detecting eye movement or eye-lid movement respectively. However one problem associated with depth of anaesthesia monitoring is the fact that some patients awaken prematurely during a medical procedure and opening of the eyes can lead to distressing views and later recall or nightmare occurrences. A further problem is the patient may litigate in such instances. An objective and accurate recording of the patient's state and amount of eye opening is therefore desirable. A system that allows the user to calibrate such an eye-opening sensor may also be of value. The HCM system of the present invention may include such a sensor (refer FIG. 34) for detecting in a calibrated manner the degree of opening of a subject's eye.

The EOS system includes an eyelid position monitor and an EOG sensor. The EOS system may include conventional surface electrode electro-physiological signal sensing in conjunction with a capability to detect the position of a subject's eyelid at any point in time. Combined sensing of eye movement and eye opening may provide a simple, minimally invasive sensing system ideally suited to a subject's eye region to provide eye blink details and rate, eye open percentage and eye movement information. The sensor can be wire or wireless connected to a monitoring system. The EOS system may also be provided in an embodiment, whereby EOG sensing is achieved within the same sensor attachment system. Special design variations may provide simple self-applied sensors, which can be safely and easily applied in a manner similar to attaching a band-aid.

A further option exists using self-applied electrodes where the electrodes may include a low cost disposable component and a more expensive reusable component. For example the connector and electronics circuit may be reusable, while the applied section of the sensor may be disposable.

The HCM system may also provide an improved capability for calibrating eye position at commencement or at any stage during a subject's use of the EOS sensor. Calibration may be applied by determining (measuring, storing and determining calibration data versus corresponding eye opening status) the output of the EOS sensor under varying conditions, e.g. by asking a subject to close their eyes, and storing the responding EOS signal. The EOS system may incorporate the format of the WEM and the EAS.

The system of the present invention may include an Integrated Sleep Electrode system (ISES)(refer FIGS. 35, 37,42). The ISES device may provide a self-applied electrode system for sleep/wake analysis of a subject. The electrode system may attach outer malbar or any two EEG electrodes to a subject's forehead as part of a monolithic self-adhesive and self-applied electrode system. An analysis method may be applied to the ISES device's signal output to provide sleep/wake or bicoherence analysis. A flexible insert may facilitate elasticity to accommodate different patient sizes. Electrodes may include varieties including an attachable version and disposable dot surface re-usable electrodes (such as from 3M) and reusable/disposable electrodes. The ISES system may include the format of the Wireless Electrode Module (WEM) and the Electrode Attachment System (EAS).

The system of the present invention may include a user programmable device with real-time display of integrated analysis index and incorporating at least two weighted and combined modes of analysis (refer FIGS. 16, 17,18,34,35,37, 41-45). The apparatus may include a capability to output one or more analysis algorithms including a combination of simultaneous, real-time analysis of R&K analysis (34), AEP (30), spectral analysis-SEF-MF (4), Bi-coherence (BIC) analysis (33), initial wave analysis (5), auditory response (30), arousal analysis (35) and body movement analysis (34), 95% spectral edge analysis (36) and anaesthetic phase and spectral energy variance measurement in association with the subject's state of consciousness (30), Pulse Transient Time (PTT) based arousal detection (31), PTT measure and PTT based blood-pressure reference measure, Pulse oximetry SA02, PTT based heart rate and blood pressure with simple non-invasive oximeter, PAT analysis for sympathetic arousal detection (104-108), EEG spike-K-complex-wave-activity-event categorisation (47) and bio-blanket heart-temperature-PTT blood-pressure-respiration-breathing sound (49). The specific types of analyses can be determined by way of signal validation, user's selection of analysis requirement (such as depth of anaesthesia, vigilance, sleep-wake and other) and electrodes input to the system.

The HCM system of the present invention addresses the limitation of the prior earlier art by presenting a simple mode of display to the user which represents a simple measure of the subject's current state of consciousness or hypnotic state. This particular aspect of the HCM system may communicate to the end-user a simple measure of the subject's consciousness despite a vast range of complex analysis measurements, as detailed herein. In addition to providing a simple overall measurement and display method the HCM system may also provide a means of storing and displaying all recorded raw data and outputs of each analysis method for complete system verification and trace ability relating to any display of conscious or vigilant state of a subject. The raw data and analysis data may be stored and available for later review, reporting and printing, as is required from time to time to verify system performance and operation.

The HCM system of the present invention may improve accuracy of prediction of the state of consciousness, or a subject's vigilance by comparing actual EEG amplitude variations with predicted EEG amplitude variations where predicted EEG behaviour may include predictions of EEG amplitude variation during anaesthesia drug administration against depth of anaesthesia prediction (29) (refer FIGS. 16, 17,18,34,35,37,41-45). The HCM system may recognize EEG amplitude variations associated with physiological phenomena such as EEG bursts as opposed to EEG amplitude variations associated with movement or other forms of artefact, such as excessive beta frequencies.

The HCM system of the present invention may apply amplitude analysis to the EEG signals. By analysing monitored EEG amplitudes from a subject and comparing this signal to a pre-known amplitude trend or signal behaviour, it may enhance accuracy of prediction of anaesthetic drug administration. The "pre-known" behaviour trend may provide a means to predict the state of the depth of anaesthesia by referencing a known or predicted sequence or trend of EEG amplitude variation (behaviour) with the subject's actual EEG amplitude or patterns of EEG amplitude variation whilst under sedation or anaesthesia, for example.

The HCM system of the present invention, may reference amplitude trend predictions and signal modelling such as described by Moira L. Steyne-Ross and D. A. Steyne-Ross, of Department of Anaesthetics, Waikato Hospital, Hamilton, New Zealand (29) in a paper entitled "Theoretical electroencephalogram stationary spectrum for white-noise-driven cortex: Evidence for a general anaesthetic-induced phase transition". This paper describes an increase in EEG spectral power in the vicinity of the critical point of transition into comatose-unconsciousness. In similar context to the above-mentioned weighting methods, the HCM system of the present invention may weight the analysis output from amplitude analysis of the EEG signal. The EEG analysis may include comparison of actual monitored EEG signal and trends and predicted signal or trend associated with the subject's transition from consciousness to consciousness and visa versa.

The output of amplitude processing may be input to a weighting table for final consideration in the monitoring, detection and alerts associated with depth of anaesthesia, hypnotic state, sedation depth, fatigue or vigilance of the subject.

The system of the present invention may include a Programmable Electrode Interface System (PEIS) (refer FIGS. 16, 17,18,34,35,37). The PEIS apparatus may provide a means for intuitive user guidance and operation. The user of the HCM system can select a desired function (for example depth of anaesthesia monitoring, vigilance monitoring, sedation monitoring) and the system may illuminate by way of LED, LCD or other display system, the required electrode connections and recommended position on subject such as the location of various surface electrodes.

The PEIS apparatus may provide a prompting capability, indicating to the user, which electrodes require attention, e.g. surface electrode may require re-attachment due to excessive impedance.

In a preferred embodiment the PEIS apparatus may include a touch screen programmable electrode attachment guidance system.

The system of the present invention may include a Biological Blanket Sensor (BBS). The BBS may enable a wired or wireless interface providing a range of measurements for assistance in determining arousal movements, body movement, breathing sounds, heart sounds, respiration, heart rate, Pulse Transient Time, Blood pressure and temperature.

The BBS apparatus may be sensitised with sensor elements whereby the sensor reacts to subject movement causing a change in impedance of a resistive element, piezo or PVD element (49).

The system of the present invention may include a Biological Sensor Oximeter with Integrated and Wireless-Linked ECG and Pulse Transient Time (PTT) Monitoring and Analysis (refer FIG. 33). The latter apparatus may monitor a subject's blood pressure variation, micro-arousal detection for detecting sleep or consciousness fragmentation (particularly useful but not limited to depth of anaesthesia consciousness monitoring and analysis), oximetry, temperature, ECG waveform and analysis, heart rate variability and cardio-balistogram respiratory monitoring output and respiratory event detection.

Prior art non-invasive blood pressure devices utilise techniques such as finger attachment probes. These finger attachment systems apply pressure to a patient's finger and can become uncomfortable after a period of attachment to the patient. Other non-invasive blood pressure measurements have been presented including qualitative methods. One such qualitative method is a qualitative derivation of Pulse Transit Time (PTT) by means of a calculation utilising the electro-cardiograph (ECG) waveform and the pulse waveform of the subject. The ECG waveform is typically derived from a chest located ECG surface electrode attachment. The pulse waveform may be derived from the plethysmograph pulse waveform of a pulse oximeter probe attachment at a location such as a patient's finger. The calculation for deriving qualitative blood pressure value is based on the relationship, which exists between PTT and Blood pressure. Plethysmograph data may also be used to establish sympathetic arousal conditions (104), which may be related to stress or anxiety and which are physiological signs of premature awakening.

However a number of patient monitoring applications require continuous and close to real-time blood pressure measures of the subject to detect a significant physiological blood-pressure change or related event.

Furthermore existing minimum invasive methods for blood-pressure measurement typically involve a cuff device placed around the subject's upper arm. The cuff device may be inflated and deflated to measure blood pressure. This method of measuring blood pressure may be applied to a patient on a periodic basis. Other methods for minimally invasive blood-pressure measurement include wristband cuffs with similar inflatable and deflateable bands. Whilst these wristband cuff blood pressure systems, are potentially less invasive than upper arm cuff type systems, it is apparent that measurement reliability of wrist systems is more vulnerable to sensitivity of positioning and difficulty in obtaining a consistent and reliable measurement. Both cuff type systems are not used routinely for real-time and continuous blood pressure monitoring applications (such as depth of anaesthesia, respiratory disorder and sleep disorder monitoring) due to obvious discomfort and complexity and inconvenience of such measurement techniques.

An object of real-time blood pressure, measurement technique is to apply a 3-point wireless localised network (raw data and analysis results may be transmitted to a remote computer, if required) to provide a minimally non-invasive, minimally obtrusive blood pressure measurement apparatus. One aspect of this apparatus is that the clinically accepted standard for upper-arm cuff inflation/deflation measurement may provide calibration and absolute blood pressure measurement, while the oximeter finger (for example—another location for oximeter pulse) SAO2 measurement together with plethysmograph (provides pulse waveform for measurement of pulse transit time) and ECG surface electrode may provide a reference heart signal to be used in conjunction with the oximeter finger pulse signal to produce a calculation in real-time for pulse transit time. Pulse transit time is recognised as a means of qualitative blood pressure measurement (31, 32).

In contrast to the prior art the HCM system of the present invention may apply periodic cuff attached (arm, wrist or other patient attachment location) blood-pressure measurement system, in conjunction with an oximeter pulse waveform and ECG waveform (for PTT calculation). The method of utilising the PTT (by way of oximeter pulse wave and ECG waveform) together with periodic cuff based blood-pressure measurement may provide a means to derive a quantitative blood-pressure measurement from the cuff value, and a qualitative blood-pressure measurement from the PTT calculated signal. In other words the baseline quantitative blood-pressure value may be derived from the cuff blood-pressure value, while a continuous and qualitative blood pressure value may be derived from the PTT value. The benefit of this type of system is accuracy and a continuous blood pressure monitoring capability, while maintaining patient comfort by implementing cuff inflation and deflation only at periodic time intervals.

Furthermore the system may simplify user operation with application of wireless interconnection of the pulse oximeter, ECG electrode and blood pressure cuff. Wireless interconnection may allow calculation of continuous blood pressure at a remote wireless or wire-linked site (such as a patient monitoring device), at the ECG electrode attachment site, at the oximeter finger probe site or the blood pressure cuff site.

The system of the present invention may include an audiovisual recall and speech sensory validation system (refer FIG. 43). The latter may provide audiovisual recall or replay and time synchronisation with depth of anaesthesia analysis data and raw data. Audiovisual recall may provide a means to correlate physiological or analysis data associated with depth of anaesthesia monitoring.

The audiovisual system may be configured in several options. One option may include a capability to store more than one audio channel synchronised with the subject's measured physiological data. The stored and monitored (and optionally analysed or condensed) audio channel may include sound or speech associated with the subject, to accommodate monitoring and detection associated with the subject's speech sensory system. This function may be deployed as a last line of defence where a partly anaesthetised patient is attempting to notify the medical team, in case of partial or complete consciousness associated with potential undesired recall of a medical procedure.

The system user may select physiological events or combinations of physiological events as event markers. The event markers may form the basis of time markers pointing to significant or relevant events. The event markers may be associated with specific audio and/or video related events. The "audio" and/or "video" related events include physiologically related or environmental related events. Physiologically related events include combinations of or single patient data changes which may be related to the patient's significant (i.e. the level exceeds a certain threshold condition) or relevant (to the users or the system's programmed detection threshold) changes in consciousness state. The system's time synchronisation between video, audio, physiological data and analysis data may provide a means for audio and video to be recalled and analysed in conjunction with the subject's state of consciousness as indicated by the status of eye opening, AEP, arousal, bi-coherence analysis, and other analysed states.

One example of an audio and/or video "relevant" event may be where a threshold level (user set or system default set) is exceeded indicating a potential for onset of consciousness. Detection that the audio evoked threshold is exceeded may be linked to detection of "environmental" and/or system generated audio threshold being exceeded, where "environmental" audio denotes audio recorded in the operating theatre from music, speech or other sources of noise. "System-generated audio" refers to the audio stimulus click, which may be applied to the patient's ear or ears during an operating procedure.

The system may detect incidence of exceeding a preset environmental audio threshold in conjunction with a physiological event such as audio evoked potential amplitude exceeding a certain threshold condition (typically a certain averaged amplitude measured with a certain time delay from a trigger point). This "capability" may provide an efficient (subject to system or user threshold programming) method for validating or evidence of a likely incidence of audio recall associated with a procedure involving application of anaesthesia. The system may present in a condensed graphic or numeric form an association between the subject's hearing status (as detected from an audio sensory nerve monitoring signal) associated with incidence of environmental sound (as detected from the recording of audio within the operating theatre environment). This "association" may allow the system user to efficiently investigate correlation of a patient's hearing response and actual alleged audio recall. For legal purposes this facility may detect whether a subject's audio sensory nerve was indeed active (as opposed to inactive during an unconscious state) and whether the alleged audio recall of specific music or words was indeed probable. The "environmental audio" recording may be achieved by means of a patient attached microphone, such as a microphone attached to an outward side of the patient's earpiece or headset speaker system (as applied for generating an audio click for Auditory Evoked Potential). This type of method has an advantage of providing a dual-purpose sensor/speaker system, while also providing specific and directional audio pick-up associated with the patient's hearing system.

Similarly, where a subject claims visual recall during an operation, an appropriately placed theatre camera that is time synchronised with physiological data and analysis may record the alleged vision. Vision recall may be compared to Systems detection (manual, automatic or computer assisted) of a subject's eye opening for example. For legal purposes this facility may detect whether a subject's alleged vision recall was indeed possible as opposed to impossible, such as when the patient's eyes are both closed.

In other words, the system may allow audio validation—i.e. if the subject's AEP data indicated that the alleged audio recall was coincident with inactive auditory evoked potential, for example, this may support data for medical defence against audio recall operation claims. Similarly video of the patient could disclose whether or not visual recall claims coincided with patient eye open status.

In another example, bi-coherence analysis of importance such as where specific threshold conditions are exceeded may be validated by reviewing it in a time-synchronised format with video and audio recorded during a subject's operation. This validation may allow quantitative data to substantiate claims such as audio or visual recall associated with an operation procedure.

The system may optionally include means for recording the subject's taste (some patient's claim taste recall, such as taste which may be associated with anaesthetic gas delivery), utilising taste biochips and again providing an association between consciousness state physiological and analysis parameters with taste and/or physiological taste sensors. In some cases the medical specialist may deem monitoring of taste sensor sensory system status as a requirement.

A further option may be to use two simultaneously acquired images, where each image is acquired at a different wavelength of light. Reflections from the patient's face may then be identical except for reflections of the eyes. By subtracting these two images, a third image consisting of the subject's eyes may be created. Finally, the image of the patient's eyes may be measured to provide a non-invasive and non-obtrusive measure of eyes opening and blink rates of the subject (99). This data utilising PERCLOS methods may be used as a relatively reliable measure in the HCM system, to ensure that a subjects eye openings particularly when the subject should be anaesthetised and unconscious (100).

The eye opening value may provide a simple measure of the percentage of eye opening of a patient and may clearly indicate risk of visual recall or potential awakening of the subject, during an anaesthesia procedure.

The system of the present invention may include a patient alarm alert system for limb-controlled alarm (refer FIG. 44). The HCM system may include a wire or wireless remote device connected to or accessible by any patient limb or other location near or attached to the patient's body. This remote device may contain at least a means for detecting or alarming system users or healthcare workers that the patient is in distress or requires attention. This remote device may allow the subject or patient a form of "final line of defence" to premature wakening or consciousness onset. If, for example, a patient is undergoing a local anaesthetic procedure, which does not allow verbal notification of pain experience by the patient, the HCM system's remote device may allow the patient to signal experience of pain level to the system operator(s). Various forms of pain or consciousness level notification may be possible. One such form is where the patient is provided a simple squeeze control such as a rubber ball, and where the pressure resulting from squeezing, signals pain experience and the level of such pain experience. Other forms (subject to type of medical procedure and anaesthetic application, for example) may include, for example, an attachment for detecting foot movement, eye movement or other appropriate means of pain or consciousness signalling.

The system of the present invention may include a Wireless Electrode system with automatic quality verification, redundant electrode substitution, and minimal sensor-electrode attachment system (refer FIGS. 34, 35, 37). The HCM system may provide a minimally invasive method and apparatus for monitoring vigilance of people, using 2 or 3 (or as many electrodes as required in a given application) forehead located surface electrodes, wireless monitoring connection, active electrode for dry electrode minimal electrode preparation, automatic electrode impedance measurement for detecting potential electrode quality problems, redundant electrode substitution for substituting back-up electrodes for poor quality electrode connections and dynamic signal quality for detecting current or pending electrode problems (refer drawings).

Paths of data storage may include localised condensed data or secondary (analysis results) data storage, or remote raw data (minimal or no compression or condensing data techniques).

A specialised identification connection system may allow automatic identification and channel characterisation (system configuration to suit particular channel type) for matching between electrode application types. "Electrode application" types may include ECG, EMG, muscle activity, piezo movement detection, bi-coherence EEG, and EOG. "Characterisation" may include sample rates, data analysis types, data condensing formats, data storage rates, data storage format, optimal power management, and electrical and processing optimisation. Data format may include on-board electrode data storage, versus remote patient worn data storage or remote linked data storage.

Characterisation may also include aliasing filter requirements, high-pass/low-pass and notch signal biological signal filtering requirements, and calibration requirements (for DC stability and gain requirements). A further embodiment of the system includes a low-cost disposable wireless electrode device such as may be required for monitoring sounds provided by a PVD sensor integrated with a "band-aid" style of attachment to a subject's face for monitoring the subject's snoring or other breathing sounds. The apparatus may include a means to incorporate the microphone sensor, amplification, filtering, storage and CPU either as a throwaway disposable system or with the more expensive electronics being part of a re-usable part of the apparatus. In the case where the apparatus is provided as a totally disposable unit, a means for sensing monitoring and recording and analysing the data may be provided for in addition to a means for displaying the analysed data results. The means for displaying the analysed data results may include a low cost means such as a permanent graphical chemical reaction associated with markers, coding or other visual based system. Alternatively a digital wired connection, optical connection or magnetic means of connection may be used to download the stored data results. A device may provide a means for recording airflow or bruxism events (via vibration or cheek muscle electrical activity) either as a disposable or re-useable device or a combination of a disposable electrode section and a re-useable electronics and wireless section. The apparatus may include means to simultaneously sense (with electrodes or transducer), monitor, record and analyse bio-physiological data within a "local" (electrode device module) memory device, while transmitting data to a "remote" (wrist watch or remote computer device) device. The "local" device may provide limited storage due to size, cost and power restraints, while the "remote" device may provide a means of transmitting and storing less condensed and more comprehensive data, as may be required for clinical or research diagnosis or validation of diagnosis.

The system may offer any combination of very low power "self-powered" system operation. Very low power operation is possible by utilising transmitted EMF or radio energy, from a remote source, as a means to supply or supplement a source of power for the system. The apparatus may be provided in a form, which is reusable or disposable.

In a form in which the electrode is disposable the device may be configured in a form, which can process and condense data such that the data can be stored in the device and may display various forms of index or output summary. This display may be in a form where the index can represent an amount of time detected in a sleep or wake state (could be any stage or combinations of state including REM, non-REM, stage 1, stage 2, stage 3, stage 4, wake) by means of say a pair of bi-coherence electrodes. Accordingly, the apparatus may record data representing the subject's sleep efficiency or related to the subjects sleep efficiency to inform a patient or healthcare worker whether the subject is receiving appropriate rest or quality of rest or quality of sleep. Similarly, a combination of a wristwatch based activity monitoring (86) and wireless electrode (such as for bi-coherence electrode monitoring) to wristwatch storage and processing may provide a low cost, minimally invasive and potentially highly accurate means of sleep, drowsiness or depth of anaesthesia monitoring.

The system may utilise special re-usable or disposable electrodes in conjunction with a miniature active electrode and transceiver device.

A combination of an active electrode and transceiver may provide a unique combination within the apparatus. The active electrode interface may provide a localised amplifier (close to or directly connected to the subject's surface electrode contact) to reduce stringent electrode application requirements of conventional electrode systems. The fact that the electrode amplifier is relatively close to the electrode (and thus the electrical signal derived from the said subject's skin surface) avoids noise pickup normally associated with conventional electrodes. Conventional electrodes have wires of up to 1 metre length, with the electrode amplifier being located some distance from the end of this wire. By buffering or amplifying the patient electrode directly at the point of patient skin surface attachment, a higher impedance may be used. Conventional (passive) electrode systems, on the other hand, have longer wires connected between the electrode and the electrode amplifier creates a pick-up zone for external noise. Accordingly, a lower electrode impedance is required to minimise this otherwise large external noise and artefact interference. An example of the benefits of an active electrode system in this application is that the driver of a vehicle may apply an electrode to his/her forehead with little or no preparation, similar to the application of a band-aid.

An electrode application with little or no preparation may result in an impedance of say 40 K to 100 K (thousand) ohms, as opposed to a well prepared (thorough skin cleansing and some-times light abrasion) or "conventional" electrode application impedance which would be typically 5 K-10 K ohms impedance. A 40 K to 100 K ohms impedance would result in such large interference (in conventional passive electrode systems) that the desired monitored physiological signal could be rendered useless or unusable, while in an active electrode system a 40 K to 100 K ohms impedance could produce acceptable results.

A wireless protocol may include a capability to continually scan for new devices and allocated bandwidth requirements to accommodate incremental or decremental demands upon the number of system channels and aggregated data bandwidth requirements. Similarly, where system bandwidth has reached or approaches system limitations, the user may be alerted. In this way the physiological electrode wireless system is a virtual plug and play system, with simple and user friendly application. The wireless protocol may also manage functions such as relaying both physiological data and commands for continuous electrode impedance checking, calibration validation or associated adjustments, signal quality checking and associated adjustments, electrode substitution and other functions.

The system may include Spread-spectrum based wireless, active electrode system suitable for in-vehicle EEG monitoring and depth of anaesthesia monitoring amongst other applications (refer FIGS. 33, 34, 37, 42, 45).

Utilisation of an active electrode system for vigilance in-vehicle monitoring, in conjunction with a wireless and battery or self-powered electrode system, may provide a self-applied driver vigilance electrode monitoring system. In one embodiment, for example, a driver could apply a self-adhesive active wireless linked forehead electrode system.

The electrode system may include a re-usable section that contains the more expensive active electronics and wireless circuitry, and a disposable section that contains the surface electrodes and some form of interconnection to the re-usable section. Such apparatus may be suitable for a minimally invasive in-vehicle vigilance system where (for example) a wireless electrode monitoring device such as a forehead attached wireless electrode system may be optionally input to an existing driver drowsiness measurement system. In this manner a driver may choose to increase reliability of driver drowsiness detection by using minimally invasive EEG bi-coherence signal monitoring and analysis. This type of function may supplement or replace other on-board vehicle real-world driver drowsiness monitoring technologies associated with measurement of driver-movement and activity sensors (Burton, 1999) and eye opening measurement.

The system of the present invention may include physiological data time delay and analysis time lag compensation. The latter may be applicable where anaesthesia drug administration can be monitored in real time against actual display changes and the apparatus is able to predict changes instantly for the user to avoid over or under drug administration associated with natural hysteresis or delay factors such as delay between the instant of drug administration and the human body's physiological parameters (as monitored by the apparatus) responding to the drug administration.

The latter is applicable to parameters such as oxygen saturation where the physiological data reading is typically delayed by between 15 and 20 seconds due to the nature of the monitoring method and the body's time delay in blood-oxygen colour change.

The system of the present invention may include a Biofeedback loop providing automatic anaesthesia drug rate or concentration of delivery (refer FIG. 48).

The HCM system may interface to various types of drug delivery systems to provide varying degrees and types of biofeedback control affecting the drug administration process. The drug delivery systems may include but are not limited to gas ventilation or ventilation or gas delivery systems, drug perfusion systems, amongst other drug delivery systems. "Varying degrees" of drug delivery may include a capability to limit drug delivery or provide degrees of drug delivery or drug delivery mixture in accordance with predetermined monitoring or analysis parameters associated with the HCM System.

The system of the present invention may include a Wireless Patient Electrode Identification and Characterisation function (IDCF). This function may provide a means for the system to automatically identify the electrode type selected by the user. Automatic identification may be by way of wireless module scanning or electrically interfacing to some resident data (contained on the disposable or reusable sensors or electrodes, which are attached to the subject) or optical or magnetic code sequence, where a unique code is associated with each unique electrode type. Various electrode types may be identified for groups of physiological variables, which share the same characteristics and processing requirements. If a user selects an ECG electrode for example, the IDSC may alert the system of optimal gain, signal range filter conditioning, aliasing filter values and types, sample-rate and data bandwidth requirements for the wireless module interface, processing, acquisition, analysis, display and other functional requirements related to the electrode channel type.

This automatic identification system may greatly simplify system application and minimise potential user errors. An example of an application and embodiment of this system may be where a nurse applies a series of clearly labelled electrodes and the rest of the system operation is automatically configured as the patient is wired up in accordance with the selected electrode types.

The IDCF is also useful if the application for the wireless electrode system is a wireless EEG electrode system that is self-applied to a vehicle driver's forehead for simple "foolproof" EEG signal monitoring. The combined application of the wireless module with automatic signal characterisation in accordance with detection of the electrode type, active electrode signal handling and later analysis techniques incorporating BIC (including bi-coherence and bi-spectral analysis) may provide a unique wireless, artefact reduced and precise method for in-vehicle or other application of cognitive performance or vigilance/fatigue monitoring.

This function may be particularly useful for depth of anaesthesia or a vehicle based vigilance system where the user needs to have a system that is as minimal and "fool-proof" as possible.

The IDCF system may also help to ensure that only known re-usable or disposable electrodes are used with the system and that optimal characterisation and system set-ups are automatically applied in accordance with the selected electrode types.

SUMMARY OF THE INVENTION

The HCM system of the present invention may provide improved accuracy in monitoring, analysis, detection, prediction, system alerts and alarms associated with, inter alia, depth of anaesthesia, depth of consciousness, hypnotic state, sedation depth, fatigue or vigilance of a subject, with as few as 3 surface electrodes. The HCM system may incorporate real-time phase, amplitude and frequency analysis of a subject's electro-encephalogram. The HCM system may provide a means to weight the output of various types of analysis and produce a combined analysis or display for precise indication or alert to various users of the system.

In particular the HMC system may monitor, store and display two or more sets of physiological data parameters or analyse one or more combinations or calculations associated with the data to display, store, condense and summarise data for a range of applications associated with monitoring human consciousness. The HMC system may analyse two or more of the physiological data to produce condensed data summaries, or indexed data (such as arousals per hour and other indexes) or tabular and graphic displays and reports associated with monitoring human consciousness. The HMC system may correlate two or more sets of the physiological data or analysis results to produce tertiary analysis results associated with monitoring human consciousness.

The HMC system may be applied to monitoring depth of anaesthesia for optimal administration of anaesthetic drugs, to sedation in tracking the subject's level of sedation for nurses or other medical professionals, to monitoring fatigue and hypnotic state for drivers, to monitoring vigilance for transport and machine workers and to controlling delivery systems for administering therapeutic treatment such as drugs, gas or the like to the subject.

The HMC system may weight the outputs of one or more analysis algorithms including combination of simultaneous, real-time analysis of R&K analysis (34, 45, 46), AEP (30), spectral analysis-SEF-MF (30), Bi-coherence (BIC) analysis (33), initial wave analysis (5), auditory response (30), arousal analysis (35) and body movement analysis (34), 95% spectral edge analysis (36) and anaesthetic phase and spectral energy variance measurement in association with a subject's state of consciousness (29), Pulse Transient Time (PTT) based arousal detection (31), PTT measure and PTT based blood-pressure reference measure, Pulse oximetry SAO2, PTT based heart rate and blood pressure with simple non-invasive oximeter (31,32), PAT analysis for sympathetic arousal detection (104-108), EEG spike-K-complex-wave-activity-event categorisation (47) and bio-blanket for monitoring of heart, temperature, respiration (49), breathing sound and PTT blood-pressure. Inclusion of sympathetic arousal may provide a unique measure of stress or mental anxiety, despite the state of a patient's state of paralysis or "apparent unconsciousness".

According to one aspect of the present invention there is provided a method of monitoring consciousness of a sentient subject and automatically detecting whether the subject is in a transition from a conscious state to a less conscious state or vice versa, by reducing effects of frequency based changes in neurological data from the subject, said method including:

(i) obtaining an EEG signal from the subject;
(ii) performing a frequency based analysis on the EEG signal to obtain a frequency based signal;
(iii) performing a phase based analysis on the EEG signal to obtain a phase based signal;
(iv) detecting by comparing the frequency based signal and the phase based signal whether the subject is in transition from said conscious state to said less conscious state or vice versa; and
(v) providing a warning signal when said subject is in said transition to said conscious state.

According to a further aspect of the present invention there is provided a method of processing a non-stationary signal including segments having increasing and decreasing amplitude representing physiological characteristics of a sentient subject, said segments including portions in which said signal changes from increasing to decreasing amplitude or vice versa, said method including:

(i) detecting each segment by determining time instants when a time derivative of said signal is substantially equal to zero;

(ii) performing syntactic analysis for each segment including assigning height, width and error parameters;

(iii) identifying noise segments present in said signal by comparing said width parameter to a preset threshold and said error parameter to said height parameter;

(iv) removing said noise segments by replacing each identified noise segment with a substantially straight line;

(v) sorting the remaining segments into a plurality of wavebands based on their width parameters; and (vi) classifying said signal as belonging to one of predefined sleep states based on relative frequency of occurrence of said segments in said wavebands.

According to a still further aspect of the present invention there is provided a method of monitoring physiological characteristics of a sentient subject including:

applying a first surface electrode to said subject to provide a first electrical signal to a remote monitoring apparatus;

applying a second surface electrode to said subject to provide a second electrical signal to said remote monitoring apparatus;

monitoring quality of said first electrical signal and in the event of a degradation in said quality of first signal;

automatically substituting said second electrical signal for said first electrical signal and in the event of a degradation in said quality of said second electrical signal and in said quality of said first electrical signal, providing a warning signal.

According to a still further aspect of the present invention there is provided an apparatus for processing a non-stationary signal including segments having increasing and decreasing amplitude representing physiological characteristics of a sentient subject, said segments including portions in which said signal changes from increasing to decreasing amplitude or vice versa, said apparatus including:

(i) means for detecting each segment by determining time instants when a time derivative of said signal is substantially equal to zero;

(ii) means for dividing said signal into said segments including data over three consecutive time instants when said time derivative is equal to zero;

(iii) means for assigning to each segment, height, width and error parameters;

(iv) means for identifying noise segments in said signal including means for comparing for each segment said width parameter to a preset threshold and said error parameter to said height parameter;

(v) means for removing said noise segments including means for substituting a straight line connecting first and third time instants when the time derivative of said signal is substantially equal to zero and reassigning segments and their parameters after the substitution;

(vi) means for sorting the remaining segments into a plurality of wave bands based on the value of their width parameter, each wave band being defined by upper and lower frequencies corresponding to lower and upper values for the width parameter respectively; and (vii) means for classifying a time interval of the signal data as belonging to one of predefined sleep states based on relative frequency of occurrence of said segments in said wave bands.

The so-called "segments" are the principal building blocks of EEG and EOG analysis. A "segment" includes a sequence of consecutively increasing and decreasing or consecutively decreasing and increasing intervals of the signal under analysis.

All "segments" may be initially detected by applying syntactic analysis to the signal, i.e. detecting all local maxima and minima. As a data structure a "segment" is represented by its orientation (i.e. "upward" or "downward"), width, height and error. In the context of visual signal interpretation, the last three parameters have a clear meaning. Width relates to the dominant frequency of the signal under analysis at this particular time interval, height relates to the magnitude of the signal variation and error, which is a measure of signal variation from a straight line connecting the start and end of the "segment", relates to the magnitude of noise in the signal if the "segment" is a part of the noise rather than a part of the actual signal that is under analysis.

After all "segments" are originally detected using a syntactic algorithm, those segments which are likely to be noise rather than the signal under analysis must be removed, and new signal "segments" must be reconstructed. To achieve this an iterative procedure of identifying noise "segments" and generating new signal "segments" may be employed. A "segment" may be classified as noise if its width is relatively small (which in the case of EEG signal indicates alpha, sigma and beta bands—where high frequency noise is typically prominent) and the error is relatively small (which ensures that genuine visible EEG high frequency components are retained). Various rules may be generated to represent meaningful conditions of small width and small error. This "segment" may then be approximated as a straight line and a new "segment" constructed as a result of this approximation. This procedure may be performed iteratively until no noise "segments" are detected. The described approach has a significant advantage over prior art FFT methods (which cannot discriminate between high-frequency noise and sharp slopes of genuine EEG patterns) and zero-crossing methods (which rely on DC offset and do not remove noise).

All remaining "segments" may then be sorted according to the value of their width parameter among conventional EEG frequency bands. This sorting may be performed for both "downward" and "upward" "segments" to enable accurate interpretation of asymmetrical "segments". Once the "segments" are sorted for an interval equal to one sleep study epoch, a simplified sleep/wake discrimination may be performed by calculating a total duration of "sleep-like" "segments" (sum of durations of all delta and theta "segments") and comparing it with the half epoch duration. This approach in fact represents a mathematical model of sleep/wake discrimination based on visual interpretation of an EEG epoch.

Various means for fine-tuning this technique to achieve more accurate detection of important EEG patterns and subsequently more accurate sleep/wake discrimination are disclosed below. These include algorithms for EEG artifact detection, delta wave detection, periodic pattern detection and modified sleep/wake discrimination rules which take into account a major role of EEG periodic patterns (which may vary beyond alpha band), role of context based decisions and the uncertainty associated with artifacts.

The apparatus may include means for detecting and processing artefact patterns in said signal including one or more of:
  means for detecting flat intervals in the signal;
  means for detecting intervals in the signal having a relatively sharp slope, being intervals in which variation in the signal exceeds a first threshold over a time interval equal to or shorter than a second threshold;
  means for detecting intervals in the signal having a relatively narrow peak, being intervals in which the width parameter is equal to or less than a third threshold and the height parameter is equal to or greater than a fourth threshold; and
  means for detecting other non-physiological pattern in the signal, being combinations of segments having a width and height of one, the segments in the combination being less than the respective total duration and signal variation of the combination by at least preset ratios.

The apparatus may include means for detecting and processing wave patterns characterised by minimum amplitude and minimum and maximum durations, including:
  means for detecting a core interval of the wave pattern as a sequence of one or more segments which starts at a first time instant of a first segment when a time derivative of the signal is substantially equal to zero and ends at a second time instant of the last segment when a time derivative of the signal is substantially equal to zero, or starts at the second time instant of the first segment when the time derivative of the signal is substantially equal to zero and ends at a third time instant of the last segment when the time derivative of the signal is substantially equal to zero, with the total signal variation of at least the minimum amplitude, duration of at least a preset share of the minimum duration, less than the maximum duration and the maximum deviation from a monotonous change of at least a preset share of the total variation.

The apparatus may include means for detecting a start and end of a main wave of the wave pattern by subsequent comparison with a preset threshold of a deviation of the slope of respective components of segments preceding and following the core interval from the slope of the core interval, and for updating the core interval if the deviation of the slope and maximum deviation from the monotonous change do not exceed respective preset thresholds, and a total updated duration is equal to at least a preset share of the minimum duration and is less than the maximum duration.

The apparatus may include means for detecting one or two side waves of the wave pattern by subsequent testing of sequences of combinations of segments preceding and following the main wave for the signal duration conditions.

The means for sorting into a plurality of wave bands may be based on the detected wave patterns. The means for classifying may include means for comparing to preset threshold values of weighted combinations of occurrences of the segments in the waveband, artefact patterns and wave patterns. The apparatus may include means for detecting periodic patterns with specified minimum and maximum frequencies, minimum amplitude and minimum number of waves including:
  means for selecting combinations of a specified number of segments;
  means for assigning for each combination, an average, minimum and maximum amplitude and an average, minimum and maximum period;
  means for testing if the average amplitude exceeds a specified minimum amplitude for a periodic pattern;
  means for testing if the maximum amplitude exceeds the minimum amplitude by not more than a specified ratio;
  means for testing if the frequency corresponding to the average period is equal to or greater than the minimum frequency of the periodic pattern and is equal to or less than the maximum frequency of the periodic pattern;
  means for testing if the maximum period for a combination of segments exceeds the minimum period by not more than a specified ratio;
  means for joining combinations of segments, which comply with the above criteria; and
  means for classifying a time interval of the signal data as belonging to one of predefined states on the basis of a comparison of the value of a weighted combination of durations of a plurality of wave bands, artefact patterns and wave patterns with a threshold which is set to a different value depending on the total relative duration of periodic patterns within the time interval.

The apparatus may include means for classifying a time interval of the signal data as belonging to one of predefined states on the basis of a comparison of the value of a weighted combination of durations of a plurality of wave bands, artefact patterns and wave patterns with a decision boundary which is set to a different value depending on the total relative duration of periodic patterns within the time interval, if the difference between the value and the decision boundary is equal to or greater than a specified margin, or otherwise, on the basis of a comparison of this value with the respective value for the preceding or following time interval providing that that interval is already classified and the difference between the respective values is equal or less than the specified margin, or otherwise, if after subsequent passes through the data, an interval is still not resolved, on the basis of comparison of this value with a threshold which is set to a different value depending on the total relative duration of periodic patterns within the time interval.

According to a still further aspect of the present invention there is provided a sensor for detecting position of an eye lid including:
  first means adapted to move substantially with said eye lid and relative to a second means; and
  means for providing an electrical signal indicative of the position of said first means relative to said second means, such that said signal includes a measure of position and/or degree of opening of said eyelid.

The first and second means may be electrically coupled such that the coupling provides the measure of position and/or degree of opening of the eyelid. The first and second means may be provided by respective arms connected for relative movement. The arms may be pivot ably connected to each other. Each arm may include a capacitive element arranged such that the extent of overlap between the arms determines the coupling between the capacitive elements. Each capacitive element may include one plate of a capacitor. Alternatively each arm may include an inductive element arranged such that the extent of overlap between the arms determines the coupling between the inductive elements. Each inductive element may include a coil. The sensor may include means such as a wien bridge for measuring the capacitive/inductive coupling between the capacitive/inductive elements.

BRIEF DESCRIPTION OF THE DRAWINGS

Preferred embodiments of the invention will now be illustrated and described with reference to the accompanying drawings wherein:

FIG. 21A shows a sample signal applied to a patient's ear(s);

FIG. 21B shows a signal similar to FIG. 21A at a lower sensitivity;

FIG. 21C shows a block diagram of hardware for generating the signals in FIGS. 21A and 21B;

FIG. 21D shows one form of hardware for collecting AEP sensory data from a subject;

FIG. 21E shows an example of the signal from the subject's ear sensory nerve when receiving signals as shown in FIGS. 21A and 21B;

FIGS. 21F and 21G show examples of AEP output graphs for a range of input frequency sweeps;

FIG. 21H shows a sample of response curves from AEP input electrodes;

FIG. 22A shows a bar graph of Context Analysis Method and FIG. 22a shows the corresponding display validation status;

FIG. 22B shows a bar graph of Context Analysis Probability and FIG. 22b shows the corresponding display validation status;

FIG. 22C shows a bar graph of Transition Analysis Method and FIG. 22c shows the corresponding display validation status;

FIG. 22D shows a bar graph of Transition Analysis Probability and FIG. 22d shows the corresponding display validation status;

FIG. 22E shows a bar graph of Movement Analysis Method and FIG. 22e shows the corresponding display validation status;

FIG. 22F shows a bar graph of Movement Analysis Probability and FIG. 22f shows the corresponding display validation status;

FIGS. 23A to 23C show graphical representations of system output alarms, indicators and displays associated with Block 15 of FIG. 18;

FIGS. 30A and 30B are tables showing examples of weighting for combined (1, 2, 3, 4, 5) analysis index in Block 35 of FIG. 18;

FIG. 38 shows a preferred embodiment of a wireless electrode;

FIG. 46 shows an indirect connected wireless module;

DETAILED DESCRIPTION OF PREFERRED EMBODIMENTS

One form of Anaesthesia Depth Monitoring System (ADMS), which utilizes a combination of Bispectral index (Bi), Audio Evoked Potential index (AEPi) and Sleep Staging Analysis (SSA) for improved Depth of Anaesthesia monitoring will now be described with reference to FIGS. 1 to 14. The ADMS may present to the user a single Index of 1 to 100, where 100 represents the highest state of a monitored patient's consciousness and 0 represents the lowest index of a monitored patient's state of consciousness.

AEPi, in the context of prior art depth of anesthesia monitoring systems, has been reported as being more sensitive (than Bi alone, for example) in the detection of the transition from unconsciousness to consciousness. AEPi has also been reported to be more responsive than Bi to patient movement in response stimuli. However, Bi has been reported to increase gradually during emergence from anesthesia and therefore may be able to predict recovery of consciousness at the end of anesthesia (Gajraj et. al. 1999).

Prior art depth of anesthesia monitoring systems typically deploy either AEPi, Bi or both indexes as separate measures. The monitoring of AEPi and Bi as a combined index (CIAi) is preferable in terms of a comprehensive depth of anesthesia monitoring system with the ability to detect transition from unconsciousness to consciousness (TUC), patient movement (AEPi) and the benefits of a measure for the gradual emergence from anesthesia (utilizing Bi).

A depth of anesthesia monitoring system should be simple and unambiguous in its' use. This presents a problem because while a single Bi or AEP index presents a simple user-friendly system, the scope of a single measure (Bi or AEP) limits the accuracy of measurement of depth of anesthesia. On the other hand, relying on two separate measures (i.e. AEPi and Bi) can complicate system operation by producing confusion, such as an ambiguity as to which of the two measures should be followed at any one point in time.

One problem with conventional depth of anesthesia systems that are dependent only upon Bi, for example, is an inability to detect a transitional change from unconsciousness to consciousness.

Figure 2:
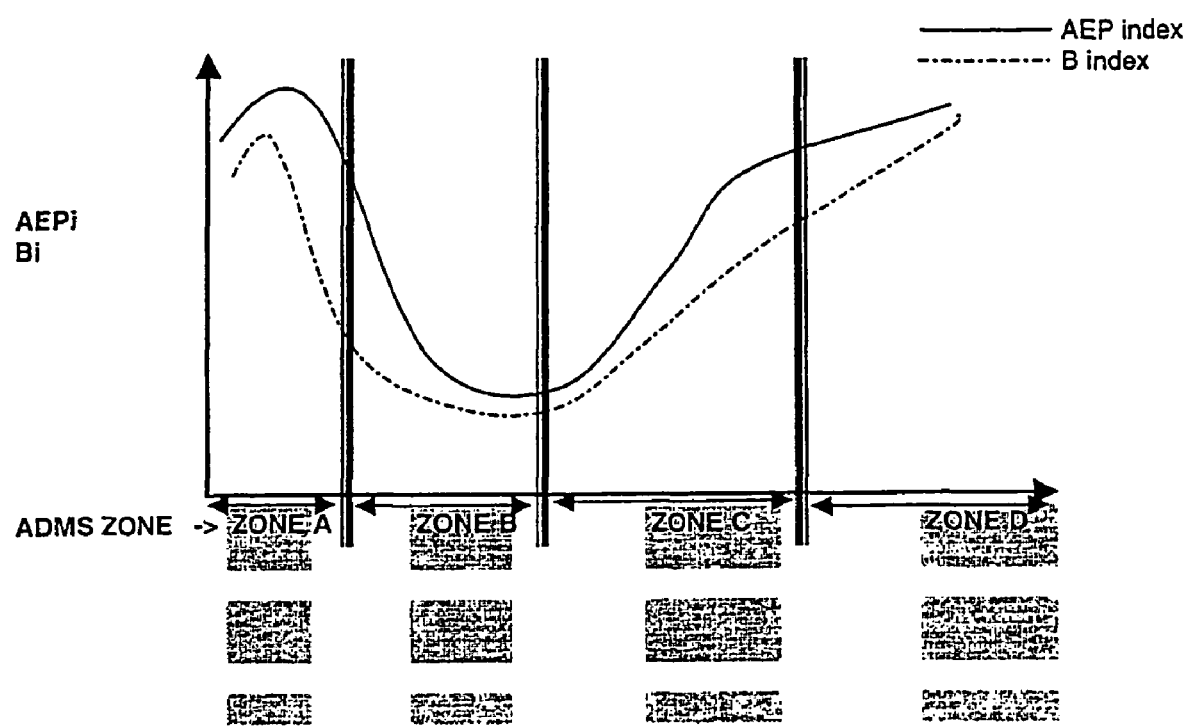
FIG. 2 shows a graphical representation of typical AEPi and Bi functions versus time for a patient undergoing general anaesthesia.

As can be seen in FIG. 2, the gradual change in the Bicoherence in Zone C presents the anesthetist with a more gradual indication of the transition from unconsciousness to consciousness. In contrast to the Bi the AEPi does not present a gradual change during emergence from unconsciousness but does provide a more clear depiction of the transition point from unconsciousness to consciousness. Concerns may exist in that the gradual changes in Bi may not distinguish clearly or quickly enough sudden transition changes, such as would be required to detect instances of a subject "prematurely" emerging from unconsciousness. These "instances" of early awakening (from anesthesia) can lead to potentially traumatic occurrences of memory recall and other associated effects. If, for example the TCU and TUC phases are not immediately apparent then the chances of instances such as audio recall will increase. Furthermore, the nature of the Bi EEG data is less likely to distinguish the audio sensory nerve shutdown and awakening as effectively as AEPi, due to the more direct hearing sensory analysis associated with AEPi analysis. Thus claims of audio recall with Bi based systems may render these technologies under greater scrutiny in future depth of anesthesia monitoring applications.

The ADMS addresses these disadvantages by integrating the strength of both AEPi and Bi, while still providing a single user-friendly Comprehensive Integrated Anesthesia index (CIAi) (refer STEP 23 and STEP 24).

A further difficulty exists with the current state of the art depth of anesthesia monitoring in that variations between different patients can alter the depth of anesthesia monitoring parameters with each individual patient. Examples of variations that can change the monitored parameters between different patients include different levels of hearing performance between the different patients. This variation can be of particular importance where the comparison of AEPi transition thresholds and critical thresholds, for example, is of importance. Other examples of variations between patients, which can affect depth of anesthesia monitoring outcomes between different patients, include gender, body mass different sleep architectures, amongst other factors.

The ADMS of the present invention may alleviate these difficulties by incorporating an automatic patient calibration function. (refer STEP 5 and STEP 6).

A further difficulty exists where a depth of anesthesia system requires ease of use but at the same time may be required to accommodate the flexibility associated with providing a range of system configurations. This range of different system configurations can exist due to the fact that some Depth Of Anesthesia (DOA) applications may not be practical, for example, to attach multiple sensor or electrode systems (such as both AEP and B sensors and electrodes). These situations may occur where the simplest electrode or sensor configuration is required. Further examples of where the system configuration may need to change include situations where various electrodes or sensors may not be performing reliably or to a minimal standard suitable for the monitoring and subsequent analysis or various parameters.

In situations where the user elects to use one or more different parameters or where electrodes or sensors are detected to not be performing appropriately, it would be desirous for the DOA monitoring system to allow the user to select or change the sensors or electrode status, or alternatively for the DOA system to notify the user and automatically compensate for the current electrode and sensor configuration or performance.

The ADMS may address these difficulties by incorporating automatic sensor and electrode scan (STEP 2) and MODE configuration (STEP 4).

A further difficulty which arises with the task of integrating AEPi and Bi is that in order to determine which of the AEPi or Bi is most appropriate at any given point in time, an independent method of arbitrating may be required to determine which of the two methods (AEPi or Bi) should be utilized or given higher weighting at any particular point in time.

The ADMS may address these difficulties by incorporating Sleep Staging Analysis (SSA) as a means of independent arbitrating for weighting of AEPi versus Bi. SSA analysis may provide a determination of the context of a patient's depth of anesthesia monitoring state and the state of a subject's consciousness based upon SSA spectral based analysis, in contrast to Bi analysis basis of phase difference and AEPi basis of averaging BSAEP amplitude signals synchronized to the patient's hearing response. Where "context analysis" refers to whether the patient's is entering a state of consciousness or emerging from unconsciousness (refer STEP 16 and STEP 24).

The ADMS of the present invention may integrate into a simple and singular index the benefits of both AEPi and Bi for the optimal monitoring of a patient during anesthesia. The new system uses an independent (to AEP or Bi) method of analysis being spectral based or ½ period amplitude analysis (34, 35, 45, 46) as a means to arbitrate which of the Bi and AEPi methods are most optimal at any point in time. Furthermore, ADMS can provide weighting to these said methods in order to combine or integrate the monitoring of a subjects depth of anesthesia into a simple but accurate single index.

Other difficulties with prior art technologies include an inability to respond to a subject who may be paralyzed due to muscle sedation and paralysis drugs administered in the course of an operation to prevent unwanted body movements during the operation. There have been incidents reported where patients were indeed conscious or partially conscious during an operation and due to the influence of paralyzing drugs were unable to alert medical staff.

ADMS may alleviate these difficulties with the use of Arousal index, Body Movement index and associated sensors, allowing the patient movement status and/or arousal status alert, independent of CIAi (STEP 23). A further difficulty that exists with the current state of the art depth of anesthesia monitoring systems is the inability to calibrate the sensitivity of the monitoring device with each patient's individual variations and sensitivity to anesthesia.

ADMS may alleviate this difficulty by incorporating a means of using Calibrated Patient (CALPAT) values to modify or adjust these said transition threshold values on an individual patient by patient basis (refer STEP 5 and STEP 6). The means of this Automatic Calibration method are based around measuring the patient's AEPi, Bi and SSA during the patient's first occurrence of transitioning from Consciousness to Unconsciousness. Thereafter Calibration of Patient transition values and display zone values can be allocated specific to the individual patient's sensitivity to AEPi and Bi.

A further difficulty with prior art AEPi based depth of anesthesia monitoring systems is the difficulty to compensate or accommodate for the varying hearing performance (or response to audible stimuli) between different patients and also between different audio stimulus apparatus and attachment of the audio stimulus apparatus thereof (Lippincott-Raven, 1997). These variations can be caused by factors such as the means used to generate the audio stimulus, the attachment method and device type (typically a single or pair of ear pieces are used to generate audio click stimulus in ear piece), or physiological variations in hearing performance evident between different subjects. The ADMS of the present invention may adjust the frequency spectrum, amplitude and phase of the audio click in order to provide optimal compensation for different audio stimulus device and attachment types and hearing variations (113).

It has been reported in recent publications (Vuyk 2002) that prior art depth of anaesthesia monitoring systems suffer several concerns. One concern relates to the use of the bispectral index monitor (Aspect Medical Systems, Inc., Natick, Mass.). This device relies upon the bispectral index (BIS) to monitor consciousness-sedation-unconsciousness levels. However it has been reported that various anaesthetic agents on the bispectral index scale appear to be agent specific. In general, it has been reported that agents such as propofol, midazolam or thiopental have a strong depressant effect on BIS. It has also been reported that inhalation anaesthetic agents propagate an intermediate depressant effect on BIS. However, it has been reported that the opioids have little or no influence on the BIS at clinically relevant concentrations. Also disconcerting is the fact that nitrous oxide and ketamine appear to have paradoxical effects on the BIS. Accordingly it has been suggested that BIS may relate well to sedation and hypnosis levels but does not properly reflect level of analgesia or depth of anaesthesia.

One inherent difficulty with the prior art depth of anaesthesia monitoring systems relying upon BIS (Aspect) as the main index or measure of depth of consciousness is the risk that a patient may lapse into a state of consciousness or indeed not enter or continue their state of unconsciousness, during critical times of an operation procedure.

The ADMS system of the present invention may alleviate or reduce risk of this difficulty by incorporating a Brain Stem Audio Evoked Potential Middle Latency (BSAEPML) signal as a precise indicator of a patient's transition from consciousness to unconsciousness and transition from unconsciousness to consciousness. This added factor of monitoring may operate in real-time and simultaneously with the measure of bispectral analysis. Thus different effects that can relate to different anaesthetic agents are reduced or alleviated by a measure of BSAEPML which is directly related to thermus and temporal lobe generators which in turn are directly related to the patients state of consciousness, and most importantly by definition of the function of (BSAEPML), to risk of memory recall associated with critical times within operation procedures.

The prior art utilises BSAEP, typically being ½ second frequency audio stimulus clicks as a method of auditory sensory stimulation. The ADMS may incorporate a steady state Audio Evoked potential capacity, including a capacity to provide higher continuous frequency of audio clicks. The range of audio frequency capacity may be from ½ Hz to 100 Hz. The steady state BSAEP may provide greater sensitivity in that more subtle changes may be measured from the subject's BSAEP. Responsiveness may also be more precise due to the fact that there is less time between consecutive stimuli clicks and therefore there is less delay and less likelihood in missing physiological responses.

The ADMS may include a capacity to provide interactive SSAEP. The latter may provide click stimulus sequences with a different or varying rate according to the patient state detected. This dynamic or programmable click stimuli may allow the system to "validate" more accurately and precisely patient status under various stimuli frequency and amplitude conditions, where these conditions can vary the stimuli test sequence.

The ADMS may include a capacity to provide multiple frequency (typically dual frequency) steady state BSAEP. In particular 40 Hz and 80 Hz continuous click stimuli frequencies may be used, where the 40 Hz and 80 Hz click rates are sequentially toggled or switched between. A typical sequence may be 5 seconds of each continuous 40 Hz audio click stimuli followed by 5 seconds of continuous 80 Hz audio click stimuli, in a continuous sequence toggling between 40 Hz and 80 Hz. The 40 Hz (or similar lower frequency rate) audio stimuli allows middle latency testing of the AEP, which may provide a graduated measure or monitoring in accordance with the subject's state of consciousness but more importantly, a precise transition state from consciousness to unconsciousness and unconsciousness to consciousness. The 80 Hz audio stimuli and corresponding AEP may allow a graduated measure and monitoring method for brain stem cortical response which is an important signal for detecting a patient's risk of neurological damage or risk of serious or fatal over sedation of anaesthesia, for example. This 80 Hz (or similar higher frequency rate) may provide an ideal alert or warning measure for the ADAMS to prevent or reduce risk of over-sedation or excessive depth of anaesthesia. This 80 Hz Continuous State and is BSAEP signal is a key measure for brain life or death status.

The ADMS integrated index and integrated monitoring capability may vastly improve upon the prior art by incorporating an important measure of hypnotic consciousness state (utilising bispectral analysis), incorporating effective transient state measure from consciousness to unconsciousness and unconsciousness to consciousness utilising lower continuous frequency such as 40 Hz click stimuli, and also incorporating critical brain stem cortical status warning and alert capability, particularly for reduced risk of over administration of anaesthetic or sedation drugs.

Multiple frequency (typically dual frequency) Brain Stem Stead State Audio Evoked Potential monitoring and subsequent electrode attachment, and bispectral monitoring and subsequent electrode attachment may be achieved with as few as one and as simple as one self-adhesive electrode attachment strip, requiring little or no electrode preparation. This is due to the ADMS system's capability to deploy the above mentioned wireless and/or battery powered audio stimulus earpiece and also a single electrode substrate with a unique combination of 2 inbuilt forehead EEG electrodes (for bispectral EEG signal-attached near patient's forehead outer malbar bones) and one further inbuilt electrode which may be positioned about 1 to 2 cm from the patients centre ear towards the patient's nose.

This single self-adhesive substrate with as few as three inbuilt electrodes may optionally include a disposable electrode format. A further option may allow a self sealed outer sterile cover typically plastic or foil to be removed to access the new electrode. The sensor may optionally contain an in-built electrode and a use by date of the electrode may be clearly marked on the outer electrode packaging. This system of inbuilt battery and due date labelling may avoid conventional technology issues and risk of both cross infection and flat batteries during critical use. A light, durable and non-obtrusive electronics module may optionally be clipped to the electrode substrate providing wireless interface to the ADMS measuring device.

The ADMS may include active electrodes, whereupon an electronics module (separate or inbuilt and disposable) may provide close location of amplifier buffering to the inbuilt electrodes. This closely located electronic buffering circuitry may provide an electrode system, which is less vulnerable to stray capacitance and external noise pick-up. Electrode impedances may be higher and may avoid issues of prior art electrode systems, whereupon extra preparation is required to clean and abrade the patient skin surface, to achieve acceptably low impedance between patient connections. Typical impedances with non-active electrodes may be 5 kilo-ohms compared to 50 Kilo-ohms or more, which is acceptable with active electrode configurations.

The electrode buffer (and/or amplification and filtering) electronics may be embedded within the substrate of the electrodes directly near the in-built electrodes, using flexible printed circuit techniques, such as circuit tracks printed on or within the electrode substrate.

A further feature of the ADMS electrode connection is that it may not require direct electrical connection to the patient. A new approach to human electrical activity detection has been made possible by recent advances in ultra-low-noise, ultra-high-input impedance probes. These probes do not require a real current conducting path and operate on the general principle of induction of a signal from a non-contact source.

This technology may provide a unique application for the ADMS electrode configuration options. Electrophysiological connection of the forehead EEG connections allowing monitoring and analysis for AEP and bispectral analysis may be implemented by electrical probes, which are embedded into the electrode substrate device and thus allow signal monitoring with minimum invasion.

The electrode and wireless systems may be used in a configuration of only forehead electrode provision for predominantly bispectral analysis. This type of simplified configuration may be especially suited to driving, operator or other vigilance monitoring and may be life saving for detection of fatigue onset (change in hypnotic and consciousness states can be detected, for example). The vehicle driver using this system may simply opt to open the disposable electrode packet, remove a battery start enable paper tag and self-attach the discrete and virtually undetectable wireless electrode to the forehead under the hairline, while a wireless mounted dash (or cigarette lighter connected) device monitors and alerts the fatigued or drowsy driver, potentially preventing a fatal road accident.

A further concern of prior art depth of anaesthesia monitoring systems which do contain some form of (BSAEPML) is that the attachment of an earpiece or other means of auditory stimulus systems to a patient during a surgical operation or other medical procedure can be disconcerting, too invasive and wires and cable can indeed cause unnecessary or potentially distracting concerns of entanglement or other adverse effects.

The ADMS system may address these difficulties and limitations by utilising a real-time wireless connected audio stimulus device, which is designed to avoid reliance on wires, may be as small as the tiniest hearing aid and may be attached to the patient with a simple non-invasive insertion process. Furthermore the device may include a disposable cover system designed to avoid cross infection while allowing the more expensive audio stimulus device to be re-used.

Furthermore the speedy disposable changeover cover system may include a unique protective-disposable-cover option providing high reliability and convenience of a wireless BSAEPML audio stimulator whilst being highly user friendly and attractive for critical environments such as operating theatres. This provides a protective cover with an integrated disposable battery and an industrial design which allows a totally fool proof attachment of the cover with a "snap in" battery function (either rechargeable or single use). The "snap in" function, denotes that when the user opens a sealed pack which displays the use by date for the cover-battery (protective cover for audio stimulus device with integrated battery), the user has a simple battery activation means such as removal of a paper or cardboard tag labelled for example "remove when ready to start. This type of methodology may ensure that the user never needs to contend with flat battery issues while the protective cover with integrated battery avoids cross infection. The "fool-proof" battery with cover method at attachment and use may be by way of the battery sliding, clipping, magnetic slotting, or slotting only into or onto or part of the wireless audio stimulus device.

The method of incorporating an anti-cross-infection and battery management system into a foolproof cover system alleviates two major issues namely, risk of the battery going flat and cross-infection and may be adopted in all sensors and electrode applications.

Figure 1:
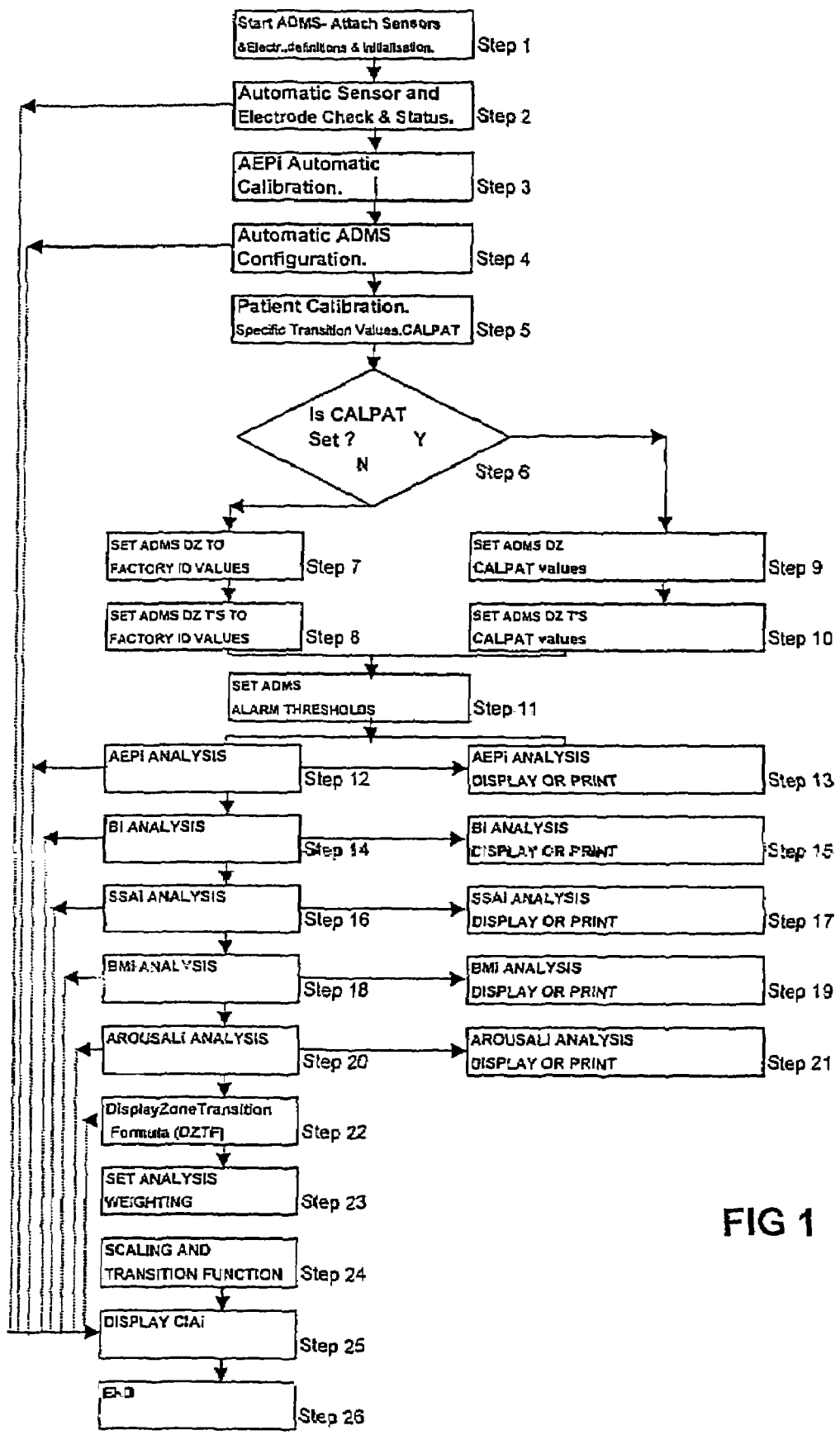
FIG. 1 shows an overview flow diagram of one form of ADMS according to the present invention.

FIG. 1 shows an overview flow diagram of an ADMS according to a preferred embodiment of the present invention. Steps 1 to 26 in the flow diagram are described below.

Step 1—Start Up ADMS and Attach Patient Electrodes and Sensors

For ease of use and minimal electrode configuration a typical electrode attachment system may include a single self-adhesive forehead electrode system. Alternatively a single sensor device extending over the patient's forehead and chin may be used, to allow the forehead EOG, EEG and reference connections/AEPi connections (where AEPi reference may include a mastoid connection), while also allowing EMG via chin surface and mastoid reference near patients ear and optionally wire or wireless connected earpiece for audio stimulus connection. The electrode device could contain 3 electrodes whereupon Bi and SSA EEG signals are derived from the forehead electrode connections (outer malbar), EOG signals are also estimated from the forehead connections and reference is derived from the central forehead connection. Alternatively the electrode device could contain 6 electrodes, being the abovementioned electrode with the addition of 2 electrodes for detection of chin EMG (for SSA EMG and arousal detection), mastoid electrode connection for bipolar reference signal where the aforementioned forehead connection provides the BSAEPi signal, and optional earpiece interface or connection for AEP audio stimulus. SSA EEG and EOG signals would be derived as estimations of conventionally placed (per sleep monitoring clinical standards (34, 114)) for EEG, EOG and EMG signal monitoring. Estimations are required in order to allow the minimal and simplified ADMS configuration, while still providing SSA.

Incorporating the self-adhesive forehead attached electrode system as a single attached substrate would provide simplification and ease of use. A wire or wireless connected ear-phone can be applied to one or both of the patient's ears for the purpose of generating the AEPi stimulus click sound. Where wireless configuration is used the earpiece could be connected to the electronics module for power and wireless control interface. One of the unique aspects of the ADMS system is the ability to adjust the volume of the stimulus click beyond a default "normal" (or standard value per empirical data (ref 1)), in order to compensate for hearing performance variations between different patients.

The electronics module can clip or attach to the outer surface of the disposable electrode substrate and provide wireless interconnection and active electrode functions. Embedded within the disposable electrode substrate could optionally be a disposable battery, thus avoiding the need otherwise for recharging of electronics module battery source (electrode may be subject of separate patent). Optionally the electrode system can be designed as a re-usable device.

The Electronics Electrode and Sensor Module (EESM) can be a fast charge system with charge capability electrically connected (for example, via electrode press-stud connections), slow charge system (via induction or RF interface to EESM recharge circuits), or a combination of both systems. Clear EESM indication (i.e. LEDs status) of remaining battery life and remote warning of pending battery flat alert is always active. An easy to clean container neatly holds EESM module and sensors, while at the same time providing ongoing charge function. One or more LEDS provide a clear status at any time for the remaining hours of charge energy.

Psuedo Code Sample (Psuedo code may be expanded upon or deleted dependent upon whether the preferred embodiment demands such detail);

ADMS Initialization;

System initializes with STARTADMS in deactivated (switch-up) position;

ADMS=0

System initializes in the uncalibrated patient mode; CALPAT=O (calibrated uninitialised).

STARTADMS=0 when start switch is de-activated (up position).

STARTADMS=1 when start switch is activated (down position).

Step 2. Automatic Sensor and Electrode Check and Status

Connected electrodes are detected for purpose of automatic system configuration and notification of automatic sensor and electrode quality status check.

Periodic impedance scanning of all electrophysiological electrodes provides the ADMS the capability to detect a deterioration of signal quality at any point in time. The operator is then provided the option to correct the poor electrode connection. Alternatively the ADMS is automatically re-configured to accommodate a revised configuration, designed to monitor a subject's depth of anesthesia in the absence of the disconnected or poor electrode contact(s).

Step 3. AEP Automatic Calibration

One of the impediments of previous art systems using BSAEPi as a marker for monitoring depth of anesthesia is the difficulty to compensate or accommodate for the variations in hearing performance (or response to audible stimuli) between different patients (Lippincott-Raven, 1997).

These variations can be caused by factors such as the generation of the audio stimulus attachment method and device type (typically a single or pair of ear pieces are used to generate audio click stimulus in ear piece), or the physiological variations in hearing performance evident between different subjects. The ADMS is capable of adjusting the frequency spectrum, amplitude and phase of the audio click in order to provide the optimal compensation for variations between different audio stimulus devices, variations due to different attachment methods (of audio stimulus device i.e. ear piece or headphones), or variations due to different hearing performance between individual patients (112).

An object of the present invention is to provide a means to calibrate the ADMS AEPi monitoring function for each specific patient's hearing response. This capability, within the ADSM, is achieved by providing a range of audio calibration stimuli signals and measuring the AEPi response to this said range of stimuli. While measuring the AEPi response the data is compared to empirical clinical data. The Sound Pressure Level (SPL) of the audio stimulus can be adjusted until the desired response, as comparable to the normal standard hearing patients, as referenced from the empirical data.

Factors such as polarity of the stimulus delivery apparatus can be checked and compensated for, as required. At all times safe SPL levels can be verified to ensure safe audio stimulus conditions.

One of the unique aspects of the ADMS system is the ability to adjust the volume of the stimulus click beyond the default "normal" value, in order to compensate for hearing performance variations between different patients.

In the circumstances, where patient's BSAEP signal does not respond to the AEP threshold levels as expected from "normal" patient hearing performance, the ADMS system provides a servo gain control function. The servo system is achieved by adjusting the AEP audio stimulus click amplitude level (while ensuring safe levels are not exceeded at any time) until the AEPi signal derived from the patient's data is similar to the levels as expected from normal patients. Further calibration of the AEPi signal can be achieved by detecting a particular patients hearing performance at different frequencies or combinations of frequencies and different levels thereof, and optimization of spectral content of the audio stimulus signal in order to compensate for each patient's individual hearing variations. In this manner the most reliable or efficient hearing performance conditions can be determined for each particular patient to ensure the AEPindex is derived for that patient under the most stable and reliable AEP stimulus frequency and amplitude conditions on an individual patient by patient basis. These same principals can be used for the automatic and optionally remote servo control of hearing aids (a subject of separate patent).

Step 4. Automatic ADMS Configuration

The ADMS system is capable of providing user adjustable or factory default MODES. A library of MODE configurations can be configured for different patient types or user specific requirements.

Subject to connected electrodes and sensors and the status of each of the said sensors and electrodes (per above step) the ADMS system determines the system configuration.

MODE 1—Integrated AEPi and Bi.

MODE 2—Bi only.

MODE 3—AEPi only.

Option 1—Body Movement Multi-zone movement Biomat sensor.

Option 2—Body Movement Single-zone movement Biomat sensor.

Option 3—Electrophysiological Arousal Detection (derived AEP and/or B EEG electrodes).

ADMS MODES 1 to 6 can be configured (automatically or with manual assistance) with options 1, 2 or 3. The ADMS system will detect the presence of a mattress sensor and type as being single or multi-zone. The ADMS system will also, by default, detect the forehead EEG electrodes and the chin EMG electrodes for arousal analysis and event detection. A logical OR function will, by default, display an arousal event if an arousal is detected from the forehead EEG OR the Chin EMG electrodes. For the purpose of this description of preferred embodiment we will assume:

MODE 4—Integrated AEPi and Bi with SSA as Bi-AEP arbitrator.
  Option 1—Body Movement Multi-zone movement Biomat sensor.
  Option 3—Electrophysiological Arousal Detection (derived from chin EMG electrodes of forehead EEG electrodes).

Automatic Electrode and Sensor Pass-Fail detect and Mode select.
  Fail condition for AEPi, Bi or SSAi is signaled when any of the respective electrodes or signals is poor quality. Poor quality electrodes (for example) would be signaled if the impedance of the said electrodes were above the acceptable electrode impedance thresholds. Typical impedance threshold would be 10 thousand ohms impedance, for example. Above this threshold (10K) value ADMS would signal the user exactly which electrode is not performing appropriately, what steps can be taken to alleviate the problem. Alternatively the user can be prompted to request the ADMS system to reconfigure the system MODE in order to ignore the poor electrode connection. The 10 K threshold can be changed to the user's selection.
  Fail condition for AEPi, Bi or SSAi would signal that the respective index should be weighted to zero. Therefore zero weighting of analysis in response to signal failure automatically changes mode in accordance to above STEP 4 and the following table.

Mode 1 impedance weighting effects are shown in Table 1 below:

TABLE 1

| AEPi | Bi | SSAi | |
|---|---|---|---|
| Pass | Pass | Fail | MODE 1 - Integrated AEPi and Bi without SSA arbitration. |

TABLE 1-continued

| Pass | Pass | Pass | MODE 1 - Integrated AEPi and Bi with SSA arbitration. |
|---|---|---|---|
| Fail | Pass | Fail | MODE 2 - Bi only. |
| Fail | Pass | Pass | MODE 2 - Bi only. |
| Pass | Fail | Fail | MODE 3 - AEPi only. |
| Pass | Fail | Pass | MODE 3 - AEPi only. |

| BM-SZ | BM-MZ | AR | |
|---|---|---|---|
| Pass | Fail | Fail | Option 1 - Body Movement (BM) movement Biomat Single-Zone (SZ) sensor. |
| Fail | Pass | Fail | Option 2 - Body Movement (BM) movement Biomat Multi-Zone (MZ) sensor. |
| Fail | Fail | Pass | Option 3 - Electrophysiological Arousal Detection. |
| Pass | Fail | Pass | Option 3 and 1- |
| Fail | Pass | Pass | Option 3 and 2- |

NOTE 1:
BM-SS = Body Movement Single Sensor;
BM-MS = Body Movement Multi-Sensor
NOTE 2:
Subject to connected electrodes and sensors (per STEP 2 above) and the status of each of the said sensors and electrodes the ADMS system determines the system configuration.

Step 5—Patient Specific Calibration Transition Values—CALPAT

The Transition thresholds of Consciousness to Unconsciousness (TCU or change of zone A to B), Transition from the deepest stage of Unconsciousness to a lesser degree of Unconsciousness (change of Zone B to C) and Transition from Unconsciousness to Consciousness (TUC or Zone C to D) in the ADMS system is determined from either default values as derived from empirical clinical data (see below) or from values as derived by way of thresholds determined with Calibration of Patient (CALPAT) function.

Graphic reference of AEP and Bi showing phases of a typical anesthesia monitoring session are shown in FIG. 2. Tables 2 to 4 below describe the associated ADMS transition zones.

TABLE 2

| 1. | Start of monitoring |
|---|---|
| 2. | Zone A . . . C |
| 3. | Transition from Zone A to B . . . TCU |
| 4. | Zone B . . . U |
| 5. | Transition from Zone B to C . . . TSW |
| 6. | Zone C . . . . . . U |
| 7. | Transition from Zone C to D . . . TCU |
| 8. | Zone D . . . C |

FIG. 2 presents a typical AEPi and Bi versus time functions for a patient undergoing general anesthesia. The Horizontal axis represents time progressing left to right from the earliest to latest time. Note the gradual Bi curve ascension in zone C versus the steeper ascension of AEPi in Zone C for the Transition of patient from Unconsciousness to Consciousness. The new ADMS system produces an ideal depth of anesthesia monitoring by incorporating a method to deploy the advantages of both AEPi and Bi, while presenting a simple single anesthesia Depth of Anesthesia monitoring index.

TABLE 3

| ADMS ZONE -> | ZONE A | | ZONE B | | ZONE C | | ZONE D |
|---|---|---|---|---|---|---|---|
| Transition Zone-> | C | TCU | U | TSW | U | TUC | C |
| Default or Empirical Data -> | IDDZA | IDTCU | IDDZB | IDTSW | IDDZC | IDTUC | IDDZD |
| Calibrated Patient Data -> | CPDZA | CPTCU | CPDZB | CPTSW | CPDZC | CPTUC | CPDZD |

NOTE:
Values exist for Bi and AEPi for each of the transition points and zones A, B, C and D.

TABLE 4

| Definition of Zones A, B, C, D Zone Ranges and Events. | CODE Key | Description |
|---|---|---|
| Zone A | C | Patient in Consciousness State. |
| | TCU | Transition from Consciousness to Unconsciousness |
| Zone B | U | Patient in unconscious state. |
| Zone C | U | Patient in unconscious state. |
| | TUC | Patient Transition from Unconsciousness to Consciousness |
| Zone D | C | Patient in Consciousness State. |
| BM | BMe | Presence of Body Movement events (ref 34). |
| Ae | Ae | Presence of Arousal events (ref 35) |

Patient Calibrated values refers to modifying or adjusting these said transition threshold values on an individual patient-by-patient basis.

The means of this Automatic Calibration method are based around measuring the patient's Bi during the patient's first occurrence of transitioning from Consciousness to Unconsciousness (in accordance with AEPi TCU empirical data transition threshold level (refer step 7).

After Calibration of Patient, transition threshold values (TCU, TUC) and display zones (C, U) can be allocated specific to the individual patient's sensitivity to AEPi and Bi.

Default empirical data values of AEPi (ref 3), Bi (ref 3) and SSA are compared to data of the patient's first Transition from Consciousness to Unconsciousness (TCU) is detected by observing AEPi, Bi and SSA transitioning through the respective TCU threshold values. This initial or first transition of consciousness state serves as a calibration point for the ADMS system to optimize to each individual patient's depth of anesthesia AEPi, Bi and SSAi monitoring sensitivity.

Once the first consciousness to unconsciousness transition has been tracked and analyzed using the ADMS system's CALPAT function, all other transitions (A to B, B to C, C to D) and monitoring Display Zones (A, B, C, D) can be optimized or fine-tuned to the individual patient's sensitivity. The relationship between AEPi and Bi at TCU is unique to each patient and can be used to extrapolate each individual patient's TUC threshold values.

The ADMS uses the basic principal that detection of the TCU for a specific patient allows all subsequent transitions and zones to be estimated with greater sensitivity and accuracy than using empirical data solely (as with prior art DOE systems).

General overview for CALPAT operation:

a) After ADMSSTART is selected the ADMS monitors patients AEPi, Bi and SSA.

b) Empirical data values derived for typical (ref 1) conditions of TCU are compared to actual and real-time patient's data for AEPi, Bi and SSA.

c) The weighting factor applied to each of AEP, Bi and SSA is dependent on the following factors.

d) When the TCU (Transition A to B) has been identified for a specific patient is derived.

e) The TCU transition is noted in terms of the AEPi, Bi and SSA value. The noting of these corresponding TUC values, allows the accurate switching and monitoring of AEPi and Bi subsequent to changing transitions (A to B, B to C and C to D) and Display Zones (A, B, C, D).

f) When the TCU (Transition A to B) has been identified for a specific patient other transitions (B to C-TSW, and C to D-TCU) can then be derived from this calibration data.

Deriving the subsequent transition states from the CALPAT.

TCU state is more sensitive and accurate for a given patient than reliance on empirical data values for these subsequent transition states (B to CTSW, C to DTUC).

Sample pseudo code sample for CALPAT function (Psuedo code may be expanded upon or deleted dependent upon whether the preferred embodiment demands such detail).

a) Select STARTADMS=1% Wait till ADMSSTART button is selected b) Assign defaults TCU, TSW and TUC values from empirical data transition thresholds (3).

TABLE 5

| Zone Transition | Empirical Bi Transition-ref1 | Empirical AEPi Transition-ref1 | SSA Conditions (Ref 34, 45, 46, 113) (ref STEP 16) |
|---|---|---|---|
| Zone A to B (TCU) | 76 | 65 | CAW > S OR CA2W > S |
| Zone B to C (TSW) | 40 | 36 | CA3W > S |
| Zone C to D (TUC) | 74 | 50 | CAW > S OR CA2W > S |

| | AEPi | Bi |
|---|---|---|
| Assign TCU | 65 | 76 |
| Assign TUC | 50 | 74 | d) Start CAP PAT procedure and determine patient specific values for TCU and TUC.

e) Read Current Patient Data value for AEPi, Bi and SSAi % read the real-time patient data and Compare this real patient TCU data values to TCU Empirical Data values for AEPi, Bi and SSAi.

If Current Patient Data AEPi Value (CDAEPi) for Transition from Consciousness to Unconsciousness (TCU) is less than or equal to (<=) Empirical Data AEPi Values (IDAEPi) for Transition from Consciousness to Unconsciousness (TCU) note the Current Data values for Bi and SSAi.

The said CD values for Bi and SSA are assigned respectively to variables for Calibrated Patient data for Transition from Consciousness to Unconsciousness for Bi (CDTCUBi) and Calibrated Patient data for Transition from Consciousness to Unconsciousness for SSAi (CDTCUSSA).

f) Assign;
CPTCUBi
CPTCUSSA g) Transition states TSW and TUC are now derived from TCU.

Calibrated Patient data for Transition from Unconsciousness to Consciousness for AEPi (CPTCUAEPi) will be derived from CPTCUAEPi transition state, i.e. CPTUCAEPi is proportional or related to CPTCUAEPi.

Note that in more complex embodiments of the ADMS more complicated calibration of the patient's variables can be applied to provide a greater degree of patient sensitive system calibration.

Once the value for CPTCUBi is established per above, CPTUCBi can be derived (in a simple embodiment as described herein) by using the ratio derived from empirical data being IDTUCBi/IDTCUBi.

h) Assign value for CPTUCbi

CPTUCBi=IDTUCBi/IDTCUBi X CPTCUBi

Further embodiments can utilize a more sensitive formula based on applying any combination of TCU, TSW and TUC derived from using patient AEPi, Bi and SSAi data to derive TSW and TUC.

PATCAL and Default Threshold Determination for TCU and TUC

The thresholds for TUC and TCU for BSAEPI and Bi can vary between patients. The current ADMS sample embodiment assumes that the relationship between these TCU and TUC values is able to be derived (refer step 7, ADMS sample embodiment) from empirical data (Gajrag et al 1999) and then modified for individual patient compliance with PATCAL function (per step 5, ADMS sample embodiment). However, as the ADMS system further evolves, the means of providing a more accurate determination of the TCU and TUC thresholds may also evolve, particularly with increased clinical data and experience with this device. Combinations of the following variables can assist the ADMS in predicting more accurate default and PATCAL TCU and TUC values; BSAEPi, Bi, SSA, eyelid opening and movement status, eye movement status, arousal and body movement status.

STEP 6. is CALPAT Set?

If no go to Step 7 and if yes go to Step 9.

STEP 7. Set to ADMS Default (Impirical Data) Display Zone Functions (DDZF). (DDZA, DDZB, DDZC, DDZD)

Empirical data values are referenced as a means of establishing the transition of zones A, B, C and D based on data collected from normal patients.

The empirical data values used for the purpose of this embodiment and simplicity of presentation is set out in Tables 6 and 7 below (3).

TABLE 6

| Zone Transition | Empirical AEPi Transition | Empirical Bi Transition | SSA Conditions (Ref 34, 45, 46, 113) |
|---|---|---|---|
| Zone A to B(TCU) | 65 | 76 | (W OR STG1) to (STG2 or STG3) |
| Zone B to C(TSW) | 36 | 40 | STG2 or STG3 to 4 or REM |
| Zone C to D(TUC) | 50 | 74 | W or STG1 to STG2 or STG3 |

TABLE 7

| Zone Ranges | Bi Range | AEPi Range | SSA Conditions ref |
|---|---|---|---|
| Zone A | 100-82 | 100-65 | W OR STG1 |
| Zone B | 82-40 | 65-35 | STG2 or STG3 or STG4 or REM |
| Zone C | 40-75 | 35-50 | STG2 or STG3 or STG4 or REM |
| Zone D | 75-100 | 50-100 | W OR STG1 |

Determination of Switching or Weighting of BSAEPi and BI.

It has been reported (Gajrag et al 1999) that AEPi provides improved detection of the transition from unconsciousness to consciousness (TUC).

This may be due to BSAEP reflecting the neural response to the auditory sensory nerve, as stimulated by the application of ADMS earphones click stimulator, to a subject's ear and auditory nerve. An increase in the AEP signal can provide a sensitive measure of the audio sensory nerves response (or lack of in state of unconsciousness) with communication paths to the brain (BSAEP), and in particular the associated vulnerability to incidence of audio recall.

The "switching on" or activation of the auditory BSAEP communication paths provides a more rapid signal change and subsequent measure of transition state than that of BIC. BIC signal, in contrast, is a measure of overall brain activity and can incorporate a mixture of control signals for the body. These "mixture" of signals may not directly relate to the consciousness factors or factors effecting depth of anesthesia status, such as vulnerability or risk of post-operative memory recall.

In MODE 1 the ADMS is capable of referring to the SSA analysis and in particular the patient's EEG spectral composition, to assess the progression from one stage of unconsciousness (sleep) to a lighter stage of consciousness (sleep). This "independent" (from BSAEP and BIS) assessment of SSA, aids the arbitration process. Improved determination of pending onset of the TUC transition can therefore be achieved with the ability to apply closer analysis and measurement focus on the rapid increase in the BSAEP signal (as would be expected with TUC).

Other MODES of the ADMS are capable of applying any combination of BSAEPi, Bi, SSA, eyelid opening and movement status, eye movement status, arousal and body movement status, as a means of determining switching or weighting between Bi and BSAEPI.

Step 8. Set to ADMS Default (Impirical Data) Display Zone Transition Functions (IDZTF). (IDZTCU, IDZTWS, IDZTUC)

Step 9. Set to ADMS CALPAT Display Zone Functions (CPDZF). (CPDZA, CPDZB, CPDZC, CPDZD)

Step 10. Set ADMS Display Zone Formulas A, B, C, D. to Calibrated Patient Display Zone Transition Formulas (CPDZTF)

Step 11. Set ADMS Alarm Thresholds

Display Zone Critical Alarms Thresholds (DZCAT) are Defined

These DZCAT consist of alarm warnings and display notification of particular importance to ADMS user, including body arousal or movement for example.

The DZCAT can be presented as markers on the CIAi display, alarms of other forms of user notification to assist the ADMS operation.

BMi and Ai can be used to weight or bias the CIAi towards patient consciousness state and/or represented as separate display, alarms of other forms of user notification to assist the ADMS operation.

STEP 12—AEPi Analysis (ref 3, 61)

STEP 13—AEPi Analysis Display or Print

STEP 14—Bi Analysis (ref 3)

Figure 3:
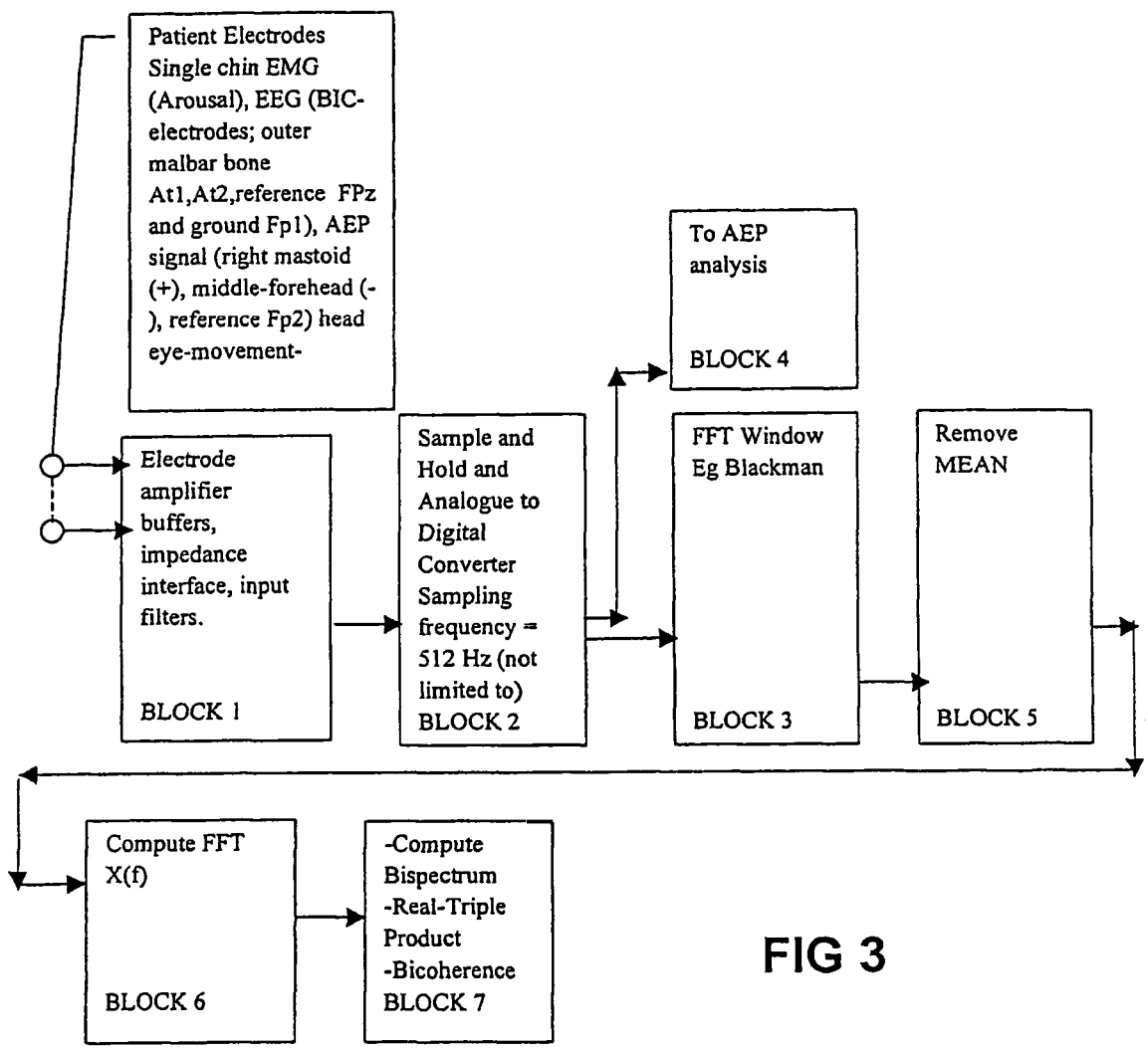
FIG. 3 shows a flow chart of one form of bicoherence, real triple product and bispectral index analysis.

FIG. 3 shows a flow chart of one form of bicoherence, real triple product and bispectral index analysis.

Computation of Bispectrum (B), Bicoherence and Real Triple Product $$B(f1f2) = \left| \sum_{I=1}^{L} Xi(f1)Xi(f2)Xi^*(f1+f2) \right|$$

Epoch length=30 seconds

75% overlap of epochs to reduce variance of bi-spectral estimate

L=epochs, i.e. 1 minute of data f1&f2 are frequency components in the FFT such that f1+f2≦fs/2 where fs is the sampling frequency Real Triple Product (RTP)

$$RTP(*f1f2) = \sum_{I=1}^{L} Pi(f1)Pi(f2)Pi(f1+f2)$$

Where Pi(f1) IS THE POWER SPECTRUM $$P(F)=|X(F)|^2$$

Bi-Coherence (BIC)

$$BIC(f1f2) = \frac{100B(f1f2)}{\sqrt{RTP(f1f2)}}$$

ranging from 0 to 100%

Step 15—Bi Analysis Display or Print

Step 16—Sleep Staging Analysis (SSA) (34, 35, 45, 46)

Figure 4:
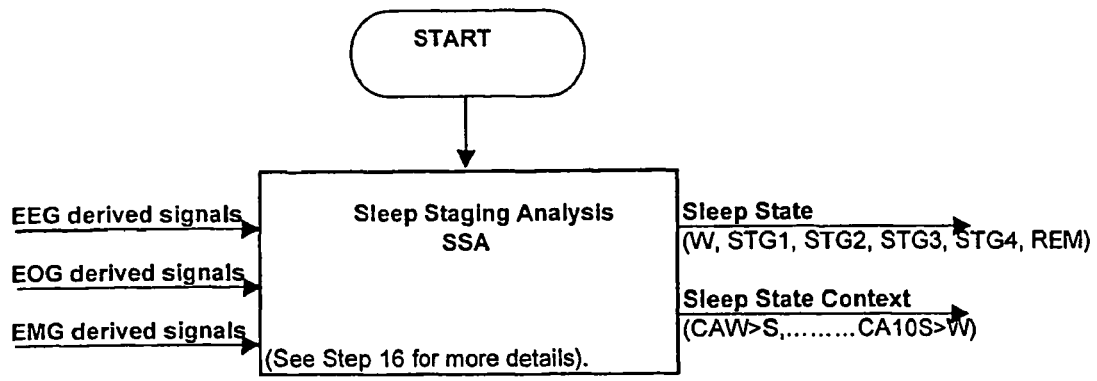
FIG. 4 shows one form of sleep staging analysis.

FIG. 4 shows one form of sleep staging analysis. Referring to FIG. 4, the Sleep Staging Analysis (SSA) provides two data descriptions, being the context analysis (described below in the form of S1W>S etc) and sleep stage estimation of a subjects (derived) EEG, EOG and EMG data (in the form of sleep stage as derived from spectral analysis of EEG and correlation of EMG and EOG signals (34, 45, 46). "Derived" in FIG. 5 denotes that these signals may be direct electrode connections to the scalp for neurology, nears patient's eyes for EOG, near patients chin or cheek for EMG signals, or alternatively may be derived from a single forehead (or forehead to chin area) electrode attachment.

If only forehead EEG electrodes are used, the EMG data will be derived as muscle electrical amplitude from signal frequency response range of (typically 70 Hz to 150 Hz bandwidth).

The SSA outputs are utilized to determine the weighting analysis and time of switching weighting analysis (STEP 23).

For simplification and minimal electrode attachments to patient Ai can be derived from existent EEG forehead (B or AEP) electrodes.

Step 17—Sleep Stage Analysis (SSA) Display or Print

Step 18—Body Movement Index (BMi) Analysis

BM detection may be by way of analysis from a mattress movement sensor device or other pressure or movement sensitive sensors/electrodes attached to the patient. Detection of Body Movement (BM) relates to a physical movement of the body such as detected by a pressure or vibration sensitive sensors.

Step 19—Body Movement Index (BMi) Analysis Display or Print

Step 20—Arousal Index (Ai) Analysis (35)

Step 21—Arousal Index (Ai) Analysis Display or Print

Step 22—Display Zone Transition Formula (DZTF)

Step 23—Set Analysis Arbitration, Weighting and Timing

This step defines the weighting ratios together with timing of changes of the weighting ratios of AEPi and Bi for each of the zones A, B, C D. for the ADMS Comprehensive & Integrated depth of Anesthesia index (CIAi).

Figure 5:
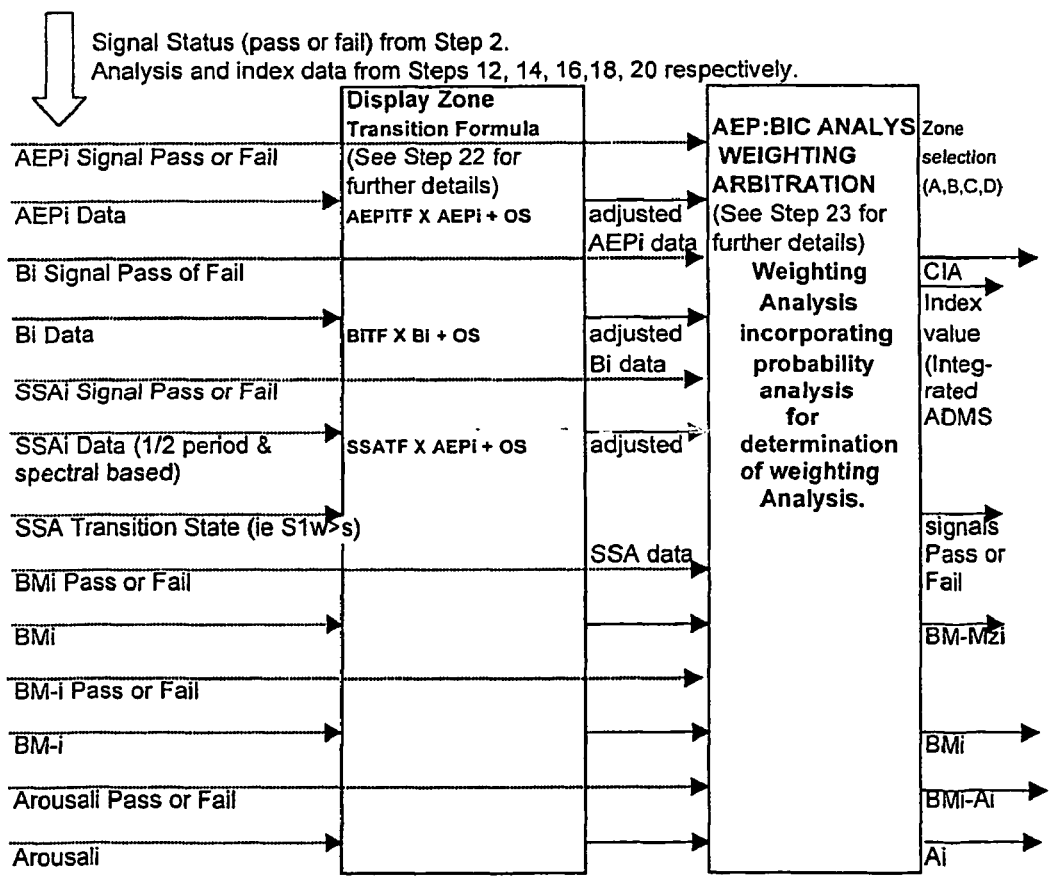
FIG. 5 shows a block diagram of sample AEP:BIC analysis (Mode 1) associated with weighting arbitration.

FIG. 5 shows a block diagram of an overview of analysis associated with weighting index. The abbreviations TF and OS in FIG. 5 are defined as follows.

TF=Transfer Formula. The transfer formula is designed to provide an adjustment or normalization of index values in order to allow all analysis input data to be comparable and allow cross-selection within the Weighting Analysis Block without mismatching or obvious level jumps, when switching between AEP, Bi or SSA analysis.

OS=Offset. The Offset is designed to provide an offset adjustment between AEPi, Bi and SSAi in order to avoid level jumps when switching between AEPI, Bi and SSA.

Figure 6:
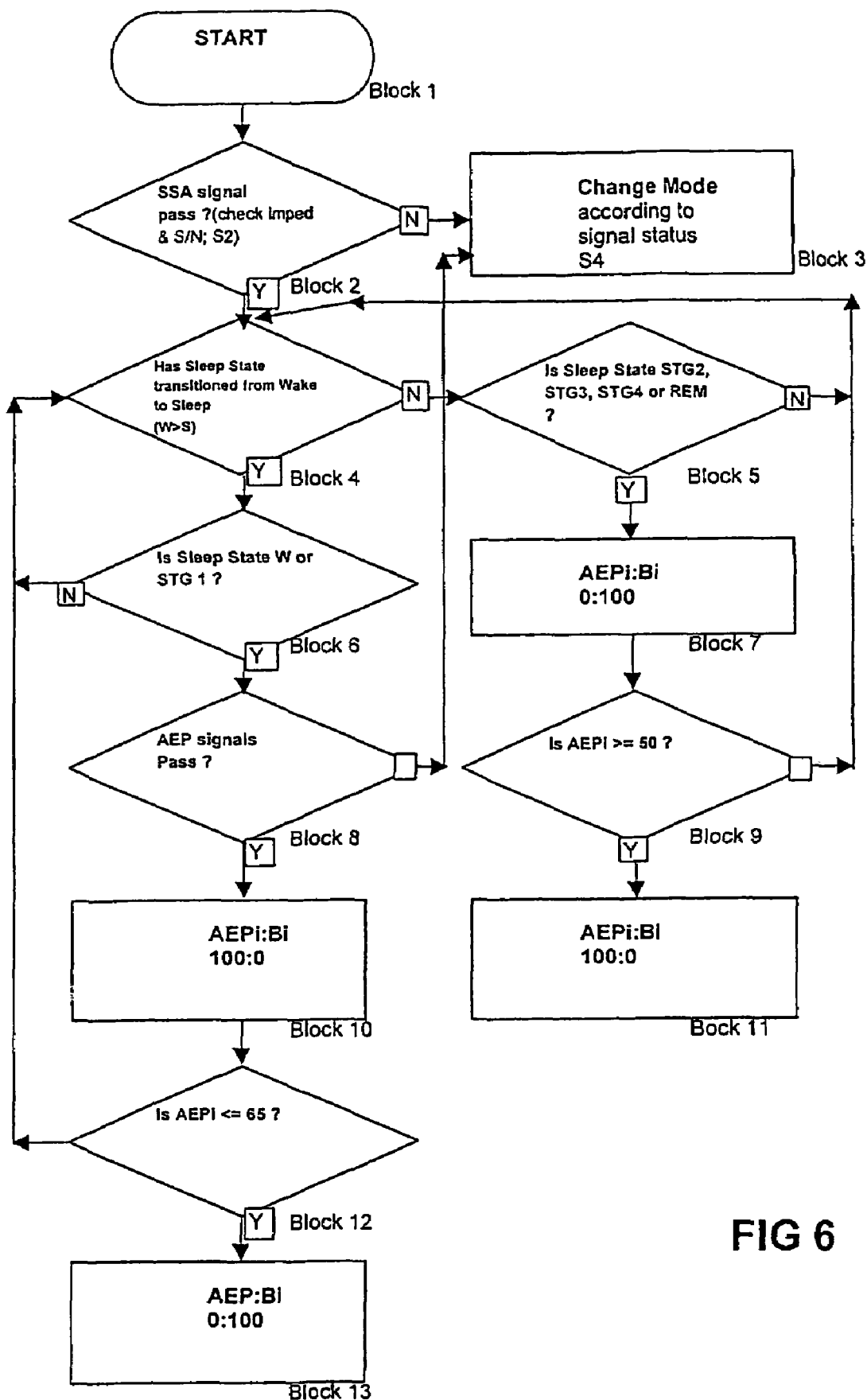
FIG. 6 shows a flow diagram of sample AEP:BIC analysis (Mode 1) associated with weighting arbitration.

FIG. 6 shows a flow diagram associated with AEP:BIC analysis weighting arbitration (Mode 1). The abbreviation S in FIG. 6 denotes a step.

The system of the present invention may allow the user to readily upgrade the system's logic and accuracy with the course of time and more advanced ADMS clinical data. The ADMS system may include a self-learning capability to evaluate any selected group of studies and via analysis of these studies allow ADMS system weighting and analysis priorities to change in accordance with more developed clinical data studies.

| | Sleep State Context | |
|---|---|---|
| KEY for SSA (where sleep stages can be 1, 2, 3, 4, REM, WAKE) | | |
| STATE | | ANALYSIS TYPE |
| CA1W > S | Change from WAKE to (sleep-stage 1 OR 2 OR 3 OR 4 OR REM) | ref 34, 35, 45, 46 |
| CA2W > S | Change from sleep-stage 1 to (2 OR 3 OR 4 OR REM) | ref 34, 35, 45, 46 |
| CA3W > S | Change from sleep-stage 2 to (3 OR 4 OR REM) | ref 34, 35, 45, 46 |
| CA4W > S | Change from sleep-stage 3 to (4 OR REM) | ref 34, 35, 45, 46 |
| CA5W > S | Change from sleep-stage 4 to REM) | ref 34, 35, 45, 46 |
| CA6S > W | Change from sleep-stage REM to (WAKE OR 1 OR 2 OR 3 OR 4) | ref 34, 35, 45, 46 |
| CA7S > W | Change from sleep-stage 4 to (WAKE or 1 OR 2 OR 3) | ref 34, 35, 45, 46 |
| CA8S > W | Change from sleep-stage 3 to (WAKE OR 1 OR 2) | ref 34, 35, 45, 46 |
| CA9S > W | Change from sleep-stage 2 to (WAKE OR 1) | ref 34, 35, 45, 46 |
| CA10S > W | Change from sleep-stage 1 to WAKE | ref 34, 35, 45, 46 |

As detailed in the steps of FIG. 6 the ADMS system highlights to the system user 4 main zones of interest, while monitoring a patient under general anesthesia, as detailed in Table 9 below. The following codes are used in Table 9.

| Definition of Zones A, B, C, D Zone Ranges | CODE Key | Description |
|---|---|---|
| Zone A | CU | Patient emerging from Consciousness to Unconsciousness. |
| Zone B | U | Patient in unconscious state. |
| Zone C | U | Patient in unconscious state. |
| Zone D | UC | Patient Transition from Unconsciousness to Consciousness. |

Table 9 presents examples of ADMS modes of operation. The ADMS may provide a capability for weighting ratios to be changed or programmed by ADMS system researchers or for a range of pre-configured weighting ratios (MODES) to be selected.

TABLE 9

| | MODE 1 | | | MODE 2 | | |
|---|---|---|---|---|---|---|
| Zone | AEP RATIO | Bi RATIO | SSAi RATIO | AEP RATIO | Bi RATIO | SSAi RATIO |
| A | 100 | 0 | 0 | 80 | 20 | 0 |
| B | 0 | 100 | 0 | 20 | 100 | 0 |
| C | 0 | 100 | 0 | 20 | | 80 |
| D | 100 | 0 | 0 | 80 | | 20 |

| | MODE 3 | | | MODE 1 + N | | |
|---|---|---|---|---|---|---|
| Zone | AEP RATIO | Bi RATIO | SSAi RATIO | AEP RATIO | Bi RATIO | SSAi RATIO |
| | 100 | 0 | 0 | | | |
| B | 0 | 50 | 50 | | | |
| C | 0 | 50 | 50 | | | |
| D | 100 | 0 | 0 | | | |

NOTE:
The range of MODES may be selected in accordance with patient or medical procedure related factors. For simplicity a simple MODE 1 configuration is presented as an example of an ADMS embodiment. N + 1 Mode represents a large library of Modes which may be selected or programmed into the ADMS system.

Step 24—Scaling and Transition Function

The scaling/range and transition functions are designed to provide a method of scaling inputs to the CIAi to minimise confusion or error associated with ADMS operation. In particular this confusion or error can occur if the two scales and ranges of BICi and AEPi (for example) are not compatible, or in a data format suitable to be combined and displayed as a single CIAi.

Scaling and range of AEPi and BICi refers to a change or adjustment of calculated values of AEPi and BICi (as detailed in steps 14 and 12) respectively, to "match" the 2 separate indices so that when weighting or switch changes occur, the CIAi does not have a sudden jump or confusing change in value or scale representation.

The switch transition function may adjust the time duration over which any switch or weighting change occurs between (for example) BICi and AEPi. Furthermore the transfer function applied to each of the respective data inputs (BICi and AEPi, for example) during this switch over duration or period may be selected from a range or transfer functions. However, as with the scaling factor the default transfer function will be X1 (linear).

Figure 7:
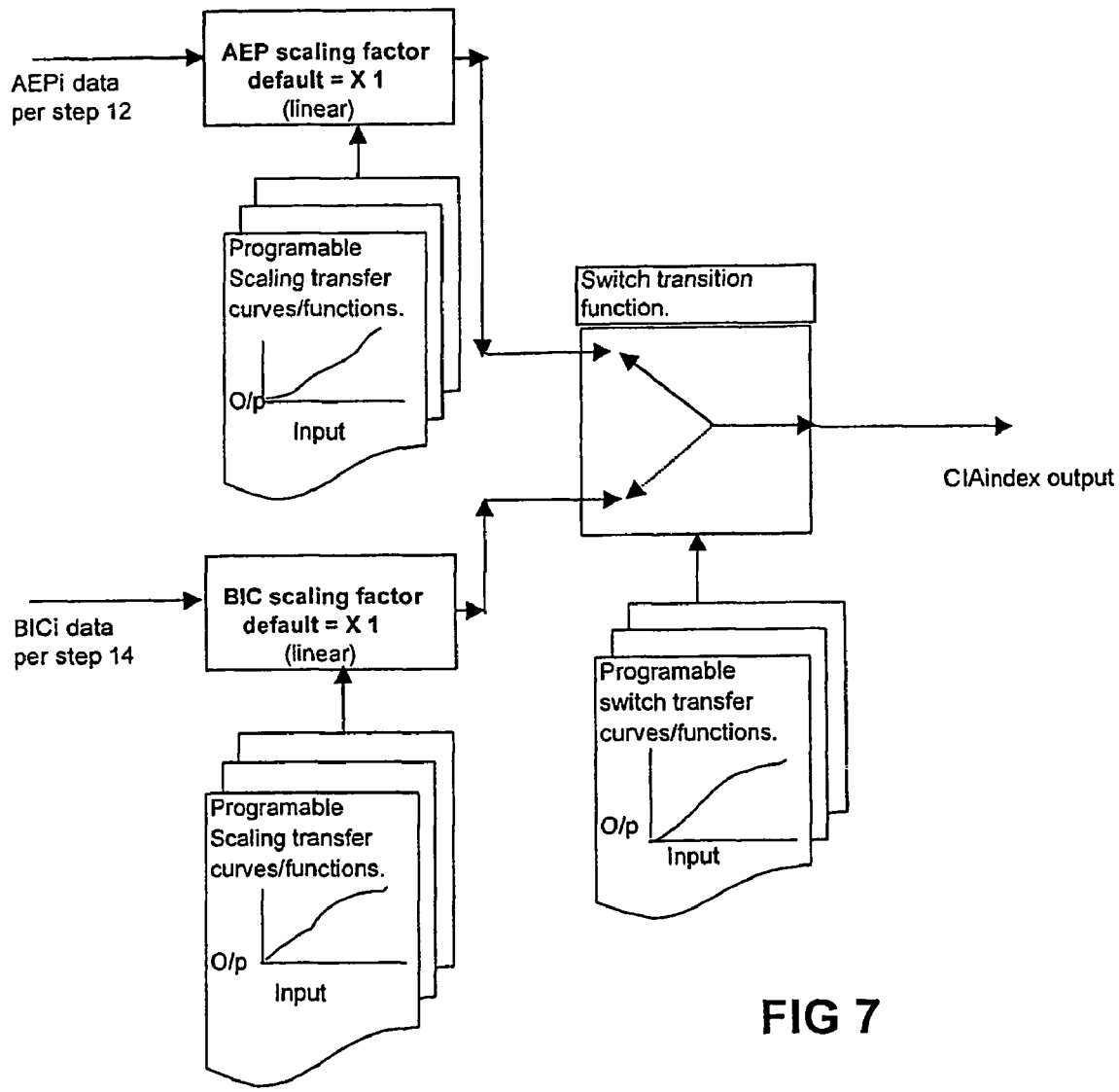
FIG. 7 shows a simplified overview of scaling factor and transition curve functions associated with the ADMS.

The diagram shown in FIG. 7 presents a simplified overview of scaling factor and transition curve functions associated with the ADMS.

Step 25—Display Comprehensive Integrated ADMS Index (CIAi)

MODE 1 CIAi Basic Assumptions

1. MODE 1 presents one of the simplest embodiments of the ADMS.

2. Table 10 below summarizes the weighting factors for zones A, B, C and D.

3. The column entitled Display transition includes a column titled display offset. This value is designed to minimize level changes during the switching of AEPi: Bi weighting from 100:0 to 0:100.

TABLE 10

| CIAi Display Zone | AEP:Bi ratio | CIA Display Translation formula | Transfer function IDO (offset) | IDO |
|---|---|---|---|---|
| A | 100:0 | X1 | 0 | 0 |
| B | 0:100 | X1 | −(76 − 65) | −11 |
| C | 0:100 | X! | −(76 − 65) | −11 |
| D | 100:0 | X! | (74 − 50) − 11 | 13 |

NOTE: 1 Offset code
IDOA AEPi
IDOB Empirical Data Offset applied for zone B = −(Bi-AEPi); for values end of first consciousness period (ref 1, FIG. 5).
IDOC Empirical Data Offset applied for zone C = −(Bi-AEPi); for values at end of first consciousness period (ref 1, FIG. 5).
IDOD Empirical Data Offset applied for zone D = (Bi-AEPi; for values at start of second consciousness period (ref 3, FIG. 5))-IDOC
NOTE 2: Values at end and start of conscious periods (TCU and TUC respectively) and TSW (ref3, FIG. 5) are set out below.

TABLE 11

| Transition | AEPi Value | Bi Value |
|---|---|---|
| TCU | 65 | 76 |
| TSW | 36 | 40 |
| TUC | 50 | 74 |

TABLE 12

| Time | DZ | AEPi | Bi | Ai | BMi | DZTF | AEPi:Bi | CIAi |
|---|---|---|---|---|---|---|---|---|
| t0 = start t10 = end ref: 1 | Display Zone See Step 8 | ** Ref. 1 | ** Ref. 1 | * | * | assume= X 1 ref: Step 22 | Ratio See Step 23 | *** See Step 24 |
| | COL 1 | COL 2 | COL 3 | COL 4 | COL 5 | COL 6 | COL 7 | COL 8 | COL 9 |
| t1 | A | 77 | 85 | 81 | 79 | (X1) | 100:0 | 77 |
| t2 | A | 76 | 90 | 73 | 75 | (X1) | 100:0 | 76 |

TABLE 12-continued

| | | | | | | | | |
|---|---|---|---|---|---|---|---|---|
| IDC(mean) | | 75 | 90 | 70 | 65 | (X1) | 100:0 | 75 |
| IDTCU | A | 65 | 76 | 80 | 64 | (X1) | 100:0 | 65 |
| IDU(mean) | | 37 | 49 | 43 | 45 | (X 1) − 11 | 0:100 | 38 |
| t3 | B | 35 | 42 | 35 | 38 | (X 1) − 11 | 0:100 | 31 |
| t4 | B | 34 | 41 | 36 | 36 | (X 1) − 11 | 0:100 | 30 |
| t5 | C | 35 | 38 | 36 | 37 | (X 1) − 11 | 0:100 | 27 |
| IDTSW | | 36 | 40 | 38 | 37 | (X 1) − 11 | 0:100 | 29 |
| t6 | C | 40 | 52 | 41 | 38 | (X 1) − 11 | 0:100 | 41 |
| t7 | C | 40 | 62 | 42 | 39 | (X 1) − 11 | 0:100 | 51 |
| t8 | C | 39 | 71 | 43 | 40 | (X 1) − 11 | 0:100 | 60 |
| IDTUC | | 50 | 74 | 40 | 38 | (X1) + 13 | 0:100 | 87 |
| t9 | D | 60 | 75 | 50 | 60 | (X1) + 13 | 100:0 | 88 |
| t10 | D | 77 | 80 | 77 | 75 | (X1) + 13 | 100:0 | 93 |

\* Data presented for sample only
\*\* The ID values present some ambiguity, particularly in relation to IDTCU, IDC (mean), IDU (mean), IDTSW and IDTUC values. However the selected ID values are designed for update with clinical data studies, currently in progress (Reference 3).
\*\*\* CIAi formula;
(AEPi (column 3) × AEPi ratio (column 8 AEPi ratio value)) + (cont'd) (Bi (column 4) × Bi ratio (column 8 Bi ratio value)) + DZTF (Column 7) = CIAi
Note:
AEPI/Bi or Bi/AEPi numerator and denominator are taken from respective AEPi and Bi ratio values per column 8 in Table 12.

Figure 8:
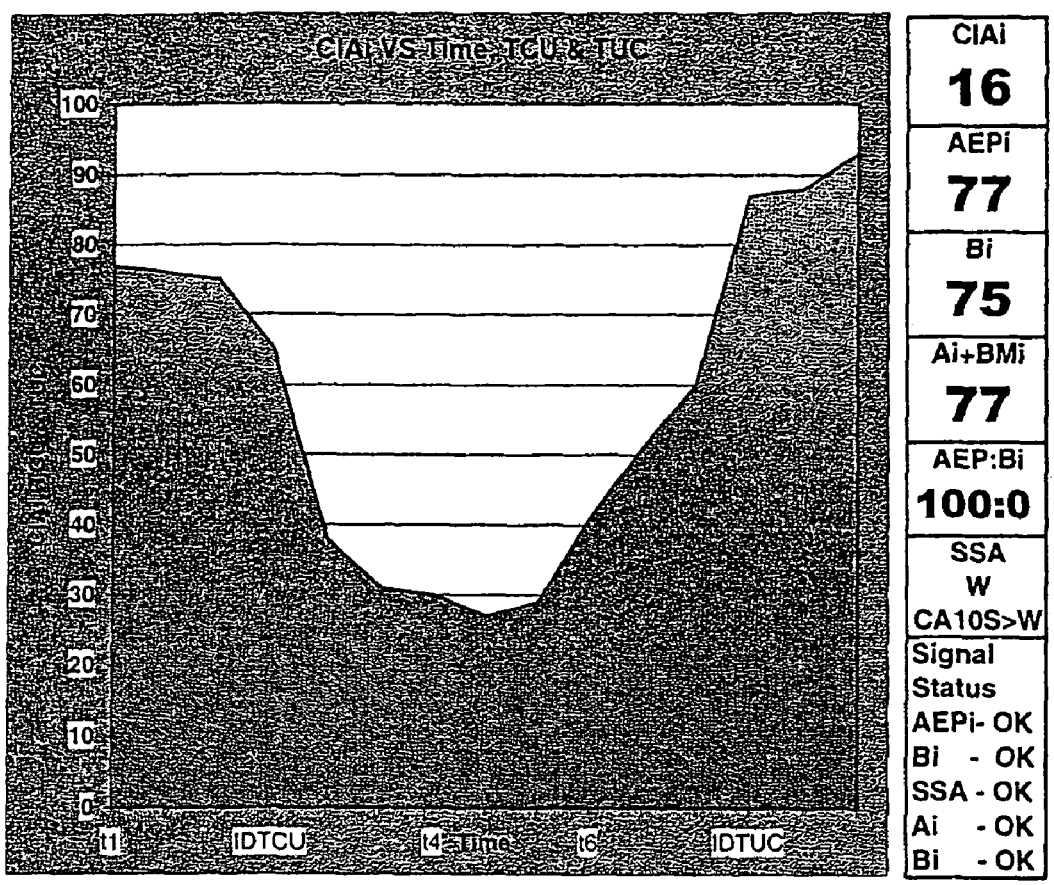
FIG. 8 shows a graphical representation of CIAi, TCU & TUC values.
Figure 9:
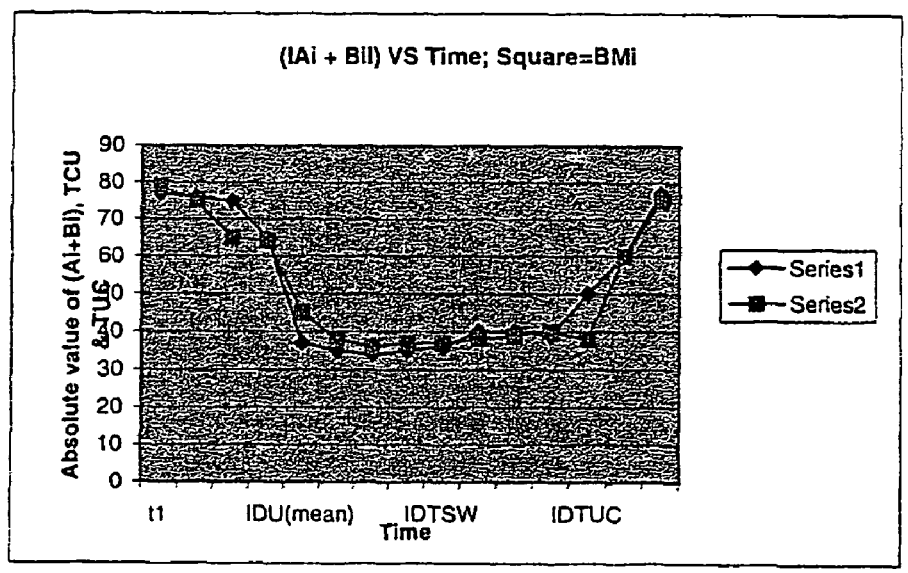
FIG. 9 shows a graphical representation of absolute value of Ai+Bi, TCU & TUC.
Figure 10:
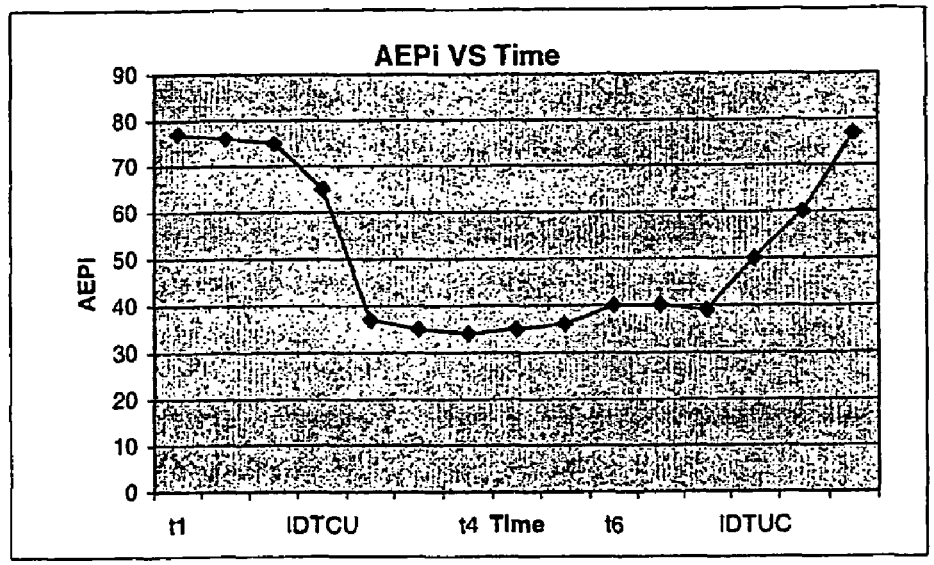
FIG. 10 shows a graphical representation of AEPi.
Figure 11:
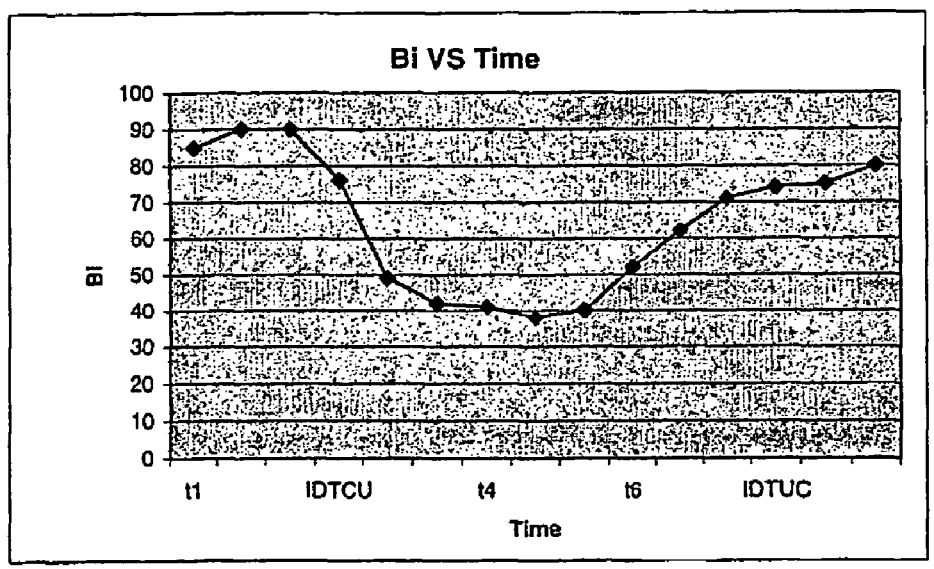
FIG. 11 shows a graphical representation of Bi.
Figure 12:
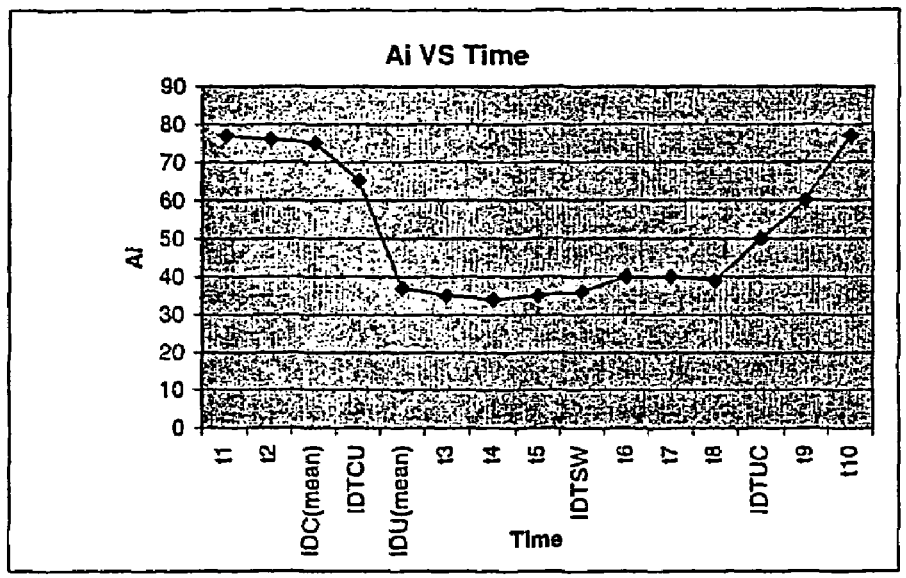
FIG. 12 shows a graphical representation of Ai.
Figure 13:
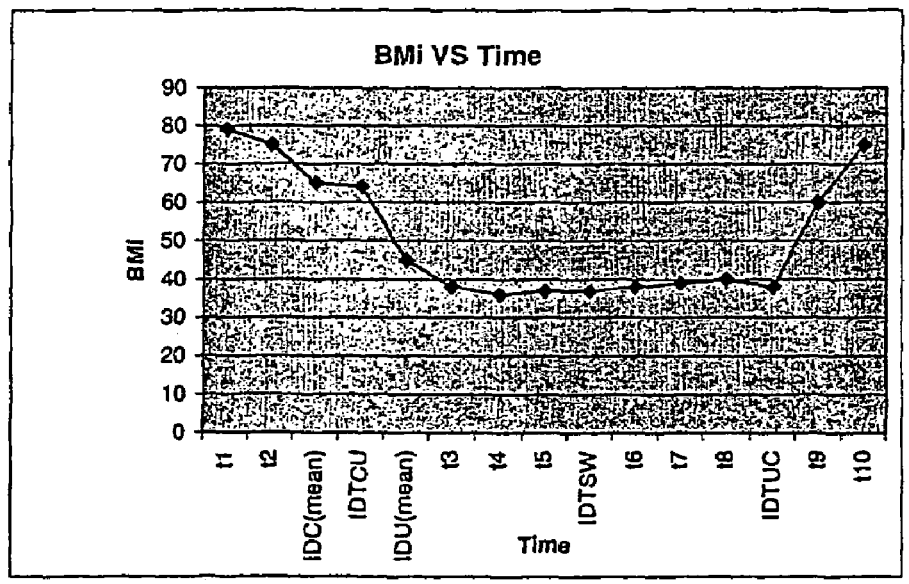
FIG. 13 shows a graphical representation of BMi.
Figure 14:
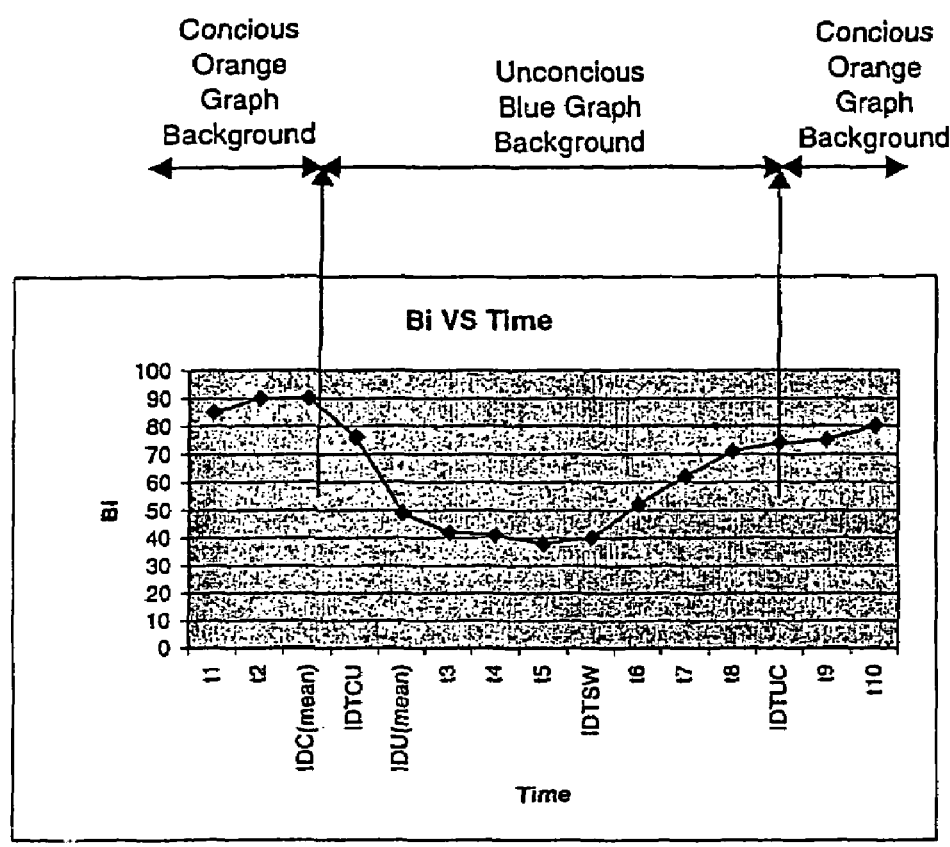
FIG. 14 shows a graphical representation of Bi with the colour of the background changing to indicate transition of consciousness state.

FIG. 8 shows a graphical representation of CIAi, TCU & TUC values;

FIG. 9 shows a graphical representation of absolute value of Ai+Bi, TCU & TUC;

FIG. 10 shows a graphical representation of AEPi;

FIG. 11 shows a graphical representation of Bi;

FIG. 12 shows a graphical representation of Ai;

FIG. 13 shows a graphical representation of BMi;

FIG. 14 shows a graphical representation of Bi with the colour of the background changing to indicate transition of consciousness state.

NOTE 1. Sleep Staging Analysis Step 16 and Analysis Weighting Step 23 are simplest embodiments as operated in MODE 1. However, the current state of clinical data (ref 11) provides only a slight correlation between bispectral values of EEG and conventional sleep staging. More advanced embodiments of the ADMS will provide greater definition and specifications in relation to spectral based sleep analysis (ref 3, 8, 9, 11). These further MODES will, in particular, deploy modified frequency distribution as opposed to the conventional frequency and amplitude analysis for sleep stage definition.

NOTE 2: Values at end and start of conscious periods (TCU and TUC respectively) and TSW (ref 3, FIG. 5) are set out below.

TABLE 13

| Transition | AEPi Value | Bi Value |
|---|---|---|
| TCU | 65 | 76 |
| TSW | 36 | 40 |
| TUC | 50 | 74 |

TABLE 14

| Time | DZ | AEPi | Bi | Ai | BMi | DZTF | AEPi:Bi |
|---|---|---|---|---|---|---|---|
| t0 = start<br>t10 = end<br>ref: 1 | Display<br>Zone<br>ref: Step | ref: Step | ref: Step 14 | \* | \* | assume=<br>X 1<br>ref: Step 22 | Ratio<br><br>ref: Step 23 |
| t1 | A | 76 | 85 | 81 | 79 | 1 | 100:0 |
| IDTCU-60 | A | 75 | 82 | 80 | 79 | 1 | 100:0 |
| t2 | A | 75 | 90 | 73 | 75 | 1 | 100:0 |
| IDC(mean) | | 75 | 90 | 60 | 65 | 1 | 100:0 |
| IDU(mean) | | 40 | 49 | 43 | 45 | 1 | 0:100 |
| t3 | B | 35 | 42 | 35 | 38 | 1 | 0:100 |
| t4 | B | 31 | 41 | 36 | 36 | 1 | 0:100 |
| t5 | C | 35 | 38 | 36 | 37 | 1 | 0:100 |
| IDTSW | | 35 | 38 | 38 | 37 | | 0:100 |
| IDTUC | | 40 | 44 | 40 | 38 | | 0:100 |
| t6 | C | 40 | 52 | 41 | 38 | 1 | 0:100 |

Figure 15:
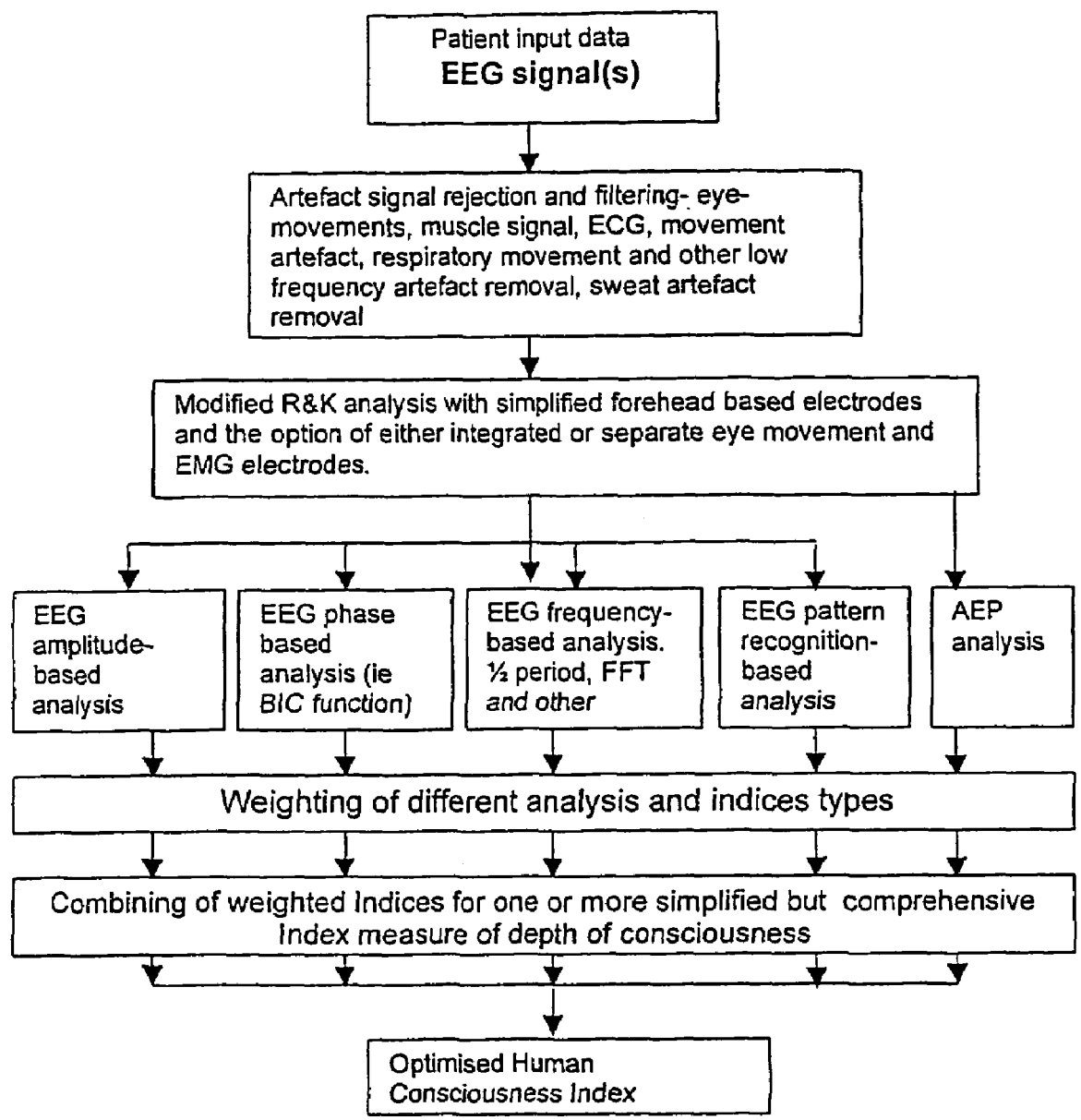
FIG. 15 shows a flow chart of an improved system for monitoring consciousness according to a preferred embodiment of the present invention.

FIG. 15 shows a flow chart of an improved system for monitoring indices associated with human consciousness and incorporating artifact rejection.

Figure 16:
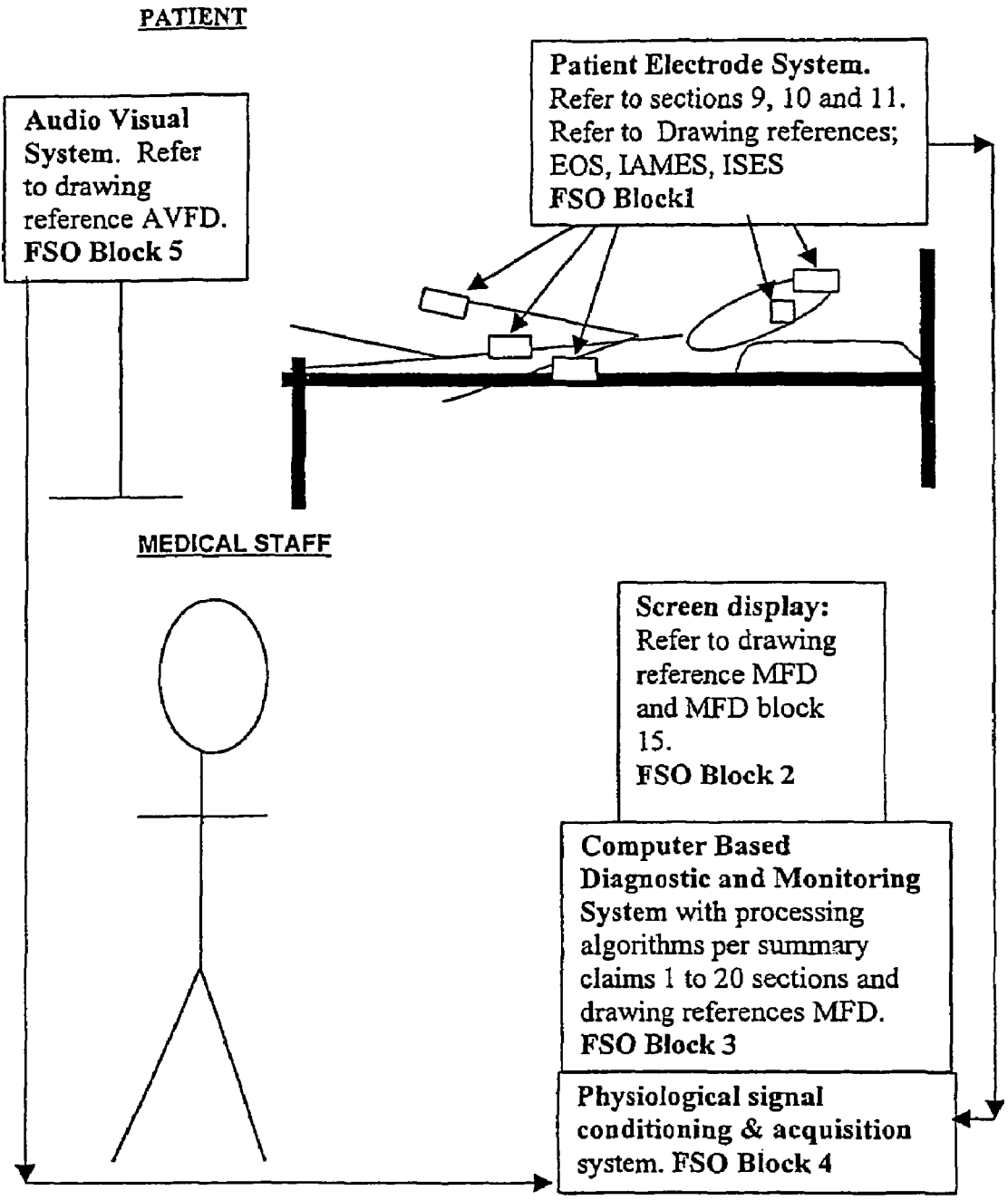
FIG. 16 shows a simplified functional system overview (FSO) of a preferred embodiment of apparatus according to the present invention.

FIG. 16 shows a simplified functional system overview (FSO) of a preferred embodiment of apparatus according to the present invention. The apparatus of FIG. 16 is a Monitoring and Diagnostic System incorporating a reduced risk Depth of Anaesthesia Analysis and Monitoring System, including Minimal Sensor-Electrode attachments for Consciousness, Audio Sensory, Movement/Arousal/Muscle Activity, Eye Movement/Opening, Stress/Anxiety/Vital Signs Parameters, and Audio-Visual Recall.

Figure 17:
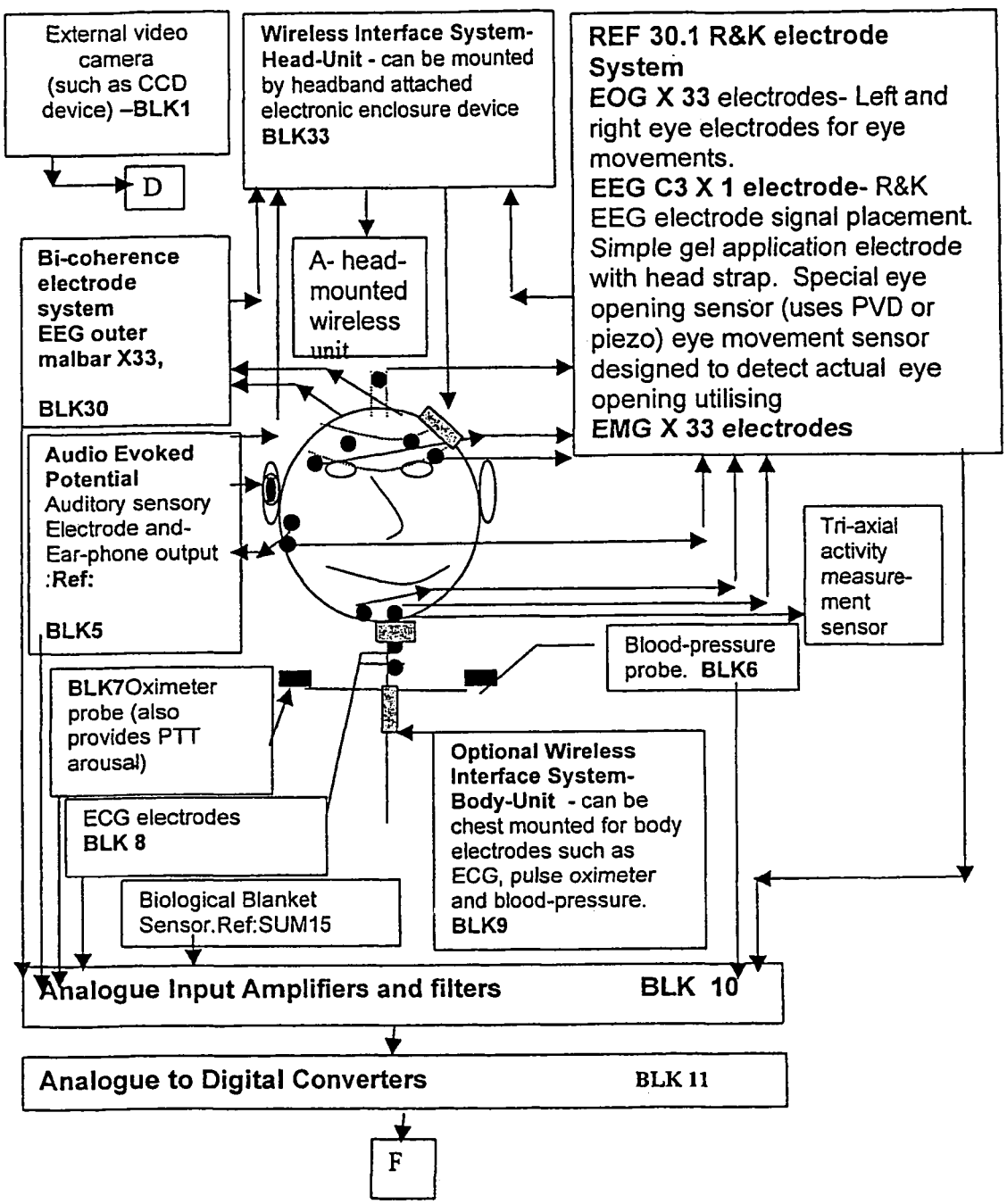
FIG. 17 shows a more detailed functional system overview (MDFSO) of a preferred embodiment of apparatus according to the present invention.
Figure 17:
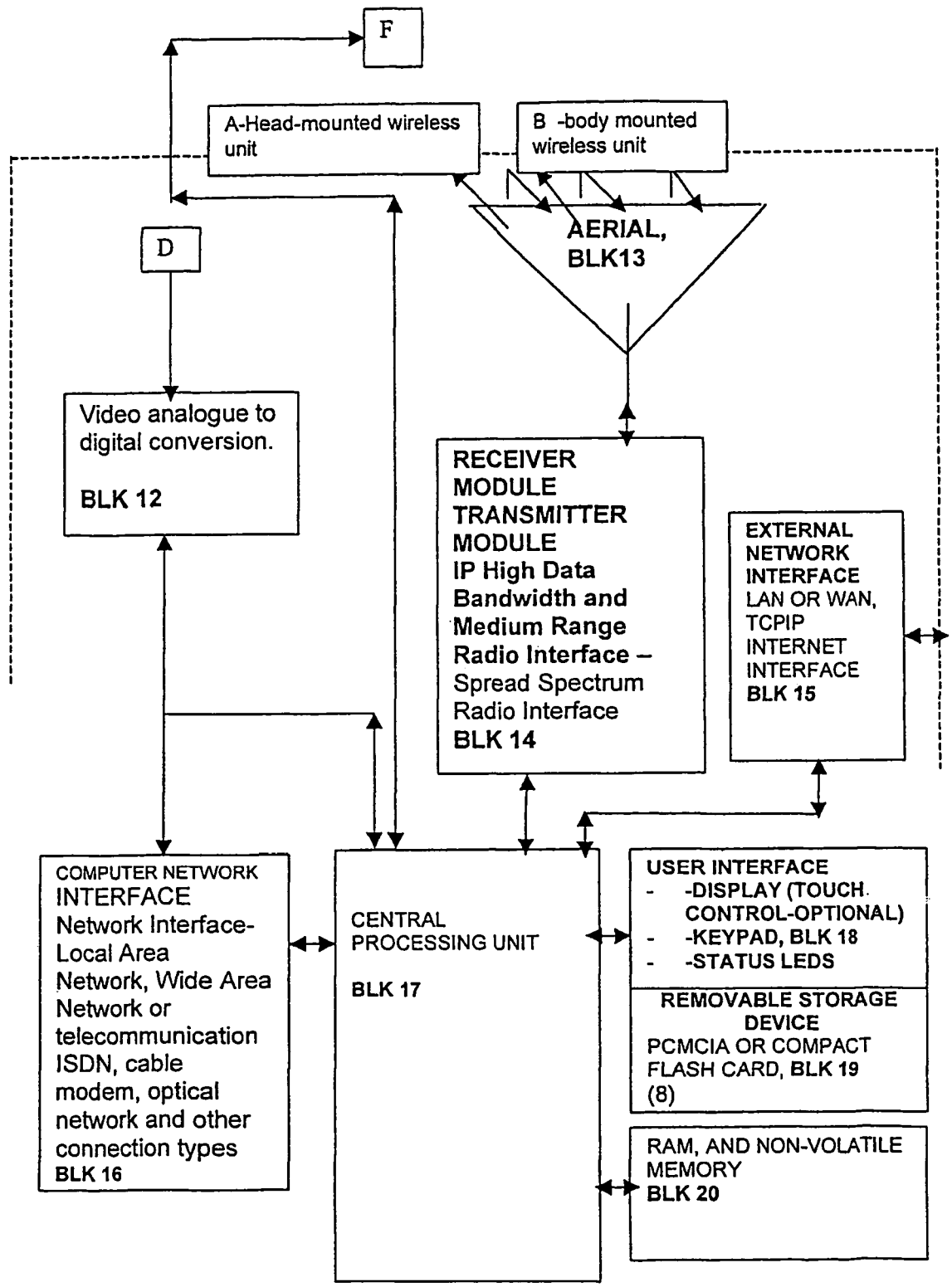

FIG. 17 shows a more detailed functional system overview (MDFSO) of a preferred embodiment of apparatus according to the present invention. The apparatus of FIG. 17 is a Depth of Anaesthesia Analysis and Monitoring System, incorporating an extended range of Sensor-Electrode attachments for Consciousness, Audio Sensory, Movement/Arousal/Muscle Activity, Eye Movement/Opening, Stress/Anxiety/Vital Signs Parameters, and Audio-Visual Recall, audio, video, PTT, activity sensor, blood pressure, oximeter, body and head wireless electrode modules.

Referring to FIG. 16, the apparatus of the HCM system includes a electrode-sensor system (Block 1) connected to a signal conditioning and data acquisition system (Block 4), an analysis and monitoring system (Block 3) and a user display and optional touch screen operator interface system (Block 2). Block 5 provides means for time stamped video and audio to be recorded.

General Overview of Human Consciousness Monitoring System Incorporates drawing FIGS. 16, 17, 35, 34, 43.

Figure 35:
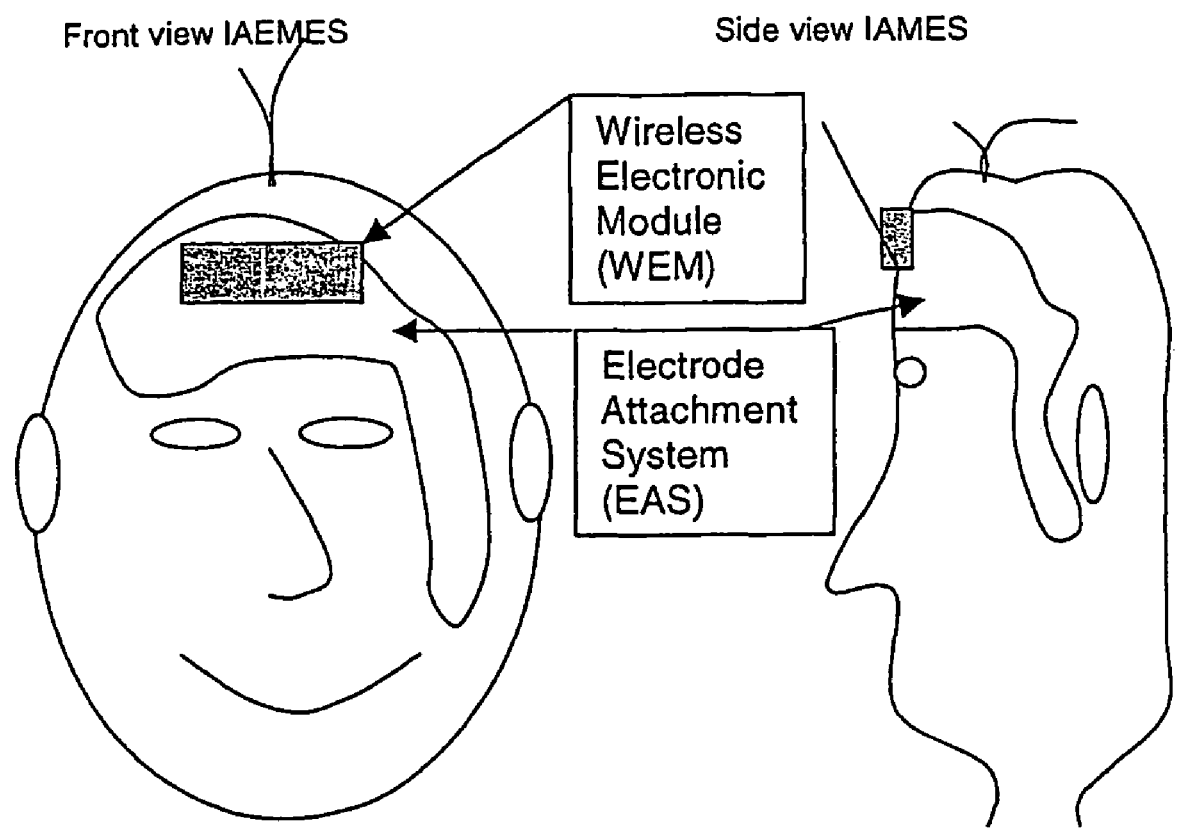
FIG. 35 shows one form of electrode system for integrated anaesthesia monitoring.

Block 1 in FIG. 16 presents that sensors and electrodes are connected to the patient body by means of a unique integrated electrode system (refer FIG. 35). The latter provides use of wireless electrode systems and special self-adhesive electrode attachment systems to achieve a minimally invasive and simple tangle-free patient connection system, desirable for anaesthesia application.

EEG electrodes are for simultaneously monitoring EEG physiological data for optimised bi-spectral and optimised Sleep/Wake analysis, EOG electrodes are for Sleep/Wake analysis, Audio Sensory Electrodes are for monitoring auditory evoked potential from a patient's auditory sensory nerve (refer Block 11 in FIG. 18), Reference Electrodes are for reference of electro-physiological signals, Chin EMG electrodes are for arousal and sleep/wake analysis and redundant or backup electrodes can be applied with various embodiments (refer FIGS. 35, 37, 34, 17). Audio stimulation can optionally be applied by means of a wireless linked patient earpiece, to minimise wiring.

The apparatus may be configured by the user for different modes of operation and furthermore is designed in a modular fashion to allow varying degrees of complexity and versatility. The most complex version of the system is configured to accommodate monitoring and analysis of a broad range of physiological parameters, as detailed above, while more basic versions can be configured to accommodate critical parameters such as "sleep-wake" analysis (34,45,46), bi-coherence analysis, audio evoked potential and arousal analysis. "Sleep-wake" analysis, for example, may be applied to optimise appropriate weighting between audio evoked potential and bi-coherence analysis in determining a subject's consciousness.

Electrode high-impedance amplifiers, signal conditioning and audiovisual monitoring and recording functions (refer Blocks 2, 3 and 4 in FIG. 16) are provided by devices such as Compumedics Siesta, E-Series and Profusion software (71, 72,73). The aforementioned devices are supplemented with specialized sensors (refer Block 1 in FIG. 16) such as addition of minimally invasive wireless and integrated function electrode and sensor systems (refer FIGS. 35,34). Time synchronized audio-visual capability of the apparatus (refer Block 5 in FIG. 16) is further detailed in FIG. 43.

Basic electrode amplification requires medical grade isolation, with special additional input circuitry for electrosurgery protection and RF input filtering for protection against extreme conditions of voltage as may occur with defibrillation procedures which are possible in a critical monitoring environment of an operating theatre, being the likely application environment for the apparatus.

Overview of Types of Physiological Sensory Monitoring parameters and analysis for depth of anaesthesia application and usefulness. The apparatus provides electrode-sensor attachment capability to a patient and includes a capability, with use of integrated and wireless electrodes (refer FIGS. 33,34,35,37) to provide a comprehensive assessment of a patient's physiological states via monitoring and analysis of the patient's critical sensory systems (critical includes avoiding incidence of recall or premature anaesthesia awakening), while the patient is undergoing anaesthesia drug delivery. Comprehensive assessment of human sensory systems includes consciousness (bi-coherence & Sleep/wake. Audio sensory (AEP analysis), arousal sensory (arousal, micro-arousal and movement states), eye opening (special EOS), anxiety & stress state and vital signs (Blood pressure, temperature, GSR, HR and oxygen saturation). Furthermore the apparatus provides a means of recording patient and operating environment audio and video with time synchronisation link to patient physiological parameters, thus providing evidence for legal implications such as claims made relating to premature depth of anaesthesia wakening or for physiological recall purposes. Block 5 in FIG. 16 presents that audio and video can be recorded in time synchronisation with the depth of anaesthesia monitoring procedure, providing an important evidence record. This may be particularly important for verifying audio recall or other type of claims by subjects undergoing depth of anaesthesia monitoring.

Figure 18:
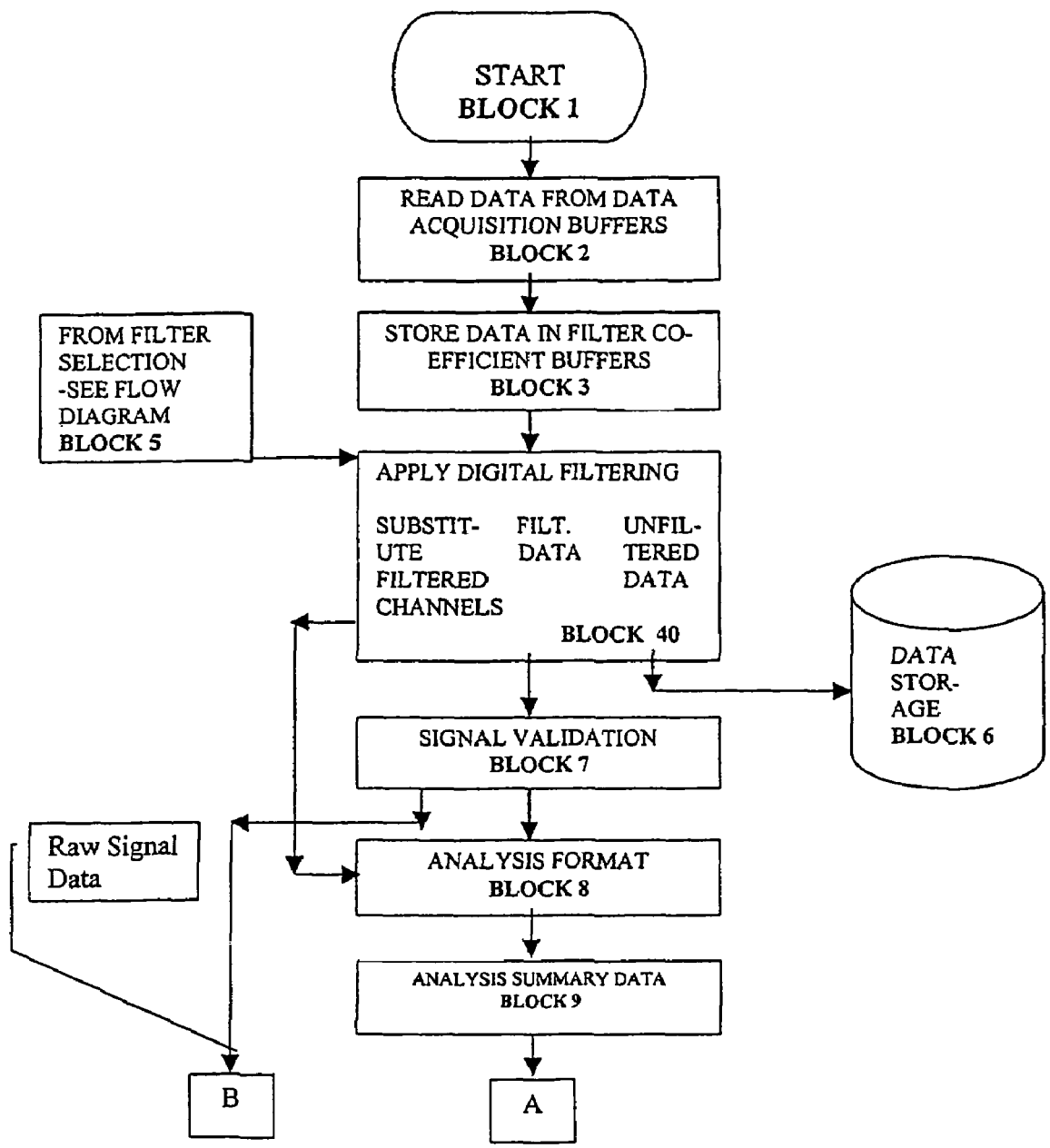
FIG. 18 shows a main flow diagram (MFD) of the HCM system according to a preferred embodiment of the present invention.

FIG. 18 shows a main flow diagram (MFD) of the HCM system according to a preferred embodiment of the present invention. Patient physiological parameters are signal conditioned and digitised in Block 4 of FIG. 16. The digitised signals are read or buffered in Block 3 of FIG. 18. Data is stored in Block 3 of FIG. 18 in buffer sizes based on filter and analysis requirements. Data from Block 3 is applied to Digital Filtering in Block 40. Block 40 provides filtering for various physiological data channels. Block 40 is also linked to signal validation Block 7 to provide a means of compensating for poor signal conditions, such as excessive mains interference noise, which may require notch filtering at 50 or 60 Hz depending on the mains frequency in the country of operation of the apparatus.

Data from Block 40 is also linked to Analysis Format Block 8 to provide specialised filtering where signals required for analysis may need to be substituted by selected alternative signals. This could occur, for example, where Sleep/Wake analysis is required and no C3 electrode scalp signal is available but outer malbar forehead signals may instead need to be optimised with digital filtering to provide the closest possible emulation of C3 EEG signal format.

Filtered signals from Block 40 are validated in Block 7, where each signal is characterised and checked for a range of potential errors, artefact and corruption. The validation of each signal allows the HCM system to present a signal validation score for each signal, so that the user can be prompted when erroneous or unreliable signals could adversely affect the systems output state determination.

This type of method provides an early warning and error reduction for critical monitoring and analysis in a depth of anaesthesia system, which otherwise could be more vulnerable to ambiguous outcomes of patient state determination.

The following provides a more detailed overview of types of physiological parameters, weighting and data translation and combining of analysed parameters for presentation of Integrated or Combined Index to provide desired functional output and achieve useful application of the HCM system and useful apparatus for depth of anaesthesia monitoring.

The following section details how the apparatus has a capability to take sensory physiological parameters including consciousness, audio, arousal-movement, eye movement-opening, stress-anxiety and vital signs parameters, and apply weighting and combining techniques to these parameters to provide a user friendly and risk minimised depth of consciousness monitoring and analysis device. For ease of presentation this overview will proceed in the order of physiological parameters set out above.

The apparatus is capable of monitoring electroencephalographic physiological parameters to provide neurological based analysis for optimised bi-spectral analysis patient state and optimised R&K sleep-wake patient states. The physiological parameters for bi-spectrum values are the outer malbar EEG electrode connections to the patient's forehead together with A1 or A2 EEG mastoid reference connections.

EEG signals are analysed in Block 10 of FIG. 18 whereupon the bi-spectrum, bi-coherence and real triple products are derived.

In accordance with empirical clinical data results (initially set with factory default values) the weighting for column 1 of table DCTT presents bands of bi-spectrum values between value 0 and 100, where the bi-spectrum values refer to between above mentioned bi-coherence and triple product and bi-spectral index together with empirical clinical data results calculate and determine these 0 to 100 values.

Column 2 of table DCTT presents Consciousness To Unconsciousness Transition Thresholds (CTUT) Negative Slope, for the BIC or bi-spectrum values critical threshold values of the bi-spectrum value normalised between values of 1 to 100 (bi-spectrum value is determined from bi-coherence, triple product and optimisation of these parameters with empirical data results).

Column 3 of table DCTT presents Unconsciousness To Consciousness Transition Thresholds (UCTCT) Negative Slope, for the BIC or bi-spectrum values critical threshold values of the bi-spectrum value normalised between values of 1 to 100 (where the bi-spectrum value is determined from bi-coherence, triple product and optimisation of these parameters with empirical data results). An object of the HCM system is to distinguish between the transition of consciousness to unconsciousness and visa versa and to apply critical threshold detection and weighting values to the analysis data in accordance with the transition. In this way the apparatus optimises visual display tracking of a subject's depth of anaesthesia to reduce risk of interpretation of state determination of a monitored patient. "Positive" and "negative" as used in this context has similar meaning throughout this document.

Column 4 of table DCTT presents the weighting values which are applied to optimised bi-spectral analysis (0-100 normalised values) to amplify the critical area of the display graph for bi-spectrum display and also to achieve a visual affect so that all sensory displays (consciousness, audio, arousal-movement, eye movement-opening, stress-anxiety and vital signs) appear to be visually aligned so that when all sensory and combined sensory index's are operating with optimal zone system the user has a simple visual alignment of various graph displays. These weighting factors are indicated as sample factory default values, but this is only indicative as the means of system to weight these parameters is achieved by allowing the apparatus to be modified and upgraded by various techniques including any form of network access, smart card or other removable storage device or specially authorised user system access and configuration.

Alignment of critical thresholds and optimal working area is an object of the HCM system, as the user has a uncomplicated method of ensuring that concentration and delivery of anaesthetic agent does not cause the display metering of the depth of anaesthesia monitor to move outside the optimal area of operation. Furthermore the display graphs associated with each sensory parameter and the combined index change colour to say, green when operating within the optimal area and orange when operating outside the optimal area, for example.

In a busy and stressful operating theatre these operational and user aspects may make a substantial difference to the useability of the apparatus. The apparatus may improve accurate assessment of rate of and concentration of, anaesthetic drug administration during depth of anaesthesia monitoring.

Column 5 of table DCTT presents Unconsciousness To Consciousness Transition Thresholds (UCTCT) Positive Slope, for the BIC or bi-spectrum values critical threshold values of the bi-spectrum value normalised between values of 1 to 100 (where bi-spectrum value is determined from bi-coherence, triple product and optimisation of these parameters with empirical data results).

An example of bi-spectrum values and weighting in accordance with the above detailed formats and processing are presented in table DCTT column 6 (sample bi-spectrum data), column 7 (weighting or translation values applied to the bi-spectrum values), column 8 (un-normalised bi-spectrum values) and column 9 (bi-spectrum values normalised between 1 and 100).

In the system's minimum and preferred configuration (for reasons of simplicity) a single pair of EEG electrodes attached to a subject's forehead (A1, A2 outer malbar bone skin surface positions) is monitored and analysed to produce a bi-spectral index (derivation of bi-coherence analysis) and also subjected to spectral analysis with artefact rejection techniques to produce an estimation of sleep state based on R&K rules but with compromised signal locations. Compromised electrode locations refer to applying forehead A1 and A2 outer malbar electrode positions as opposed to the clinical standard. (refer Principles and Practice of Sleep Medicine—Kryger Roth and Dement Roth) instead of the typical A3 (requires specialised scalp electrode application).

The apparatus has a capability to present reports and analysis display and reports in a simple condensed tabular or graphic form, or more detailed reports and displays detailing raw or basic physiological data. In this way expedient and effective validation of condensed raw data results is accessible to the user. Furthermore graphic and condensed display graphs provide a means of combining or integrating various combinations of consciousness input monitoring variables (including one or more of the various sensory monitored inputs). In this way the user has a capability of combining sets of consciousness index including for example bi-spectral analysis combined with audio-evoked potential analysis, arousal analysis combined with bi-spectral and audio evoked potential analysis, amongst other combinations of analysis and subsequent index measures.

Note 1: Any combination of 1, 2, 3, 4 and 5 can be utilized for display purposes.

Note 2: 1, 2, 3 4, 5 and 6 represent analysis outputs for BIC, AEP, Arousal, Eye opening and movement, anxiety and sleep-unconsciousness/wake-consciousness respectively.

Note 3: A, B, C, D, E represents analysis data after critical threshold detection, Display data translation and display normalization.

BLOCK 7 - FIG. 18

SIGNAL VALIDATION

| Channel | Signal Type | Signal Group Type | Electrode Placement | Raw Data Actual Value Range (MilliVolts) or per unit | Frequency Actual set Pass band High Pass Low Pass (Hz) | Impedance Measure Value | Impedance Weight Factor | a) Impedance Normalised 1-10 Value | Distortion Measure Value |
|---|---|---|---|---|---|---|---|---|---|

SIGNAL CONFIGURATION AND TABLE REFERENCES

| Channel | Signal Type | Signal Group Type | Electrode Placement | Raw Data Range | Freq Pass band | | | Impedance | |
|---|---|---|---|---|---|---|---|---|---|
| 1 | EEG | R&K | C3 | 0-.300 | 0.3-30 | | 1 | Imped-1 | |
| 2 | EOG | R&K | Left eye | 0-.300 | 0.3-30 | | 1 | Imped-1 | |
| 3 | EOG | R&K | Right eye | 0-.300 | 0.3-30 | | 1 | Imped-1 | |
| 4 | EMG | R&K | subment | 0-.260 | 0.3-30 | | 1 | Imped-1 | |
| 5 | EMG | R&K | selectEMG | 0-.260 | 0.3-30 | | 1 | Imped-1 | |
| 6 | EEG | BIC | Fp1 | 0-.300 | 0.3-30 | | 1 | Imped-1 | |
| 7 | EEG | BIC | Fp2 | 0-.300 | 0.3-30 | | 1 | Imped-1 | |
| 8 | EEG | BIC | Fpz | 0-.300 | 0.3-30 | | 1 | Imped-1 | |
| 9 | EEG | AEP | Mastoid+ | 0-.300 | 70-260 | | 1 | Imped-1 | |
| 10 | EEG | AEP | mld-foreh– | 0-.300 | 70-260 | | 1 | Imped-1 | |
| 11 | EMG | EP | L-EP+ | 0-.260 | 70-260 | | 1 | Imped-1 | |
| 12 | EMG | EP | L-EP– | 0-.260 | 70-260 | | 1 | Imped-1 | |
| 13 | EYE TRK | EYE-LID | + | 0-500 | .01-15 | | 1 | Peizo-1 | |
| 14 | EYE TRK | EYE-LID | – | 0-500 | .01-15 | | 1 | Peizo-1 | |
| 15 | ECG | Vital-Signs | | 0-5 | .03-30 | | 1 | Imped-1 | |
| 16 | Sa02-HR | Vital-Signs | | BPM | NA | | | SAO2-1 | |
| 17 | Sa02 | Vital-Signs | | 0-100% | NA | | | SAO2-1 | |
| 18 | SAO2-PTT | Vital-Signs | | arous/min | NA | | | SAO2-1 | |
| 19 | BloodPres | Vital-Signs | | 0-300 mmHg | NA | | | | |

| Channel | Signal Type | Distortion Weight Factor | b) Distortion Normalised 1-10 Value | DC-Offset Measure Value | DC-Offset Weight Factor | c) DC-Offset Normalised 1-10 Value | Dc Stability Measure Value | Dc Stability Weight Factor | d) Dc Stability Normalised 1-10 Value |
|---|---|---|---|---|---|---|---|---|---|
| 1 | EEG | Distn-1 | | DC-Offset 1 | 1 | 0-10 | | DC-Stab1 | |
| 2 | EOG | Distn-1 | | DC-Offset 1 | | 0-10 | | DC-Stab1 | |
| 3 | EOG | Distn-1 | | DC-Offset 1 | | 0-10 | | DC-Stab1 | |
| 4 | EMG | Distn-1 | | DC-Offset 1 | | 0-10 | | DC-Stab1 | |
| 5 | EMG | Distn-1 | | DC-Offset 1 | | 0-10 | | DC-Stab1 | |
| 6 | EEG | Distn-1 | | DC-Offset 1 | | 0-10 | | DC-Stab1 | |
| 7 | EEG | Distn-1 | | DC-Offset 1 | | 0-10 | | DC-Stab1 | |
| 8 | EEG | Distn-1 | | DC-Offset 1 | | 0-10 | | DC-Stab1 | |
| 9 | EEG | Distn-1 | | DC-Offset 1 | | 0-10 | | DC-Stab1 | |
| 10 | EEG | Distn-1 | | DC-Offset 1 | | 0-10 | | DC-Stab1 | |
| 11 | EMG | Distn-1 | | DC-Offset 1 | | 0-10 | | DC-Stab1 | |
| 12 | EMG | Distn-1 | | DC-Offset 1 | | 0-10 | | DC-Stab1 | |
| 13 | EYE TRK | NA | | NA | | 0-10 | | NA | |
| 14 | EYE TRK | NA | | NA | | 0-10 | | NA | |
| 15 | ECG | NA | | NA | | 0-10 | | NA | |
| 16 | Sa02-HR | | | | | | | | |
| 17 | Sa02 | | | | | | | | |
| 18 | SAO2-PTT | | | | | | | | |
| 19 | BloodPres | | | | | | | | |

| Channel | Signal Type | Amp-headr Measure Value | Amp-headr Weight Factor | e) Amp-headr Normalised 1-10 Value | Mains int. Measure Value | Mains int. Weight Factor | f) Mains int. Normalised 1-10 Value | Sig/Noise Measure Value | Sig/Noise Weight Factor |
|---|---|---|---|---|---|---|---|---|---|
| 1 | EEG | | Amp-Head1 | | | Mains-Int1 | | | S/N-1 |
| 2 | EOG | | Amp-Head1 | | | Mains-Int1 | | | S/N-1 |
| 3 | EOG | | Amp-Head1 | | | Mains-Int1 | | | S/N-1 |
| 4 | EMG | | Amp-Head1 | | | Mains-Int1 | | | S/N-1 |
| 5 | EMG | | Amp-Head1 | | | Mains-Int1 | | | S/N-1 |
| 6 | EEG | | Amp-Head1 | | | Mains-Int1 | | | S/N-1 |
| 7 | EEG | | Amp-Head1 | | | Mains-Int1 | | | S/N-1 |
| 8 | EEG | | Amp-Head1 | | | Mains-Int1 | | | S/N-1 |
| 9 | EEG | | Amp-Head1 | | | Mains-Int1 | | | S/N-1 |
| 10 | EEG | | Amp-Head1 | | | Mains-Int1 | | | S/N-1 |
| 11 | EMG | | Amp-Head1 | | | Mains-Int1 | | | S/N-1 |
| 12 | EMG | | Amp-Head1 | | | Mains-Int1 | | | S/N-1 |
| 13 | EYE TRK | | NA | | | NA | | | NA |
| 14 | EYE TRK | | NA | | | NA | | | NA |
| 15 | ECG | | NA | | | NA | | | NA |
| 16 | Sa02-HR | | | | | | | | |
| 17 | Sa02 | | | | | | | | |

-continued

BLOCK 7 - FIG. 18

| | |
|---|---|
| 18 | SAO2-PTT |
| 19 | BloodPres |

| Channel | Signal Type | Sig/Noise Normalised g) 1-10 Value | Filters Actual Settings | Filters Recom. | h) Filters Alarm | Signal Validity NB 30 sample formula |
|---|---|---|---|---|---|---|
| 1 | EEG | | | Filt-1 | | |
| 2 | EOG | | | Filt-1 | | |
| 3 | EOG | | | Filt-1 | | |
| 4 | EMG | | | Filt-1 | | |
| 5 | EMG | | | Filt-1 | | |
| 6 | EEG | | | Filt-1 | | |
| 7 | EEG | | | Filt-1 | | |
| 8 | EEG | | | Filt-1 | | |
| 9 | EEG | | | Filt-1 | | |
| 10 | EEG | | | Filt-1 | | |
| 11 | EMG | | | Filt-1 | | |
| 12 | EMG | | | Filt-1 | | |
| 13 | EYE TRK | | | NA | | |
| 14 | EYE TRK | | | NA | | |
| 15 | ECG | | | NA | | |
| 16 | Sa02-HR | | | | | |
| 17 | Sa02 | | | | | |
| 18 | Sa02-PTT | | | | | |
| 19 | BloodPres | | | | | |

NB 1 - Valid Impedance Table
NB 2 - NA = Not Applicable
NB 3 - KEY
a) Impedance normalised 1-10 value
b) Distortion normalised 1-10 value
c) DC Off-set normalised 1-10 value
d) DC stability normalised 1-10 value
e) Amp-Headroom normalised 1-10 value
f) Mains Interference normalised 1-10 value
g) Signal to Noise normalised 1-10 value
NB 4 For current channel mark as Valid if (a > A)&(b > B)&(c > C)&(d > D)&(e > E)&(f > F)&(g > G) - see NB3

The Following Tale is Set-Up in System Configuration Options

| Valid Table Number | Imped-1 | Valid Table Number | Peizo-1 |
|---|---|---|---|
| Valid Table Name | Electro-Impedance | Valid Table Name | Eye Track-Validate |
| Signal | EEG, EOG, EMG, ECG | Signal | Eye Track Sensor |
| Groups | Electro | Groups | Eye Piezo |
| Impedance Value (K) | Weighted Value | Impedance Value (K) | Weighted Value |
| 1 to 10 | 4 | 100K-200K | 3 |
| 10 to 15 | 3 | 201K-300K | 2 |
| 15 to 25 | 2 | >300K | 1 |
| >25 | 1 | | |

| Valid Table Number | SAO2-1 | Valid Table Number | Distn-1 |
|---|---|---|---|
| Valid Table Name | SAO2 | Valid Table Name | Electro-Impedance |
| Signal | SaO2 | Signal | EEG, EOG, EMG, ECG |
| Groups | SaO2 | Groups | Electro |
| DC Value (V) | Weighted Value | Distortion Value (%) | Weighted Value |
| 0-1 | 3 | 1 | |
| <1 or >1 | 1 | 2 | |
| | | 3 | |
| | | >3 | |

-continued

| Valid Table Number | DC-Offset 1 | Valid Table Number | DC-Stab1 |
|---|---|---|---|
| Valid Table Name | DC-Offset | Valid Table Name | DC-stability |
| Signal Groups | Electrophysiological Electro | Signal Groups | Electrophysiological Electro |
| DC Value (mV) | Weighted Value | DC Value (mV) | Weighted Value |
| 1-100 mV | 4 | 1-100 mV | |
| 1-200 mV | 3 | 1-200 mV | |
| 200-300 mV | 2 | 200-300 mV | |
| >300 mV | 1 | >300 mV | |

| Valid Table Number | Amp-Head1 | Valid Table Number | Mains-Int1 |
|---|---|---|---|
| Valid Table Name | Amp-Head1 | Valid Table Name | Mains-Interference |
| Signal Groups | Electrophysiological Electro | Signal Groups | Electrophysiological Electro |
| DC Value (mV) | Weighted Value | DC Value (dB) | Weighted Value |
| No-Clip | 4 Bn | <20 | |
| Clip+ | 3 | 20-30 | |
| Clip− | 2 | 30-40 | |
| Clip+&− | 1 | >40 | 1 |

| Valid Table Number | S/N-1 | Valid Table Number | Filt-1 |
|---|---|---|---|
| Valid Table Name | Signal to Noise | Valid Table Name | Filters |
| Signal Groups | Electrophysiological Electro | Signal Groups | Electrophysiological Electro |
| DC Value (mV) | Weighted Value | Deviation from rec. Value (% Hz) | Weighted Value |
| >40 | 4 | HP >20 | |
| 30-40 | 3 EEG amp | HP 0-20 | |
| 20-30 | 2 | LP >20 | |
| <20 | 1 | LP 0-20 | |

Ref: 3.2
Analysis Weighting Table
See Table 2

Output Complexity Levels 1, 2, 3 and 4

Signal Validation

Provides a means for Automatic signal validation of a subject's monitored variables by way of automatic impedance measurement, frequency response, mains interference, signal to noise and signal distortion characteristics as part of the analysis algorithm for monitoring, detection or prediction of a subject's state of consciousness, sedation or vigilance.

Patient Calibration

Provides a means for a patient's calibration data to be utilised in analysis algorithm for monitoring, detection or prediction of a subject's state of consciousness, sedation or vigilance.

Analysis Validation

Provides a means for Automatic Analysis Adaptation linked to signal validation. Where the analysis types are determined in accordance to status and quality of patient signals being monitored.

Automatic determination of available analysis processes by way of validating input signal quality and activating analysis only in accordance to validated signal sets associated with the analysis.

Once analysis types have been activated, weighting techniques are applied to apply optimal emphasis for each analysis type. Furthermore various analysis types are combined to simplify the display method of tracking, prediction or detection of consciousness, sedation level or a subject's vigilance.

Analysis Format

Provides a means for Automatic Analysis format linked to signals connected, such as in the case of sleep and wake analysis where the analysis parameters applied will depend on the validated signals. If, for example, only EEG outer malbar electrodes are validated, then frequency optimised EEG outer malbar signals can be utilised for analysis, as opposed to more complex analysis signal combinations including EMG and EOG signals.

Furthermore, weighting associated with each analysis type will depend on the complexity and signal types available for each analysis type.

Analysis

Incorporates an integrated BIC and AEP algorithm, predicting EEG amplitude, integration of frequency (95% spectral edge, FFT) and, ½ period amplitude analysis.

By utilising sleep and wake state determination as a means of context analysis to assist in determining which analysis method, from 5 or more methods (auditory evoked potential (AEP) index (a numerical index derived from the AEP), 95% spectral edge frequency (SEF), median frequency (MF) and the coherence (CHI) and R&K sleep staging) is most suitable for optimal accuracy off tracking each phase of the human vigilance stages.

Provides a means for Localised Evoked potential analysis to detect muscle or nerve response to incisions during localised or gas delivered anaesthetic drug administration.

Provides a means for Eyelid tracking for vigilance monitoring and detection with wireless electrode option. A further option exists using self-applied electrodes where the electrodes consist of a low cost disposable component and a more expensive reusable component.

Patient Information

Provides a means for a patient's body Mass Index, age, medical history and other relevant information to be utilised in an analysis algorithm for monitoring, detection or prediction of a subject's state of consciousness, sedation or vigilance.

BIC Vigilance Application

Provides a means for BIC analysis for vehicle and machine operator vigilance detection with wireless electrode option. A further option exists using self-applied electrodes where the said electrodes consist of a low cost disposable component and a more expensive reusable component. The said EEG monitoring can be by way of self-applied wireless or headrest attached electrodes.

BLOCK 7, EXAMPLE
EXAMPLE OF SIGNAL VALIDATION PRESENTING LOGIC EXAMPLE,
BEHIND DETERMINATION OF VALIDATION OR RELIABILITY LEVEL
OF VARIOUS SETS OF PHYSIOLOGICAL DATA STATES,
FOR PURPOSE OF R&K SLEEP-WAKE STATE DETERMINATION.
THIS VALIDATION LEVELK CAN BE DISLAYED FOR PURPOSE
OF PROVIDING THE SYSTEM USER A CONFIDENCE LEVEL
OF ANALYSIS MONITORING AND DISPLAY.
Example of Sleep Staging Signals Validity and Weighting

| R&K Signals H-High, L-Low, M-Medium | Weighting factor | | | | | | | | | | | | | | | |
|---|---|---|---|---|---|---|---|---|---|---|---|---|---|---|---|---|
| | L | L | L | M | L | M | L | H | L | M | L | H | M | M | M | H |
| EEG-C3 | 0 | 1 | 0 | 1 | 0 | 1 | 0 | 1 | 0 | 1 | 0 | 1 | 0 | 1 | 0 | 1 |
| EMG | 0 | 0 | 1 | 1 | 0 | 0 | 1 | 1 | 0 | 0 | 1 | 1 | 0 | 0 | 1 | 1 |
| EOG | 0 | 0 | 0 | 0 | 1 | 1 | 1 | 1 | 0 | 0 | 0 | 0 | 1 | 1 | 1 | 1 |
| BIC | 0 | 0 | 0 | 0 | 0 | 0 | 0 | 0 | 1 | 1 | 1 | 1 | 1 | 1 | 1 | 1 |

Note:
1 = Signal Valid
0 = Signal not valid
X = do not care

Figure 19:
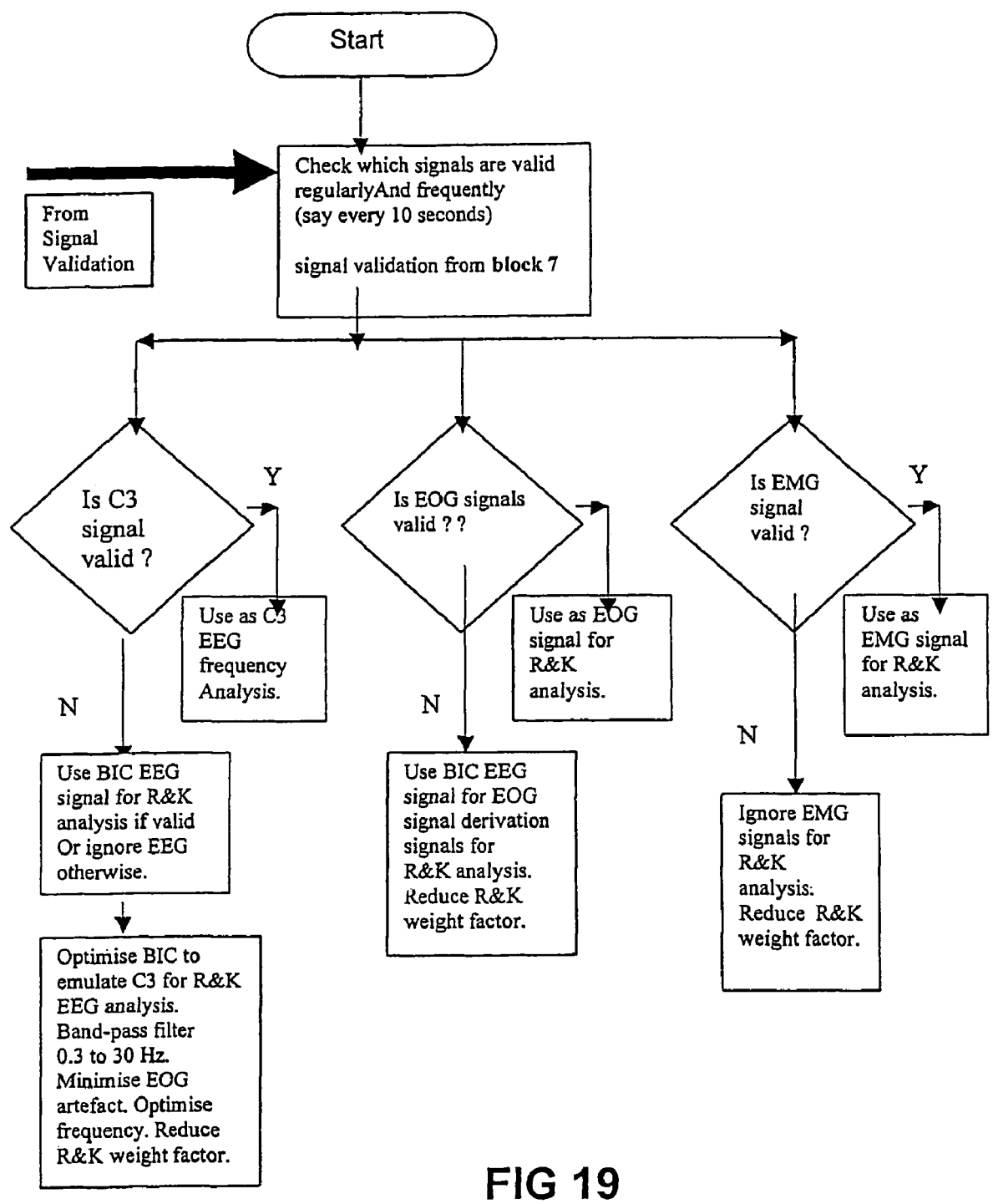
FIG. 19 shows a flow diagram of one form of EEG analysis format validation in Block 8 of FIG. 18.

BLOCK 8 - FIG. 18
ANALYSIS FORMAT EXAMPLE PRESENTING EEG FORMAT
ANALYSIS DETERMINATION IN PREPARATION FOR
SLEEP/WAKE ANALYSIS PER BLOCK 18.
An Analysis format Validation Flow Diagram is shown in FIG. 19
based on analysis confidence level,
signal combination and analysis crosscheck.

| Channel | Signal Type | Signal Group Type | Electrode Placement | Actual Analysis Options Level 1 BIC Weight Value = 10 | Actual Analysis Options Level 2 BIC Weight Value = 5 | Actual Analysis Options Level 1 R&K Weight Value = 10 | Actual Analysis Options Level 2 R&K Weight Value = 5 | Actual Analysis Options Level 3 R&K Weight Value = 3 |
|---|---|---|---|---|---|---|---|---|
| 1 | EEG | R&K, NB1, 18 | C3 | YES | | YES | YES | YES |
| 2 | EOG | R&K, NB18 | Left eye | | | YES | YES | |
| 3 | EOG | R&K, NB18 | Right eye | | | YES | YES | |
| 4 | EMG | R&K, NB18 | subment | | | YES | | |
| 5 | EMG | R&K, NB18 | selectEMG | | | YES | | |
| 6 | EEG | BIC, NB18 | Fp1 | YES | YES | | | |
| 7 | EEG | BIC, NB1, 18 | Fp2 | YES | YES | | | |
| 8 | EEG | BIC, NB1, 18 | Fpz | YES | YES | | YES | |
| 9 | EEG | AEP | Mastoid+ | | | | | |
| 10 | EEG | AEP | mid-foreh− | | | | | |
| 11 | EMG | EP | L-EP+ | | | | | |
| 12 | EMG | EP | L-EP− | | | | | |
| 14 | EYE TRK | EYE-LID | + | | | | | |
| 15 | EYE TRK | EYE-LID | − | | | | | |
| 16 | ECG | Vital-Signs | | | | | | |
| 17 | SAO2-HR | Vital-Signs | | | | | | |
| 18 | SAO2 | Vital-Signs | | | | | | |
| 19 | SAO2-PTT | Vital-Signs | | | | | | |
| 20 | BloodPres | Vital-Signs | | | | | | |

BLOCK 8 - FIG. 18
ANALYSIS FORMAT EXAMPLE PRESENTING EEG FORMAT
ANALYSIS DETERMINATION IN PREPARATION FOR
SLEEP/WAKE ANALYSIS PER BLOCK 18.
An Analysis format Validation Flow Diagram is shown in FIG. 19
based on analysis confidence level,
signal combination and analysis crosscheck.

| Channel | Signal Type | Signal Group Type | Electrode Placement | Actual Analysis Options Level 1 Arousal Weight Value = 10 | Actual Analysis Options Level 2 Arousal Weight Value = 9 | Actual Analysis Options Level 3 Arousal Weight Value = 8 | Actual Analysis Options Level 4 Arousal Weight Value = 7 | Actual Analysis Options Level 5 Arousal Weight Value = 6 |
|---|---|---|---|---|---|---|---|---|
| 1 | EEG | R&K, NB1, 18 | C3 | YES | YES | YES | YES | |
| 2 | EOG | R&K, NB18 | Left eye | YES | | | | |
| 3 | EOG | R&K, NB18 | Right eye | YES | | | | |
| 4 | EMG | R&K, NB18 | subment | YES | YES | YES | | YES |
| 5 | EMG | R&K, NB18 | selectEMG | YES | YES | YES | | |
| 6 | EEG | BIC, NB18 | Fp1 | YES | YES | | | |
| 7 | EEG | BIC, NB1, 18 | Fp2 | YES | YES | | | |
| 8 | EEG | BIC, NB1, 18 | Fpz | YES | | | | |
| 9 | EEG | AEP | Mastoid+ | YES | | | | |
| 10 | EEG | AEP | mid-foreh− | YES | | | | |
| 11 | EMG | EP | L-EP+ | YES | | | | |
| 12 | EMG | EP | L-EP− | YES | | | | |
| 13 | EYE TRK | EYE-LID | + | YES | | | | |
| 14 | EYE TRK | EYE-LID | − | YES | | | | |
| 15 | ECG | Vital-Signs | | | | | | |
| 16 | SAO2-HR | Vital-Signs | | | | | | |
| 17 | SAO2 | Vital-Signs | | | | | | |
| 18 | SAO2-PTT | Vital-Signs | | | | | | |
| 19 | BloodPres | Vital-Signs | | | | | | |

BLOCK 9 (FIG. 18)
ANALYSIS SUMMARY DATA

| | Analysis Summary Data | | | | | INSERT INDEPTHANESTH, BLOCK 9 | | | |
|---|---|---|---|---|---|---|---|---|---|
| Channel | Signal Type | Signal Group Type | Electrode Placement | User Input Select On/Off | Signal Validity Valid or Invalid See SigVal | Analysis Format & Priority | Analysis Priority (Reference: Analysis Interface Version | Analysis Algorithm Type & Version | Algorithm Period | Algorithm Period Type |
| | | | | NB1 | NB 1 | NB 3 | NB 4 | NB 5 | NB 6 | NB 7 | NB 8 |
| | | | | SIGNAL CONFIGURATION AND TABLE REFERENCES | | | | | | | |
| 1 | EEG | R&K, NB1, 18 | C3 | | | | | | | | |
| 2 | EOG | R&K, NB18 | Left eye | | | | | | | | |
| 3 | EOG | R&K, NB18 | Right eye | | | | | | | | |
| 4 | EMG | R&K, NB18 | subment | | | | | | | | |
| 5 | EMG | R&K, NB18 | selectEMG | | | | | | | | |
| 6 | EEG | BIC, NB18 | Fp1 | | | | | | | | |
| 7 | EEG | BIC, NB1, 18 | Fp2 | | | | | | | | |
| 8 | EEG | BIC, NB1, 18 | Fpz | | | | | | | | |
| 9 | EEG | AEP | Mastoid+ | | | | | | | | |
| 10 | EEG | AEP | mid-foreh− | | | | | | | | |
| 11 | EMG | EP | L-EP+ | | | | | | | | |
| 12 | EMG | EP | L-EP− | | | | | | | | |
| 13 | EYE TRK | EYE-LID | + | | | | | | NA | | |
| 14 | EYE TRK | EYE-LID | − | | | | | | NA | | |
| 15 | ECG | Vital-Signs | | | | | | | NA | | |
| 16 | SAO2-HR | Vital-Signs | | | | | | | | | |
| 17 | SAO2 | Vital-Signs | | | | | | | | | |
| 18 | SAO2-PTT | Vital-Signs | | | | | | | | | |
| 19 | BloodPres | Vital-Signs | | | | | | | NA | | |

-continued

BLOCK 9 (FIG. 18)
ANALYSIS SUMMARY DATA

| Channel | Signal Type | Analysis Inputs, Outputs, Conditions | Analysis Index Unit | Analysis Index Measure | Analysis Calibrate Reference | Analysis Patient Data | Analysis State | Analysis Reference Weight table | Analysis Validity Weighted Value | Analysis Depth |
|---|---|---|---|---|---|---|---|---|---|---|
| | | NB 9 | NB 10 | NB 11 | NB 12 | NB 13 | NB 14 | NB 15 | NB 16 | NB 17 |
| | | | | SIGNAL CONFIGURATION AND TABLE REFERENCES | | | | | | |
| 1 | EEG | | | | | | | | | |
| 2 | EOG | | | | | | | | | |
| 3 | EOG | | | | | | | | | |
| 4 | EMG | | | | | | | | | |
| 5 | EMG | | | | | | | | | |
| 6 | EEG | | | | | | | | | |
| 7 | EEG | | | | | | | | | |
| 8 | EEG | | | | | | | | | |
| 9 | EEG | | | | | | | | | |
| 10 | EEG | | | | | | | | | |
| 11 | EMG | | | | | | | | | |
| 12 | EMG | | | | | | | | | |
| 13 | EYE TRK | | | | | | | | | |
| 14 | EYE TRK | | | | | | | | | |
| 15 | ECG | | | | | | | | | |
| 16 | SAO2-HR | | | | | | | | | |
| 17 | SAO2 | | | | | | | | | |
| 18 | SAO2-PTT | | | | | | | | | |
| 19 | BloodPres | | | | | | | | | |

NB 1

These channels can be referenced for 95% edge analysis and/or ½ period amplitude analysis for purpose of validating neurological hypnosis, wake or sleep state. The following table is set-up in system configuration options.

NB 2

User select on/off-user can configure which input channels are selected

NB 3

Signal validity (valid or invalid) Signal validity table determines whether the signal status is valid or invalid. Analysis format Validation Flow Diagram shows an example of how the selected channels and processing format.

NB 4

Analysis priority is determined by combination of input signals and validity of input signals. See diagram: Analysis format Validation Flow Diagram, which details example low diagrams detailing selection of appropriate analysis, subject to input signal type and signal validation.

NB 5

Analysis Interface version is necessary to ensue that the analysis type and version is compatible with analysis algorithm interface.

NB 6

Analysis algorithm type and version. Each analysis algorithm is interfaced to main program by way of a standard analysis interface, which can be in the form of a DLL or other defined and standard interface method. This function provides a means of configuring, updating and convenient definition and display of a system's analysis status and configuration.

NB 7

Algorithm Period 1 sec 10 secs 30 secs 1 min 2 min 5 min 10 min 20 min 30 min 40 min 60 min

NB 8

Algorithm Period Type Options

Average over past period

Running Average over period

Running Average since start

NB 9

Analysis inputs, outputs and conditions describe standard variables associated with interface between analysis algorithms and main program analysis interface.

NB 10

Analysis index units refer to measure associated with Index, such as respiratory events per hour for RDI.

NB 11

Analysis index measure refers to name of specific index—example is RDI or Respiratory Disturbance Index.

NB 12

Analysis calibrate reference refers to calibration data which was compiled from measurements associated with a specific patient. This data could be, for example, normal wake and/or sleep EEG bi-coherence reference data measured as part of a preparatory study to assist more accurate depth of anaesthesia monitoring during a patient's operation.

NB 13

Analysis patient data refers to special patient data such as Body Mass Index (BMI), patient age and patient sex, which can affect the amount of anaesthetic drug required for a particular patient.

NB 14

Analysis state refers to the state of analysis such as wake, sleep, conscious or unconscious.

NB 15

Analysis reference weight table refers to specific table referenced for purpose of allocating correct analysis weighted value.

NB 16

Analysis weighted value refers to value assigned for current analysis output

NB 17

Analysis Depth refers to the degree or depth of the analysis, where 1 represents conscious or wake state and 10 represent greatest depth of unconsciousness. In other words we could have an analysis depth of say 8 (see NB 17) for BIC analysis state and weighted value (see NB 16) of 7 (for example only). In this example the weighted value is determined by the signal validity associated with— a) Signal quality associated with BIC signals b) Analysis priority associated with BIC signals c) Analysis probability and consolidation

NB 18

Arousal detection can also be detected from this channel by way of frequency shift detection.

Figure 20A:
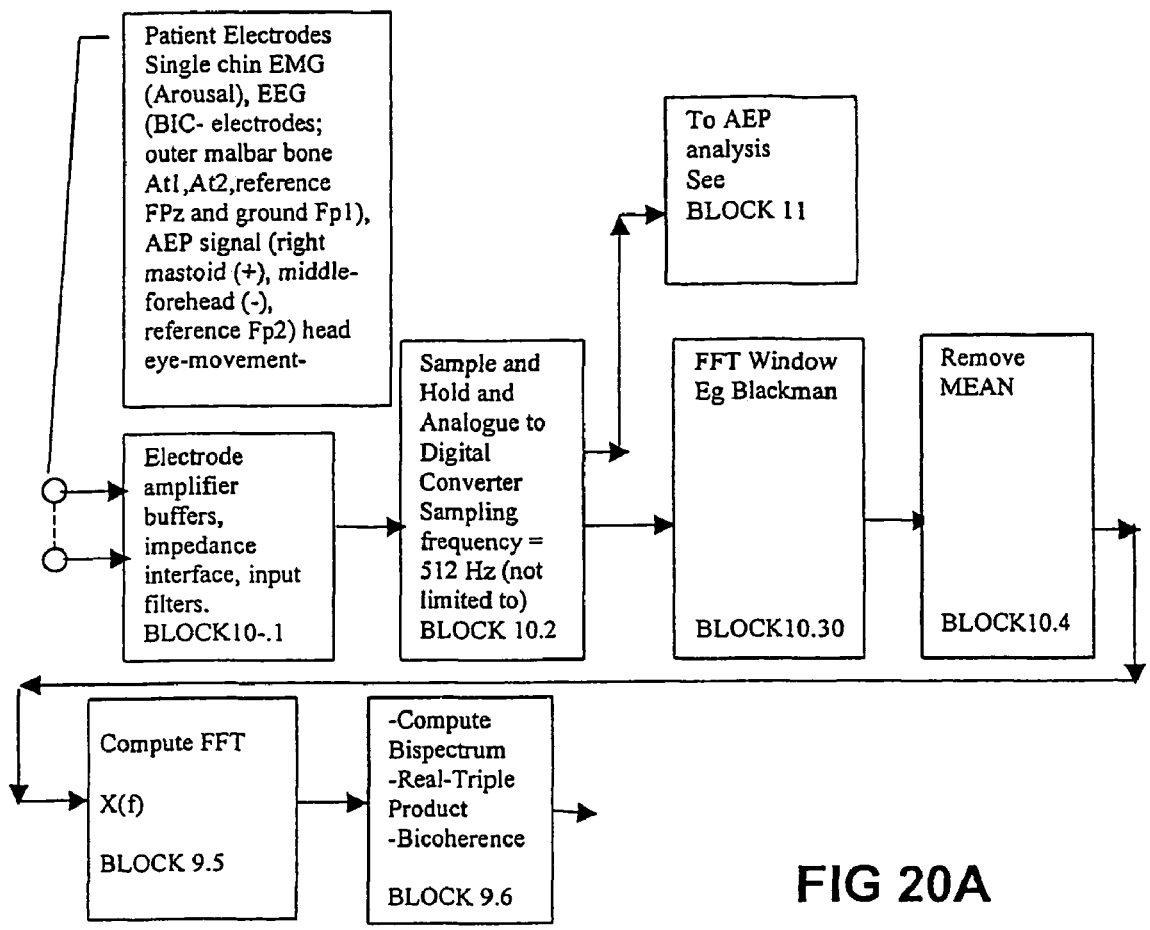
FIG. 20A shows a flow diagram of computation of bicoherence, real triple product and bispectral index in Block 10 of FIG. 18.

FIG. 20A shows a flow diagram of computation of bicoherence, real triple product and bispectral index in Block 10 of FIG. 18.

Computation of Bispectrum (B), Bicoherence and Real Triple Product $$B(f1f2) = \left| \sum_{l=1}^{L} Xi(f1)Xi(f2)Xi^*(f1+f2) \right|$$

Epoch length=30 seconds

75% overlap of epochs to reduce variance of bi-spectral estimate

L=epochs, i.e. 1 minute of data f1&f2 are frequency components in the FFT such that f1+f2≦fs/2 where fs is the sampling frequency Real Triple Product (RTP)

$$RTP(^*f1f2) = \sum_{l=1}^{L} Pi(f1)Pi(f2)Pi(f1+f2)$$

Where $Pi(f1)$ IS THE POWER SPECTRUM $$P(F) = |X(F)|^2$$

Bi-Coherence (BIC)

$$BIC(f1f2) = \frac{100B(f1f2)}{\sqrt{RTP(f1f2)}}$$

ranging from 0 to 100%

Figure 20B:
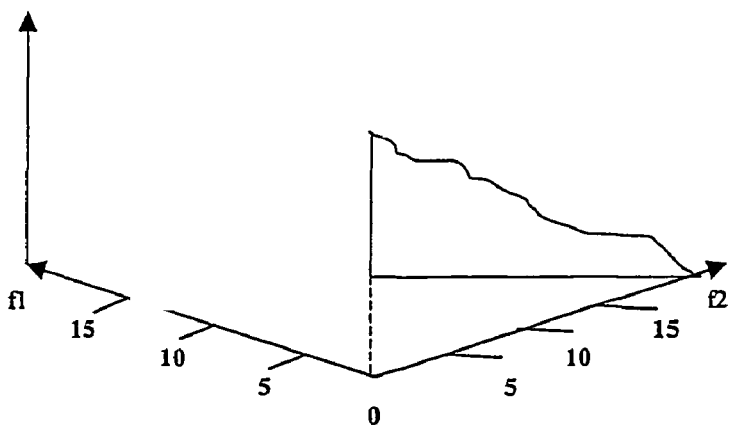
FIG. 20B shows a graphical representation of bispectrum, bicoherence and real triple product in Block 10 of FIG. 18.

FIG. 20B shows a graphical representation of bispectrum, bicoherence and real triple product in Block 10 of FIG. 18.

Block 11—FIG. 18

Audio Evoked Potential Depth of Hypnosis Frequency Sensitivity Analysis

FIG. 21A shows waveform trace 1 representing a sample of frequency sweep signals which can are applied to one or both of a patient's ears.

FIG. 21B shows waveform trace 2 representing the frequency sweep signal at a sensitivity lower than trace 1. FIG. 21C shows one form of hardware for generating the signals shown in FIGS. 21A and 21B. FIG. 21D shows one form of hardware for collecting AEP sensory data from a subject.

FIG. 21E shows Waveform Trace 3 representing a sample of the signal resulting from monitoring the ear sensory nerve when the patient's ear is receiving signals such as trace 1 or trace 2. The system has the capability of applying a range of frequencies at various sensitivity levels to provide a gauge of the patient's response to frequency and sensitivity variations whilst undergoing anaesthesia. In this manner relatively complex audio performance evaluation of a patient is possible. Detailed and precise performance evaluation assists in obtaining an accurate measure of critical thresholds (as determined by empirical clinical data for varying patient ages and types). Furthermore more accurate determination is possible by calibrating the system detection (consciousness and unconsciousness) thresholds for a specific patient. This may be achieved by measuring normal consciousness values and in some circumstances values as the subject transitions into sleep.

FIGS. 21F and 21G show graph 1 and graph 2 respectively representing examples of AEP output results from measuring a sequence of input signal amplitudes at selected sensitivities for a range of frequency sweeps. By outputting the same sequence of frequency sweeps but with varying sensitivities (e.g. trace 1 and trace 2) it is possible to graph the effect of the subjects hearing during anaesthesia and provide an accurate assessment based on deterioration of frequency response and sensitivity of the Audio Evoked Potential signal, the likely critical points in the process of anaesthesia (i.e. the points where the patient is at low risk of audio-recall while undergoing operation procedure).

The above provides an extremely sensitive performance evaluation system for ear-related operations where monitoring of a patient's audio sensory nerve function can be critical. The same system may also be applied to comprehensive measurement and evaluation of audio performance.

FIG. 21H shows graph 3 demonstrating a sample of varying response curves expected from the AEP electrode output when outputting to a patient a series of frequencies at different sensitivities.

The same type of graphical curves are stored as part of the reference block to determine various stages of a subjects monitored anaesthesia—i.e. thresholds for a patient in consciousness and unconsciousness with low risk of audio recall.

BLOCK 15 - FIG. 18
system output alarms, indicators and displays
COMBINED CONSCIOUSNESS-TRANSITION NEW INDEX WEIGHTED ANALYSIS
Display Level 1

| Context Analysis Type | Context Analysis Method | | | Analysis Value | Context Analysis Method | Analysis Probability Weight Factor (1-10) 10- max | |
|---|---|---|---|---|---|---|---|
| Consciousness (anaes depth) | Spectral & 1/2 period | | | 7 | Spectral & 1/2 period | 10 | |
| Consciousness (anaes depth) | R&K | | | 5 | R&K | 8 | |
| Sleep/Wake | Bi-coherence | | | 6 | Bi-coherence | 7 | |
| | | | | | | | |
| Transition Analysis Type | Transition Analysis Method | | | | Transition Analysis Method | | |
| Alertness | AEP | | | 10 | AEP | 9 | |
| | | | | | | | |
| Movement Response Type | Movement Analysis Method | | | | Movement Analysis Method | 6 | |
| Eye Lid | Eye Lid | | | 8 | Eye Lid | 7 | |
| Local Evoked Potential | Local Evoked Potential | | | 7 | Local Evoked Potential | 6 | |
| Arousal | Arousal | | | 5 | Arousal | 8 | |
| | | | | | Vital Signs | | |
| | | | | | ECG HR | 60 | |
| | | | | | SAO2 | 76 | |
| | | | | | Blood Pressure | 305 | |

FIG. 22A shows a bar graph of Context Analysis Method and FIG. 22a shows the corresponding display validation status. Validation status is represented by a colour coded bar display wherein green indicates that the parameter is operating in an optimal area, orange indicates that it is operating in a marginal area outside the optimal area and red indicates that the parameter is operating in an invalid or unreliable area.

FIG. 22B shows a bar graph of Context Analysis Probability and FIG. 22b shows the corresponding display validation status. FIG. 22C shows a bar graph of Transition Analysis Method and FIG. 22c shows the corresponding display validation status. FIG. 22D shows a bar graph of Transition Analysis Probability and FIG. 22d shows the corresponding display validation status. FIG. 22E shows a bar graph of Movement Analysis Method and FIG. 22e shows the corresponding display validation status. FIG. 22F shows a bar graph of Movement Analysis Probability and FIG. 22f shows the corresponding display validation status.

Block 15—FIG. 18

Figure 23C:
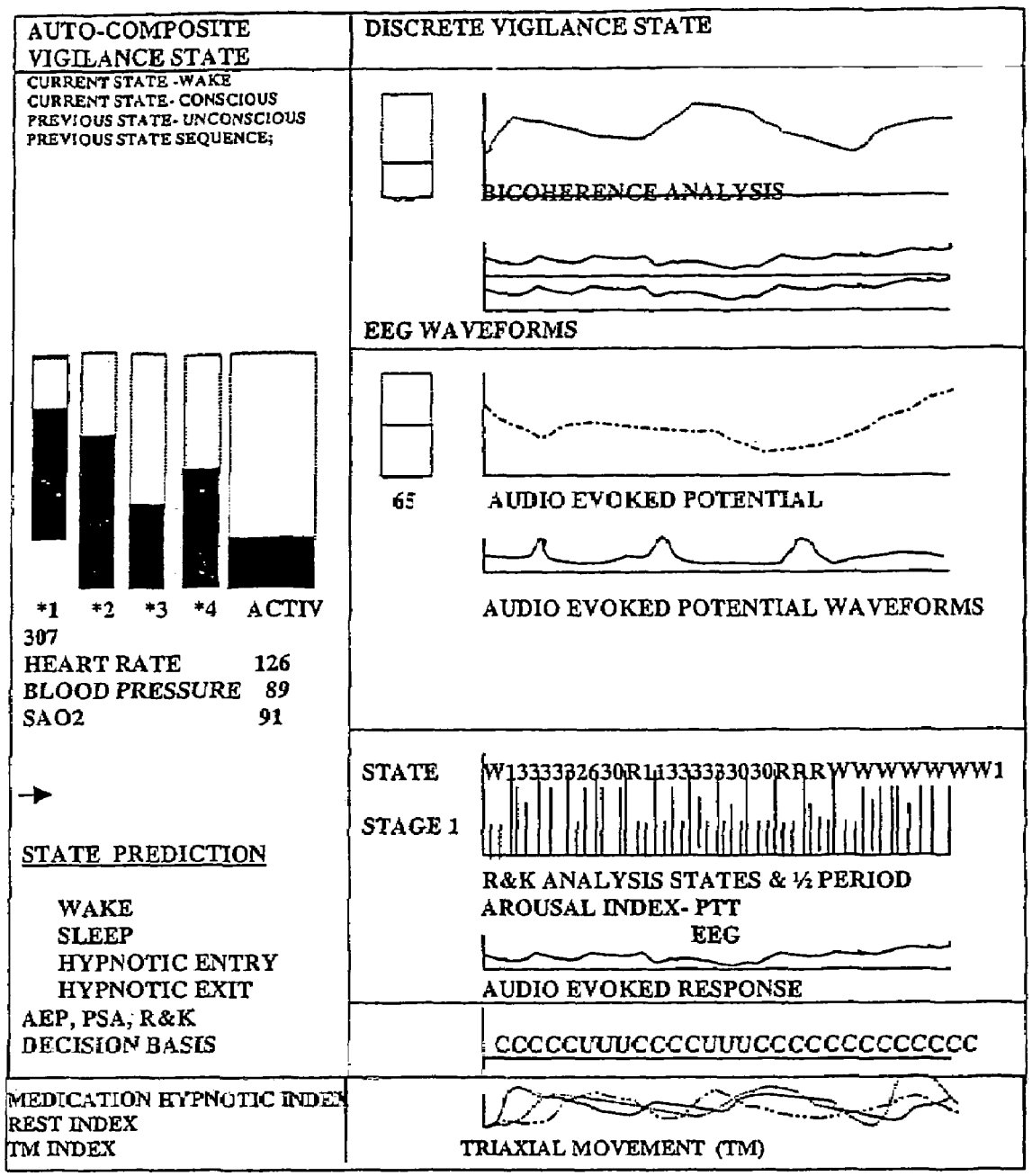

System Output Alarms, Indicators and Displays
  Consciousness Index (Derivation of BIC).
  Transition Index (derivation of AEP and Arousal Index), with cross-linked verification and feedback (transition state holding precedent and over-riding priority over BIC derived Index).
  FIGS. 23A to 23C show graphical representations of system output alarms, indicators and displays associated with Block 15 in FIG. 18. FIG. 23A shows a typical AEP and BIC display and report output together with an integrated and weighted example display of auto track AEP-BIC index wherein the colour of the display indicates its value as set forth in the figure. FIG. 23B shows a bar graph display of discrete sensory index wherein the colour of the display indicates its validation status as set forth in the figure. FIG. 23C shows a sample display screen associated with a hospital in depth anaesthesia meter/hospital ward rest meter with depth anaesthesia analysis embodiment.

Block 16—FIG. 18

Figure 24:
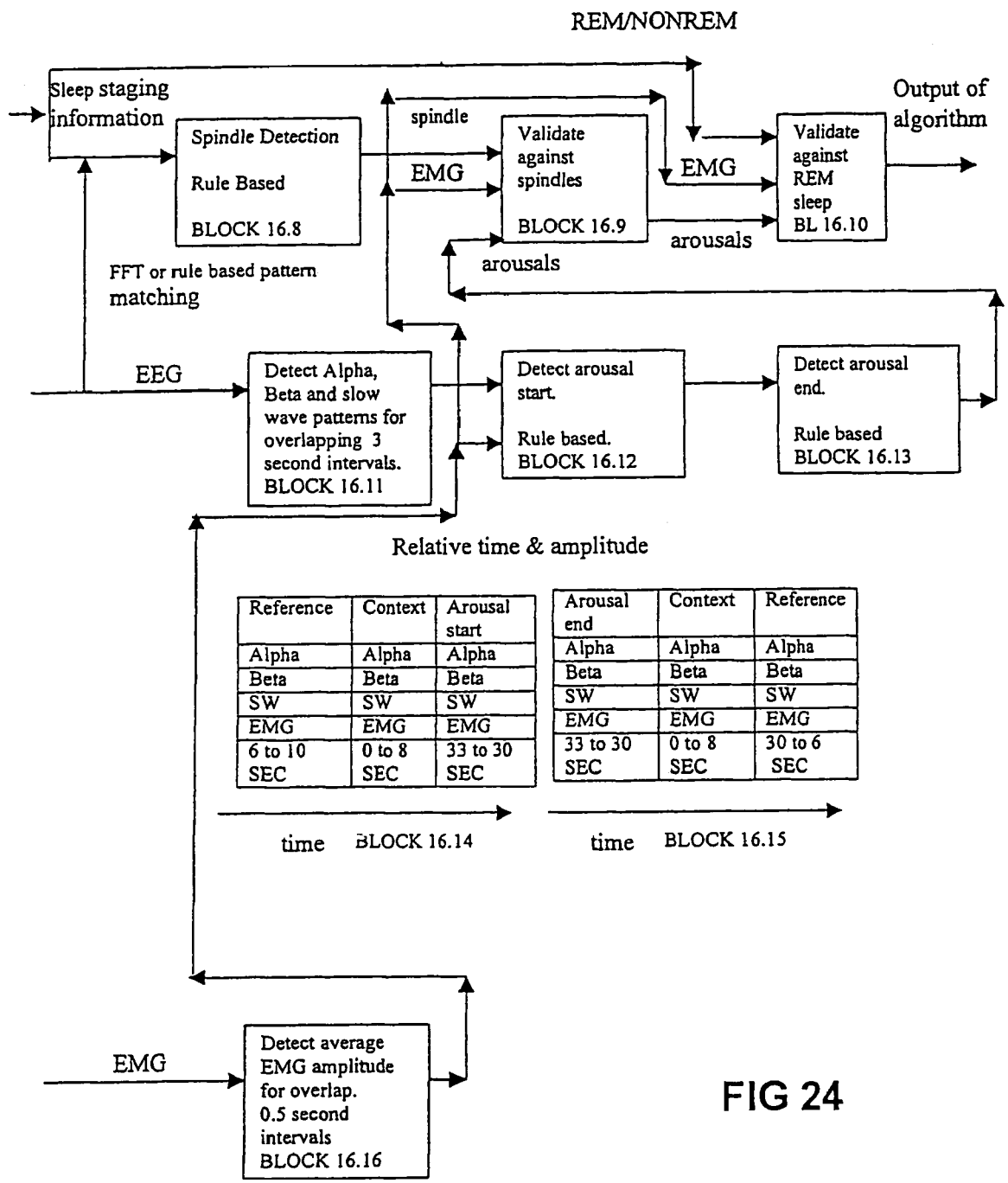
FIG. 24 shows a flow diagram of arousal detection in Block 16 of FIG. 18.

Arousal Detection
  FIG. 24 shows a flow diagram of arousal detection in Block 16 of FIG. 18.

Block 17—FIG. 18

Determination of Eyeopen Index (EOI)
  Eye Opening Sensor Device (EOSD) outputs a unique voltage level in response to each eye opening status. The Actual Eye Opening Value (AEOV) is determined by detecting periods from the subject's consecutive blinks and detecting a maximum value of eye opening during these periods. This procedure excludes blinks and effects of blinks, but rather extracts a maximum eye opening during the period.
  The Reference Eye Opening Wake Value (REOWV) can be determined by instigating the systems REOWV calibration procedure. This procedure records the Actual Eye Opening Value (AEOV) during a designated period, say for example 60 seconds, and then determines the average AEOV during this 60-second period.

$$REOWV = \frac{\text{total addition of } AEOV \text{ for calibration time-(60 seconds)}}{\text{total number of } AEOV\text{'s for calibration time period}}$$

The Percentage Eye Opening (PEO) value can be calculated by dividing the Actual Eye Opening Value (AEOV) by the Reference Eye Opening Wake Value (REOWV) and multiplying this value by 100 in order to determine the PEO value.

PEO=(AEOV/REOWV)×100

Eye Opening Index (PEOI) is calculated with the following formula $$\frac{100}{1} \times \frac{\text{Total addition of } AEOV \text{ for 1-minute period}}{\text{Total number of } AEOV \text{ during said 1-minute period}}$$

PEOI=Percentage Eye Opening Index

AEOV=The Actual Eye Opening Value

REOWV=Reference Eye Opening Wake Value

AEOV=Actual Eye Opening Value

PEO=Percentage Eye Opening

Determination of Eye Movement Index

The Eye Movement Index (EMI) is determined by detecting each Eye Movement and using a running average formula determining the EMI for the past time period t;

EMI=Total number of EM for period 1 minute(last minute for running average calculation)

wherein:

t=time period under measurement—this is typically running time window and for the EMI can be typically 1 minute (i.e. representing EM's over the past 1 minute for EMI running average)

EM=Eye Movements. The eye movements are detected by way of output from EOSD sensor and detecting for minimum period and threshold values EMI=Eye Movement Index Block 21—FIG. 18

Sleep—Wake Analysis

Block 21 performs automatic recognition of sleep and wake states.

Figure 25:
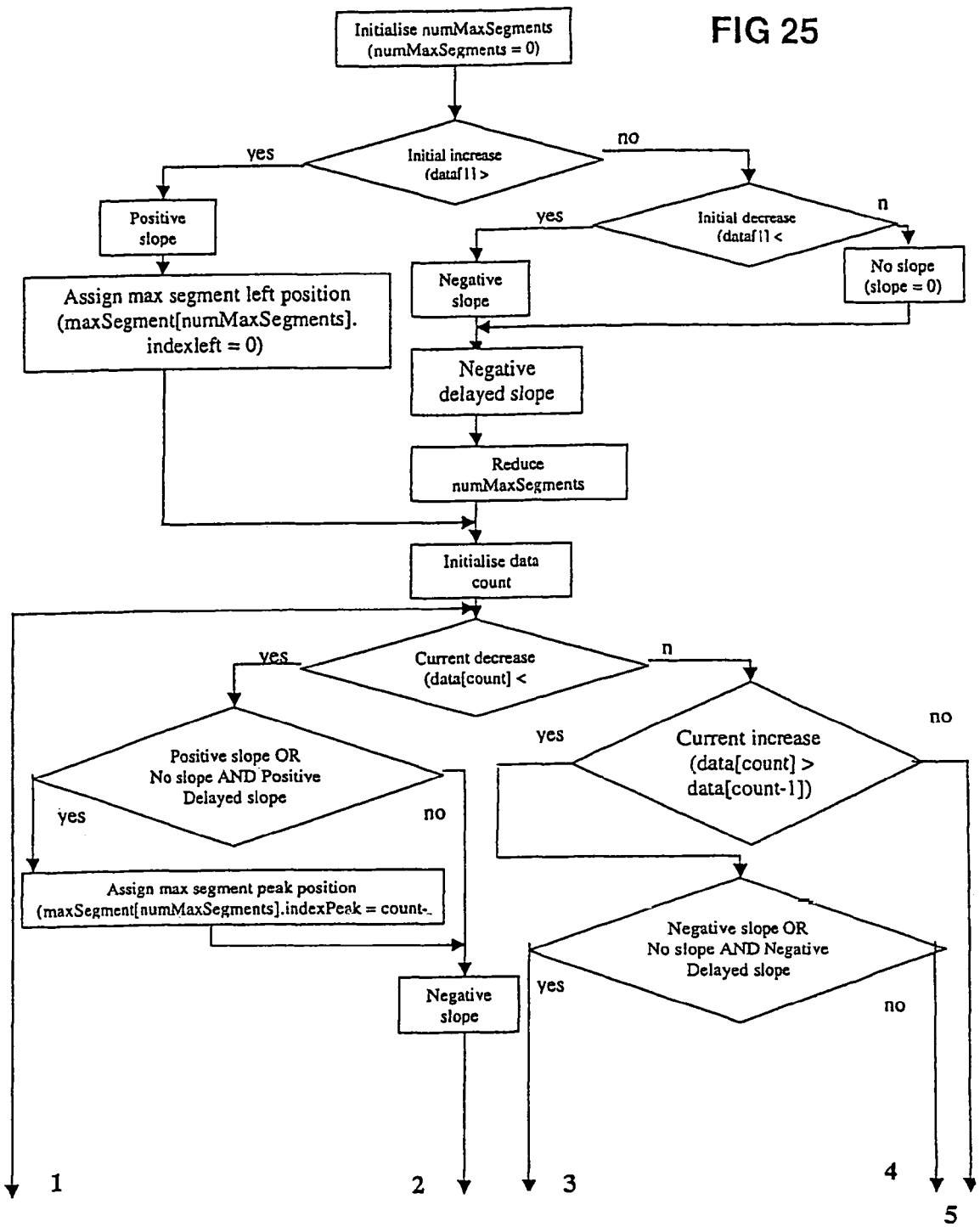
FIG. 25 shows a flow diagram of the process of detecting zero derivative time instants and elementary maximum segments in Block 21 of FIG. 18.
Figure 25:
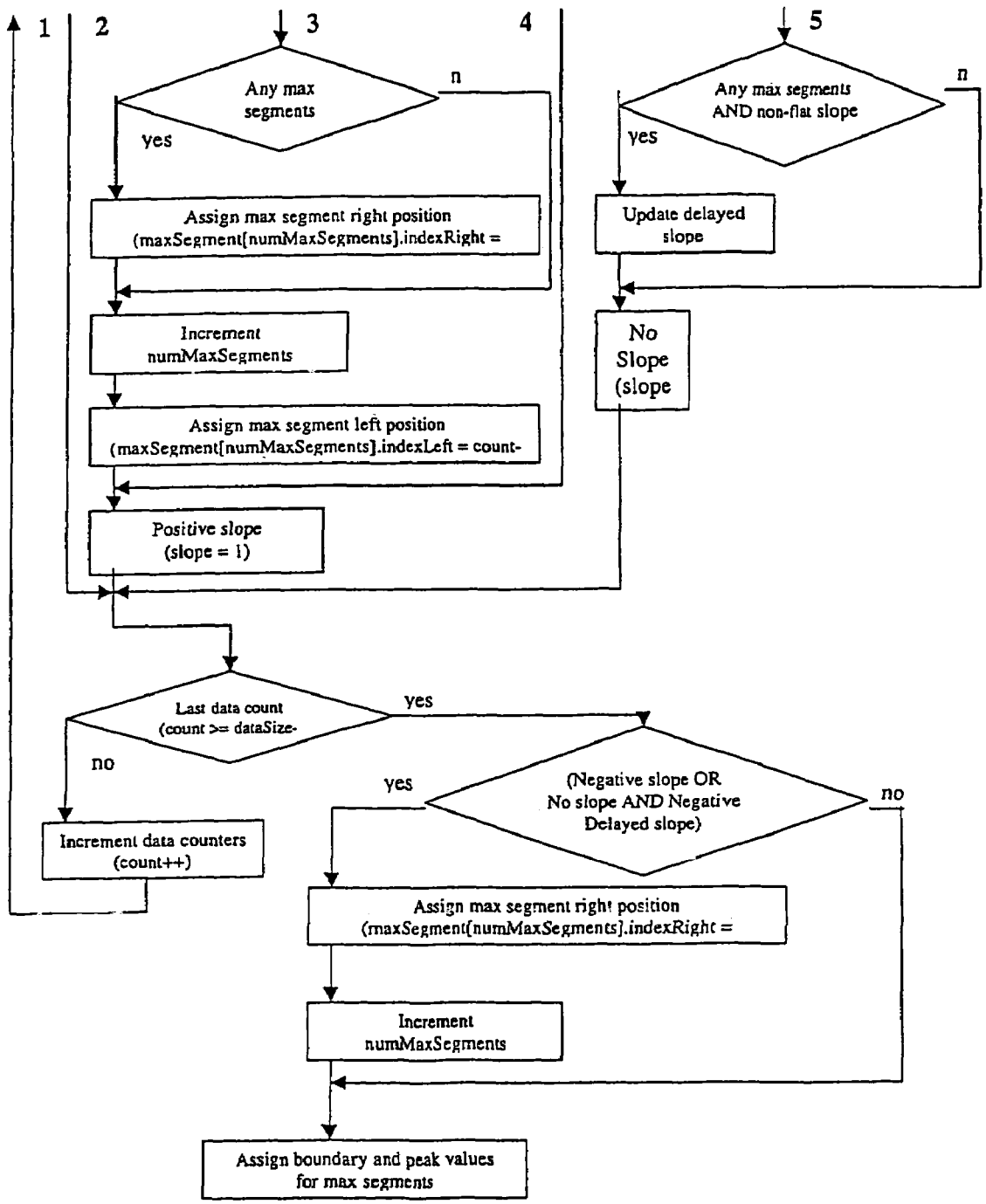

FIG. 25 shows a flow diagram of the process of detecting zero derivative time instants and elementary maximum segments—1 in Block 21 of FIG. 18.

Figure 26:
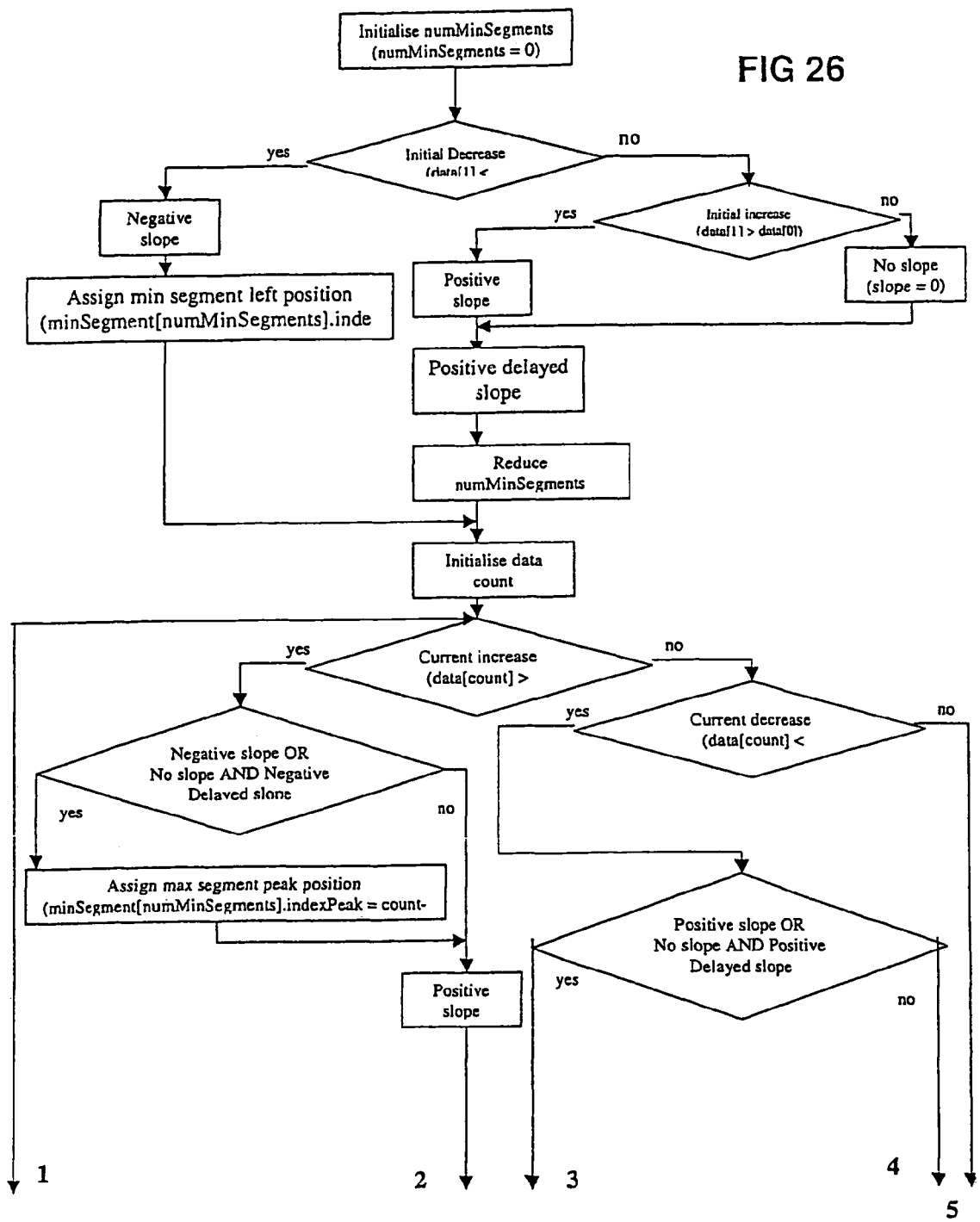
FIG. 26 shows a flow diagram of the process of detecting zero derivative time instants and elementary minimum segments in Block 21 of FIG. 18.
Figure 26:
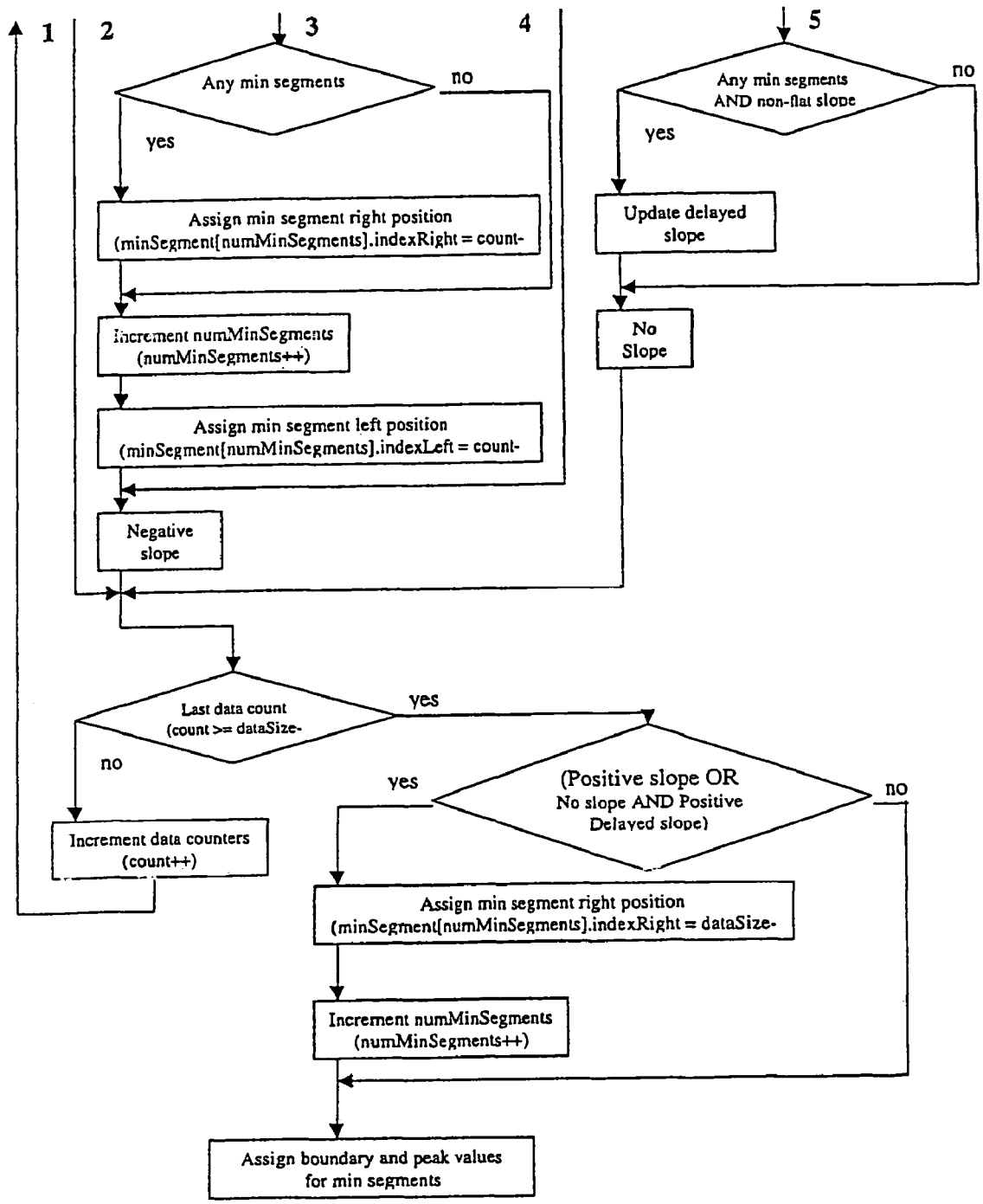

FIG. 26 shows a flow diagram of the process of detecting zero derivative time instants and elementary minimum segments—1 in Block 21 of FIG. 18.

Block 21—FIG. 18

Sleep-Wake Analysis and BIC EEG Artifact Removal

Figure 27:
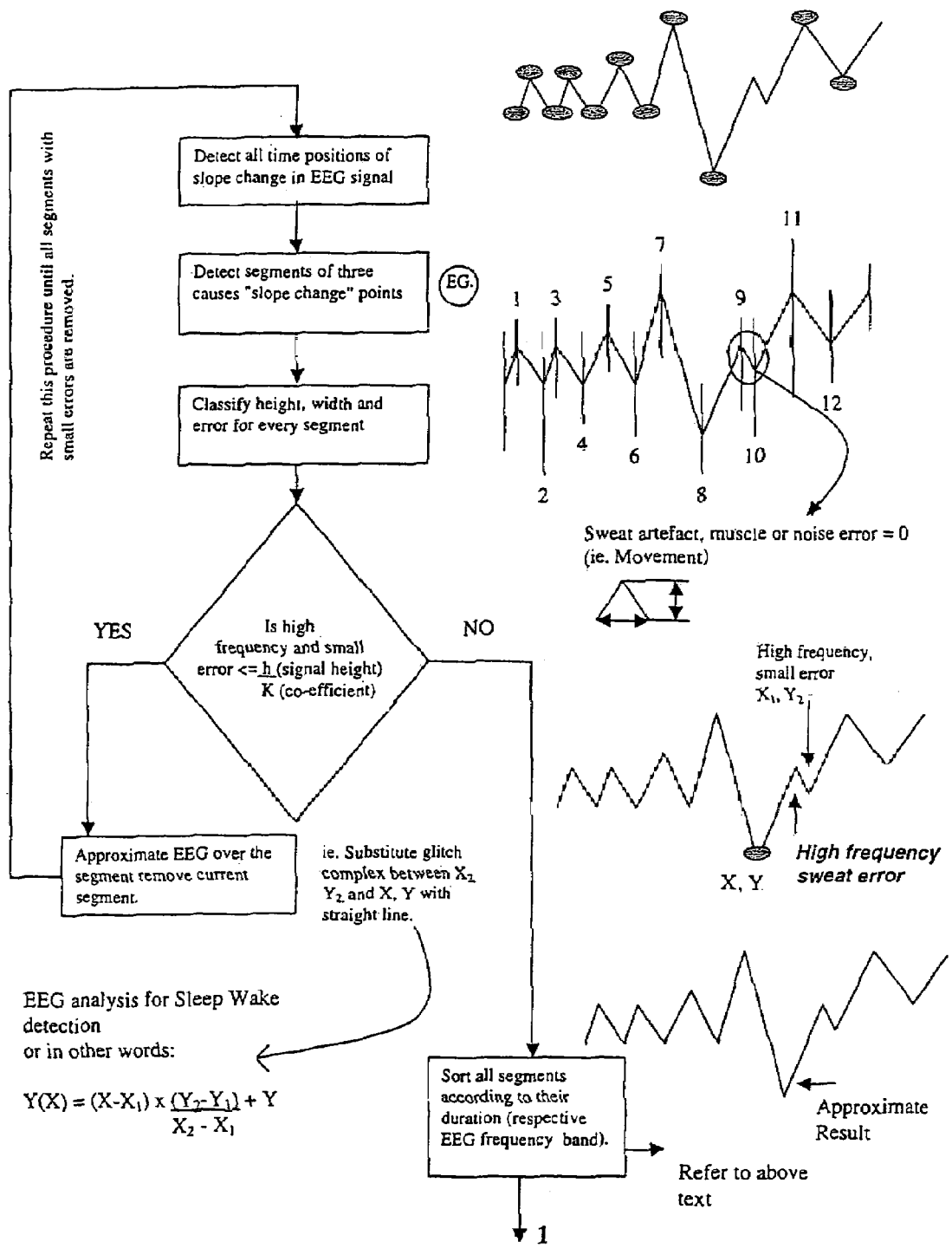
FIG. 27 shows a flow diagram of the process of sleep/wake analysis and BIC EEG artefact removal in Block 21 of FIG. 18.

FIG. 27 shows a flow diagram of the process of sleep/wake analysis and BIC EEG artefact removal in Block 21 of FIG. 18;

Blocks 23, 24, 25, 26, 27, 42, 29, 30, 31, 32, 33, 43 Display Range Scaling and Samples of Display Output (Block 15) Display Range Scaling Display scaling is designed to provide the system end-user with a simple and intuitive view of important analysis data whilst monitoring a patient.

A Display Range and Display Translation table has been designed from empirical data (derived from clinical studies) to convert actual analysis data values to normalised or weighted Display Unit Values (DUV). Accordingly, the Display Translation table can distort or provide a non-linear translation across various sections of display translation, to improve visual tracking across critical regions of analysis data.

The Display Unit Values (DUV) are formulated to provide the system user with a means to display the critical working range of each measured variable in a convenient and user friendly manner.

Furthermore, one or more Display Range Translation Tables (DRTT) may be dynamically allocated to a single Display Unit. The specific DRTT applied at any point in time to a DU can be determined by the context of or change sequence associated with a subject's hypnotic state. In this manner typically different slopes or rates of change associated with a subjects measured variables may be displayed to present a maximised and Auditory Evoked Potential critical transition of a subject's state from consciousness to unconsciousness and visa versa.

Calculation of Display Scale Range Calculation $$DVD = \frac{AV - MNS}{SR} \times 100 \, (\text{FULL SCALE RANGE})$$

Variables:

Display Range Transition Table (DRTT)

DSV=Display Screen View

DU=Display Unit which is one meter or trace that forms part of the Display Screen View MXS=maximum Scale Value is the Actual input data minimum or "cut-off" lower value displayed MNS=minimum Scale Value is the Actual input data maximum or "cut-off" higher value displayed DVD=Display Value Deflection

SRAD=MXS−MNS

AV=Actual Value, or the value that is currently being displayed by a DU.

DR=Display Range. This can be, for example any value between 1 to 100.

DUV=Display Unit Values

OWR=Optimal Working Range

BIC Function and AEP Typical Values

Example of Display Range Translation tables for BIC function and AEP Indexes (note this is an example presenting 10 data points translation but a complete table would present at least 100 data points).

Display Transition

Step 1.

Define Critical Zones of Display

The critical zone of display represents the values, which are desired to be displayed in such a manner that the user has an expanded viewing range (on meter display, for example) compared to less critical display zones. In the HCM system the ability exists to define these "critical display zones" and in particular the critical display zones can change subject to both the context of a subjects current and past states of conscious/wake or unconscious/sleep.

Step 2.

Define Critical Threshold Values.

These values are typically the following data points.

The following table defines the default critical values. These default values can be changed or modified in accordance with the user interface or different system configuration requirements.

Display Critical Threshold Value and Display Transition for BIC analysis (DCTT)

TABLE

DCTT

| BIC DATA RANGE COLUMN 1 | BIC critical CTUT Thresholds Negative Slope COLUMN 2 | BIC critical UCTCT Thresholds Positive Slope COLUMN 3 | BIC\CTUT Display transition Factor- Negative slope COLUMN 4 | BIC\UCTCT Display transition Factor- Positive slope COLUMN 5 | COLUMN 6 | Translation value as derived from columns 4 and 5 above. COLUMN 7 | Weighted BIC function (weighted in accordance with CTUT and UCTCT translation values. (per column 4 & 5) COLUMN 8 | Display 1-100 normalised values. (divide by 300/100 and rounded to nearest whole unit) COLUMN 9 |
|---|---|---|---|---|---|---|---|---|
| 0-10 | | | .5 | 1 | T1-85-(pos slope) | 3 | 255 | 75 |
| 11-20 | | | .5 | 1 | T2-90-(pos slope) | 3 | 270 | 90 |
| 21-30 | | | .5 | 1 | T3-42-(pos slope) | 1 | 42 | 14 |
| 31-40 | DCTTW Threshold-35 | DCTTW Threshold-35 | 2 | 1 | T4-41-(neg slope) | 2 | 82 | 27 |
| 41-50 | | | 2 | 1 | T5-38-(neg slope) | 2 | 76 | 25 |
| 51-60 | | | 2 | 1 | T6-52-(pos slope) | 1 | 52 | 17 |
| 61-70 | CTUT Threshold-80 | | 2 | 3 | T7-62-(pos slope) | 3 | 186 | 62 |
| 71-80 | | UTCT Threshold-75 | 2 | 3 | T8-71-(pos slope) | 3 | 213 | 71 |
| 81-90 | | | 2 | 3 | T9-75-(pos slope) | 3 | 225 | 75 |
| 91-100 | | | 2 | 3 | T10-80 (pos slope) | 3 | 240 | 80 |

Display Critical Threshold Value and Display Transition for AEP Analysis

| AEP DATA RANGE COLUMN 1 | AEP critical CTUT Thresholds Negative Slope +/−10%- see block 39[1] COLUMN 2 | AEP critical UCTCT Thresholds Positive Slope +/−10%- see block 39[1] COLUMN 3 | AEP\CTUT Display transition Factor- Negative slope COLUMN 4 | AEP\UCTUT Display transition Factor-Positive slope COLUMN 5 | Typical AEP values for time sequence T1 to T10 COLUMN 6 | Translation value as derived from columns 4 and 5 above. COLUMN 7 | Weighted AEP values (weighted in accordance with CTUT and UCTCT translation values. (per column 4 & 5) COLUMN 8 | Display 1-100 normalised values. (divide by 160/100 and rounded to nearest whole unit) COLUMN 9 |
|---|---|---|---|---|---|---|---|---|
| 0-10 | | | 1 | 1 | T1-77-(neg slope) | 2 | 154 | 96 |
| 11-20 | | | 1 | 1 | T2-76-(neg slope) | 2 | 152 | 95 |
| 21-30 | DCTTW Threshold-25 | DCTTW Threshold-25 | 1 | 1 | T3-37-(neg slope) | 1 | 37 | 23 |
| 31-40 | | | 1 | 1 | T4-35-(neg slope) | 1 | 35 | 22 |
| 41-50 | | UTCT Threshold-50 | 2 | 2 | T5-36-(pos slope) | 1 | 36 | 23 |
| 51-60 | | | 2 | 2 | T6-40-(pos slope) | 1 | 40 | 25 |
| 61-70 | CTUT Threshold-65 | | 2 | 2 | T7-39-(neg slope) | 1 | 39 | 24 |
| 71-80 | | | 2 | 1 | T8-38-(neg slope) | 1 | 38 | 24 |
| 81-90 | | | 1 | 1 | T9-60-(pos slope) | 2 | 120 | 75 |
| 91-100 | | | 1 | 1 | T10-75(pos slope) | 1 | 75 | 47 |

Note 1
refer block 39 for details on selector logic for BIC and AEP combined output.

Figure 28:
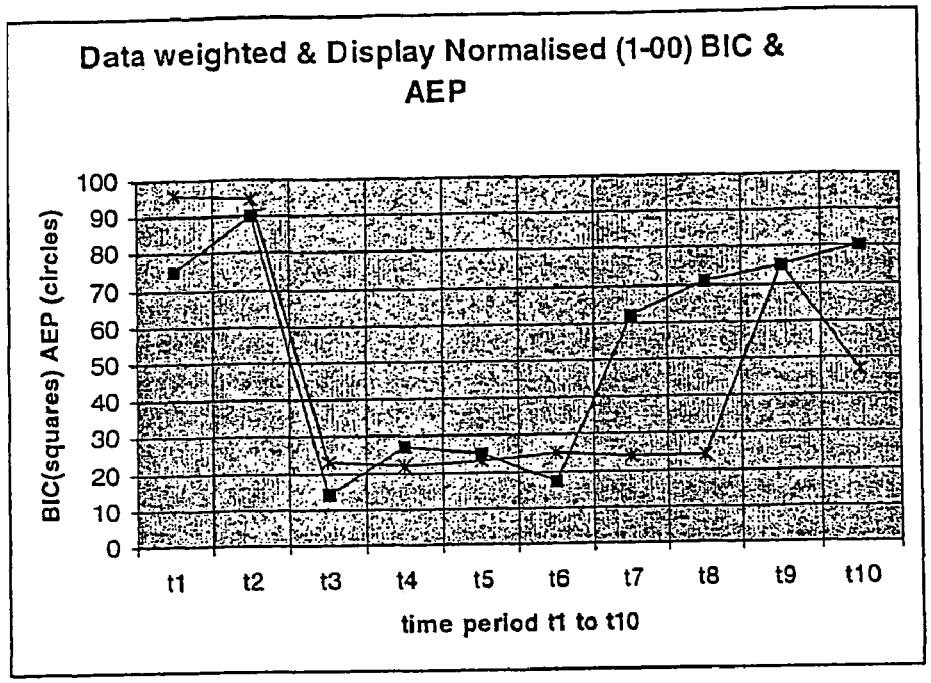
FIG. 28 shows weighted and display normalized BIC and AEP data.

FIG. 28 shows weighted and display normalized (1-00) BIC and AEP data.

Above Example with combined BIC and AEP Display (refer blocks 12, 14 and 34)

Note that switching between BIC and AEP is in accordance with Block 12 logic or;

1. Consciousness (wake) to unconsciousness (sleep) state transition—switch to BIC function
2. Unconsciousness (sleep) to consciousness (wake) state transition—switch to AEP value
3. During consciousness (wake) state—switch to AEP value
4. During unconsciousness (sleep) state—switch to BIC function

| Time period COLUMN 1 | State Conscious Unconscious Wake* sleep* (example indicates only consciousness and unconsciousness state). COLUMN 2 | Weighted and Normalised (1-100) BIC function COLUMN 3 | Weighted and Normalised (1-100) AEP Value COLUMN 4 | Weighted, Normalised (1-100) and combined BIC function and AEP Value Greater of values from columns 3 and 4. COLUMN 5 |
|---|---|---|---|---|
| T1 | consciousness | 75 | 96 | 96 |
| T2 | consciousness | 90 | 95 | 95 |
| T3 | unconsciousness | 14 | 23 | 23 |
| T4 | unconsciousness | 27 | 22 | 27 |
| T5 | unconsciousness | 25 | 23 | 25 |
| T6 | unconsciousness | 17 | 25 | 25 |
| T7 | unconsciousness | 62 | 24 | 62 |
| T8 | unconsciousness | 71 | 24 | 71 |
| T9 | consciousness | 75 | 75 | 75 |
| T10 | consciousness | 80 | 47 | 80 |

Sleep and wake states can include stage 1 sleep, stage 2 sleep, stage 3 sleep, stage 4 sleep, REM sleep, movement sleep, arousal sleep and micro-arousal sleep subject to the HCM system's application configuration and user's required sensitivity (i.e. system may be configured and selected for application as a sedation or activity monitor for the aged or subjects undergoing drug administration, in which cases the HCM system may be configured and selected for full-sleep state sensitivity. Alternatively the HCM system may be selected for vigilance monitoring with a jet pilot or other transport driver or pilot steering a ship or other sea vehicle and in this case electrode attachments to the subject may be as minimal as a disposable wireless linked electrode for BIC parameters. Accordingly only level and state of conscious or unconsciousness may be required.

Figure 29:
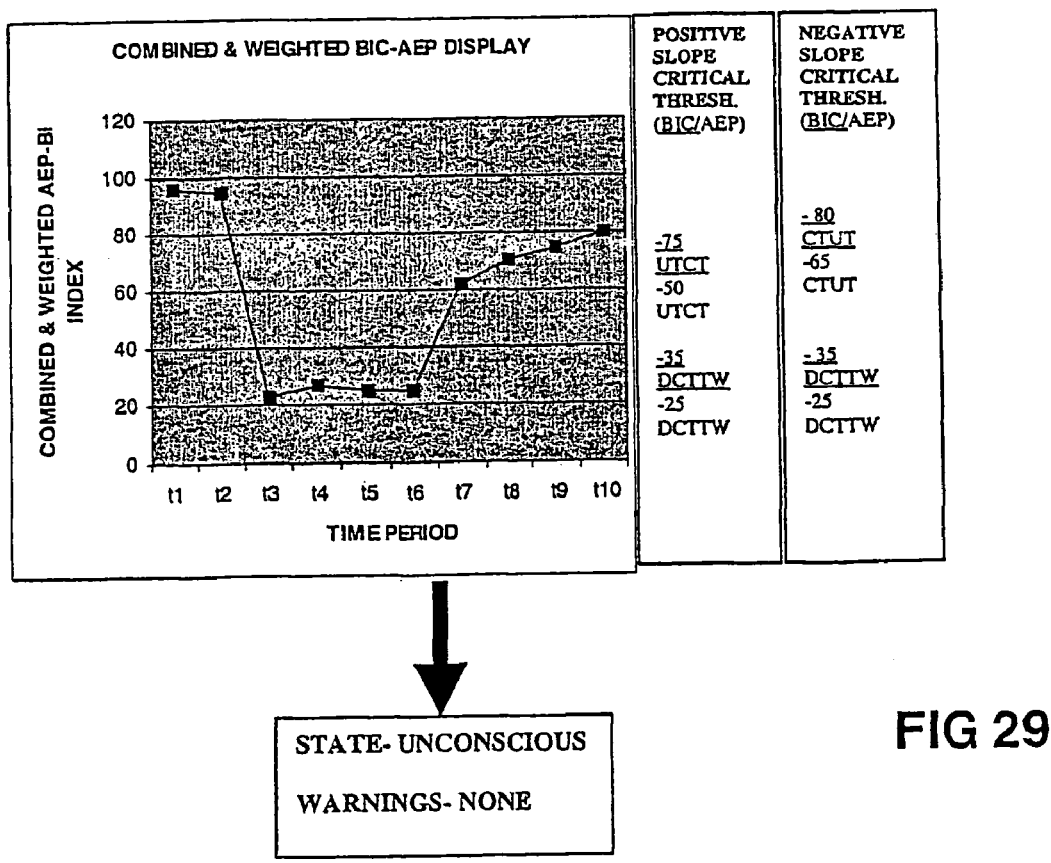
FIG. 29 is a sample of combined and weighted BIC and AEP data with critical threshold and patient state display.

Sample of Combined AEP and BIC with Critical Threshold and Patient State Display FIG. 29 is a sample of combined and weighted BIC and AEP data with critical threshold and patient state display.

Status and Critical Threshold Display—LAST 10, 20, 30, 40, 50, 60, 70, 80, 90, or 100 Epochs of 30 Seconds (Subject to User Requirements and Application)

sample for above t1 to t10 period with basic main states.

The data appearing to roll down in the format provides users a clear graphic means of detecting the monitored subject's progression of consciousness states, consciousness transitions and critical thresholds.

Sample for above t1 to t10 period can include basic main states and sleep states (would be the same as above table with the inclusion of states wake, stage 1 sleep, stage 2 sleep, stage 3 sleep, stage 4 sleep, REM sleep, movement sleep, arousal sleep and micro-arousal sleep).

Key;

CTUT—Consciousness To Unconsciousness Transition

UTCT—Unconsciousness To Consciousness Transition

DCTTW—Deep Consciousness Transition Threshold Warning

CS—Conscious state

US—Unconscious State

*Slope indicates that value is measured in conjunction with increasing (positive slope) or decreasing (negative slope).

Step 3

Define the transition formula associated with each segment or section of the display. Transition formula refers to a single co-efficient (such as 0.5 or 2, for example) for the formula such as log of input value. This transition formula defines the method whereby different display sections are amplified, divided, distorted, stretched. For a viewing perspective the display may be contracted or expanded. The display transition may be important to simplify verification of the subjects status, i.e. Index of BIC or Index of AEP or Arousal Index.

| TIME | EPOCH # | CONSCIOUS | CTUT | UNCONSCIOUS | UTCT | DCTTW |
|---|---|---|---|---|---|---|
| 10:44:16 | 300 | | | | | |
| 10:44:00 | 299 | | | | | |
| 10:43:30 | 298 | | | | | |
| 10:43:00 | 297 | | | | | |
| 10:42:30 | 296 | | | | | |
| 10:42:00 | 295 | | | | | |
| 10:31:30 | 294 | | | | | |
| 10:31:00 | 293 | | | | | |
| 10:30:30 | 292 | | | | | |
| 10:30:00 | 291 | | | | | |

Using the application of display transition method, the HCM system presents to the user a clear and concise operation method whereupon each compliance or optimal status of each parameter can be quickly and easily verified by ensuring that the metered level falls within the optimal display range. Furthermore, each critical parameter being measured (such as Hypnosis Sensory-BIC Index, Auditory Sensory-AEP Index, Muscle Sensory-Arousal Index, Visual Sensory-Eye Opening Index, Eye Movement Sensory-Eye Movement Index-EOI) may be viewed across a common optimal working and the display graphs can be colour coded so that the user is given colour and positional information which instantly verifies whether or not the subject's physiological parameters are measured in the optimal zone or display area at any point in time. With dangerous and critical drug administration the ability to monitor a number of critical variables with simple and accurate verification can avert an otherwise fatal or critical situation for the subject under monitoring. For example, the system user may be instructed to administer the anaesthesia drug while ensuring that each sensory graph such as Hypnosis Sensory-BIC Index, Auditory Sensory-AEP Index, Muscle Sensory-Arousal Index, Visual Sensory-Eye Opening Index, Eye Movement Sensory-Eye Movement Index-EOI or an Integrated Sensory Index (combined discrete sensory Indexes) are within the optimal range (colour and position) during drug administration.

In particular the current method may provide users a simple and precise method of metering critical variables being analysed for a subject undergoing administration of potentially dangerous drugs such as drugs promoting anaesthesia.

BIC and AEP Index Typical Unweighted Data

FIG. 23A shows typical AEP and BIC index display together with an integrated and weighted example display of auto track AEP-BIC index.

BIC and AEP Index Typical Weighted Data with Expansion of Critical Display Regions FIG. 23B shows a discrete sensory index display example including:
HYPNOSIS (45)
AUDITORY (78)
MUSCLE (44)
EYE MOVE (76)
EYE OPEN (50)
INTEGRATED AND WEIGHTED SENSORY EXAMPLE Step 4

Verify or modify Display Translation coefficients or critical thresholds using empirical data derived from clinical studies.

Block 29 FIG. 18

CSCA Data Translation Table (DTT) & Alarm Thresholds (AT) & Level Normalisation (LN)

The translation tables provide a means to translate raw analysis output data into a non-linear or linear manner. The translated data is output in a form suitable for user display viewing. The working or optimal value range for various analysis functions can be transposed in order to fit the screen display and resolution for ease of user system operation.

Important or critical threshold values, associated with analysis data output provide a means for the system to automatically generate alarm indicators or displays. For example, transition from conscious to unconscious and transition from unconscious are critical thresholds, which would be displayed as critical status displays.

Block 35—FIG. 18

Weighting for Combined (1, 2, 3, 4, 5) Index

The analysis index from 1) CORTICAL SENSORY (EEG) CONSCIOUSNESS ANALYSIS, 2) AUDITORY SENSORY TRANSITION ANALYSIS (ASTA) AEP, 3) MUSCLE SENSORY AROUSAL ANALYSIS, 4) VISUAL SENSORY ANALYSIS, 5) SLEEP/WAKE SENSORY ANALYSIS input and combined with a formula to provide a single index designed to register the maximal value of 1, 2, 3, 4 and 5 at any point in time;

Select output value to maximal value from 1, 2, 3, 4 and 5 inputs.

FIGS. 30A and 30B show tables of examples of weighting for combined (1, 2, 3, 4, 5) analysis index in Block 35 of FIG. 18.

Block 37—FIG. 18

Transition State Analysis

Body Movement, (34), Arousal (35), AEP (30) Analysis Algorithms.

Block 37

Contest & Transition Weighting Analysis

Figure 31:
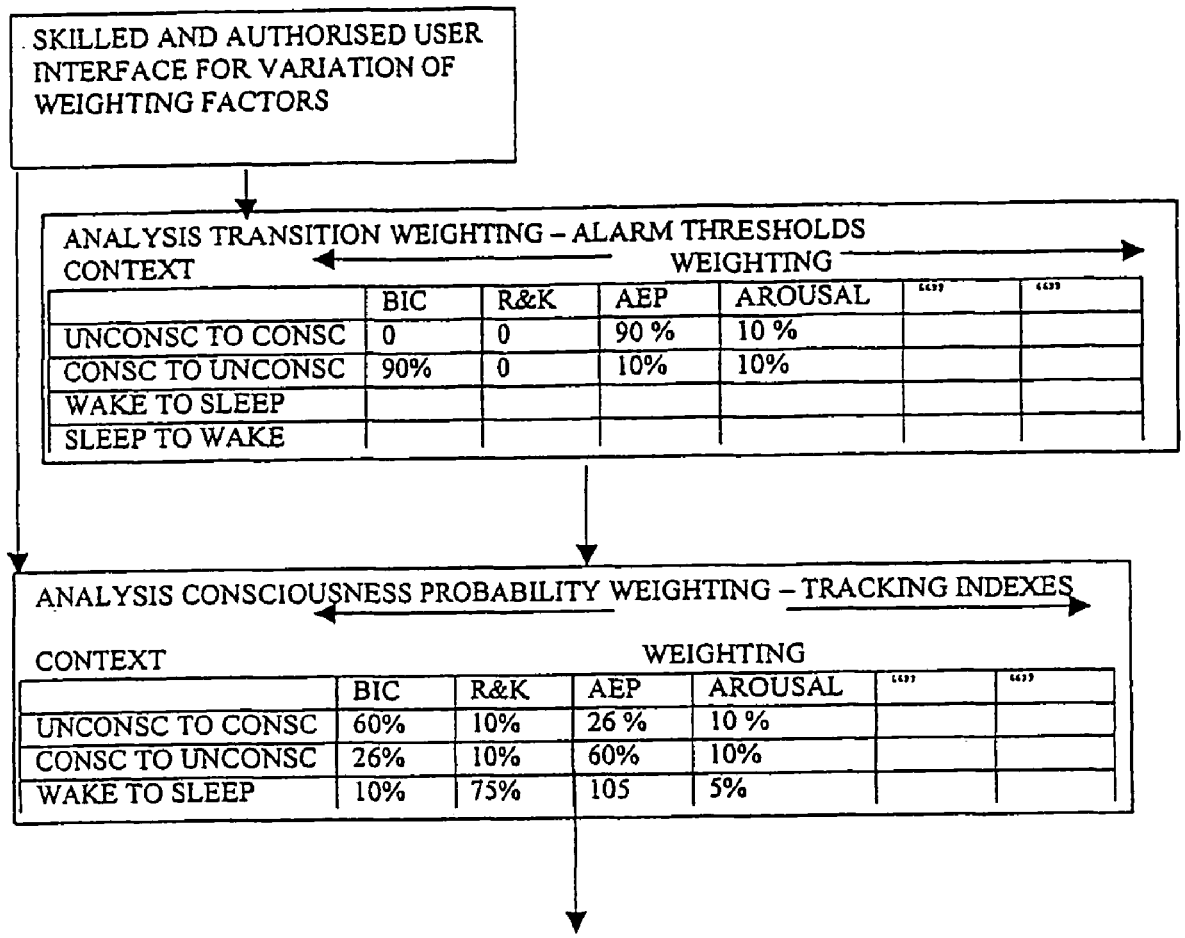
FIG. 31 shows an example format for transition weighting based upon context analysis in Block 37 of FIG. 18.

FIG. 31 shows an example format for transition weighting based upon context analysis in Block 37 of FIG. 18.

Weighting based upon context analysis, BIC co-efficient table (range of BIC function versus critical thresholds, and weighting value versus BIC function).

Consciousness Probability
Compute Bi-spectrum
Real-Triple Product
Bi-coherence

Transition State
AEP
Arousal
Eye movement Analysis
EOG analysis
EMG analysis (Chin)

Figure 32:
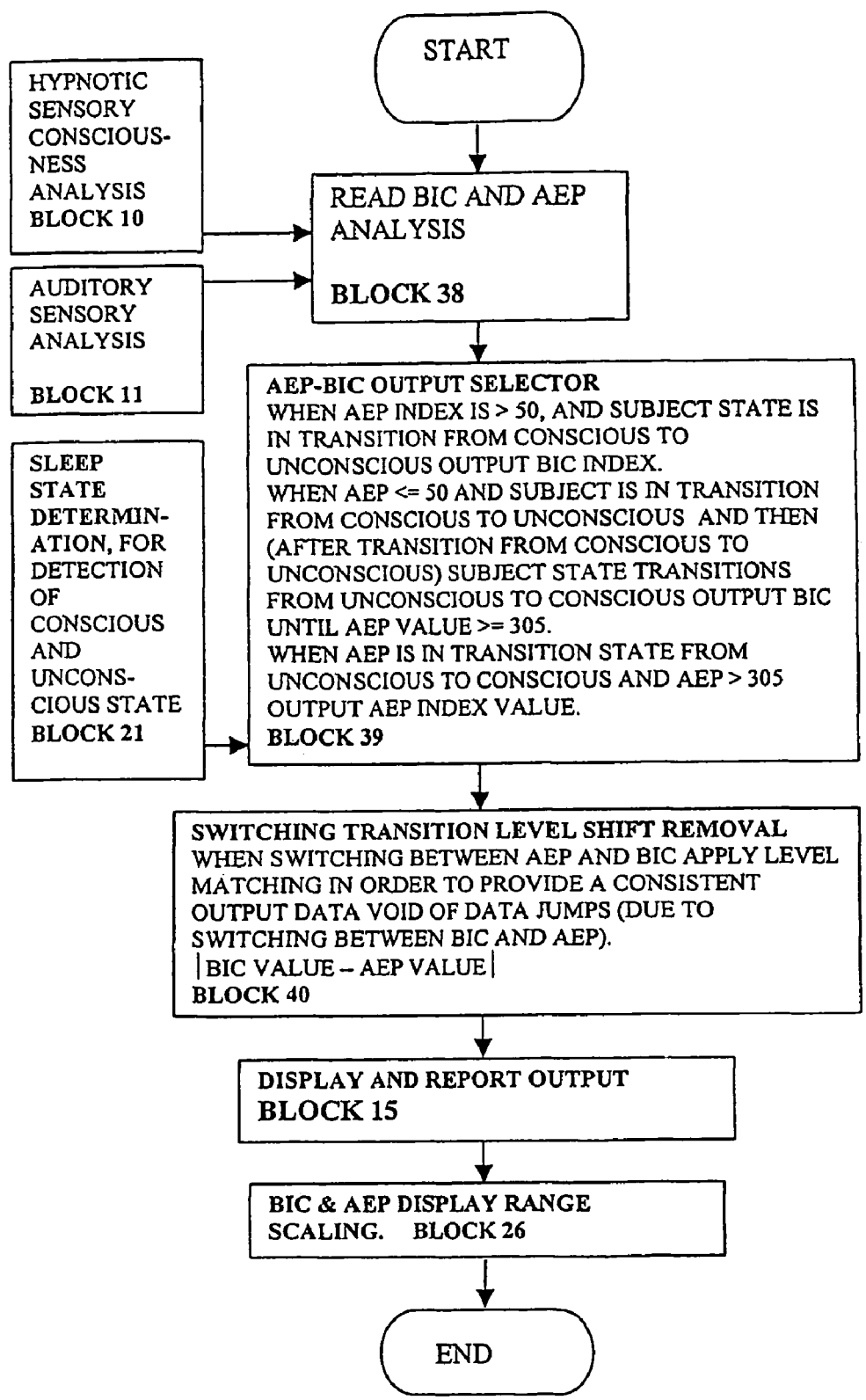
FIG. 32 shows a flow diagram for determining consciousness/unconsciousness using combined AEP and BIC index and R & K in decision context in Block 37 of FIG. 18.

Combined AEP and BIC Index for Consciousness & Unconsciousness Determination Using BIC and R&K in Unique Decision Context FIG. 32 shows a flow diagram for determining consciousness/unconsciousness using combined AEP and BIC index and R & K in decision context in Block 37 of FIG. 18.

Block 44

GSR (Galvanic Skin Response) or EDA (Electrodermal Activity) or SCR (Skin Conductivity Response)

GSR (galvanic skin response) or EDA (electro dermal activity) or SCR (skin conductivity response) as it is now called, is a measure of the conductivity of the skin from the fingers and/or palms. In practice the measurement is made by passing a constant current through the electrodes to determine the skin resistance.

Physiologically the EDA is a measure of sweat gland activity. Increased sympathetic nervous activity will cause sweat to be released onto the palms, thus increasing the conductance. Many emotions such as fear, anger and being startled will elicit increased sympathetic activity—hence its use in lie-detectors and biofeedback relaxation training.

Block 44-51—FIG. 18

Stress and Anxiety Analysis

The HCM system proposes to apply periodic cuff attached (arm, wrist or other patient attachment location) blood-pressure measurement system, in conjunction with an oximeter pulse waveform and ECG waveform (for PTT calculation). The method of utilising the PTT (by way of oximeter pulse wave and ECG waveform) together with periodic cuff based blood-pressure measurement provides a means to derive the quantitative blood-pressure measurement from the cuff value, and the qualitative blood-pressure measurement from the PTT calculated signal. In other words the baseline quantitative blood-pressure value is derived from the cuff blood-pressure value, while continuous and qualitative blood pressure value is derived from the PTT value. Furthermore the application of PAT (104-108) measurement as a means of sensitive EEG arousal detection potentially provides a new method for minimally invasive and maximally sensitive arousals detection. In the context of monitoring a subject in a minimally invasive fashion, and with the intent of reducing the risk associated with premature awakening during an anaesthesia related procedure this new method provides promising scope and application. The benefit of this type of system is its accuracy and continuous blood pressure monitoring capability, while maintaining patient comfort by only implementing the cuff inflation and deflation at periodic time intervals.

Furthermore the system has a capability to simplify user operation with application of wireless interconnection of the pulse oximeter, ECG electrode and blood pressure cuff. This wireless interconnection may allow calculation of continuous blood pressure at a remote wireless or wire-linked site (such as a patient monitoring device), at the EFCG electrode attachment site, at the oximeter finer probe site or the blood pressure cuff site (refer FIG. 33).

Respiration and In-Depth Anaesthesia Monitoring

Effects of paced respiration and expectations on physiological and physiological responses to threat, anxiety or stress conditions can be detected by monitoring a subject's respiration rate.

These states of threat, anxiety, or stress may be expected in a case where a patient partially or fully awakens during a medical procedure. In many cases muscles are paralyzed through special muscle relaxants, and the ability to alert surrounding people may be disabled.

Measurement of Respiration Rate and Respiration Rate Variability

Step 1. Determine the respiration rate for the past 60 second period. This is repeated after every second for the past 30 seconds of respiratory data to produce a running average respiratory rate variability.

Step 2. A similar method as described in block 21 is applied to provide a syntactic or breath-by-breath detection of the respiratory waveform. The respiratory waveform data can be derived (subject to system configuration) from Respiratory Inductive Plethysmography or other type of respiratory bands or patient airflow sensors. Alternatively the respiratory waveform can be derived indirectly from channels such as PTT, ECG, ECG, amongst others.

Step 3. An average baseline (AB) for the past 5 minutes (period is nominal but adjusted with reference to empirical clinical data) is calculated as a mean average. The change of respiration (CR) for the past 1 minute (period is nominal but adjusted with reference to empirical clinical data) is measured against the stated AB value, to produce the current Respiration Variability Rate value (RVRV).

$$RVRV = CR/AB$$

RVRV is compared to threshold values (TV) alarm or notification indication for user or user display. This notification can be in the form of color changes of screen display, meter threshold or the like. TV's are determined from empirical clinical data for the range of normal respiration, anxious or high level respiration and below normal respiration.

Step 4. The RVRV, AB, CR are available for display against the various threshold guide values (i.e. TV's) (53).

Heart Rate and In-Depth Anaesthesia Monitoring (see refs. 54, 55, 56, 57, 60)

Galvanic Skin Response

Galvanic Skin Response is one physiological parameter, which has been found to be associated with threatening or stressful conditions and may be correlated with patients under stress. Galvanic Skin Response may be evident during premature waking associated with an anesthetic procedure.

Blood Pressure and In-Depth Anaesthesia Monitoring

Figure 33:
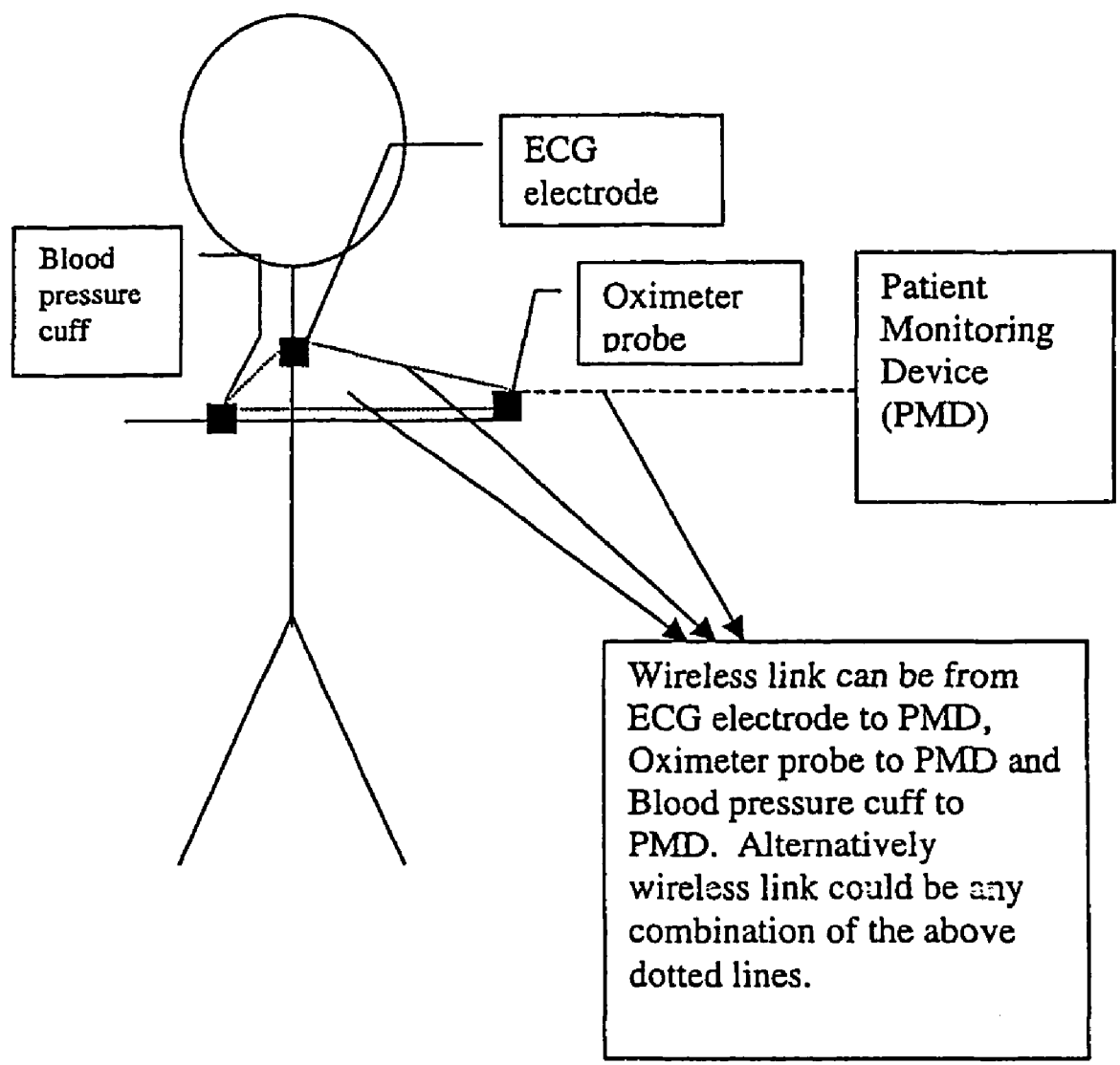
FIG. 33 shows one form of apparatus for wireless linked continuous blood pressure measurement.

FIG. 33 shows one form of apparatus for wireless linked continuous blood pressure measurement (see ref. 58).

Improved Biological Sensor for Sensing and Measuring Eye Opening

Figure 34A:
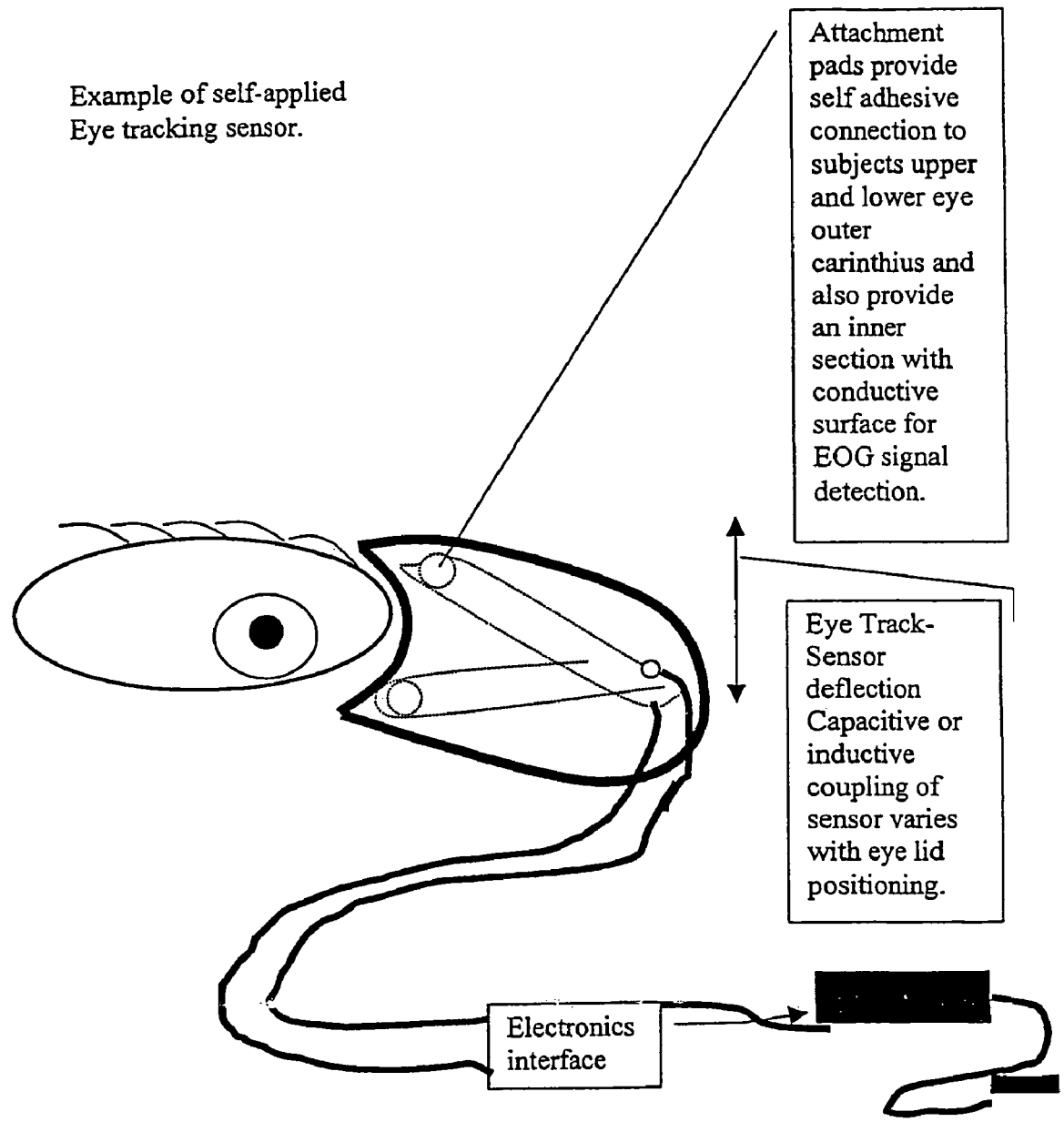
FIG. 34A shows one form of sensor device for sensing and measuring eye opening.

FIG. 34A shows one form of biological sensor device for sensing and measuring eye opening. The biological sensor includes a pair of scissor arms 34, 35 connected for pivot able movement at hinge 36. Arm 34 is adapted to move substantially with an eyelid. In one form the free end of arm 34 may be fixed to a movable part of the eyelid by means of an adhesive such as double-sided tape. The free end of arm 35 may be fixed to part near the eye that substantially does not move with the eyelid. Each arm 35, 36 includes conductive carbon tracks 37. Tracks 37 may form an inductor on each arm. Alternatively tracks 37 may form a plate of a capacitor on each arm. It may be seen that as arms 34, 35 move or pivot relative to each other the degree of over lap between carbon tracks 37 on the respective arms changes with the movement. Tracks 37 are connected to an Electronics Interface for converting the position of arms 35,36 to an electrical signal.

Figure 34B:
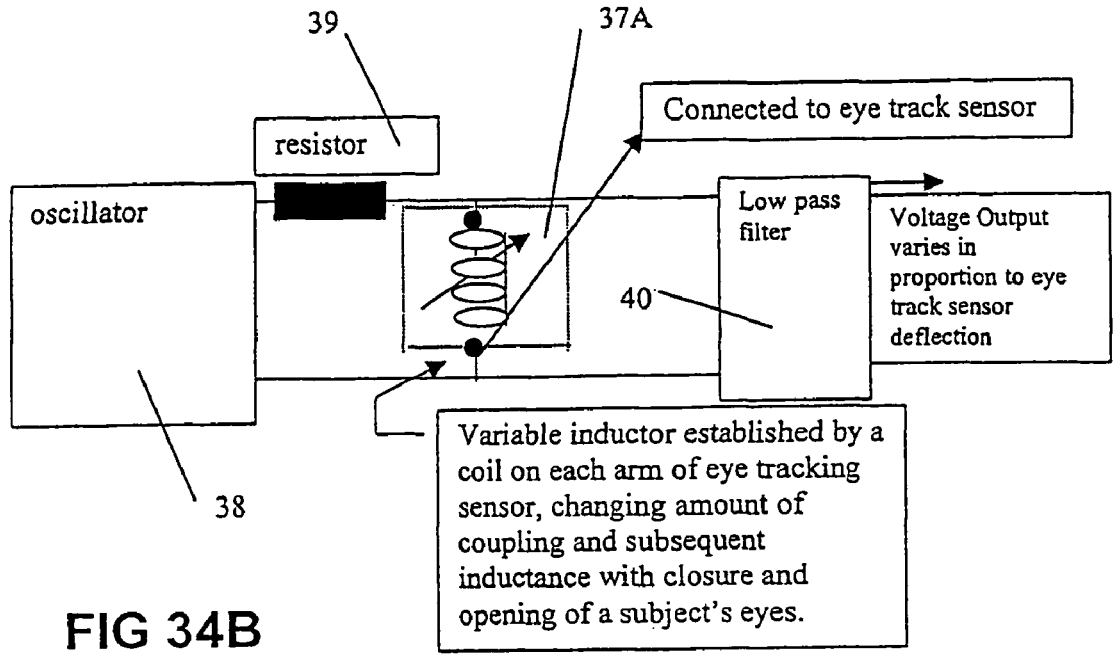
FIGS. 34B and 34C show alternative forms of the electronic interface shown in FIG. 34A.

FIG. 34B shows one form of Electronics Interface wherein the eye track sensor is represented by a variable inductor 37A for tracking eyelid position. Variable inductor 37A is formed with carbon tracks on respective arms 34, 35. Variable inductor 37A includes a coil on each arm 34, 35 arranged such that movement of the arms changes the amount of coupling between the coils and therefore the inductance value of each coil.

The inductance value may be measured in any suitable manner and by any suitable means such as a wien bridge. In one form the inductance value may be measured by a circuit including oscillator 38, resistor 39 and low pass filter 40. The output of low pass filter 40 provides a signal that is indicative of the relative position of arms 34, 35 and hence provides a measure of eye opening. An additional measure of eyelid activity is provided via EOG electrodes 41, 42 at the free ends arms 34,35. Electrodes 41, 42 are connected to suitable monitoring apparatus via respective wires 43, 44.

Figure 34C:
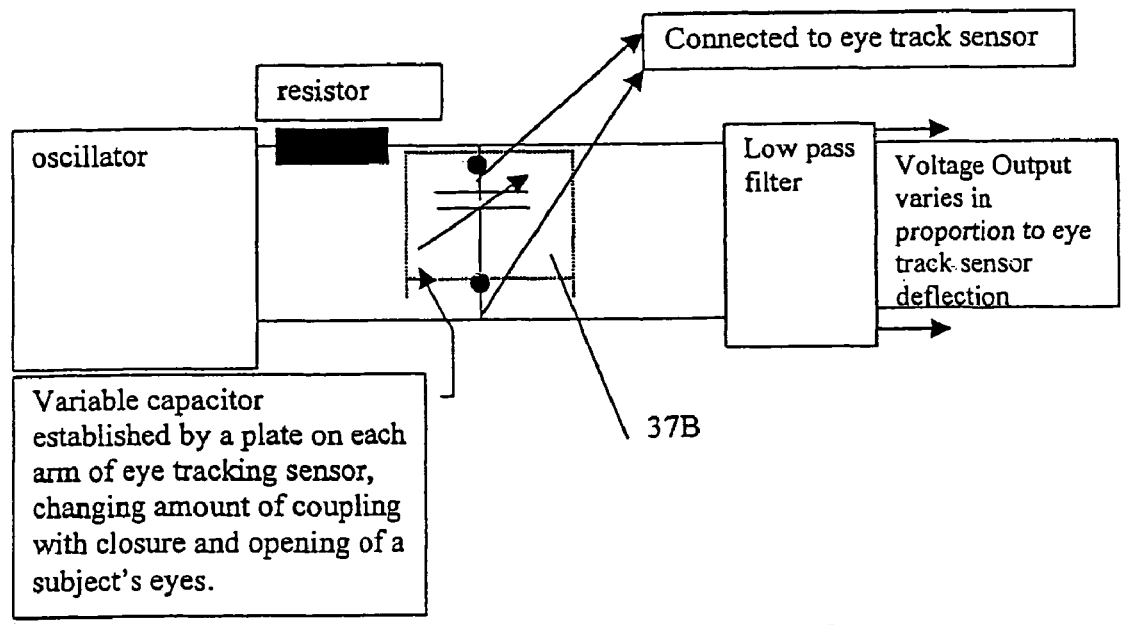

FIG. 34C shows one form of Electronics Interface wherein the eye track sensor is represented by a variable capacitor 37B for tracking eyelid position. The embodiment shown in FIG. 34C is similar to the embodiment of FIG. 34B except that variable capacitor 37B is formed with carbon tracks on the respective arms 34, 35. Variable capacitor 37B includes a capacitor plate on each arm separated by an insulator (dielectric) and is arranged such that movement of the arms changes the amount of coupling between the plates and therefore the capacitance value of the variable capacitor. The capacitance value is measured by the circuit shown in FIG. 37C which is similar to the circuit in FIG. 34B.

Integrated Anaesthesia Monitoring Electrode System (IAMES) Block Diagram—Wireless or Wired Version—refer FIG. 35

FIG. 35 shows one form of electrode system for integrated anaesthesia monitoring. The IAMES system may be applied for each wireless electrodes set. 2 unique components may be utilised, including the Electrode Attachment System (EAS) and the Wireless Electronic System (WES).

Figure 36:
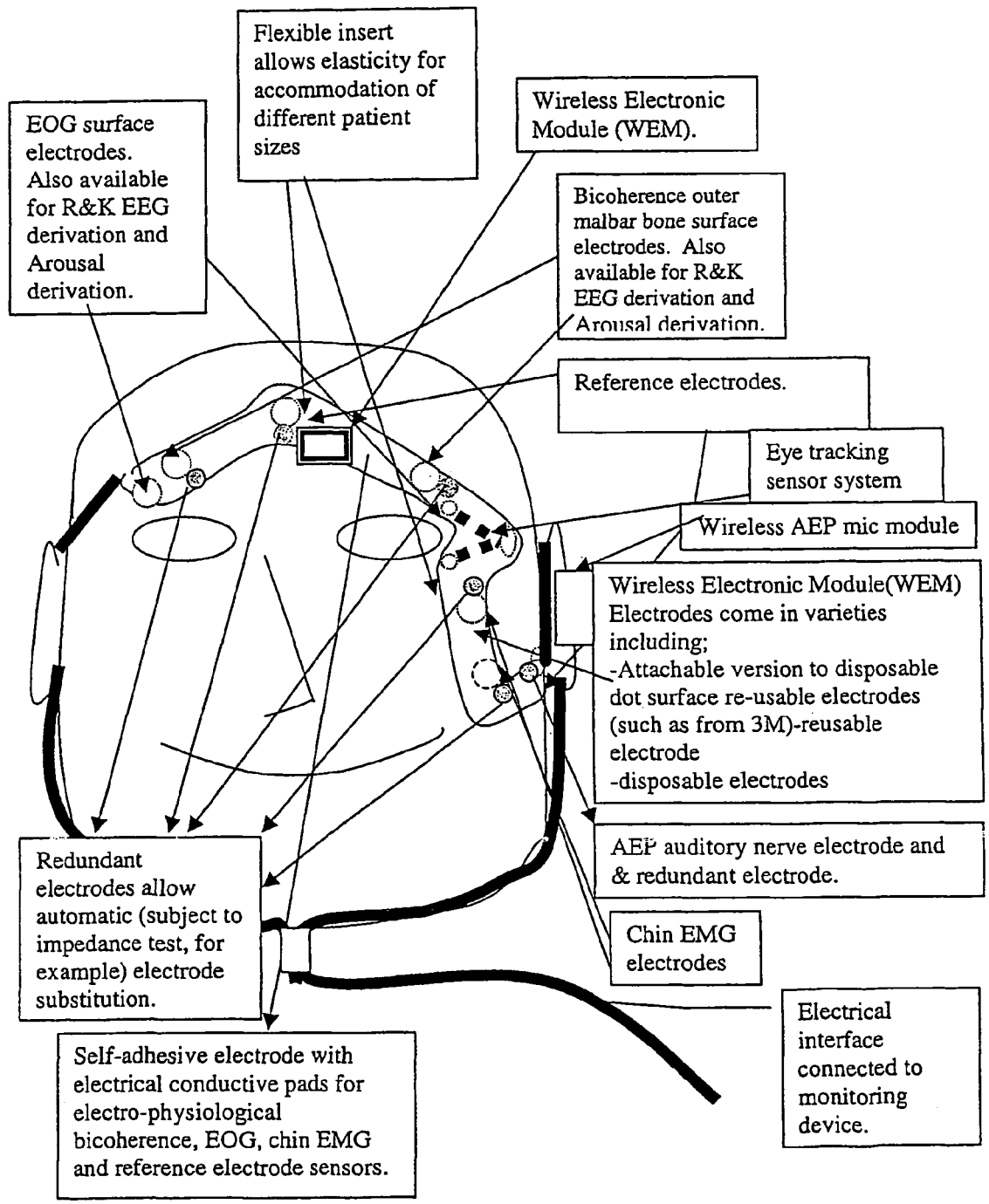
FIG. 36 shows one embodiment of a wire connected sensor device including bi-coherence, EOG, chin EMG and eye opening.

FIG. 36 shows a sample embodiment of a wire connected sensor device including bi-coherence, EOG, chin EMG and Eye Opening.

Figure 37:
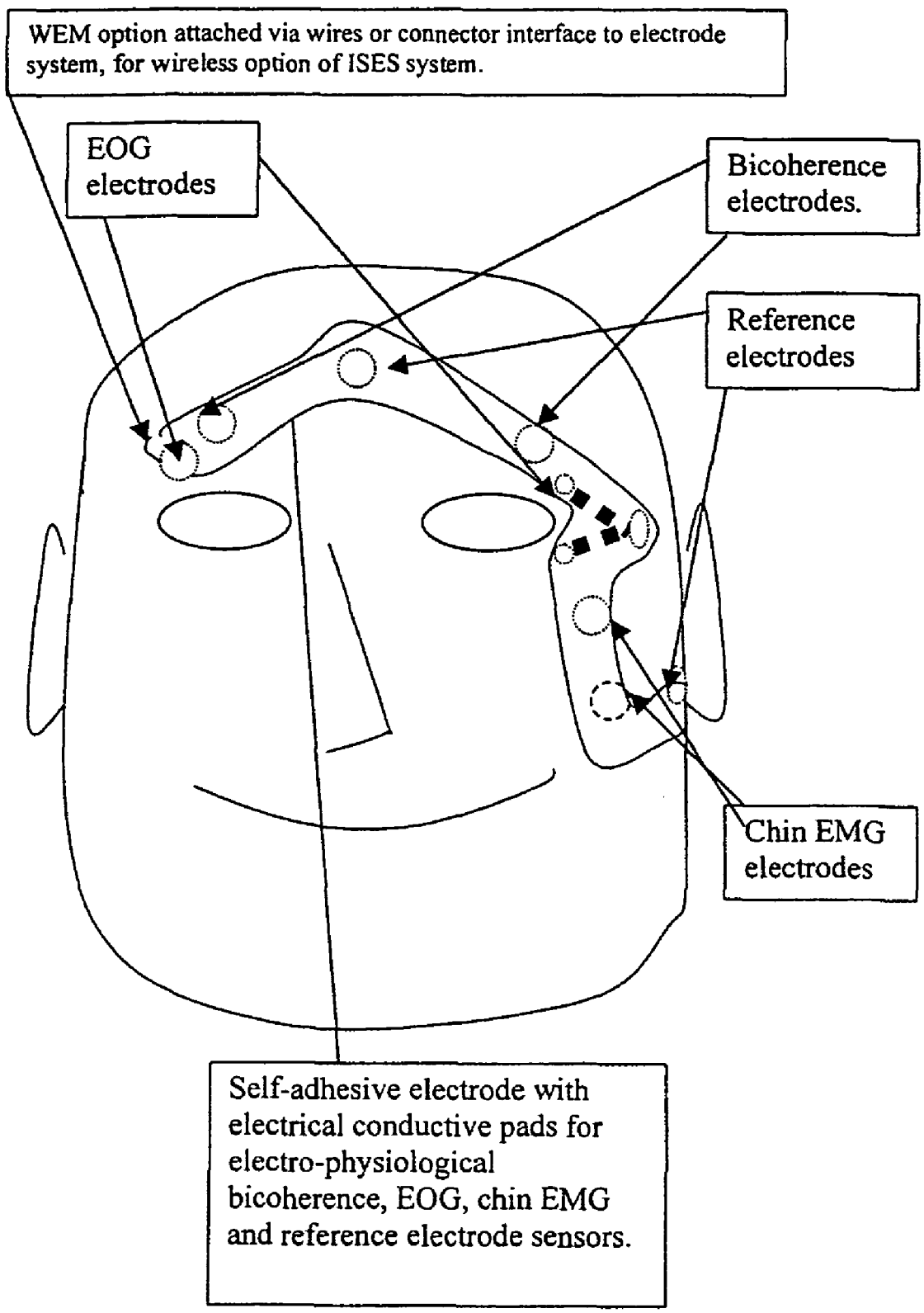
FIG. 37 shows one embodiment of a wireless integrated electrode system including bi-coherence, EOG chin EMG and eye opening.

Integrated Sleep Electrode System (ISES)—refer FIG. 37

Sample of embodiment including bi-coherence, EOG, chin EMG and Eye Opening Wireless Sensor Device.

FIG. 37 shows a sample embodiment of a wireless integrated electrode system including bi-coherence, EOG chin EMG and Eye Opening.

The ISES system may be applied for each wireless electrodes set. 2 unique components may be utilised, including the Electrode Attachment System (EAS) and the Wireless Electronic System (WES).

Note—all above electrode positions may include an optional redundant electrode system to allow automatic electrode switching or exchange where a poor quality or excessively high impedance electrode is detected.

Wireless Electrode Preferred Embodiment (WEPE)—refer FIG. 38

FIG. 38 shows a preferred embodiment of a wireless electrode.

A radio transmitter sends data to a PC within the same room (operating theatre) which analyses EEG and determines depth of anaesthesia.

Transmitter Unit

Battery powered—Maxell rechargeable lithium cell. 3V 65 mAh 3 mm×20 mm diameter ML2033.

Should provide at least 12 hours operation from a single charge, ideally 24 hours—so that it may be used for other applications.

Radio Transmitter
  Prefer use 915 MHz ISM band or 2.4 GHz ISM band.
  Prefer spread spectrum so that signal is less prone to interference than a single carrier frequency.
  Lower power average <65 mA/12.
  Transmission range 10 m.
  Data rate average 256×12=3000 bps min. i.e. 256 samples per second, 12 bits/sample prefer 16 bits/sample.
  Would expect to have much higher Tx data rate but only use low duty cycle to save power.
  Prefer operate at 3V or less.
  Blue tooth has too much protocol overhead to get really low power consumption Data Acquisition
  Done by micro-controller, which also controls radio transmitter. Use 16 bit or 12 bit with differential end—(INA122) or discrete op. amps.
  Spread spectrum transmitters normally have receivers to convey hopping sequence and/or that data has been correctly received.
  Texas Instruments TRF6900 3V single chip radio transceiver.
  Tx 21 mA @ 20 dB attenuation, 37 mA @ 0 dB attenuation.
  Rx 24 mA
  Power down 2 mA
  Using MSP430 micro-controller to perform base band operations and data acquisition.

A system with one master unit may collect acquisition data from up to 12 slaves. Each slave may collect 512 bytes of data per second and transmit this to the master. The whole system may operate at the LIPD (Low Interference Potential Device) ISM band at 915-928 MHz. This is an "unlicensed band" and is subject to the "no interference, no protection" policy. No protection implies that several methods have to be devised to make the whole system as interference-immune as possible.

The main design criteria are listed below in order of importance.
  Minimal current consumption in slave (ideally <2 mA).
  Maximum immunity to interference.
  Small physical size.
  Component lead-time <8-12 weeks.
  System manufacturing cost.

Channel Assignment

The ISM band is located between the GSM mobile and GSM base station band at 915-928 MHz. Channel spacing is decided to be 500 kHz, giving 24 usable channels for the frequency-hopping scheme.

Figure 39:
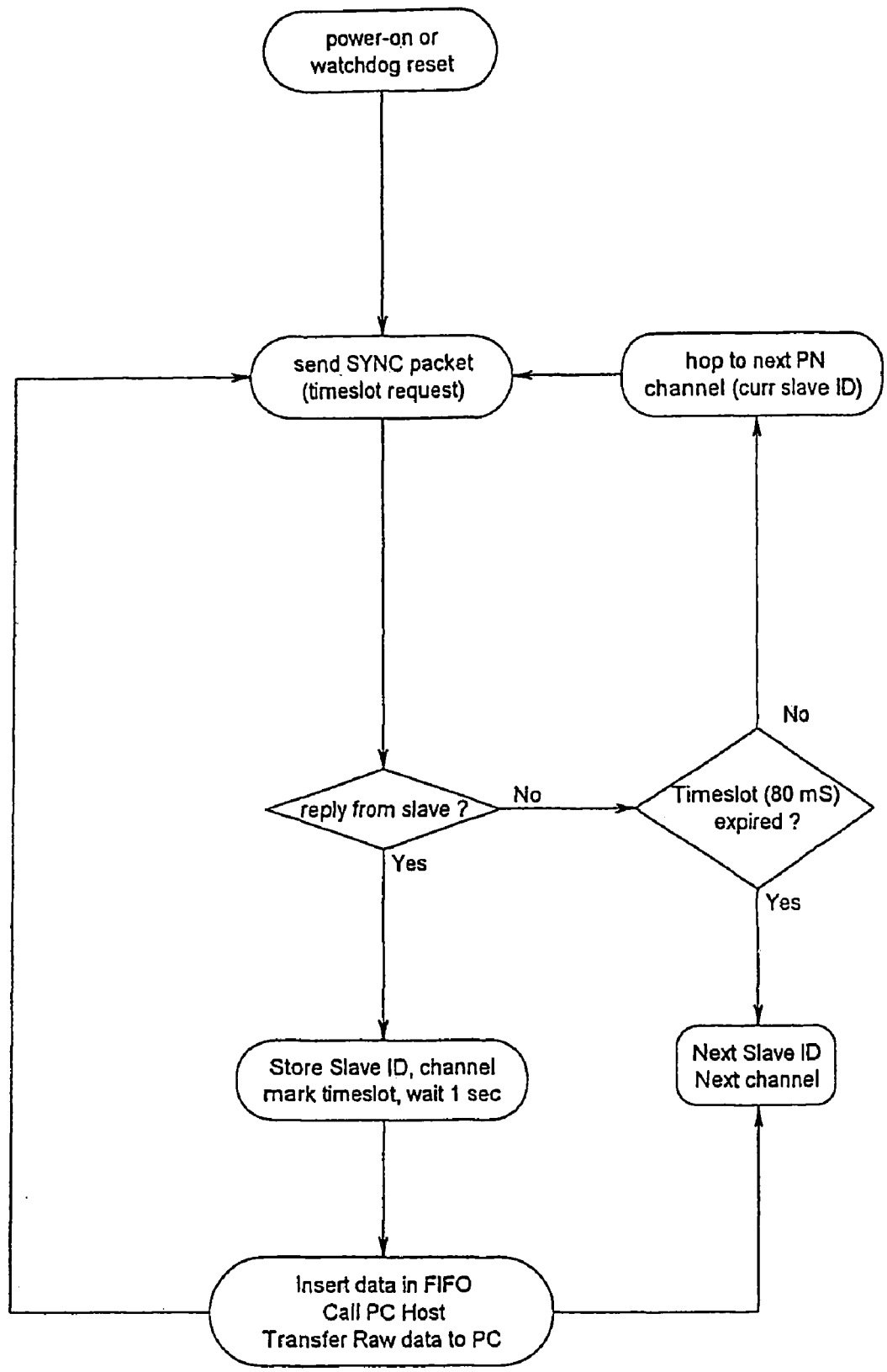
FIG. 39 shows a flow chart of master firmware.

Master Unit—Refer FIG. 39

Current consumption is not an adverse factor on the master unit, so the master will have to control all RF traffic. In each 1-second time slice up to 12 slave transactions of 512 bytes may be made.

Referring to FIG. 39, the following scheme is proposed:

At a data rate of approximately 110 kBps a 512 byte NRZ packet will take 46.5 mS. Timeslots of approx. 70 mS are allocated for each slave, totalling 840 mS. The remaining 160 mS are arbitrary timeslots reserved for retries on unsuccessful slave transfers (up to 2 for each second).

On power-up, the master starts "calling" for slaves using short format packets. During this acquisition process all channels are sequentially scanned to find free channels for each timeslot subsequently assigned to a slave. Each time a slave is found a "time marker" is set in the master indicating which slave needs to be acquired on which channel in the next timeslot (1000 mS later). When a transfer from slave to master is due, the master first sends a synchronisation packet and waits for the relevant slave's acknowledge. If the slave does not reply, the master starts sending sync packets while hopping the channels based on a PN sequence seeded by the current targeted slave's ID. The slave itself also follows the same PN sequence. About 20 retries are allowed for so a new channel can be found for the slave to transfer its 512 byte acquisition packet in case of "jamming".

Once data transfer with one or more slaves starts, a host PC will collect the data via an RS232 interface, possibly incorporating RTS/CTS lines for hardware handshake. Since the MSP430F149 has 2 KB of RAM, it is expected that 1.5 KB will be reserved for the acquisition data, so a 3 level deep "FIFO" can be implemented on the master. This may be useful in case the host PC has say Windows calling it to perform other functions. This implies that the PC host software can have a maximum latency of 2 seconds to collect the data, otherwise an overrun will occur.

Figure 40:
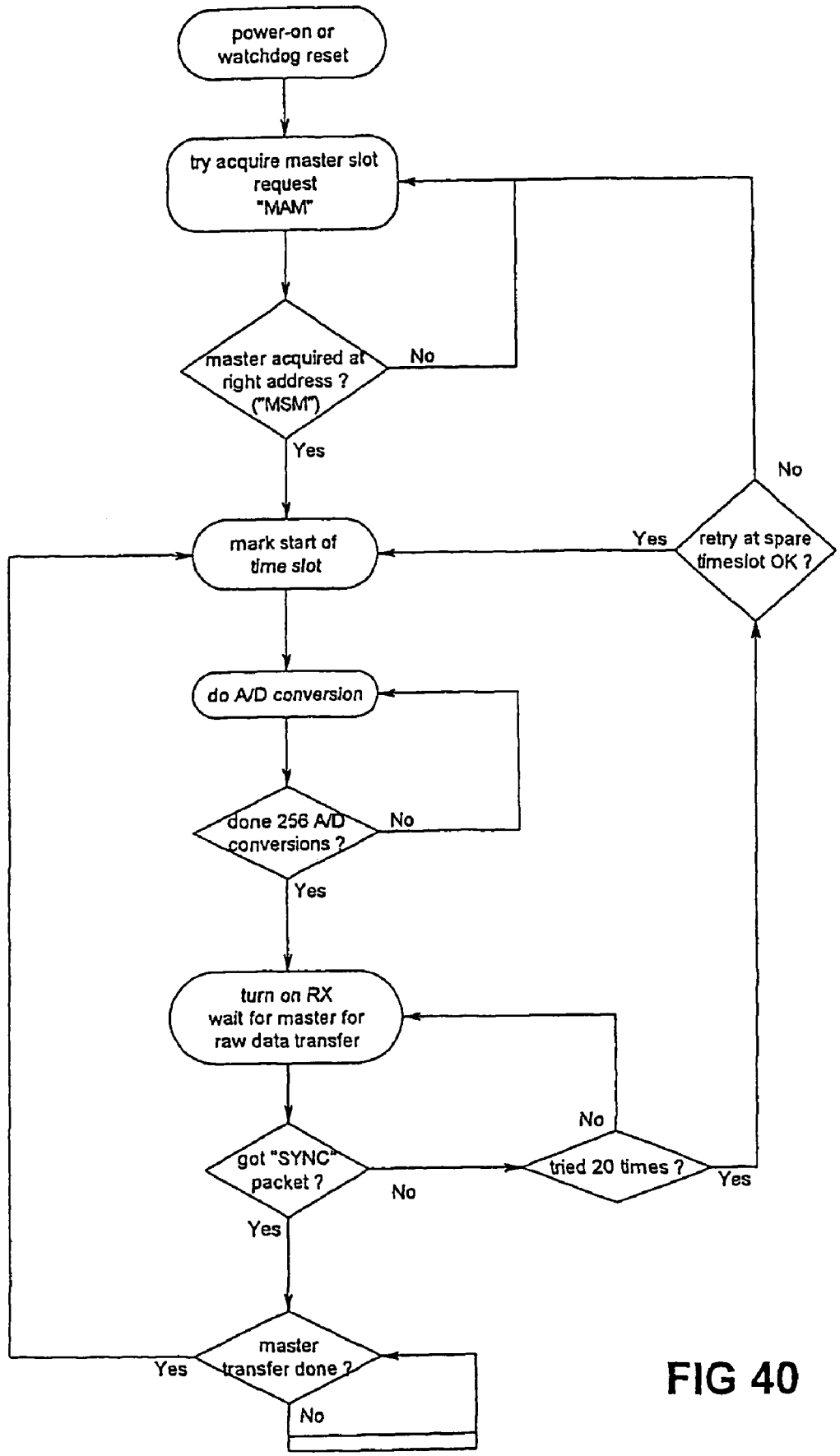
FIG. 40 shows a flow chart of slave firmware.

Slave Unit—Refer FIG. 40

On power-up, the slave goes into receive mode waiting for a master sync packet (Master Acquisition Mode—MAM).

A sync packet will approximately take 1.4 mS, including preamble, frame header, descriptor and CRC (approx. 150 bits)

An arbitrary amount of time is designated for the slave to spend in MAM, say 10 seconds. If a master sync is not acquired, the slave waits for 20 seconds and enters MAM again.

This is to avoid excessive current consumption in case the master is not present or fails during operation of the network.

Once sync is achieved with the master (Master Sync Mode—MSM), the slave starts taking 256 A/D samples with a resolution of 12-16 bits every second. These are stored in a RAM buffer and will be transferred to the master at the end of each 1-second time slice.

The PCB for the slave is intended to be identical to the master's HAN.

The RS232 pads will be used to assign an ID to the slave and store it in Flash.

Slave Current Consumption

The Slave's current consumption is made up of 3 components, namely the continuous current, peak transceiver current component, and peak A/D conversion component and works out to be approx. 1.82 mA. Each retry for a slave in a 1 second time slice incurs an extra 1.74 mA. This is anticipated to be unlikely since 24 channels are available at +5 dBm output.

Continuous Slave Current

The MSP430F149's LFXTAL is running with a 32.768 kHz crystal and clocks the internal Timer A. This Timer has a three-channel Capture/Compare Unit and will be used to interrupt the core at a 256 Hz rate for A/D conversion. This is the continuous component.

Transceiver Peak Current

In each 1-second time slice the TRF6900 will be active for about 50 mS total. The sequence is as follows:
- On wake-up, The XT2 oscillator is started and is allowed start-up (Crystal oscillators typically will start from 5-10 mS), together with the DDS reference.
- The CPU is now turned on and provides ample processor throughput to handle the 110 kBps link and SPI communication with the TRF6900 transceiver block. About 1 mS is needed to set-up the TRF6900 into receive and lock.
- The slave has CPU+TRF6900 activated for approx. 2 mS, assuming good BER and clear channel.
- The TRF6900 is put in TX mode. It is decided to initially output the full output power on the TRF6900. This results in a higher peak current but will ensure minimal BER and therefore retries thereby minimising current.

A/D Conversion Peak Current

The A/D converter has its own RC internal clock and does a conversion in max 4 uS. (12 bit resolution).

Software

The firmware will be written in "C" to allow for clarity and easy expansion. It is worth noting that after production the design can be ported to a MSP430F147 to reduce cost. Further expansion and addition should be made easier by a considerable amount of spare program memory (the F149 has 60 KB Flash memory). The presence of a 1 cycle signed/unsigned 16×16 into 32 bit H/W MAC will be useful for possible future DSP additions like wave filtering.

Hardware

The Slave and Master PCB should be identical and will be implemented on a 4 layer PCB.

Figure 41:
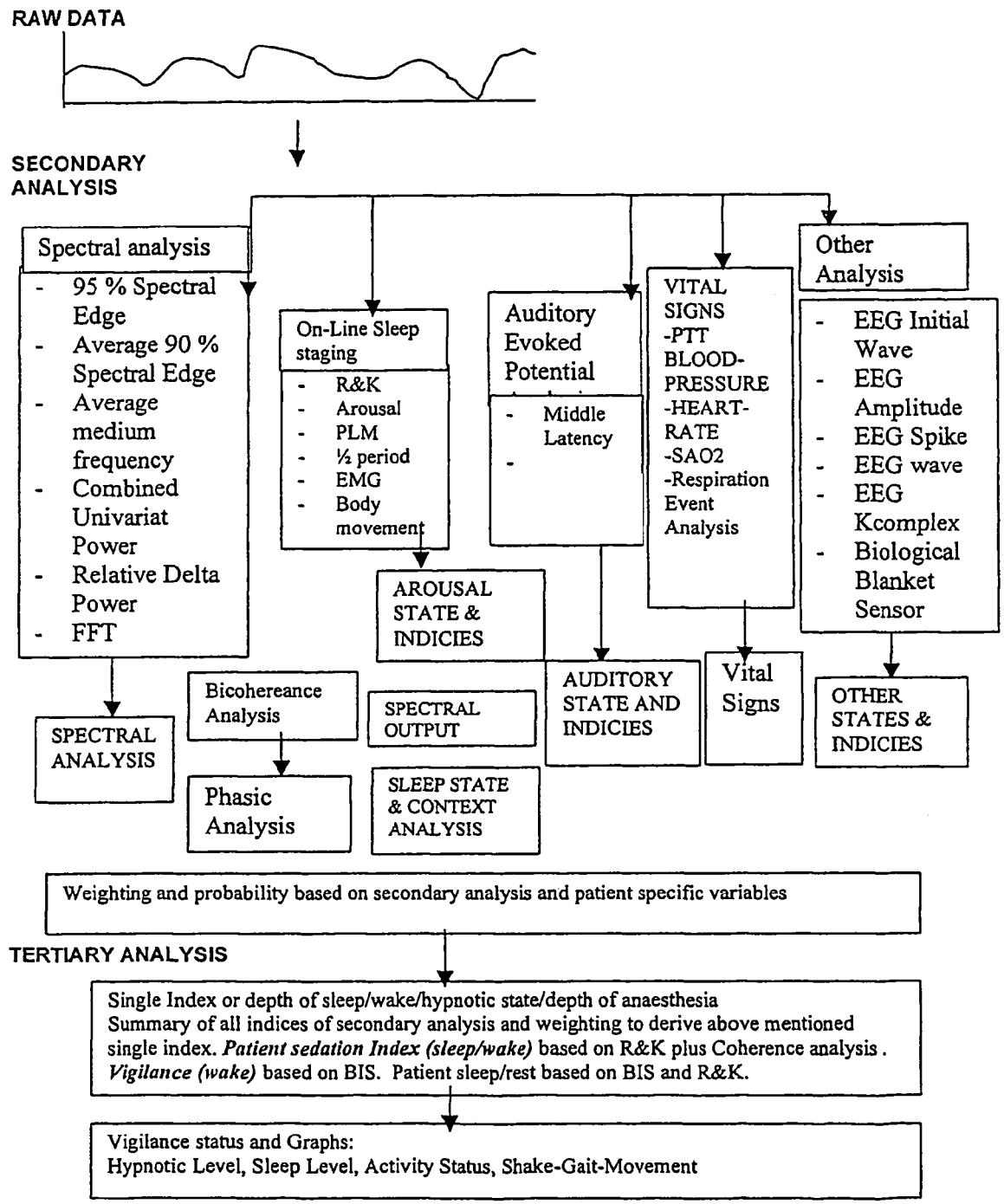
FIG. 41 shows an overview of primary, secondary and tertiary analysis.

Analysis Overview—a Breakdown of Primary, Secondary and Tertiary Analysis—Refer FIG. 41

Figure 42:
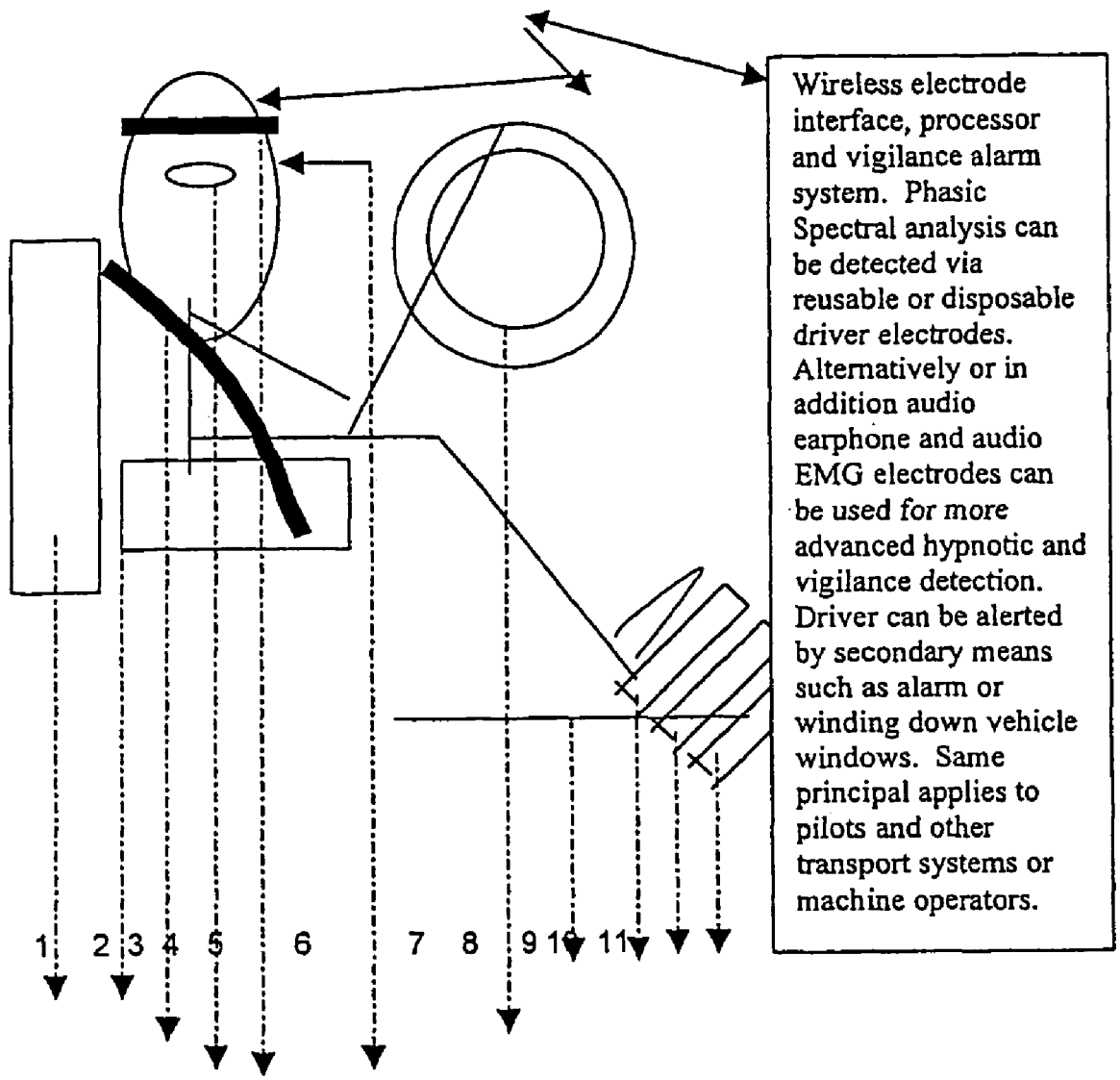
FIG. 42 shows one form of vehicle bicoherence wireless system.

Vehicle Bicoherence Wireless System (VBWS)—Refer FIG. 42—Car Vigilance System

System Hardware Block Diagram

The block diagram in FIG. 42 shows a system consisting of wireless attached electrodes to patient's forehead and wireless interface for electrode signal pick-up and EEG processing, within a driving environment. EEG processing can include coherence spectral analysis and/or Audio Evoked Response.

The VBWS system can be applied for each wireless electrodes set. 2 unique components can be utilised, including the Electrode Attachment System (EAS) and the Wireless Electronic System (WES).

Figure 43:
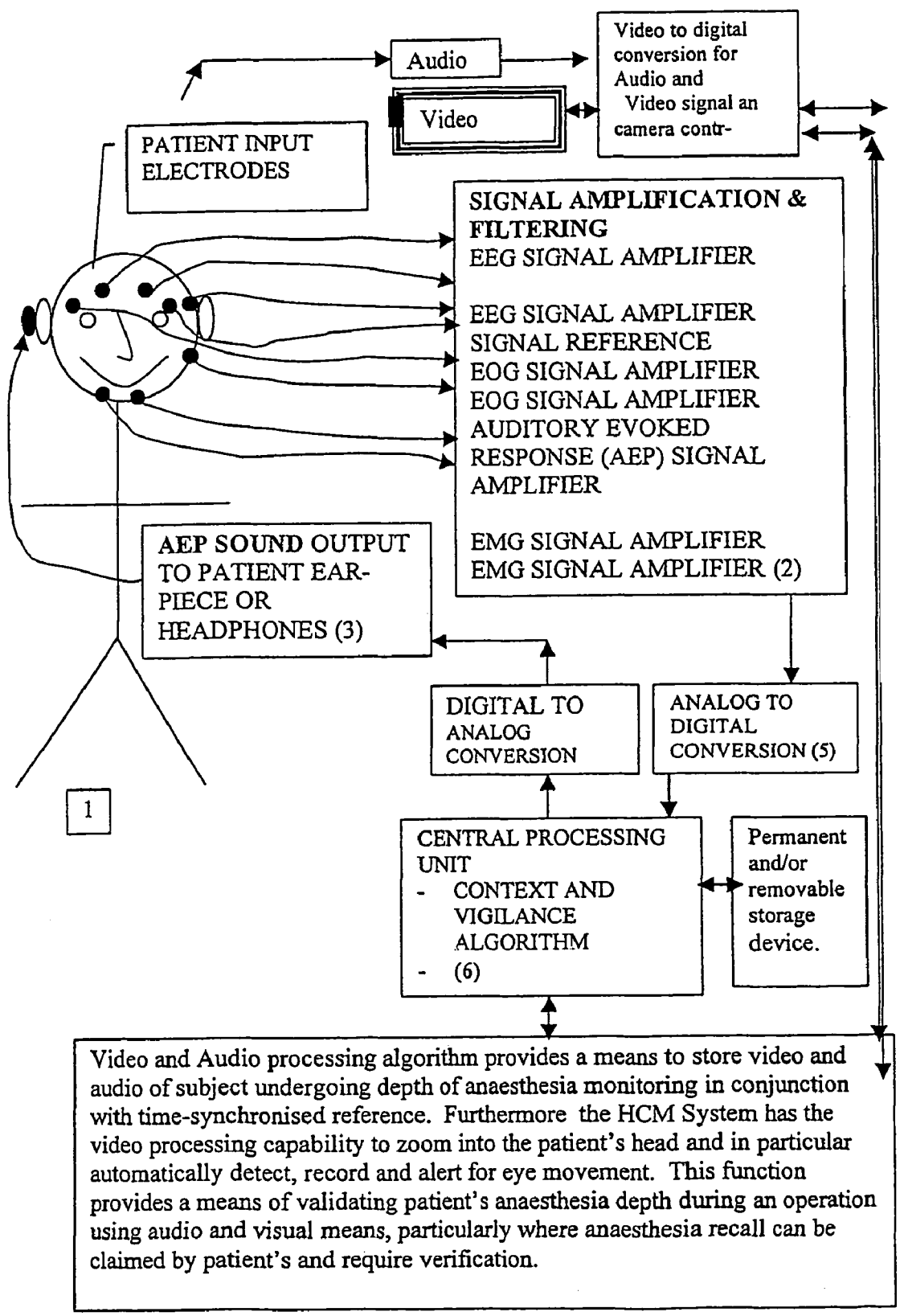
FIG. 43 shows a flow diagram of one form of audio and video apparatus used for validating and replay in an in-depth anaesthesia system.

Audio Visual Flow Diagram (AVF)—Refer FIG. 43

FIG. 43 shows a sample embodiment using synchronized audio and video as a means for in-depth anesthesia system validation and recall apparatus.

The embodiment includes use of bi-phasic and AEP in-depth anaesthesia monitoring system with synchronised video detection and recording capability.

Figure 44:
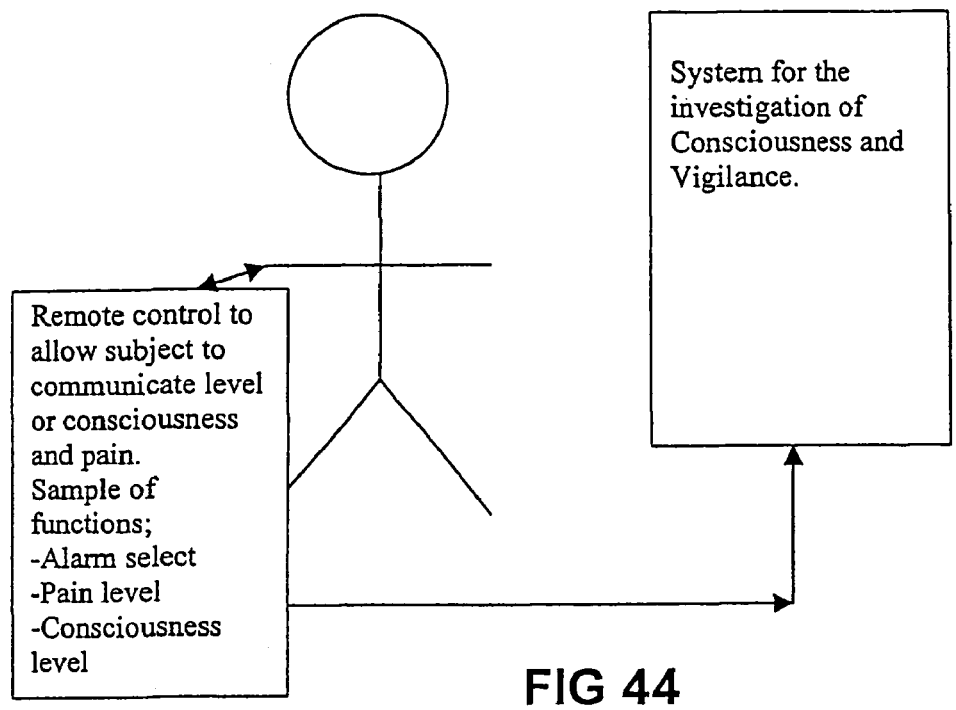
FIG. 44 shows one form of pain level or consciousness level remote indicator.

Pain Level or Consciousness Level Remote Indicator (PLCLRI)—Refer FIG. 44

Pain Level or Consciousness Level Remote Indicator

Figure 45:
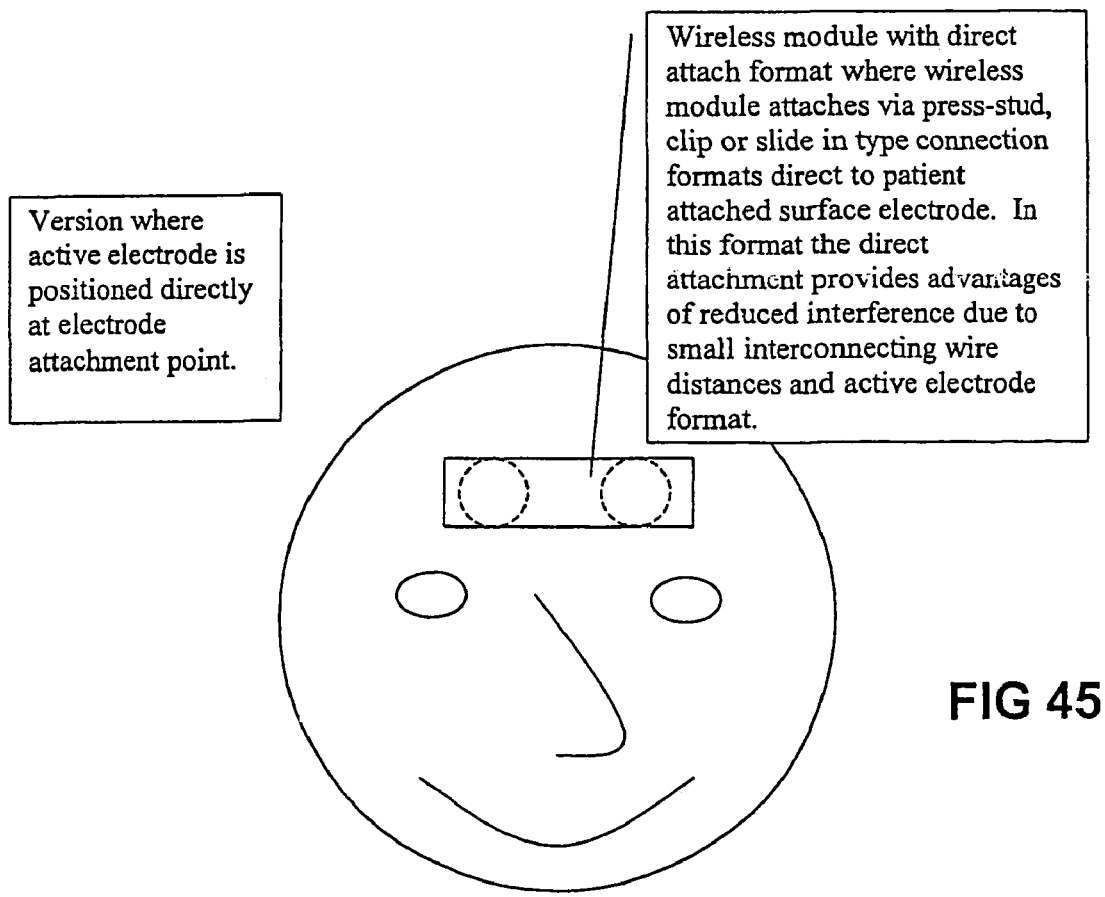
FIG. 45 shows a spread spectrum based wireless, active electrode system.

Spread Spectrum Based Wireless, Active Electrode System (SSBWAES)—Refer FIGS. 45 and 46

Spread Spectrum Based Wireless, Active Electrode System, with redundant electrode substitution, dynamic signal quality verification, impedance verification and calibration.

FIG. 45 shows a direct connected wireless module.

FIG. 46 shows an indirect connected wireless module.

The SSBWAES system may be applied for each wireless electrodes set. 2 unique components may be utilised, including the Electrode Attachment System (EAS) and the Wireless Electronic System (WES).

Example of embodiment of wireless based active electrode system.

Figure 47:
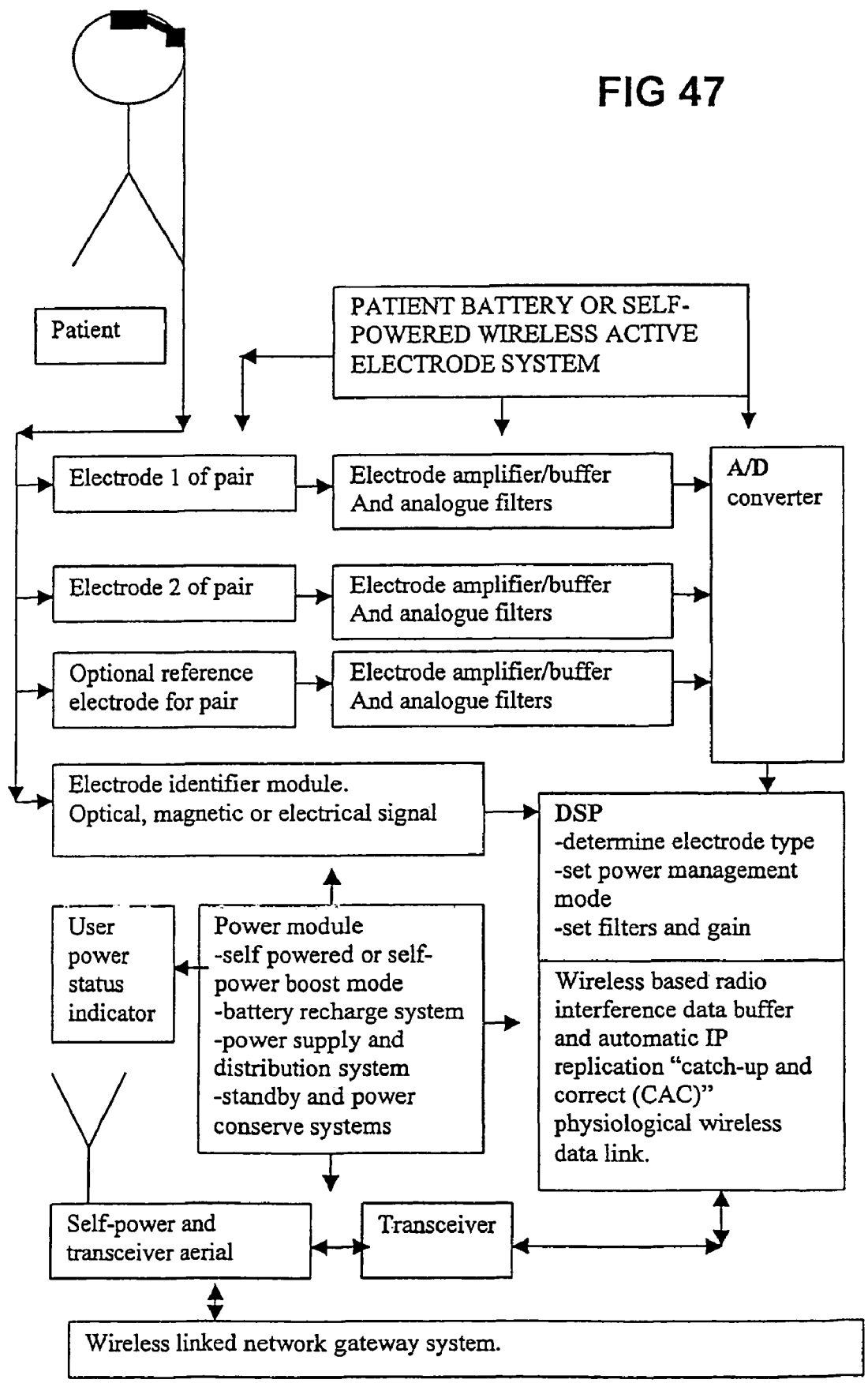
FIG. 47 shows one embodiment of a wireless based active electrode system.

FIG. 47 shows one embodiment of a wireless based active electrode system.

Figure 48:
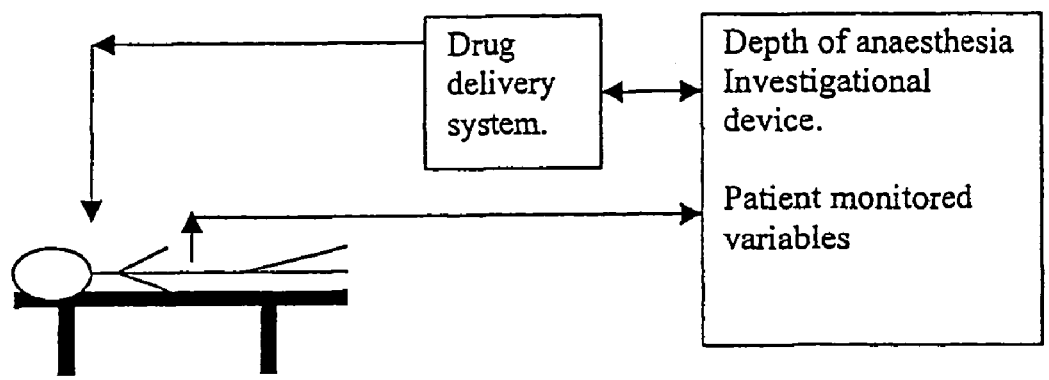
FIG. 48 shows a drug delivery system linked to a consciousness monitoring device.

Biofeedback Controlled Drug Delivery System Linked to Consciousness Monitoring Investigational Device (BCDDSLCIG)—Refer FIG. 48

FIG. 48 shows a drug delivery system linked to a consciousness-monitoring device.

Finally, it is to be understood that various alterations, modifications and/or additions may be introduced into the constructions and arrangements of parts previously described without departing from the spirit or ambit of the invention.

APPENDIX I

References Adjoining Patent Application

The HCM system utilises a range of different parameters, which allow the user to establish a library or range of patient input variables, a range of different secondary analysis and a range of different weighting and summary tertiary analysis as the means to determine the depth of anaesthesia for a particular subject. The following studies demonstrate that the use of a simple or single dimension or measure for depth of anaesthesia, while desirable, is not practical with such a complex physiological state and change of state:

1.

Barr G, Anderson R E, Samuelsson S, Owall A, Jakobsson J G, described in British Journal of Anaesthesia June 2000, PMID: 10895750, UI: 20354305 "Fentanyl and midazolam anaesthesia for coronary bypass surgery: a clinical study of bi-spectral electroencephalogram analysis, drug concentrations and recall." In this study, Barr and colleagues describe: "Bi-spectral index (BIS) was assessed as a monitor of depth of anaesthesia during fentanyl and midazolam anaesthesia for coronary bypass surgery." "BIS decreased during anaesthesia, but varied considerably during surgery (range 36-91) with eight patients having values >60. Midazolam and fentanyl drug concentrations did not correlate with BIS. No patient reported explicit or implicit recall. During clinically adequate anaesthesia with midazolam and fentanyl BIS varies considerably. The most likely reason is that BIS is not an accurate measure of the depth of anaesthesia when using this combination of agents."

2.
Schraag S, Bothner U, Gajraj R, Kenny G N, Georgieff M, described in Anesth Analg April 2000, PMID: 10553858, UI: 20019286 "The performance of electroencephalogram bi-spectral index and auditory evoked potential index to predict loss of consciousness during propofol infusion." In this study, Schraag and colleagues describe: "The bi-spectral index (BIS) of the electroencephalogram and middle latency auditory evoked potentials are likely candidates to measure the level of unconsciousness and, thus, may improve the early recovery profile." "The electroencephalogram BIS and the auditory evoked potential index (AEPi), a mathematical derivative of the morphology of the auditory evoked potential waveform, were recorded simultaneously in all patients during repeated transitions from consciousness to unconsciousness." "We conclude that both the BIS and AEP are reliable means for monitoring the level of unconsciousness during propofol infusion. However, AEPi proved to offer more discriminatory power in the individual patient. IMPLICATIONS: Both the bi-spectral index of the electroencephalogram and the auditory evoked potentials index are good predictors of the level of sedation and unconsciousness during propofol infusion. However, the auditory evoked potentials index offers better discriminatory power in describing the transition from the conscious to the unconscious state in the individual patient."

3.
Gajraj R J, Doi M, Mantzaridis H, Kenny G N, described in British Journal of Anaesthesia May 1999, PMID: 10536541, UI: 20006623 "Comparison of bi-spectral EEG analysis and auditory evoked potentials for monitoring depth of anaesthesia during propofol anaesthesia." In this study, Gajraj & colleagues describe: "We have compared the auditory evoked potential index (AEP Index) and bi-spectral index (BIS) for monitoring depth of anaesthesia in spontaneously breathing surgical patients." "The average awake values of AEP Index were significantly higher than all average values during unconsciousness but this was not the case for BIS. BIS increased gradually during emergence from anaesthesia and may therefore be able to predict recovery of consciousness at the end of anaesthesia. AEPIndex was more able to detect the transition from unconsciousness to consciousness."

4.
Gajraj R J, Doi M, Mantzaridis H, Kenny G N, described in Br J Anaesth January 1998, PMID: 9505777, UI: 98166676 "Analysis of the EEG bispectrum, auditory evoked potentials and the EEG power spectrum during repeated transitions from consciousness to unconsciousness." In this study, Gajraj & colleagues describe: "We have compared the auditory evoked potential (AEP) index (a numerical index derived from the AEP), 95% spectral edge frequency (SEF), median frequency (MF) and the bi-spectral index (BIS) during alternating periods of consciousness and unconsciousness produced by target-controlled infusions of propofol." "Our findings suggest that of the four electrophysiological variables, AEP index was best at distinguishing the transition from unconsciousness to consciousness."

5.
Witte H, Putsche P, Eiselt M, Hoffmann K, Schack B, Arnold M, Jager H, described in: Neurosci Lett November 1997, PMID: 9406765, UI: 98068600 "Analysis of the interrelations between a low-frequency and a high-frequency signal component in human neonatal EEG during quiet sleep." In this study, Witte and colleagues describe: "It can be shown that dominant rhythmic signal components of neonatal EEG burst patterns (discontinuous EEG in quiet sleep) are characterised by a quadratic phase coupling (bi-spectral analysis). A so-called 'initial wave' (narrow band rhythm within a frequency range of 3-12 Hz) can be demonstrated within the first part of the burst pattern. The detection of this signal component and of the phase coupling is more successful in the frontal region. By means of amplitude demodulation of the 'initial wave' and a subsequent coherence analysis the phase coupling can be attributed to an amplitude modulation, i.e. the envelope curve of the 'initial wave' shows for a distinct period of time the same qualitative course as the signal trace of a 'lower' frequency component (0.75-3 Hz)."

6.
Schneider G, Sebel P S, described in Eur J Anaesthesiol Suppl May 1997, PMID: 9202934, UI: 97346517 "Monitoring depth of anaesthesia". In this study, Schneider & Sebel describe: "In clinical practice, indirect and non-specific signs are used for monitoring anaesthetic adequacy. These include haemodynamic, respiratory, muscular and autonomic signs. These measures do not indicate adequacy of anaesthesia in a reliable manner." "EEG information can be reduced, condensed and simplified, leading to single numbers (spectral edge frequency and median frequency). These methods appear insufficient for assessing anaesthetic adequacy. The bi-spectral index, derived from bi-spectral analysis of the EEG, is a very promising tool for measuring adequacy of anaesthesia. An alternative approach is to monitor evoked potentials. Middle latency auditory evoked potentials may be helpful in assessing anaesthetic adequacy. Both techniques need further validation."

The following studies indicate the use of BIS as a strong indicator of depth of anaesthesia and accordingly the HCM System utilises BIS as one of the indices for in-depth anaesthesia but provides multiple concurrent indices to ensure that the user is able to ultimately provide an informed decision on the depth of a patient's anaesthesia as opposed only the reliance of one indicator:

7.
Sandler N A, Sparks B S, described in J Oral Maxillofac Surg April 2000, PMID: 10759114, UI: 20220864 "The use of bi-spectral analysis in patients undergoing intravenous sedation for third molar extractions." In this study, Sandler describes: "The Observer's Assessment of Alertness and Sedation (OAA/S) scale was used to subjectively assess the level of sedation observed by the anaesthetist before initiating the sedation procedure and then at 5-minute intervals until the end of the procedure. The BIS level was simultaneously recorded." "The time and dose of the drug given were recorded. The level of sedation based on a single anaesthetist's interpretation (OAA/S) and the BIS readings were then compared. RESULTS: A strong positive relationship between the BIS index and OAA/S readings was found (P<0.0001)." "CONCLUSION: BIS technology offers an objective, ordinal means of assessing the depth of sedation. There was a strong relationship between the objective BIS values and subjective assessment (OAA/S scale) of the depth of anaesthesia. This can be invaluable in providing an objective assessment of sedation in oral and maxillofacial surgery where it may be difficult to determine the level of sedation clinically."

8.

Denman W T, Swanson E L, Rosow D, Ezbicki K, Connors P D, Rosow C E, described in Anesth Analg April 2000, PMID: 10735791, UI: 20200014 "Pediatric evaluation of the bi-spectral index (BIS) monitor and correlation of BIS with end-tidal sevoflurane concentration in infants and children." In this study, Denman & colleagues describe: "The bispectral index (BIS) has been developed in adults and correlates well with clinical hypnotic effects of anesthetics. We investigated whether BIS reflects clinical markers of hypnosis and demonstrates agent dose-responsiveness in infants and children." "BIS correlated with clinical indicators of anesthesia in children as it did in adults: as depth of anesthesia increased, BIS diminished. BIS correlated with sevoflurane concentration in infants and children." "The use of bispectral index (BIS) during general anesthesia improves the titration of anesthetics in adults."

9.

Hirota K, Matsunami K, Kudo T, Ishihara H, Matsuki A, described in Eur J Anaesthesiol August 1999, PMID: 10500939, UI: 99430726 "Relation between bispectral index and plasma catecholamines after oral diazepam premedication." In this study, Hirota and colleagues describe: "Venous blood samples (6 mL) were collected in the case of patients in group D(+) for the measurement of plasma catecholamines levels using high-performance liquid chromatography. The bispectral index level (mean+/− SD) in group D(+): 93.5+/−773.5 was significantly lower than that in group D(−): 96.1+/−1.8 (P<0.05). There was a significant correlation between bispectral index and plasma norepinephrine levels (r=0.567, P<0.05). study suggests that the bispectral index monitor may detect the effect of oral diazepam premedication."

10.

Muthuswamy J, Roy R J, described in IEEE Trans Biomed Eng March 1999, PMID: 10097464, UI: 99197537 "The use of fuzzy integrals and bispectral analysis of the electroencephalogram to predict movement under anesthesia." In this study, Muthuswamy and Roy describe: "The objective of this study was to design and evaluate a methodology for estimating the depth of anesthesia in a canine model that integrates electroencephalogram (EEG)-derived autoregressive (AR) parameters, hemodynamic parameters, and the alveolar anesthetic concentration." "Since the anesthetic dose versus depth of anesthesia curve is highly nonlinear, a neural network (NN) was chosen as the basic estimator and a multiple NN approach was conceived which took hemodynamic parameters, EEG derived parameters, and anesthetic concentration as input feature vectors. Since the estimation of the depth of anesthesia involves cognitive as well as statistical uncertainties, a fuzzy integral was used to integrate the individual estimates of the various networks and to arrive at the final estimate of the depth of anesthesia." "The fuzzy integral of the individual NN estimates (when tested on 43 feature vectors from seven of the nine test experiments) classified 40 (93%) of them correctly, offering a substantial improvement over the individual NN estimates."

11.

Muthuswamy J, Sherman D L, Thakor N V, described in IEEE Trans Biomed Eng January 1999, PMID: 9919830, UI: 99118483 "Higher-order spectral analysis of burst patterns in EEG." In this study, Muthuswamy & Colleagues describe: "We study power spectral parameters and bispectral parameters of the EEG at baseline, during early recovery from an asphyxic arrest (EEG burst patterns) and during late recovery after EEG evolves into a more continuous activity. The bicoherence indexes, which indicate the degree of phase coupling between two frequency components of a signal, are significantly higher within the delta-theta band of the EEG bursts than in the baseline or late recovery waveforms. The bispectral parameters show a more detectable trend than the power spectral parameters." "The bicoherence indexes and the diagonal elements of the polyspectrum strongly indicate the presence of nonlinearities of order two and in many cases higher, in the EEG generator during episodes of bursting. This indication of nonlinearity in EEG signals provides a novel quantitative measure of brain's response to injury."

12.

Lipton J M, Dabke K P, Alison J F, Cheng H, Yates L, Brown T I, described in: Australas Phys Eng Sci Med March 1998, PMID: 9633147, UI: 98296803 "Use of the bispectrum to analyse properties of the human electrocardiograph." In this study, Lipton & colleagues describe: "The bispectrum and bicoherence spectrum have been shown to be powerful techniques for identifying different types of nonlinear system responses. This paper presents an introduction to bispectral techniques applied to biomedical signals and examines the bispectral properties of the human electrocardiograph (ECG). The bispectrum proves to be an effective tool for representing and distinguishing different ECG response types. Bispectral ECG analysis is non-invasive and may prove to be a useful discriminant diagnostic."

13.

Hall J D, Lockwood G G, described in Br J Anaesth March 1998, PMID: 9623435, UI: 98286638 "Bispectral index: comparison of two montages." In this study, Hall & Lockwood describe: "We have compared fronto-central and bifrontal montages using a new EEG monitor, the Aspect A-1000. The monitor uses bispectral analysis to derive an index of anaesthetic depth, the bispectral index (BIS)." "ECG electrodes placed in a bifrontal montage were more reliable than silver dome electrodes in a fronto-central montage and both types of electrodes had impedances in the clinically useful range. However, BIS values derived from each montage were found to differ in an unpredictable manner." "We conclude that the BIS may be useful for following trends in anaesthetic depth in individual cases but it is less helpful when making comparison between patients or as a single value."

14.

Struys M, Versichelen L, Byttebier G, Mortier E, Moerman A, Rolly G, described in Anaesthesia January 1998, PMID: 9505735, UI: 98166634 "Clinical usefulness of the bispectral index for titrating propofol target effect-site concentration." In this study, Struys and colleagues describe: "A greater percentage of bispectral index readings lying outside the target range (i.e. <40 or >60) and more movement at incision and during maintenance were found in Group 1. There was a trend towards more implicit awareness in patients in Group 1." "Propofol dosage could not be decreased but a more consistent level of sedation could be maintained due to a more satisfactory titration of target effect-site concentration."

15.
Kearse L A Jr, Rosow C, Zaslavsky A, Connors P, Dershwitz M, Denman W, described in Anaesthesia January 1998, PMID: 9447852, UI: 98107541 "Bispectral analysis of the electroencephalogram predicts conscious processing of information during propofol sedation and hypnosis." In this study, Kearse & colleagues describe: "BACKGROUND: The bispectral index (BIS) measures changes in the interfrequency coupling of the electroencephalogram (EEG). The purposes of this study were (1) to determine whether BIS correlates with responses to command during sedation and hypnosis induced by propofol or propofol and nitrous oxide, and (2) to compare BIS to targeted and measured concentrations of propofol in predicting participants' responses to commands." "CONCLUSIONS: Bispectral index accurately predicts response to verbal commands during sedation and hypnosis with propofol or propofol plus nitrous oxide. Accuracy is maintained in situations likely to be encountered during clinical use: when propofol concentrations are increasing or decreasing and when repeated measurements are made over time".

16.
Glass P S, Bloom M, Kearse L, Rosow C, Sebel P, Manberg P, described in Anesthesiology April 1997, PMID: 9105228, UI: 97259091 "Bispectral analysis measures sedation and memory effects of propofol, midazolam, isoflurane, and alfentanil in healthy volunteers." In this study, Glass & colleagues describe: "At each pseudo-steady-state drug concentration, a BIS score was recorded, the participant was shown either a picture or given a word to recall, an arterial blood sample was obtained for subsequent analysis of drug concentration, and the participant was evaluated for level of sedation as determined by the responsiveness portion of the observers assessment of the alertness/sedation scale (OAAS). An OAAS score of 2 or less was considered unconscious. The BIS (version 2.5) score was recorded in real-time and the BIS (version 3.0) was subsequently derived off-line from the recorded raw EEG data." "CONCLUSIONS: The BIS both correlated well with the level of responsiveness and provided an excellent prediction of the loss of consciousness. These results imply that BIS may be a valuable monitor of the level of sedation and loss of consciousness for propofol, midazolam, and isoflurane."

17.
Sebel P S, Lang E, Rampil I J, White P F, Cork R, Jopling M, Smith N T, Glass P S, Manberg P, described in Anesth Analg April 1997, PMID: 9085977, UI: 97240517 "A multicenter study of bispectral electroencephalogram analysis for monitoring anesthetic effect." In this study, Sebel & colleagues describe: "Bispectral analysis (BIS) of the electroencephalogram (EEG) has been shown in retrospective studies to predict whether patients will move in response to skin incision." "EEG was continuously recorded via an Aspect B-500 monitor and BIS was calculated in real time from bilateral frontocentral channels displayed on the monitor." "Therefore, the adjunctive use of opioid analgesics confounds the use of BIS as a measure of anesthetic adequacy when movement response to skin incision is used as the primary end point."

18.
Muthuswamy J, Sharma A, described in J Clin Monit September 1996, PMID: 8934342, UI: 97088404 "A study of electroencephalographic descriptors and end-tidal concentration in estimating depth of anesthesia." In this study, Muthuswamy and Sharma describe: "OBJECTIVE: To study the usefulness of three electro-encephalographic descriptors, the average median frequency, the average 90% spectral edge frequency, and a bispectral variable were used with the anesthetic concentrations in estimating the depth of anesthesia. METHODS: Four channels of raw EEG data were collected from seven mongrel dogs in nine separate experiments under different levels of halothane anesthesia and nitrous oxide in oxygen." "CONCLUSIONS: The bispectral variable seems to reduce the non-linearity in the boundary separating the class of non-responders from the class of responders. Consequently, the neural network based on the bispectral variable is less complex than the neural network that uses a power spectral variable as one of its inputs."

19.
Shils J L, Litt M, Skolnick B E, Stecker M M, described in Electroencephalogram Clin Neurophysiol February 1996, PMID: 8598171, UI: 96173435 "Bispectral analysis of visual interactions in humans." In this study, Shils & colleagues describe: "We used non-linear spectral analysis, in particular the bispectrum, to study interactions between the electrocerebral activity resulting from stimulation of the left and right visual fields. The stimulus consisted of two squares, one in each visual field, flickering at different frequencies. Bispectra, bichoherence and biphase were calculated for 8 subjects monocularly observing a visual stimulus." "These results illustrate how bispectral analysis can be a powerful tool in analyzing the connectivity of neural networks in complex systems. It allows different neuronal systems to be labeled with stimuli at specific frequencies, whose connections can be traced using frequency analysis of the scalp EEG."

20.
Leslie K, Sessler D I, Schroeder M, Walters K, described in Anesth Analg December 1995, PMID: 7486115, UI: 96079788 "Propofol blood concentration and the Bispectral Index predict suppression of learning during propofol/epidural anesthesia in volunteers." In this study, Leslie & colleagues describe: "Propofol is often used for sedation during regional anesthesia. We tested the hypothesis that propofol blood concentration, the Bispectral Index and the 95% spectral edge frequency predict suppression of learning during propofol/epidural anesthesia in volunteers. In addition, we tested the hypothesis that the Bispectral Index is linearly related to propofol blood concentration." "The Bispectral Index value when learning was suppressed by 50% was 91+/−1. In contrast, the 95% spectral edge frequency did not correlate well with learning. The Bispectral Index decreased linearly as propofol blood concentration increased (Bispectral Index=−7.4.[propofol]+90; r2=0.47, n=278). There was no significant correlation between the 95% spectral edge frequency and propofol concentration. In order to suppress learning, propofol blood concentrations reported to produce amnesia may be targeted. Alternatively, the Bispectral Index may be used to predict anesthetic effect during propofol sedation."

21.
Sebel P S, Bowles S M, Saini V, Chamoun N, described in J Clin Monit March 1995, PMID: 7760092, UI: 95280046 "EEG bispectrum predicts movement during thiopental/isoflurane anesthesia." In this study, Sebel & colleagues describe: "OBJECTIVE. The objective of our study was to test the efficacy of the bispectral index (BIS) compared with spectral edge frequency (SEF), relative delta power, median frequency, and a combined univariate power spectral derivative in predicting movement to incision during isoflurane/oxygen anesthesia." "CONCLUSIONS. When bispectral analysis of the EEG was used to develop a retrospectively determined index, there was an association of the index with movement. Thus, it may be a useful predictor of whether patients will move in response to skin incision during anesthesia with isoflurane/oxygen."

22.

Kearse L A Jr, Manberg P, Chamoun N, deBros F, Zaslavsky A, described in Anesthesiology December 1994, PMID: 7992904, UI: 95085072 "Bispectral analysis of the electroencephalogram correlates with patient movement to skin incision during propofol/nitrous oxide anesthesia." In this study, Kearse & colleagues describe: "BACKGROUND: Bispectral analysis is a signal-processing technique that determines the harmonic and phase relations among the various frequencies in the electroencephalogram. Our purpose was to compare the accuracy of a bispectral descriptor, the bispectral index, with that of three power spectral variables (95% spectral edge, median frequency, and relative delta power) in predicting patient movement in response to skin incision during propofol-nitrous oxide anesthesia." "CONCLUSIONS: The bispectral index of the electroencephalogram is a more accurate predictor of patient movement in response to skin incision during propofol-nitrous oxide anesthesia than are standard power spectrum parameters or plasma propofol concentrations."

23.

Sigl J C, Chamoun N G, described in J Clin Monit November 1994, PMID: 7836975, UI: 95138762 "An introduction to bispectral analysis for the electroencephalogram." In this study, Sigl and Chamoun describe: "The goal of much effort in recent years has been to provide a simplified interpretation of the electroencephalogram (EEG) for a variety of applications, including the diagnosis of neurological disorders and the intraoperative monitoring of anesthetic efficacy and cerebral ischemia. Although processed EEG variables have enjoyed limited success for specific applications, few acceptable standards have emerged. In part, this may be attributed to the fact that commonly used signal processing tools do not quantify all of the information available in the EEG. Power spectral analysis, for example, quantifies only power distribution as a function of frequency, ignoring phase information. It also makes the assumption that the signal arises from a linear process, thereby ignoring potential interaction between components of the signal that are manifested as phase coupling, a common phenomenon in signals generated from nonlinear sources such as the central nervous system (CNS)."

24.

Kearse L A Jr, Manberg P, DeBros F, Chamoun N, Sinai V, described in Electroencephalogr Clin Neurophysiol March 1994, PMID: 7511501, UI: 94192475 "Bispectral analysis of the electroencephalogram during induction of anesthesia may predict hemodynamic responses to laryngoscopy and intubation." In this study, Kearse and colleagues describe: "The use of electroencephalography as a measure of adequacy of anesthesia has achieved limited success. Our purpose was to determine whether the non-linear properties of the electroencephalogram (EEG) as defined by the bispectral index was a better predictor of autonomic responses to endotracheal intubation during opioid-based anesthesia than the linear statistical properties of the EEG formulated by power spectral analysis." "There was a significant difference between response groups as measured by the bispectral index which distinguished responders from non-responders independently of the amount of drug given. None of the variables of power spectral analysis accurately distinguished responder from non-responder."

The HCM System is designed to use conventional low cost electrodes in conjunction with wireless interface device to reduce the hazards and difficulties associated with wiring patients during operational procedures. Furthermore the HCM System utilises a unique method of displaying the charge status of the wireless electrode module by way of simple led display representing the available charge time, where each hour (or 2 hours) of charged usage time available is represented by a LED display. The HCM System wireless device also provides a simple fool-proof means of recharging the wireless module by utilising a unique proximity RF charging technique.

The following papers present some of the difficulties of state of the art which are overcome by the HCM System:

25.

Yli-Hankala A, Vakkuri A, Annila P, Korttila K, described in Acta Anaesthesiol Scand May 1999, PMID: 10342003, UI: 99273549 "EEG bispectral index monitoring in sevoflurane or propofol anaesthesia: analysis of direct costs and immediate recovery." In this study, Yli-Hankala and colleagues describe: "BIS monitoring decreased the consumption of both propofol and sevoflurane and hastened the immediate recovery after propofol anaesthesia. Detailed cost analysis showed that the monitoring increased direct costs of anaesthesia treatment in these patients, mainly due to the price of special EEG electrodes used for relatively short anaesthesias."

26

EEG power spectrum during repeated transitions from consciousness to unconsciousness. R. J Gajrai, M. Doi, H. Mantzzaridis and G. N. C. Kenny. British Journal of Anaesthesia 1998.

29

Moira L. Steyne-Ross and D. A. Steyne-Ross, of Department of Anaesthetics, Waikato Hospital, Hamilton, New Zealand describe "Theoretical electroencephalogram stationary spectrum for white-noise-driven cortex: Evidence for a general anaesthetic-induced phase transition" This paper describes an increase in EEG spectral power in the vicinity of the critical point of transition into comatose-unconsciousness.

The HCM System applies the capability to predict the amplitude of an EEG signal during administration of an anaesthetic drug as one of the weighted inputs for an improved in depth anaesthesia monitoring system.

30.

Analysis of the EEG Bispectrum, auditory evoked potentials and the EEG power spectrum during repeated transitions from consciousness to unconsciousness. R. J. Gajraj, M. Doi, H. Mantzaridis and G. N. C. Kenny. British Journal of Anaesthesia 1998.

31.

Differentiating Obstructive and Central Sleep Apnea Respiratory Events through Pulse Transit Time. Jerome Argod, Jean-Louis Pepin, and Patrick Levy. Resp Crit Care Med 1998 Vol 158 pp 1778-1783.

32.

Pulse Transit Time: an appraisal of potential clinical applications. Robin P Smithj, Jerome Argod, Jean-Louis Pepin, Patrick A Levy. Thorax 1999; 54:452-458.

33.

An Introduction to Bispectral Analysis for the electroencephelogram. Jeffrey C. Sigl. PhD, and Nassib G. Chamoun, M S. 1994 Little, Brown and Company.

34.

Allan Rechtschaffen and Anthony Kales, Editors of A Manual of Standardized Terminology, Techniques and Scoring System for Sleep Stages of Human Subjects, Brain Information Service/Brain Research Institute, University of California, Los Angeles, Calif. 90024.

35.

EEG Arousals: Scoring Rules and Examples. A Preliminary Report from the Sleep Disorders Atlas Task Force of the American Sleep Disorders Association. Sleep, Vol. 15 No. 2, 1992.

36.

95% spectral edge analysis is the point on the spectral power curve of a sample of data, which is measured at the 95% point on the frequency axis, where the Y axis represents the frequency band power.

Figure 49:
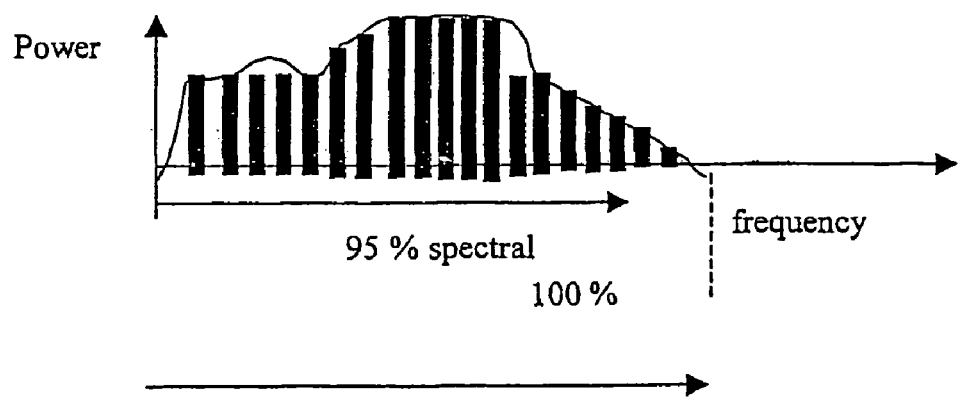
FIG. 49 shows a power spectral curve of sample data.

For example refer to FIG. 49 which shows a power spectral curve of sample data.

37.

The Biomedical Engineering Handbook. Joseph D. Bronzino. 1995 pages 840 to 852. Signal averaging.

38. The Fourier Transform in Biomedical Engineering. Introduction to the Fourier Transform. T. M. Peters. 1998. Chapter 1.

39.

Biomedical Instruments Theory and Design. Second Edition. Walter Welkowitz 1992. The frequency spectrum. Pages 10 to 19.

40.

The Biomedical Engineering Handbook. Joseph D. Bronzino. 1995 Bioloectric Phenomena. Craig S. Henriquez. Chapter 11.

41.

The Biomedical Engineering Handbook. Joseph D. Bronzino. 1995 Biomedical Signals: Origin and Dynamic Characteristics; Frequency-Domain Analysis. Chapter 54.

42.

The Biomedical Engineering Handbook. Joseph D. Bronzino. 1995 Anaesthesia Delivery Systems. Chapter 86.

43.

The Biomedical Engineering Handbook. Joseph D. Bronzino. 1995 Measurement of Sensory-Motor Control Performance Capacities. Chapter 145.

44.

Principles and Practice of Sleep Medicine, Second edition 1994, Kryger Roth Dement. Chapter 89 Monitoring and Staging Human Sleep by Mary Carskadon and Allan Rechtschaffen.

45.

Patent Reference: AU 632432 Analysis System for Physiological Variables. Burton and Johns, 1989.

46.

An improved method for EEG analysis and computer aided sleep scoring. (½ period amplitude abstract—Johns and Burton 1989. Abstracts of Conference Manual.

47.

Atlas of Adult Electroencephalography. Warren T Blume, Masaka Kaibara, Raven Press, 1995. Artifacts, Chapter 2.

48.

The Biomedical Engineering Handbook. Joseph D. Bronzino. 1995 Higher-Order Spectra in Biomedical Signal Processing. Pages 915-916.

49.

Barrett-Dean Michelle, Preliminary Investigation of the Compumedics Mattress sensor in a clinical setting. St Frances Xavier Cabrini Hospital, Malvern, Victoria. ASTA, 1999.

50.

Modified R&K utilising frequency compensation techniques to best approximate non-conventional R&K EEG electrode position recommendations (34).

51.

Bispectral Analysis of the Rat EEG During Various Vigilance States. Taiking Ning and Joseph D. Bronzino. IEEE transactions on biomedical engineering. April 1989.

52.

Trademarks associated with Aspect monitoring;

BIS®

Bispectral Index®

A-2000™

53.

Effects of paced respiration and expectations on physiological and physiological responses to threat.

McCaul K D, Solomon S, Holmes D S, Journal of Personality and Social Psychology 1979, Vol 37, No 4, 564-571

54.

Casino gambling increases heart rate and salivary cortisol in regular gamblers. Meyer G, Hauqffa B P, Schedlowski M, Pawlak C, Stadler M A, Exton M S Biol Psychiatry 2000 November 1; 48(9):948-53

ABSTRACT

55.

Heart rate variability, trait anxiety, and perceived stress among physically fit men and women.

Dishman R K, Nakamura Y, Garcia M E, Thompson R W, Dunn A L, Blair S N Int J Psychophysiol 2000 August; 37(2):121-33

56.

Effects of short-term psychological stress on the time and frequency domains of heart variability Delaney J P, Brodie D A Percept Mot Skills 2000 October; 9(2):515-24

ABSTRACT

57.

Heart rate variability in depressive and anxiety disorders

Gorman J M, Sloan R P

Am Heart J 2000 October; 140(4 Suppl):77-83

ABSTRACT

58.

Chronic stress effects blood pressure and speed of short-term memory.

Brand N, Hanson E, Godaert G

Percept Mot Skills 2000 August; 91(1):291-8

ABSTRACT

59.

Effects of Paced Respiration and Expectations on Physiological and Psychological Responses to Threat.

Kevin D. McCaul, Sheldon Solomon, and David S. Holmes

University of Kansas, Journal of Personality and Social Psychology

1979, Vol. 37, No 4, 564-571

PAPER

60.

Heart. Rate Variability, trait anxiety, and perceived stress among physically fit men and women Rod K. Dishman, Yoshia Nakamura, Melissa E. Garcia, Ray W. Thompson, Andrea L. Dunn, Steven N. Blair 16th Nov. 1999, International Journal of Psychophysiology 37 (2000) 121-133

61

Auditory evoked potential index: a quantitative measure of changes in auditory evoked potentials during general anaesthesia H. Mantzaridis and G. N. C. Kenny
Anaesthesia, 1997, 52 pages 1030-1036

62
Concept for an intelligent anaesthesia EEG monitor
W. NAHM, G. STOCKMANNS, J. PETERSEN, H. GEHRING, E. KONECNY, H. D. KOCHS and E. KOCHS
Med. Inform. (1999), vol. 24. NO. 1-9

63
Monitoring depth of anaesthesia
G. Schneider and P. S. Sebel
European Journal of Anaesthesiology 1997, 14 (Suppl. 15), 21-28

64
Clinical usefulness of the bispectral index for titrating propofol target effect-site concentration
M. Struys, L. Versichelen, G. Byttebier, E. Mortier, A. Moerman and G. Rolly Anaesthesia, 1998, 53, pages 4-12

65
Genetic dependence of the electroencephalogram bispectrum
JOEL. WHITTON, SUSAN M. ELGIE, HERB KUGEL, AND HARVY MOLDOFSKY
Electroencephalography and clinical Neurophysiology, 1985, 60; 293-298

66
Assessment of power spectral edge for monitoring depth of anaesthesia using low methohexitone infusion
Peter S. Withington, John Morton, Richard Arnold, Peter. S. Sebel and Richard Moberg
International Journal of Clinical Monitoring and Computing 3: 117-122, 1986

67
Analysis of the interrelations between frequency band of the EEG by means of the bispectrum.
Electroencephalography and clinical neurophysiology. International Federation-7th Congress. Free communications in EEG.
Kleiner B; Huber P J, Dumermuth G;

68
GSR or Skin Response
Biomedical instruments, Inc.
WWW.bio-medical.com/Gsr.html 26/0201

69
Awareness during general anaesthesia: is it worth worrying about ?
MJA Vol 174 5 Mar. 2001

70
Women take longer to recover from operations and are more likely to suffer side-effects than men during surgery.
British Medical Journal, Mar. 23 2001.
(reference—Age Mar. 24, 2001)

71
Compumedics Siesta patient monitoring system.

72
Compumedics E-Series patent monitoring system.

73
Compumedics Profusion Software patient monitoring system.

74
Recall of intraoperative events after general anaesthesia and cardiopulmonary bypass; Phillips A A, McLean R F, Devitt J H, Harrington E M; Canadian Journal of Anaesthesia; 1993 Oct.

75
Patient satisfaction after anaesthesia and surgery: results of a prospective survey of 10,811 patients; Myles P S, Williams D L, Hendrata M, Anderson H, Weeks A M; British Journal of Anaesthesia; 2000 Jan.

76
EEGs, EEG processing, and the bispectral index; Todd M M; Anesthesiology; 1998 Oct.

77
Detecting awareness during general anaesthetic caesarean section. An evaluation of two methods; Bogod D G, Orton J K, Yau H M, Oh T E; Anaesthesia; 1990 Apr.

78
Oesophageal contractility during total i.v. anaesthesia with and without glycopyrronium; Raftery S, Enever G, Prys-Roberts C; British Journal of Anaesthesia; 1991 May.

79
Effect of surgical stimulation on the auditory evoked response; Thornton C, Konieczko K, Jones J G, Jordan C, Dore C J, Heneghan C P H; British Journal of Anaesthesia; 1988 Mar.

80
Comparison of bispectral index, 95% spectral edge frequency and approximate entropy of the EEG, with changes in heart rate variability during induction of general anaesthesia; Sleigh J W, Donovan J; British Journal of Anaesthesia; 1999 May.

81
Bispectral index monitoring allows faster emergence and improved recovery from propofol, alfentanil, and nitrous oxide anesthesia. BIS Utility Study Group; Gan T J, Glas P S, Windsor A, Payne F, Rosow C, Sebel P, Manberg P; Anesthesiology; 1997 Oct.

82
Why we need large randomized studies in anaesthesia; Myles P S; British Journal of Anaesthesia; 1999 Dec.

83
U.S. Pat. No. 5,381,804, Aspect Medical Systems, Inc Jan. 17 1995 describes a monitor for receiving electrical signals from a living body.

84
U.S. Pat. No. 5,458,117, Aspect Medical Systems, Inc Oct. 17 1995 describes a cerebral biopotential analysis system and method.

85
U.S. Pat. No. 5,320,109 Aspect Medical Systems, Inc Jun. 14 1994 describes a cerebral biopotential analysis system and method.

86
It has been reported that Wrist actigraphic recordings may differentiate sleep and wakefulness with a 94.5% agreement with standard polysomnography (Mullaney et al. 1980).
Other Wrist actigraphic studies have reported a 91.8% agreement in healthy subjects, 85.7% in patients with obstructive sleep apnea syndrome, 78.2% in patients with insomnia, and 89.9% in children Sadeh et al. (1989) (21).

87.
Medical Dictionary. 1997 Merriam-Webster, Incorporated.
http://www.intelihealth.com/IH/

88.
The American Heritage® Dictionary of the English Language
http://www.bartleby.com/61/

89.
William Thomas Gordon Morton first demonstrated what is today referred to as surgical anaesthesia (89).

Pubmed search

90

In Australia about 1 million people a year undergo general anaesthesia. Of these 1 million people about 5 people die each year, as a direct result of the anaesthesia, while about 3000 more will be inadequately anaesthetised. These people inadequately anaesthetised will experience a range of symptoms from hearing recall while undergoing a medical procedure, sight recall from premature recovery and the early opening of eyes, stress and anxiety from experiencing paralysis while some degree of mental awareness to the medical procedure being instigated, memory recall from having some degree of consciousness, operation mishaps can occur in cases where the subject's state of paralysis is not adequate and leads to movement of the subject's body during incision.

91

In fact, even hospitals such as Melbourne's Alfred Hospital, which demonstrated one of the world's lowest reported incidences of consciousness under general anaesthesia, still have an incidence rate of 1 in 1000 patients (for consciousness under anaesthesia) (91).

Pubmed search

92

Up-to-date there has been no way to determine whether a patient is asleep during a medical procedure (according to University of Sydney-Australia's Web site, introductory paper on anaesthesia).

Pubmed search

93

Furthermore, the discovery in 1942 Canadian anaesthetists determined (Sir Walter Raleigh had known in 1596 that the indigenous people of Bolivia had been using an American plant derivative called curare to cause paralysis) that neuromuscular blocking drugs could be developed (93). Since 1942 these drugs have revolutionised surgery, particularly abdominal and chest operations where muscle contraction had made cutting and stitching almost impossible.

Pubmed search

94

Anaesthetists tend to overestimate the amount of anaesthetic drug usage by up to 30%. This overestimation has consequences in relation to a patient's health, recovery time and financial costs to health services.

(Age article—eyes wide shut)

Pubmed search

95

The challenge to monitor for appropriate or optimum anaesthesia is even further demonstrated with classic experiments such as that of psychiatrist Bernard Levin in 1965, when 10 patient's who were read statements during anaesthesia, later had no recall of the statements when questioned after surgery. However, of the same patient's under hypnosis four could quote the words verbatim and another four could remember segments, but became agitated and upset during questioning.

Pubmed search

96

An adequately anaesthetised patient should not "feel", "smell", "see" or "taste" anything until they regain consciousness.

(Age article—eyes wide shut)

Pubmed search

97

In 1998 Dr David Adams of New York's Mount Sinai Medical Centre replayed audiotapes of paired words (boy/girl, bitter/sweet, ocean/water . . . ) to 25 unconscious heart surgery patients. Approximately four days after the operation, the patients listened to a list of single words. Some of these words had been played while they were unconscious during their former operation. The patients were asked to respond to each word with the first word that came into their minds. The patient was found to be significantly better at free-associating the word pairs they had already encountered than those they had not. It was apparent that the patients had heard the information and remembered it.

(Age article—eyes wide shut)

Pubmed search

98

It appears that while a smaller number of patient's have conscious memories of their experiences on the operating table, a larger number have unconscious recollections. While positive messages during surgery may have desired consequences others can have undesirable results.

Pubmed search

99

The PERCLOS Monitor

Reference: http://www.cmu.edu.cmri/drc/drcperclosfr.html, 12/10/2000

100.

Drowsy Driver Detection System http://www.jhuapl.edu/ott/newtech/soft/DDDSystem/benefits.htm

101.

Driver Drowsiness Literature Review & Perspective; Cause, effects, detection, PSG methods, Bio-behavioural, Physiological, safety air-bags business case, practicality, ease-of-use, ethical implications & alarms.

Burton, June 2001.

102.

Proprietary, Zilberg Eugene, Ming Xu May 2001. Compumedics preliminary Vigilance Project Report on Drowsiness and movement sensor (seat & steering wheel)—correlation analysis (May, 2001).

103.

Burton David, Methods and Apparatus for Monitoring Human Consciousness, U.S. Provisional Patent Application 60/298,011 filed 13 Jun. 2001.

104.

Iani C, Gopher D, Lavie P

Effects of Task Difficulty and Invested Mental Effort of Peripheral Vascoconstriction. SLEEP, Vol-24, Abstract Supplement 2001.

105

Autonomic Activation Index (MI)—A New Marker of Sleep Disruption. Pillar G, Shlitner A, Lavie P. SLEEP, Vol-24, Abstract Supplement 2001.

106.

Lac, Leon. PAT perspective—how well is pulse wave amplitude related top PAT?. Correspondence with DB. Jun. 27 2001.

107.

Peter G. Catcheside, R. Stan Orr, Siau Chien Chiong, Jeremy Mercer, Nicholas A, Saunders. Peripheral cardiovascular responses provide sensitive markers of acoustically induced arousals from NREM sleep.

108.

Michael H. Pollok and Paul A. Obrist. Aortic-Radial Pulse Transit Time and ECG Q-Wave to Radial Pulse Wave Interval as Indices of Beat-By-Beat Blood Pressure Change. Psychophysiology. Vol. 20 No. 11983.

109.
PAT signal Provides New Marker of Sleep Quality, Respiratory and Cardiovascular Disorders. http://www.talkaboutsleep.com/news/PAT signal.htm. Chicago, Ill., Jun. 7, 2001

110.
Todd, Michael M. MD. EEGs, EEG Processing, and Bispectral Index. Anaesthesiology. Vol. 89(4), pp 815-817. October 1998

111.
A Primer for EEG Signal Processing in Anaesthesia. Anaesthesiology. Vol. 89(4), pp 980-1002. October 1998

112. Lippincott-Raven, 1997. Evoked Potentials in Clinical Medicine. Third Edition. a) Click Intensity. CH8, 179. b) Click Polarity. CH8, PP183. c) Stimulus Delivery Apparatus. CH8, PP188.

113. Nieuwenhuijs, D.; Coleman, E. L.; Douglas, N. J.; Drummond, G. B.; Dohan, A. Bispectral index values and spectral edge frequency of different stages of physiologic sleep. Anesth. Analg.

114. Kryger, Roth, Dement. Principles and Practice of Sleep Medicine. Second edition, 2000.

APPENDIX II

| | GLOSSARY: |
|---|---|
| AMPLITUDE | One half the peak-to-peak height of a sinusoid, usually measured in volts or microvolts ($\mu$V). (33) |
| Anesthesia or Anaesthesia | Noun: 1. Total or partial loss of sensation, especially tactile sensibility, induced by disease, injury, acupuncture, or an anesthetic, such as chloroform or nitrous oxide. 2. Local or general insensibility to pain with or without the loss of consciousness, induced by an anesthetic. 3. A drug, administered for medical or surgical purposes, that induces partial or total loss of sensation and may be topical, local, regional, or general, depending on the method of administration and area of the body affected. Word History: The following passage, written on Nov. 21, 1846, by Oliver Wendell Holmes, a physician-poet and the father of the Supreme Court justice of the same name, allows us to pinpoint the entry of anesthesia and anesthetic into English: "Every body wants to have a hand in a great discovery. All I will do is to give you a hint or two as to names—or the name—to be applied to the state produced and the agent. The state should, I think, be called 'Anaesthesia' [from the Greek word anaisth$\bar{\text{e}}$sia, "lack of sensation"]. This signifies insensibility . . . The adjective will be 'Anaesthetic.' Thus we might say the state of Anaesthesia, or the anaesthetic state." This citation is taken from a letter to William Thomas Green Morton, who in October of that year had successfully demonstrated the use of ether at Massachusetts General Hospital in Boston. Although anaesthesia is recorded in Nathan Bailey's Universal Etymological English Dictionary in 1721, it is clear that Holmes really was responsible for its entry into the language. The Oxford English Dictionary has several citations for anesthesia and anesthetic in 1847 and 1848, indicating that the words gained rapid acceptance |
| BICOHERENCE | A normalised measure of phase coupling in a signal, ranging from 0% to 100%. (33) |
| BISPECTRAL INDEX | A mutlivariate measure incorporating bispectral and time-domain parameters derived from the EEG. (33) |
| BISPECTRUM | A measure of the level of phase coupling in a signal, as well as the power in the signal. The bispectrum can be described as a measure of the actual level of phase coupling that exists in the EEG signal, with the phase angles of the components at their actual values.(33) |
| COMPONENT | One of the sinusoids summed together in a Fourier series to represent a signal. (33) |
| Consciousness | Function: noun 1 : the totality in psychology of sensations, perceptions, ideas, attitudes, and feelings of which an individual or a group is aware at any given time or within a given time span <altered states of con·scious·ness, such as sleep, dreaming and hypnosis-Bob Gaines> 2 : waking life (as that to which one returns after sleep, trance, or fever) in which one's normal mental powers are present <the ether wore off and the patient regained con·scious·ness> 3 : the upper part of mental life of which the person is aware as contrasted with unconscious processes (87) 1. The state or condition of being conscious. 2. A sense of one's personal or collective identity, including the attitudes, beliefs, and sensitivities held by or considered characteristic of an individual or group: Love of freedom runs deep in the national consciousness. 3a. Special awareness or sensitivity: class consciousness; race consciousness. b. Alertness to or concern for a particular issue or situation: a movement aimed at raising the general public's consciousness of social injustice. 4. In psychoanalysis, the conscious. (88) |
| EPOCH | A series of successive, equal time segments (overlapping or contiguous) into which the data series x(k) is divided. (33) |

APPENDIX II-continued

GLOSSARY:

| | |
|---|---|
| FEATURES | Descriptive parameters extracted from a signal and correlated with some information of interest, such as a particular cerebral state. (33) |
| FOURIER SERIES | A representation of a signal as a sum of sinusoid components of different frequencies and amplitudes. (33) |
| FOURIER TRANSFORM | A mathematical process that converts a time signal to its representation in terms of the amplitudes and frequencies of its sinusoid components. (33) |
| FREQUENCY | The rate at which a signal or sinusoid oscillates, usually measured in cycles per second (Hz). (33) |
| FREQUENCY DOMAIN | A representation of a signal in which amplitude or power is a function of frequency. (33) |
| FREQUENCY RESOLUTION | The spacing in hertz between successive values of the Fourier transform. (33) |
| FUNDAMENTAL | A component of an output signal that is not an IMP. (33) |
| HERTZ (Hz) | A measure of frequency; equivalent to cycles per second. (33) |
| REAL TRIPLE PRODUCT (RTP) | A measure of the maximum possible degree of phase coupling that would result if the phase angle of each and every component of a signal were exactly identical. It is also a function of signal power. The ratio of the bispectrum to the square root of the real triple product, which expresses the normalized degree of phase coupling in the EEG range (ranging from 0 to 100%) is defined as the bicoherence. |
| System | Refers to the device or apparatus forming the basis of invention. This system typically contains physiologically recording capabilities for 1 or more channels of physiological data, display viewing capabilities for viewing or reviewing one or more channels of physiological data, data analysis and reporting capabilities, and data recording and archiving and retrieval capabilities, for the purpose of providing a device for the investigation of a patient's state of consciousness or vigilance. |
| HCM system | Denotes Human Consciousness Monitoring system including methods and apparatus for monitoring, sensing, tracking, analysing, storing, logging and/or displaying, in the context of the present invention, data related to the state of mind or state of consciousness of human and other sentient subjects. |
| System-generated audio | Refers to the audio click, which can be applied to the patient's ear or ears during an operating procedure, for example. |
| Unconscious | Adjective: Lacking awareness and the capacity for sensory perception; not conscious. 2. Temporarily lacking consciousness. 3. Occurring in the absence of conscious awareness or thought: unconscious resentment; unconscious fears. 4. Without conscious control; involuntary or unintended: an unconscious mannerism. Noun: The division of the mind in psychoanalytic theory containing elements of psychic makeup, such as memories or repressed desires, that are not subject to conscious perception or control but that often affect conscious thoughts and behavior. Other forms: un·con'scious·ly—ADVERB un·con'scious·ness—NOUN (88) |
| Unconsciousness | Function: adjective 1 : not marked by conscious thought, sensation, or feeling <un·con·scious motivation> 2 : of or relating to the unconscious 3 : having lost consciousness <was un·con·scious for three days> un·con·scious·ly adverb un·con·scious·ness noun (87) Alert watchfulness (88) |
| Vigilance | Function: noun :the quality or state of being wakeful and alert: degree of wakefulness or responsiveness to stimuli vig·i·lant/$_{-l\&nt}$/adjective (87) |
| Unconsciousness | Function: adjective 1 : not marked by conscious thought, sensation, or feeling <un·con·scious motivation> 2 : of or relating to the unconscious 3 : having lost consciousness <was un·con·scious for three days> un·con·scious·ly adverb un·con·scious·ness noun (87) |
| Subject | This word can be interchanged within context of this document for "patient". |
| Patient | This word can be interchanged within context of this document for "subject". |

APPENDIX II-continued

GLOSSARY:

| | |
|---|---|
| Vagal modulation definition; | The parasympathetics to the heart are contained in the vagus nerves. The vagus nerves. Stimulation of these nerves causes slowing of the heart while cuffing the parasympathetics causes the heart rate to increase. Vagal modulation relates to the modulation of the vagus nerves (Stedmans, Medical Dictionary, 2000), which in turn relates to the slowing of the heart (Vander etal, Human Physiology, 1970 PP 241). |
| Relationship of Bispectrum, Real Triple Product and Bicoherence | The bispectrum can be described as a measure of the actual level of phase coupling that exists in the EEG signal, with the phase angles of the components at their actual values.<br>The real triple product is a measure of the maximum possible degree of phase coupling, which could result if the phase angle of each and every component of the EEG were exactly identical. The ratio of the bispectrum to the square root of the real triple product, which expresses the normalized degree of phase coupling in the EEG range (ranging from 0 to 100%) is defined as the bicoherence. |
| CONTEXT ANALYSIS | Refers to whether the patient's is entering a state of consciousness or emerging from unconsciousness. 1/2 period amplitude analysis (ref 3,4,8,9) is a method for determining the stage od sleep a subject is in. Stages include WAKE, STAGE 1, STAGE 2, STAGE 3, STAGE 4 AND REM SLEEP. |

ABBREVIATIONS

| | |
|---|---|
| ADMS | Anaesthesia Depth of Monitoring System. |
| Bi | Bispectral index. |
| B | Bicoherence derivattive of the EEG signal. |
| SSA | Sleep Staging Analysis. |
| AEPi | Audio Evoked Potential index. |
| TUC | Transition From Unconsciousness to Consciousness. |
| TCU | Transition From Consciousness to Unconsciousness |
| CIAi | Comprehensive Integrated Anaesthesia index. The main function and output of the ADMS. |
| DOA | Depth Of Anaesthesia. |
| CALPAT | Calibrated Patient (values). |
| CP | Calibrated Patient. |
| IDDZA | Impirical Data Display Zone A. |
| IDDZB | Impirical Data Display Zone B. |
| IDDZC | Impirical Data Display Zone C. |
| IDDZD | Impirical Data Display Zone D. |
| CPDZA | Calibrated Patient DisplayZone A. |
| CPDZB | Calibrated Patient DisplayZone B. |
| CPDZC | Calibrated Patient DisplayZone C. |
| CPDZD | Calibrated Patient DisplayZone D. |
| CPTUCBi | Calibrated Patient data for Transition from Unconsciousness to Consciousness for Bi. |
| CPTUCAEPi | Calibrated Patient data for C1260Transition from Unconsciousness to Consciousness C1230 for AEPi. |
| CPTUCSSA | Calibrated Patient Transition from Unconsciousness to Consciousness for SSA. |
| FE | Forehead Electrodes |
| EOG | Electrooculogram<br>The study of electrophysiology eye movement<br>surface electrode signals (which show rapid activity with WAKE and REM sleep stages). |
| EEG | Electroencephelogram<br>The study of electrophysiology surface<br>electrode signals (electrical muscle energy, which decreases with sleep state). |
| EMG | Electromyography<br>The study of electrophysiology eye movement surface electrode signals (which show rapid activity with WAKE and REM sleep stages). |
| SPL | Sound Pressure Level |
| C | Consciousness |
| U | Unconsciousness |
| TSW | Transition from Sleep to Wake |
| S1W > S | SSA Stage 1 Wake to Sleep |
| Bme | Body Movement Event<br>Detection of Body Movement (BM) relates to a physical movement of the body such as detected by a pressure or vibration sensitive sensors. |

-continued

| ABBREVIATIONS | |
|---|---|
| Bmi | Body Movement index |
| Ae | Arousal event<br>Arousal refers to physiological events as can be cause by the Central Nervous System (CNS), and may not always constitute a body movement detection. |
| Ai | Arousal index |
| DZ | Display Zone Display Zones (DZ) of display represents the zones of the ADMS display where defined phases or states can be measured. |
| DZCT | The critical Display Zones Critical Threshold (DZCT) of display represents the values which are desired to be displayed in such a manner that the user has an expanded viewing range (on meter display, for example) compared to less critical display zones. In the present invention the ability exists to define these said "critical display zones" and in particular the critical display zones can change subject to both the context of a subjects current and past states of conscious/wake or unconscious/sleep. |
| CD | Current Data |
| CDAEPi | Current Patient Data AEPi (Value) |
| IDAEPi | Impirical Data AEPi (Value) |
| CDTCUAEPi | Current Data for TCU of AEPi. Current Data refers to latest analysed real time data value. |
| CDTCUBi | Current Data for TCU of Bi. Current Data refers to latest analysed real time data value. |
| ID | Impirical Data |
| IDAEPi | Impirical Data value for AEPi |
| IDBi | Impirical Data value for Bi |
| CDTCUSSA | Current Data for TCU of SSA. Current Data refers to latest analysed real time data value. |
| CPTUCSSA | Calibrated Patient for Transition from Unconsciousness to Consciousness for Sleep Staging Analysis. |
| CDTUCAEPi | Current Data for TUC of AEPi. Current Data refers to latest analysed real time data value. |
| CPTSWAEPi | Calibrated Patient for Transition Context State from Sleep to Wake for AEPi. |
| DZTF | Display Zone Transition Formula |
| Zone A | Patient emerging from Consciousness to Unconsciousness. |
| Zone B | Patient in unconscious state. |
| Zone C | Patient in unconscious state. |
| Zone D | Patient Transition from Unconsciousness to Consciousness. |
| CA1W > S | Context Analysis change from WAKE to (sleep-stage 1, 2, 3, 4 or REM) ref 3, 4, 8, 9 |
| CA2W > S | context Analysis Change from sleep-stage 1 to (2 OR 3 OR 4 OR REM) ref 3, 4, 8, 9 |
| CA3W > S | Context Analysis Change from sleep-stage 2 to (3 OR 4 OR REM) ref 3, 4, 8, 9 |
| CA4W > S | Context Analysis Change from sleep-stage 3 to (4 OR REM) ref 3, 4, 8, 9 |
| CA5W > S | Context Analysis Change from sleep-stage 4 to REM) ref 3, 4, 8, 9 |
| CA6S > W | Context Analysis Change from sleep-stage REM to (WAKE OR 1, 2, 3 or 4) ref 3, 4, 8, 9 |
| CA7S > W | Context Analysis Change from sleep-stage 4 to (WAKE or 1 OR 2 OR 3) ref 3, 4, 8, 9 |
| CA8S > W | Context Analysis Change from sleep-stage 3 to (WAKE OR 1 OR 2 ) ref 3, 4, 8, 9 |
| CA9S > W | Context Analysis Change from sleep-stage 2 to (WAKE OR 1) ref 3, 4, 8, 9 |
| CA10S > W | Context Analysis Change from sleep-stage 1 to WAKE ref 3, 4, 8, 9 |
| W | Wake State |
| STG1 | Stage 1 of Sleep |
| STG2 | Stage 2 of Sleep |
| STG3 | Stage 3 of Sleep |
| STG4 | Stage 4 of Sleep |
| REM | REM Stage of Sleep % Represents start of comments, as applicable to psuedo coding or lines of program code. |
| IDOA | Impirical Data Offset applied for zone A |
| IDOB | empirical Data Offset applied for zone B |
| IDOC | Impirical Data Offset applied for zone C |
| IDOD | Impirical Data Offset applied for zone D |
| IDC | Impirical Data Consciousness. |
| IDU | Impirical Data Unconsciousness. |
| BM-Mz | Body Movement Multi-zone sensor |
| AEPiTF | Audio Evoked Potential Transition Formula |
| BiTF | Bicoherence index Transition Formula |
| SSATF | Sleep Staging Analysis Transition Formula. |
| EESM | Electronics Electrode and Sensor Module |

We claim:

1. A method for acquiring, characterising and classifying biosignals from a living being for determining the state of consciousness of said being comprising:

acquiring at least one continuous biosignal;

stimulating an evoked potential response signal in said being;

deriving at least one evoked potential response signal from said at least continuous biosignal using a processor;

deriving a first index of consciousness from said continuous biosignal;
deriving a second index of consciousness from said evoked potential response signal; and
classifying said indices as being representative of entering or leaving consciousness according to a weighting process.

2. The method of claim 1 wherein the continuous biosignal is an EEG (electroencephalogram) signal or a muscular activation signal or both.

3. The method of claim 2 wherein the muscular activation signal is a measure of eyelid movement.

4. The method of claim 2 wherein the EEG signal is a continuous signal.

5. The method of claim 1 further comprising monitoring signals for signal quality.

6. The method of claim 1 wherein said acquiring said at least one continuous biosignal includes using at least one disposable or semi-disposable sensor.

7. The method of claim 6 wherein said at least one disposable or semi-disposable sensor includes means for activating an electrical energy source.

8. The method of claim 7 wherein the means for activating said energy source includes the packaging of said electrical energy source.

9. The a method of claim 1 wherein said evoked potential response signal comprises any one or a combination of somatosensory, auditory, or visual evoked response.

10. The method of claim 1 whereby said stimulating induces a steady state response signal or any combination of signals inducing associated auditory evoked response or responses classified as the following either singly or in combination greater than: 60 Hz ASSR (auditory steady state response), 40 Hz ASSR, or less than 20 Hz ASSR.

11. The method of claim 1 further comprising displaying a functional or operational status of a sensor.

12. The method of claim 1 wherein said stimulating includes producing any one of or a combination of evoked response paradigms including:
at least one type of click stimulus;
at least one response at spaced intervals within a click stimulus
sounds of white noise or speech
oddball sound characteristics
unusual sound characteristics
masked noise sounds
unanticipated noise sounds
composite sounds
familiar sounds
recognizable sounds in reference to said being
wherein a combination of any sound stimulus is generated according to a predetermined sequence.

13. The method of claim 12 wherein the predetermined sequence is determined by determination means.

14. The method of claim 13 including alerting an operator of a status of at least one sensor.

15. The method of claim 1 wherein said at least one evoked potential response signal includes one or more of:
a first latency signal acquired from any of a cochlear, eighth nerve or eighth nerve compound action potential, said signal having a duration substantially of 0 to 5 ms (milliseconds);
a second fast latency signal acquired from any of an auditory brainstem response, wave I, wave 11, wave 111, wave IVY or wave V, said signal having a duration substantially of 2 to 20 ms;
a third early cortical or middle latency signal said signal including any of MLAEP (middle latency audio evoked potential), Na, Pa, TP41, Pb, or Nb, said signal having a duration substantially of 10 to 100 m sec;
a fourth slow latency vertex audio evoked potential signal including any of P1, N1, P2, or N2 having a duration substantially of 50 to 300 ms; and a fifth contingent potential processing signal (PCP), including any one of or a combination of mismatched negativity, Nd, N2b, P3a, P3b, N400, or P600.

* * * * *